United States Patent
Shen et al.

(10) Patent No.: US 12,329,823 B2
(45) Date of Patent: *Jun. 17, 2025

(54) LONG-ACTING DUAL GIP/GLP-1 PEPTIDE CONJUGATES AND METHODS OF USE

(71) Applicant: The Scripps Research Institute, La Jolla, CA (US)

(72) Inventors: Weijun Shen, Shenzhen (CN); Zaid Amso, El Cajon, CA (US); Peter G. Schultz, La Jolla, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 66 days.

This patent is subject to a terminal disclaimer.

(21) Appl. No.: 18/366,653

(22) Filed: Aug. 7, 2023

(65) Prior Publication Data

US 2024/0148884 A1 May 9, 2024

Related U.S. Application Data

(63) Continuation of application No. PCT/CN2022/097662, filed on Jun. 8, 2022.

(60) Provisional application No. 63/208,952, filed on Jun. 9, 2021.

(51) Int. Cl.
*A61K 47/64* (2017.01)
*A61K 47/54* (2017.01)
*A61K 47/59* (2017.01)
*A61P 3/04* (2006.01)
*A61P 3/10* (2006.01)

(52) U.S. Cl.
CPC ............ *A61K 47/64* (2017.08); *A61K 47/542* (2017.08); *A61K 47/595* (2017.08); *A61P 3/04* (2018.01); *A61P 3/10* (2018.01)

(58) Field of Classification Search
CPC .... A61K 47/64; A61K 47/542; A61K 47/595; A61P 3/04; A61P 3/10
See application file for complete search history.

(56) References Cited

U.S. PATENT DOCUMENTS

| | | |
|---|---|---|
| 3,773,919 A | 11/1973 | Boswell et al. |
| 3,854,480 A | 12/1974 | Zaffaroni |
| 3,887,699 A | 6/1975 | Yolles |
| 4,452,775 A | 6/1984 | Kent |
| 4,485,045 A | 11/1984 | Regen |
| 4,544,545 A | 10/1985 | Ryan et al. |
| 4,675,189 A | 6/1987 | Kent et al. |
| 5,133,974 A | 7/1992 | Paradissis et al. |
| 5,407,686 A | 4/1995 | Patel et al. |
| 5,654,010 A | 8/1997 | Johnson et al. |
| 5,736,152 A | 4/1998 | Dunn |
| 5,750,497 A | 5/1998 | Havelund et al. |
| 5,759,807 A | 6/1998 | Breece et al. |
| 5,811,395 A | 9/1998 | Schwabe et al. |
| 5,863,552 A | 1/1999 | Yue |
| 5,866,538 A | 2/1999 | Norup et al. |
| 6,011,007 A | 1/2000 | Havelund et al. |
| 6,051,551 A | 4/2000 | Hughes et al. |
| 6,268,343 B1 | 7/2001 | Knudsen et al. |
| 6,372,716 B1 | 4/2002 | Bush et al. |
| 6,444,641 B1 | 9/2002 | Flora |
| 6,566,329 B1 | 5/2003 | Meyn et al. |
| 6,685,940 B2 | 2/2004 | Andya et al. |
| 6,869,930 B1 | 3/2005 | Havelund et al. |
| 6,890,518 B2 | 5/2005 | Patton et al. |
| 7,563,770 B2 | 7/2009 | Larsen et al. |
| 7,781,567 B2 | 8/2010 | Wagner et al. |
| 7,928,058 B2 | 4/2011 | Sinha Roy et al. |
| 7,960,506 B2 | 6/2011 | Nash |
| 7,981,998 B2 | 7/2011 | Nash |
| 7,981,999 B2 | 7/2011 | Nash |
| 8,071,541 B2 | 12/2011 | Arora et al. |
| 8,129,343 B2 | 3/2012 | Lau et al. |
| 8,217,145 B2 | 7/2012 | Wang et al. |
| 8,288,339 B2 | 10/2012 | Gegg, Jr. et al. |
| 8,399,405 B2 | 3/2013 | Nash et al. |
| 8,420,598 B2 | 4/2013 | Lee et al. |
| 8,454,971 B2 | 6/2013 | Day et al. |
| 8,486,384 B2 | 7/2013 | Shen et al. |
| 8,507,428 B2 | 8/2013 | DiMarchi et al. |
| 8,524,653 B2 | 9/2013 | Nash et al. |

(Continued)

FOREIGN PATENT DOCUMENTS

| CA | 1176565 A | 10/1984 |
|---|---|---|
| CA | 2924109 A1 | 3/2015 |

(Continued)

OTHER PUBLICATIONS

Yifang Yang, Design of potent and proteolytically stable biaryl-stapled GLP-1R/GIPR peptide dual agonists, ACS Chem Biol. May 20, 2022; 17(5): 1249-1258.*
Backus et al. Proteome-wide covalent ligand discovery in native biological systems. Nature 534(7608):570-574 (2016).
Bondeson, et al., Catalytic in vivo protein knockdown by small-molecule PROTACs. Nat Chem Biol 11(8):611-617 (Aug. 2015).
Bondeson et al. Lessons in PROTAC Design from Selective Degradation with a Promiscuous Warhead. Cell Chem Biol 25:78-87.e5 (2018).
Buckley et al. Small-molecule inhibitors of the interaction between the E3 ligase VHL and HIF1α. Angew Chem Int Ed Engl 51:11463-11467 (2012).
Cal et al. Cysteine-selective reactions for antibody conjugation. Angewandte Chemi International Edition 53:10585-10587 (2014).

(Continued)

*Primary Examiner* — Julie Ha
*Assistant Examiner* — Erinne R Dabkowski
(74) *Attorney, Agent, or Firm* — WILSON SONSINI GOODRICH & ROSATI

(57) ABSTRACT

Provided herein are peptides and peptide conjugates comprising a dual glucose-dependent insulinotropic polypeptide (GIP) and GLP-1 receptor agonist. The peptides may be used for blood glucose management and treating conditions such as diabetes, obesity, non-alcoholic fatty liver disease (NAFLD), and non-alcoholic steatohepatitis (NASH).

8 Claims, 25 Drawing Sheets

Specification includes a Sequence Listing.

(56) References Cited

U.S. PATENT DOCUMENTS

| | | |
|---|---|---|
| 8,637,686 B2 | 1/2014 | Nash |
| 8,703,701 B2 | 4/2014 | DiMarchi |
| 8,735,539 B2 | 5/2014 | Kraynov et al. |
| 8,808,694 B2 | 8/2014 | Nash et al. |
| 9,062,124 B2 | 6/2015 | DiMarchi et al. |
| 9,156,901 B2 | 10/2015 | Riber et al. |
| 9,254,311 B2 | 2/2016 | Bancel et al. |
| 9,474,780 B2 | 10/2016 | Bokvist et al. |
| 10,039,809 B2 | 8/2018 | Shen et al. |
| 10,683,353 B2 | 6/2020 | Wang et al. |
| 11,007,252 B2 | 5/2021 | She et al. |
| 11,865,160 B2 | 1/2024 | Shen et al. |
| 2003/0158376 A1 | 8/2003 | Schwabe et al. |
| 2005/0176108 A1 | 8/2005 | Kim et al. |
| 2005/0192217 A1 | 9/2005 | Muhlradt et al. |
| 2007/0212355 A1 | 9/2007 | Baker et al. |
| 2008/0262200 A1 | 10/2008 | Nash |
| 2008/0305519 A1 | 12/2008 | Lin et al. |
| 2009/0047711 A1 | 2/2009 | Nash |
| 2009/0088553 A1 | 4/2009 | Nash |
| 2009/0117104 A1 | 5/2009 | Baker et al. |
| 2009/0186817 A1 | 7/2009 | Ghosh et al. |
| 2009/0239784 A1 | 9/2009 | Jonassen et al. |
| 2009/0275519 A1 | 11/2009 | Nash et al. |
| 2009/0326192 A1 | 12/2009 | Nash et al. |
| 2010/0029554 A1 | 2/2010 | Ghosh et al. |
| 2010/0093086 A1 | 4/2010 | Lin et al. |
| 2010/0184133 A1 | 7/2010 | Norgaard et al. |
| 2010/0184628 A1 | 7/2010 | Nash |
| 2010/0210515 A1 | 8/2010 | Nash et al. |
| 2010/0216688 A1 | 8/2010 | Nash et al. |
| 2010/0239554 A1 | 9/2010 | Schellenberger et al. |
| 2010/0292172 A1 | 11/2010 | Ghosh et al. |
| 2010/0298201 A1 | 11/2010 | Nash et al. |
| 2011/0046056 A1 | 2/2011 | Bianchi et al. |
| 2011/0144303 A1 | 6/2011 | Nash et al. |
| 2011/0166321 A1 | 7/2011 | Garibay et al. |
| 2011/0223149 A1 | 9/2011 | Nash et al. |
| 2011/0243942 A1 | 10/2011 | Wang |
| 2011/0263815 A1 | 10/2011 | Nash |
| 2012/0040889 A1 | 2/2012 | Nash et al. |
| 2012/0046229 A1 | 2/2012 | Kraynov et al. |
| 2012/0149648 A1 | 6/2012 | Nash et al. |
| 2012/0172311 A1 | 7/2012 | Nash et al. |
| 2012/0178700 A1 | 7/2012 | Nash et al. |
| 2012/0190818 A1 | 7/2012 | Nash |
| 2012/0264674 A1 | 10/2012 | Nash et al. |
| 2013/0023646 A1 | 1/2013 | Nash et al. |
| 2013/0040884 A1 | 2/2013 | Lau et al. |
| 2013/0123169 A1 | 5/2013 | Kawahata et al. |
| 2013/0203673 A1 | 8/2013 | Drucker et al. |
| 2013/0210745 A1 | 8/2013 | Guerlavais et al. |
| 2013/0237481 A1 | 9/2013 | Kraynov et al. |
| 2014/0057857 A1 | 2/2014 | Lin et al. |
| 2014/0128581 A1 | 5/2014 | Darlak et al. |
| 2014/0135255 A1 | 5/2014 | Nash et al. |
| 2014/0135473 A1 | 5/2014 | Nash |
| 2014/0148390 A1 | 5/2014 | Haupts et al. |
| 2014/0309168 A1 | 10/2014 | Rosendahl |
| 2014/0329742 A1 | 11/2014 | Dock et al. |
| 2016/0317623 A1 | 11/2016 | Shen et al. |
| 2017/0260248 A1 | 9/2017 | Walensky et al. |
| 2018/0118758 A1 | 5/2018 | Jacques |
| 2018/0207276 A1 | 7/2018 | Shen |
| 2018/0228907 A1 | 8/2018 | Crew et al. |
| 2019/0000928 A1 | 1/2019 | Shen et al. |
| 2020/0024322 A1 | 1/2020 | Abraham et al. |
| 2022/0000981 A1 | 1/2022 | Shen et al. |
| 2022/0072104 A1 | 3/2022 | Shen et al. |
| 2022/0168396 A1 | 6/2022 | Wu et al. |
| 2023/0057847 A1 | 2/2023 | Shen et al. |
| 2023/0071371 A1 | 3/2023 | Shen et al. |
| 2024/0207363 A1 | 6/2024 | Shen et al. |

FOREIGN PATENT DOCUMENTS

| | | |
|---|---|---|
| CA | 2933701 A1 | 6/2015 |
| CN | 101568350 A | 10/2009 |
| CN | 103201285 A | 7/2013 |
| DE | 3218121 A1 | 11/1983 |
| EP | 0133988 A2 | 3/1985 |
| JP | 2008533105 A | 8/2008 |
| WO | WO-9315722 A1 | 8/1993 |
| WO | WO-9420069 A1 | 9/1994 |
| WO | WO-9607399 A1 | 3/1996 |
| WO | WO-9629998 A1 | 10/1996 |
| WO | WO-9633193 A1 | 10/1996 |
| WO | WO-9640072 A2 | 12/1996 |
| WO | WO-9703692 A1 | 2/1997 |
| WO | WO-2004100997 A2 | 11/2004 |
| WO | WO-2006066258 A2 | 6/2006 |
| WO | WO-2006097537 A2 | 9/2006 |
| WO | WO-2007109135 A2 | 9/2007 |
| WO | WO-2008057298 A2 | 5/2008 |
| WO | WO-2010011439 A2 | 1/2010 |
| WO | WO-2010096052 A1 | 8/2010 |
| WO | WO-2010096142 A1 | 8/2010 |
| WO | WO-2011039096 A1 | 4/2011 |
| WO | WO-2012003995 A1 | 1/2012 |
| WO | WO-2012006598 A1 | 1/2012 |
| WO | WO-2012011752 A2 | 1/2012 |
| WO | WO-2012024452 A2 | 2/2012 |
| WO | WO-2012088116 A2 | 6/2012 |
| WO | WO-2012088379 A2 | 6/2012 |
| WO | WO-2012149563 A1 | 11/2012 |
| WO | WO-2013004607 A1 | 1/2013 |
| WO | WO-2013007563 A1 | 1/2013 |
| WO | WO-2013100704 A1 | 7/2013 |
| WO | WO-2013130683 A2 | 9/2013 |
| WO | WO-2013192131 A1 | 12/2013 |
| WO | WO-2014059213 A1 | 4/2014 |
| WO | WO-2015038938 A1 | 3/2015 |
| WO | WO-2015095406 A1 | 6/2015 |
| WO | WO-2015095684 A1 | 6/2015 |
| WO | WO-2016111971 A1 | 7/2016 |
| WO | WO-2016149501 A2 | 9/2016 |
| WO | WO-2016205488 A1 | 12/2016 |
| WO | WO-2017007612 A1 | 1/2017 |
| WO | WO-2017024317 A2 | 2/2017 |
| WO | WO-2017024318 A1 | 2/2017 |
| WO | WO-2017210600 A1 | 12/2017 |
| WO | WO-2018119448 A1 | 6/2018 |
| WO | WO-2018148440 A1 | 8/2018 |
| WO | WO-2018148443 A1 | 8/2018 |
| WO | WO-2018187401 A1 | 10/2018 |
| WO | WO-2019165229 A1 | 8/2019 |
| WO | WO-2019203645 A1 | 10/2019 |
| WO | WO-2020077278 A1 | 4/2020 |
| WO | WO-2020207477 A1 | 10/2020 |
| WO | WO-2021093883 A1 | 5/2021 |
| WO | WO-2021113524 A2 | 6/2021 |
| WO | WO-2021113535 A1 | 6/2021 |
| WO | WO-2022257979 A1 | 12/2022 |

OTHER PUBLICATIONS

Chen et al. Plant E3 Ligases: Flexible Enzymes in a Sessile World. Molecular Plant 6(5):1388-1404 (2013).
Co-pending U.S. Appl. No. 15/104,807, inventors Shen; Weijun et al., filed Jun. 15, 2016.
Co-pending U.S. Appl. No. 15/735,898, inventors Shen; Weijun et al., filed Dec. 12, 2017.
Co-pending U.S. Appl. No. 16/000,829, inventors Shen; Weijun et al., filed Jun. 5, 2018.
Co-pending U.S. Appl. No. 17/317,631, inventors Shen; Weijun et al., filed May 11, 2021.
Co-pending U.S. Appl. No. 17/485,171, inventors Shen; Weijun et al., filed Sep. 24, 2021.
Co-pending U.S. Appl. No. 17/782,560, inventors Shen; Weijun et al., filed Jun. 3, 2022.
Co-pending U.S. Appl. No. 17/782,573, inventors Shen; Weijun et al., filed Jun. 3, 2022.

(56) References Cited

OTHER PUBLICATIONS

Co-pending U.S. Appl. No. 18/514,838, inventors Shen; Weijun et al., filed Nov. 20, 2023.
Co-pending U.S. Appl. No. 18/568,244, inventors Shen; Weijun et al., filed Dec. 7, 2023.
Deshaies et al.RING Domain E3 Ubiquitin Ligases. Annual Review of Biochemistry 78(1):399-434 (2009).
Filippakopoulos et al.: Selective inhibition of BET bromodomains. Nature 468:1067-1073 (2010).
Gadd et al. Structural basis of PROTAC cooperative recognition for selective protein degradation. Nat Chem Biol 13:514-521 (2017).
Huang et al. A Chemoproteomic Approach to Query the Degradable Kinome Using a Multi-kinase Degrader. Cell Chem Biol 25:88-99 (2018).
Ito et al. Identification of a primary target of thalidomide teratogenicity. Science 327:1345-1350 (2010).
Japanese Patent Application No. 2016-542823 Office Action dated Jul. 22, 2019.
Jin et al., A family of diverse Cul4-Ddb1-interacting proteins includes Cdt2, which is required for S phase destruction of the replication factor Cdt1. Molecular Cell. 23(5):709-721 (2006).
Nabet et al. The dTAG system for immediate and target-specific protein degradation. Nat Chem Biol 14:431-441 (2018).
PCT/US2019/055958 International Search Report and Written Opinion dated Feb. 3, 2020.
Raina et al. PROTAC-induced BET protein degradation as a therapy for castration-resistant prostate cancer. PNAS USA 113:7124-7129 (2016).
Soucy et al. An inhibitor of NEDD8-activating enzyme as a new approach to treat cancer. Nature 458:732-736 (2009).
U.S. Appl. No. 16/600,326 Office Action dated Apr. 27, 2021.
U.S. Appl. No. 16/600,326 Office Action dated Dec. 2, 2021.
U.S. Appl. No. 16/600,326 Office Action dated May 23, 2022.
Vassilev et al. In vivo activation of the p53 pathway by small-molecule antagonists of MDM2. Science 303:844-848 (2004).
Weerapana et al. Quantitative reactivity profiling predicts functional cysteines in proteomes. Nature 468:790-795 (2010).
Winter et al. Drug Development. Phthalimide conjugation as a strategy for in vivo target protein degradation. Science 348:1376-1381 (2015).
Xu et al. ProLuCID: An improved SEQUEST-like algorithm with enhanced sensitivity and specificity. J Proteomics 129:16-24 (2015).
Zhang et al. Electrophilic PROTACs that degrade nuclear proteins by engaging DCAF16. Nature Chemical Biology 15:737-746 (2019).
Aicart-Ramos et al. Protein palmitoylation and subcellar trafficking. Biochim Biophys Acta 1808:2981-2994 (2011).
Altschul et al. Gapped BLAST and PSI-BLAST: a new generation of protein database search programs. Nucleic Acids Res. 25(17):3389-402 (1997).
Amso et al., A Peptide Engineering Platform for PEG-FA Stapled Long-acting Peptide Hormones. (2020).
Backer et al. Chapter 16: Cysteine-Containing Fusion Tag for Site-Specific Conjugation of Therapeutic and Imaging Agents to Targeting Proteins, Peptide-Based Drug Design Methods and Protocols, Springer Protocols, pp. 275-294 (2008).
Bader et al., Bioorganic synthesis of lipid-modified proteins for the study of signal transduction. Nature, 403:223-226 (Jan. 13, 2000).
Baosheng. Peptide PEGylation: The Next Generation Linking peptides to polythylene glycol, or PEGylation, has helped improve pharmaceutical therapeutics in several ways. A wave of new techniques is now ushering in further advances. Pharmaceutical Technology 2011(3):1-3 (May 1, 2011).
Bird et al. Hydrocarbon double-stapling remedies the proteolytic instability of a lengthy peptide therapeutic. PNAS USA 107(32):14093-14098 (2010).
Chalker et al. Chemical modification of proteins at cysteine: opportunities in chemistry and biology. Chem Asian J 4(5):630-640 (2009).

Chang et al. Stapled α-helical peptide drug development: A potent dual inhibitor of MDM2 and MDMX for p53-dependent cancer therapy. PNAS USA 110(36):E3445-E3454 (2013).
Cheng et al. Design, synthesis, characterization and in-vivo activity of a novel salmon calcitonin conjugate containing a novel PEG-lipid moiety. J Pharm Pharmacol 62(3):296-304 (Mar. 2010).
Cheng et al. Lipeo-sCT: A novel reversible lipidized salmon calcitonin derivative, its biophysical properties and hypocalcemic activity. Euro J Pharm Sci 37(2):151-159 (May 12, 2009).
Coskun et al. LY3298176, a novel dual GIP and GLP-1 receptor agonist for the treatment of type 2 diabetes mellitus: From discovery to clinical proof of concept. Clinical Trial 18:3-14 (2018).
Day et al. A new glucagon and GLP-1 co-agonist eliminates obesity in rodents. Nat Chem Biol 5(10):749-757 (2009).
Day et al. Optimization of co-agonism at GLP-1 and glucagon receptors to safely maximize weight reduction in DIO-rodents. Biopolymers, 98(5):443-450 (2012).
Druce et al. Investigation of Structure-Activity Relationships of Oxyntomodulin (Oxm) Using Oxm Analogs. Endocrinology 150(4):1712-1721 (Apr. 2009).
Eppstein et al. Biological activity of liposome-encapsulated murine interferon gamma is mediated by a cell membrane receptor. PNAS USA 82(11):3688-92 (1985).
Finan et al. Unimolecular Dual Incretins Maximize Metabolic Benefits in Rodents, Monkeys, and Humans. Sci Transl Med 5(209):209ra151 (2013).
Fusion proteins releasing Relaxin and uses thereof. pp. 1-75 (2013).
Guldenhaupt et al. Secondary structure of lipidated Ras bound to lipid bilayer. FEBS J 275:5910-5918 (2008).
Havelund et al. The mechanism of protraction of insulin detemir, a long-acting, acylated analog of human insulin. Pharm Res 21(9):1498-1504 (Aug. 2004).
Hossain et al. Chimeric relaxin peptides highlight the role of the A-chain in the function of H2 relaxin. Peptides 35:102-106 (May 2012).
Hossain et al. The Minimal Active Structure of Human Relaxin-2. J Biol Chem 286(43):37555-37565 (2011).
Janout et al. Bioconjugate-Based Molecular Umbrellas. Bioconjugate Chemistry 20(2):183-192 (E-Pub Nov. 20, 2008).
Joregensen et al. Oxyntomodulin differentially affects glucagon-like peptide-1 receptor beta-arrestin recruitment and signaling through Gas. The Journal of Pharmacology and Experimental Therapeutics 322(1):148-154 (2007).
Karlin et al. Applications and statistics for multiple high-scoring segments in molecular sequences. PNAS USA 90(12):5873-7 (1993).
Koonin et al. Chapter 2: Evolutionary Concept in Genetics and Genomics. Sequence—Evolution—Function: Computational Approaches in Comparative Genomics. Boston: Kluwer Academic (2003).
Langer. Controlled release of macromolecules. Chem. Tech. 12:98-105 (1982).
Langer et al. Biocompatibility of polymeric delivery systems for macromolecules. J Biomed Mater Res. 15(2):267-277 (1981).
Lau et al., Peptide stapling techniques based on different macrocyclisation chemistries. Chemical Society Reviews. 44(1):91-102 (2015).
Lear et al. Chapter 8: Engineering PEG-fatty acid stapled, long-acting peptide agonists for G protein-coupled receptors. Methods in Enzymology 622:183-200 (2019).
Lear et al. Engineering of a Potent, Long-Acting NPY2R Agonist for Combination with a GLP-1R Agonist as a Multi-Hormonal Treatment for Obesity. J Med Chem 63(17):9660-9671 (2020).
Lear et al. Peptide Engineering Strategies for Long-Acting Peptide Hormones. (2019) Abstract.
Lorenz et al. Recent progress and future options in the development of GLP-1 receptor agonists for the treatment of diabesity. Bioorg Med Chem Lett 23(14):4011-4018 (May 16, 2013).
Metra et al. Effect of Serelaxin on Cardiac, Renal, and Hepatic Biomarkers in the Relaxin in Acute Heart Failure (RELAX-AHF) Development Program. J Am Coll Cardiol 61(2):196-206 (Jan. 15, 2013).
Muller et al. Chapter 2: Peptide carrier conjugation, Synthetic Peptides as Antigens, Laboratory Techniques in Biochemstry and Molecular Biology. 28:79-131 (1999).

(56) References Cited

OTHER PUBLICATIONS

Muppidi et al. Design and Synthesis of Potent, Long-Acting Lipidated Relaxin-2 Analogs. Bioconjugate Chem. 30:83-89 (Dec. 2018).
Muppidi et al., Design of Potent and Proteolytically Stable Oxyntomodulin Analogs. ACS Chem. Biol. 11:324-328 (2016).
Muppidi et al. Rational design of proteolytically stable, cell-permeable peptide-based selective Mcl-1 inhibitors. J. Am. Chem. Soc. 134:14734-14737 (Aug. 2012).
Pan et al. Design of a Long Acting Peptide Functioning as Both a Glucagon-like Peptide-1 Receptor Agonist and a Glucagon Receptor Antagonist. J Biol Chem 281(18):12506-12515 (May 5, 2008).
Patterson et al. Functional association of the N-terminal residues with the central region in glucagon-related peptides. J. Pept. Sci. 17:659-666 (2011).
PCT/US2014/070977 International Search Report and Written Opinion dated Mar. 27, 2015.
PCT/US2016/022880 International Search Report and Written Opinion dated Oct. 7, 2016.
PCT/US2016/037834 International Search Report and Written Opinion dated Oct. 26, 2016.
PCT/US2020/063130 International Search Report and Written Opinion dated May 24, 2021.
PCT/US2020/063149 International Search Report and Written Opinion dated Apr. 29, 2021.
Pflimlin et al. Design of a Long-Acting and Selective MEG-Fatty Acid Stapled Prolactin-Releasing Peptide Analog. ACS Med. Chem. Lett. 10:1166-1172 (2019).
Pflimlin et al. Engineering a Potent, Long Acting and Periphery-Restricted Oxytocin Receptor Agonist with Anorexigenic and Body Weight Reducing Effects. J. Med. Chem. 63(1):382-390 (2020).
Pollaro et al., Strategies to prolong the plasma residence time of peptide drugs. Med. Chem. Commun. 1:319-324 (2010).
Rost. Twilight zone of protein sequence alignments. Protein engineering 12(2):85-94 (1999).
Santoprete et al. DPP-IV-resistant, long-acting oxyntomodulin derivatives. J Pep Sci 17:270-280 (2011).
Schultz et al. General Approach to the Synthesis of Short a-Helical Peptides. J. Am. Chem. Soc. 113:9391-9392 (1991).
Shah. Bioconjugates: The Adaptable Challenge. BioPharm International the Science & Business of Biopharmaceuticals 26(1):1-4 (Jan. 1, 2013).
Sidman et al. Controlled release of macromolecules and pharmaceuticals from synthetic polypeptides based on glutamic acid. Biopolymers 22(1):547-556 (Jan. 1983).
Soloff et al. Cloning, characterization, and expression of the rat relaxin gene. Gene 323:149-155 (2003).
Teerlink et al. Serelaxin, recombinant human relaxin-2, for treatment of acute heart failure (RELAX-AHF): a randomised, placebo-controlled trial. Lancet 381:29-39 (Jan. 2013).
Trussel et al. New strategy for the extension of the serum half-life of antibody fragments. Bioconjug Chem. 20(12):2286-92 (2009).
Underwood et al. Crystal Structure of Glucagon-like Peptide-1 in Complex with the Extracellular Domain of the Glucagon-like Peptide-1 Receptor. J Biol Chem 285(1):723-730 (Jan. 1, 2010).
U.S. Appl. No. 16/000,829 Non-Final Office Action dated Mar. 5, 2020.
U.S. Appl. No. 15/104,807 Non-Final Office Action dated Nov. 27, 2017.
U.S. Appl. No. 15/735,898 Final Office Action dated Jun. 22, 2020.
U.S. Appl. No. 15/735,898 Final Office Action dated May 25, 2021.
U.S. Appl. No. 15/735,898 Non-Final Office Action dated Jan. 8, 2020.
U.S. Appl. No. 16/000,829 Non-Final Office Action dated Aug. 27, 2020.
U.S. Appl. No. 17/317,631 Final Office Action dated May 12, 2023.
U.S. Appl. No. 17/317,631 Non-Final Office Action dated Dec. 23, 2022.
U.S. Appl. No. 17/485,171 Non-Final Office Action dated May 10, 2023.
Verdine et al. Chapter 1: Stapled Peptides for Intracellular Drug Targets. Methods in Enzymology 503:3-33 (Dec. 2012).
Wade et al. The Chemical Synthesis of Relaxin and Related peptides: A Historical Perspective. Ann. N.Y. Acad. Sci. 1160:11-15 (2009).
Walensky et al. Hydrocarbon-Stapled Peptides: Principles, Practice, and Progress. J Med Chem 57:6275-6288 (2014).
Webber et al. Genes and homology. Current Biology 14(9):R332-R333 (2004).
Wisniewski et al., Synthesis and Pharmacological Characterization of Novel Glucagon-like Peptide-2 (GLP-2) Analogues with Low Systemic Clearance. J Med Chem 59:3129-3139 (Mar. 2016).
Wu et al. Addition of a cysteine to glucagon-like peptide-1 (GLP-1) conjugates GLP-1 to albumin in serum and prolongs GLP-1 action in vivo. Reg Pept 164(2):83-89 (2010).
Yang et al. Engineering a long-acting, potent GLP-1 analog for microstructure-based transdermal delivery. PNAS USA 113(15):4140-4145 (2016).
Yang et al., New Generation Oxyntomodulin Peptides with Improved Pharmacokinetic Profiles Exhibit Weight Reducing and Anti-Steatotic Properties in Mice. Bioconjugate Chem. 31(4):1167-1176 (2020).
Lear et al. Recombinant Expression and Stapling of a Novel Long-Acting GLP-1R Peptide Agonist. Molecules 25(11):2508 (2020).
U.S. Appl. No. 17/485,171 Office Action dated Nov. 3, 2023.
Yang et al. Stapled, Long-Acting Glucagon-like Peptide 2 Analog with Efficacy in Dextran Sodium Sulfate Induced Mouse Colitis Models. J Med Chem 61(7):3218-3223 (2018).
Das, Shinjita. Psoriasis. Merck Manual, Professional Version, Sep. 2023; [retrieved on Sep. 28, 2024]. Available at URL:merckmanuals.com/professional/dermatologic-disorders/psoriasis-and-scaling-diseases/psoriasis? query=psoriasis pp. 1-20.
Dermatitis from Merck Manual, (2020). Accessed on Aug. 30, 2020, pp. 1-4.
Inflammation from Merck Manual, (2020). Accessed on Aug. 30, 2020, pp. 1-3.
Inflammatory disorders from Merck Manual, (2020). Accessed on Aug. 30, 2020, pp. 1-4.
Kontzias, Apostolos. Osteoarthritis. Merck Manual, Professional Version, May 2020; [retrieved on Oct. 24, 2020]. Available at URL:https://www.merckmanuals.com/professional/musculoskeletal-and-connective-tissue-disorders/joint-disorders/osteoarthritis-oa pp. 1-10.
Korczyn, Amos D. et al. Emerging therapies in the pharmacological treatment of Parkinson's disease. Drugs 62(5):775-786 (2002).
Margolis, Russell L. et al. Ross. Diagnosis of Huntington disease. Clinical chemistry 49(10):1726-1732 (2003).
Nguyen, Minhhuyen. Colorectal Cancer. Merck Manual, Consumer Version, Jul. 2019; [retrieved on Oct. 24, 2020]. Available at URL:https://www.merckmanuals.com/home/digestive-disorders/tumors-of-the-digestive-system/colorectal-cancer pp. 1-8.
Obesity. NHS, May 2019; [retrieved on Oct. 24, 2020]. Available at URL:https://www.nhs.uk/conditions/obesity/ pp. 1-6.
Prevention of Cardiovascular Disease: Guidelines for assessment and management of cardiovascular risk. World Health Organization, Jan. 2007; [retrieved on Mar. 16, 2015]. Available at URL:who.intJcardiovascular_diseases/guidelines/Full%20text.pdf pp. 1-92.
U.S. Appl. No. 17/485,171 Office Action dated May 28, 2024.
U.S. Appl. No. 18/514,838 Office Action dated Jan. 22, 2025.
U.S. Appl. No. 18/514,838 Office Action dated Sep. 29, 2024.

\* cited by examiner

D-Phe

D-Asn

D-Glu

D-Gln

D-Asp

D-Tyr

D-Leu

L-Phe (2-F)

L-Phe (3-F)

L-Phe (4-F)

N-Methyl-Tyr

N-Methyl-L-Leu

N-Methyl-L-Phe

A. Vehicle, B. ZP3-K4, C. 2050-K4, D. Semaglutide, E. Cotadutide

SEQUENCE LISTING

```
Sequence total quantity: 62
SEQ ID NO: 1            moltype = AA  length = 39
FEATURE                 Location/Qualifiers
REGION                  1..39
                        note = Description of Artificial Sequence: Synthetic
                         polypeptide
MOD_RES                 2
                        note = Aminoisobutyric acid
VARIANT                 14
                        note = any amino acid
MOD_RES                 20
                        note = Aminoisobutyric acid
VARIANT                 21
                        note = any amino acid
source                  1..39
                        mol_type = protein
                        organism = synthetic construct
SEQUENCE: 1
YXEGTFTSDY SIYXDKQAAX XFVNWLLAGG PSSGAPPPS                          39

SEQ ID NO: 2            moltype = AA  length = 39
FEATURE                 Location/Qualifiers
REGION                  1..39
                        note = Description of Artificial Sequence: Synthetic
                         polypeptide
MOD_RES                 2
                        note = Aminoisobutyric acid
VARIANT                 14
                        note = any amino acid
MOD_RES                 20
                        note = Aminoisobutyric acid
VARIANT                 21
                        note = any amino acid
source                  1..39
                        mol_type = protein
                        organism = synthetic construct
SEQUENCE: 2
YXEGTFHSDY DIYXDKQAAX XFVQWLLAGG PSSGAPPPS                          39

SEQ ID NO: 3            moltype = AA  length = 39
FEATURE                 Location/Qualifiers
REGION                  1..39
                        note = Description of Artificial Sequence: Synthetic
                         polypeptide
MOD_RES                 2
                        note = Aminoisobutyric acid
VARIANT                 14
                        note = any amino acid
MOD_RES                 20
                        note = Neuroleucine
VARIANT                 21
                        note = any amino acid
source                  1..39
                        mol_type = protein
                        organism = synthetic construct
SEQUENCE: 3
YXEGTFHSDY DIYXDKQAAX XFVAWLLAGG PSSGAPPPS                          39

SEQ ID NO: 4            moltype = AA  length = 39
FEATURE                 Location/Qualifiers
```

```
REGION                  1..39
                        note = Description of Artificial Sequence: Synthetic
                         polypeptide
MOD_RES                 2
                        note = Aminoisobutyric acid
MOD_RES                 8
                        note = D-Serine
MOD_RES                 11
                        note = D-Serine
VARIANT                 14
                        note = any amino acid
MOD_RES                 20
                        note = Neuroleucine
VARIANT                 21
                        note = any amino acid
source                  1..39
                        mol_type = protein
                        organism = synthetic construct
SEQUENCE: 4
YXEGTFTSDY SIYXDKQAAX XFVAWLLAGG PSSGAPPPS                                 39

SEQ ID NO: 5            moltype = AA  length = 39
FEATURE                 Location/Qualifiers
REGION                  1..39
                        note = Description of Artificial Sequence: Synthetic
                         polypeptide
MOD_RES                 2
                        note = Aminoisobutyric acid
VARIANT                 14
                        note = any amino acid
MOD_RES                 20
                        note = Aminoisobutyric acid
VARIANT                 21
                        note = any amino acid
source                  1..39
                        mol_type = protein
                        organism = synthetic construct
SEQUENCE: 5
YXEGTFTSDY SIYXDKQAAX XFVNWLIAGG PSSGAPPPS                                 39

SEQ ID NO: 6            moltype = AA  length = 39
FEATURE                 Location/Qualifiers
REGION                  1..39
                        note = Description of Artificial Sequence: Synthetic
                         polypeptide
MOD_RES                 2
                        note = Aminoisobutyric acid
VARIANT                 17
                        note = any amino acid
MOD_RES                 20
                        note = Aminoisobutyric acid
source                  1..39
                        mol_type = protein
                        organism = synthetic construct
VARIANT                 24
                        note = any amino acid
SEQUENCE: 6
YXEGTFTSDY SIYLDKXAAX EFVXWLIAGG PSSGAPPPS                                 39

SEQ ID NO: 7            moltype = AA  length = 39
FEATURE                 Location/Qualifiers
REGION                  1..39
                        note = Description of Artificial Sequence: Synthetic
                         polypeptide
MOD_RES                 2
                        note = Aminoisobutyric acid
VARIANT                 6
                        note = Alpha-methyl Phe, N-methyl Phe, D-Phe, beta3-Phe,
                         alpha-methyl Phe, alpha-methyl Phe (2-F), alpha-methyl Phe
                         (3-F), and alpha-methyl (4-F), Phe (2-F), Phe (3-F), or
                         Phe (4-F)
VARIANT                 10
                        note = Alpha-methyl Tyr, N-methyl Tyr, D-Tyr, beta3-Tyr,
                         4-Pyr-Ala, Phe (2-F), Phe (3-F), or Phe (4-F)
VARIANT                 13
                        note = Alpha-methyl Leu, N-methyl Leu, D-Leu, beta3-Leu,
                         Leu, Val, Ile, Aminoisobutyric acid, alpha-methyl Tyr,
                         N-methyl Tyr, D-Tyr, beta3-Tyr, 4-Pyr-Ala, Phe (2-F), Phe
                         (3-F), or Phe (4-F)
```

```
VARIANT               16
                      note = L-Orn, alpha-methyl Lys, N-methyl Lys, D-Lys, or
                      beta3-Lys
MOD_RES               20
                      note = Aminoisobutyric acid
VARIANT               28
                      note = A or E
source                1..39
                      mol_type = protein
                      organism = synthetic construct
VARIANT               25
                      note = Alpha-methyl Trp, N-methyl Trp, D-Trp, beta3-Trp,
                      alpha-methyl Tyr, or Aminoisobutyric acid
VARIANT               17
                      note = any amino acid
VARIANT               24
                      note = any amino acid
SEQUENCE: 7
YXEGTXTSDX SIXLDXXAAX EFVXXLIXGG PSSGAPPPS                              39

SEQ ID NO: 8          moltype = AA  length = 39
FEATURE               Location/Qualifiers
REGION                1..39
                      note = Description of Artificial Sequence: Synthetic
                      polypeptide
MOD_RES               2
                      note = Aminoisobutyric acid
VARIANT               6
                      note = Alpha-methyl Phe, N-methyl Phe, D-Phe, beta3-Phe,
                      alpha-methyl Phe, alpha-methyl Phe (2-F), alpha-methyl Phe
                      (3-F), and alpha-methyl (4-F), Phe (2-F), Phe (3-F), or
                      Phe (4-F)
VARIANT               10
                      note = Alpha-methyl Tyr, N-methyl Tyr, D-Tyr, beta3-Tyr,
                      4-Pyr-Ala, Phe (2-F), Phe (3-F), or Phe (4-F)
VARIANT               13
                      note = Alpha-methyl Leu, N-methyl Leu, D-Leu, beta3-Leu,
                      Leu, Val, Ile, Aminoisobutyric acid, alpha-methyl Tyr,
                      N-methyl Tyr, D-Tyr, beta3-Tyr, 4-Pyr-Ala, Phe (2-F), Phe
                      (3-F), or Phe (4-F)
VARIANT               17
                      note = any amino acid
MOD_RES               20
                      note = Aminoisobutyric acid
VARIANT               24
                      note = any amino acid
VARIANT               25
                      note = Alpha-methyl Trp, N-methyl Trp, D-Trp, beta3-Trp,
                      alpha-methyl Tyr, or Aminoisobutyric acid
source                1..39
                      mol_type = protein
                      organism = synthetic construct
VARIANT               16
                      note = Orn, alpha-methyl Lys, N-methyl Lys, D-Lys, or
                      beta3-Lys
VARIANT               28
                      note = A or E
SEQUENCE: 8
YXEGTXTSDX SIXLDXXAAX EFVXXLIXGG PSSGAPPPS                              39

SEQ ID NO: 9          moltype = AA  length = 39
FEATURE               Location/Qualifiers
REGION                1..39
                      note = Description of Artificial Sequence: Synthetic
                      polypeptide
MOD_RES               2
                      note = Aminoisobutyric acid
VARIANT               10
                      note = Alpha-methyl Tyr, N-methyl Tyr, D-Tyr, beta3-Tyr,
                      4-Pyr-Ala, Phe (2-F), Phe (3-F), Phe (4-F), or
                      4-pyridyl-Ala
VARIANT               13
                      note = Alpha-methyl Leu, N-methyl Leu, D-Leu, beta3-Leu,
                      Val, Ile, or Aminoisobutyric acid
VARIANT               14
                      note = any amino acid
MOD_RES               20
                      note = Aminoisobutyric acid
```

```
VARIANT                 21
                        note = any amino acid
VARIANT                 24
                        note = Alpha-methyl Asn, N-methyl Asn, beta3-Asn,
                         Aminoisobutyric acid, D-Asn, D-Asp, D-Glu, or D-Gln
VARIANT                 28
                        note = A or E
source                  1..39
                        mol_type = protein
                        organism = synthetic construct
VARIANT                 16
                        note = Alpha-methyl Leu, N-methyl Leu, D-Leu, beta3-Leu,
                         Val, Ile, or Aminoisobutyric acid
VARIANT                 6
                        note = Alpha-methyl Phe, N-methyl Phe, D-Phe, beta3-Phe,
                         alpha-methyl Phe (2-F), alpha-methyl Phe (3-F), and
                         alpha-methyl (4-F), Phe (2-F), Phe (3-F), or Phe (4-F)
VARIANT                 25
                        note = Alpha-methyl Trp, N-methyl Trp, D-Trp, beta3-Trp,
                         alpha-methyl Tyr, or Aminoisobutyric acid
SEQUENCE: 9
YXEGTXTSDX SIXXDXQAAX XFVXXLIXGG PSSGAPPPS                      39

SEQ ID NO: 10           moltype = AA  length = 39
FEATURE                 Location/Qualifiers
REGION                  1..39
                        note = Description of Artificial Sequence: Synthetic
                         polypeptide
VARIANT                 2
                        note = Gly, Val, Leu, Ile, or Aminoisobutyric acid
VARIANT                 13
                        note = Alpha-methyl Leu, N-methyl Leu, D-Leu, beta3-Leu,
                         Leu, Val, Ile, Aminoisobutyric acid, alpha-methyl Tyr,
                         N-methyl Tyr, D-Tyr, beta3-Tyr, 4-Pyr-Ala, Phe (2-F), Phe
                         (3-F), or Phe (4-F)
VARIANT                 17
                        note = any amino acid
VARIANT                 20
                        note = Gly, Val, Leu, Ile, or Aminoisobutyric acid
VARIANT                 24
                        note = any amino acid
source                  1..39
                        mol_type = protein
                        organism = synthetic construct
SEQUENCE: 10
YXEGTFTSDY SIXLDKXAAX EFVXWLIAGG PSSGAPPPS                      39

SEQ ID NO: 11           moltype = AA  length = 28
FEATURE                 Location/Qualifiers
REGION                  1..28
                        note = Description of Artificial Sequence: Synthetic peptide
VARIANT                 2
                        note = Gly, Val, Leu, Ile, or Aminoisobutyric acid
VARIANT                 17
                        note = any amino acid
VARIANT                 24
                        note = any amino acid
source                  1..28
                        mol_type = protein
                        organism = synthetic construct
VARIANT                 20
                        note = G, V, L, I, or Aminoisobutyric acid
VARIANT                 13
                        note = Alpha-methyl Leu, N-methyl Leu, D-Leu, beta3-Leu,
                         Leu, Val, Ile, Aminoisobutyric acid, alpha-methyl Tyr,
                         N-methyl Tyr, D-Tyr, beta3-Tyr, 4-Pyr-Ala, Phe (2-F), Phe
                         (3-F), or Phe (4-F)
SEQUENCE: 11
YXEGTFTSDY SIXLDKXAAX EFVXWLIA                                  28

SEQ ID NO: 12           moltype = AA  length = 39
FEATURE                 Location/Qualifiers
REGION                  1..39
                        note = Description of Artificial Sequence: Synthetic
                         polypeptide
VARIANT                 2
                        note = Gly, Val, Leu, Ile, or Aminoisobutyric acid
```

```
VARIANT                 13
                        note = Alpha-methyl Leu, N-methyl Leu, D-Leu, beta3-Leu,
                         Leu, Val, Ile, Aminoisobutyric acid, alpha-methyl Tyr,
                         N-methyl Tyr, D-Tyr, beta3-Tyr, 4-Pyr-Ala, Phe (2-F), Phe
                         (3-F), or Phe (4-F)
VARIANT                 14
                        note = any amino acid
VARIANT                 20
                        note = Gly, Val, Leu, Ile, or Aminoisobutyric acid
source                  1..39
                        mol_type = protein
                        organism = synthetic construct
VARIANT                 21
                        note = any amino acid
SEQUENCE: 12
YXEGTFTSDY SIXXDKQAAX XFVNWLIAGG PSSGAPPPS                                  39

SEQ ID NO: 13           moltype = AA  length = 28
FEATURE                 Location/Qualifiers
REGION                  1..28
                        note = Description of Artificial Sequence: Synthetic peptide
VARIANT                 2
                        note = G, V, L, I, or Aminoisobutyric acid
VARIANT                 21
                        note = any amino acid
source                  1..28
                        mol_type = protein
                        organism = synthetic construct
VARIANT                 20
                        note = G, V, L, I, or Aminoisobutyric acid
VARIANT                 13
                        note = Alpha-methyl Leu, N-methyl Leu, D-Leu, beta3-Leu,
                         Leu, Val, Ile, Aminoisobutyric acid, alpha-methyl Tyr,
                         N-methyl Tyr, D-Tyr, beta3-Tyr, 4-Pyr-Ala, Phe (2-F), Phe
                         (3-F), or Phe (4-F)
VARIANT                 14
                        note = any amino acid
SEQUENCE: 13
YXEGTFTSDV SIXXDKQAAX XFVNWLIA                                              28

SEQ ID NO: 14           moltype = AA  length = 39
FEATURE                 Location/Qualifiers
REGION                  1..39
                        note = Description of Artificial Sequence: Synthetic
                         polypeptide
MOD_RES                 2
                        note = Aminoisobutyric acid
MOD_RES                 6
                        note = Alpha-methyl Phe
MOD_RES                 10
                        note = 4-pyridyl-Ala
MOD_RES                 13
                        note = Alpha-methyl Leu
MOD_RES                 16
                        note = Ornithine
VARIANT                 17
                        note = any amino acid
MOD_RES                 20
                        note = Aminoisobutyric acid
VARIANT                 24
                        note = any amino acid
MOD_RES                 25
                        note = Alpha-methyl tyrosine
source                  1..39
                        mol_type = protein
                        organism = synthetic construct
SEQUENCE: 14
YXEGTFTSDX SILLDXXAAX EFVXYLIAGG PSSGAPPPS                                  39

SEQ ID NO: 15           moltype = AA  length = 39
FEATURE                 Location/Qualifiers
REGION                  1..39
                        note = Description of Artificial Sequence: Synthetic
                         polypeptide
MOD_RES                 2
                        note = Aminoisobutyric acid
MOD_RES                 6
                        note = Alpha-methyl Phe
```

```
MOD_RES            10
                   note = 4-pyridyl-Ala
MOD_RES            13
                   note = Alpha-methyl Leu
VARIANT            14
                   note = any amino acid
MOD_RES            16
                   note = Ornithine
MOD_RES            20
                   note = Aminoisobutyric acid
VARIANT            21
                   note = any amino acid
MOD_RES            24
                   note = D-Glutamic acid
MOD_RES            25
                   note = Alpha-methyl tyrosine
source             1..39
                   mol_type = protein
                   organism = synthetic construct
SEQUENCE: 15
YXEGTFTSDX SILXDXQAAX XFVEYLIAGG PSSGAPPPS                   39

SEQ ID NO: 16      moltype = AA   length = 39
FEATURE            Location/Qualifiers
REGION             1..39
                   note = Description of Artificial Sequence: Synthetic
                    polypeptide
MOD_RES            2
                   note = Aminoisobutyric acid
MOD_RES            20
                   note = Aminoisobutyric acid
VARIANT            21
                   note = any amino acid
source             1..39
                   mol_type = protein
                   organism = synthetic construct
VARIANT            14
                   note = any amino acid
SEQUENCE: 16
YXEGTFTSDY SIYXDKQAAX XFVQWLLAGG PSSGAPPPS                   39

SEQ ID NO: 17      moltype = AA   length = 39
FEATURE            Location/Qualifiers
REGION             1..39
                   note = Description of Artificial Sequence: Synthetic
                    polypeptide
MOD_RES            2
                   note = Aminoisobutyric acid
VARIANT            14
                   note = any amino acid
MOD_RES            20
                   note = Aminoisobutyric acid
source             1..39
                   mol_type = protein
                   organism = synthetic construct
VARIANT            21
                   note = any amino acid
SEQUENCE: 17
YXEGTFISDV SIYXDKQAAX XFVNWLIAGG PSSGAPPPS                   39

SEQ ID NO: 18      moltype = AA   length = 39
FEATURE            Location/Qualifiers
REGION             1..39
                   note = Description of Artificial Sequence: Synthetic
                    polypeptide
MOD_RES            2
                   note = Aminoisobutyric acid
VARIANT            17
                   note = any amino acid
MOD_RES            20
                   note = Aminoisobutyric acid
source             1..39
                   mol_type = protein
                   organism = synthetic construct
VARIANT            24
                   note = any amino acid
SEQUENCE: 18
YXEGTFTSDY SIYLDKXAAX EFVXWLLAGG PSSGAPPPS                   39
```

-continued

```
SEQ ID NO: 19              moltype = AA  length = 39
FEATURE                    Location/Qualifiers
REGION                     1..39
                           note = Description of Artificial Sequence: Synthetic
                            polypeptide
MOD_RES                    2
                           note = Aminoisobutyric acid
VARIANT                    17
                           note = any amino acid
MOD_RES                    20
                           note = Aminoisobutyric acid
VARIANT                    24
                           note = any amino acid
source                     1..39
                           mol_type = protein
                           organism = synthetic construct
SEQUENCE: 19
YXEGTFTSDY SIYLDKXAQX AFVXWLIAQG PSSGAPPPS                              39

SEQ ID NO: 20              moltype = AA  length = 39
FEATURE                    Location/Qualifiers
REGION                     1..39
                           note = Description of Artificial Sequence: Synthetic
                            polypeptide
MOD_RES                    2
                           note = Aminoisobutyric acid
MOD_RES                    20
                           note = Aminoisobutyric acid
VARIANT                    24
                           note = any amino acid
source                     1..39
                           mol_type = protein
                           organism = synthetic construct
VARIANT                    17
                           note = any amino acid
SEQUENCE: 20
YXEGTYTSDY SIYLDKXAAX EFVXWLIAGG PSSGAPPPS                              39

SEQ ID NO: 21              moltype = AA  length = 39
FEATURE                    Location/Qualifiers
REGION                     1..39
                           note = Description of Artificial Sequence: Synthetic
                            polypeptide
MOD_RES                    2
                           note = Aminoisobutyric acid
VARIANT                    17
                           note = any amino acid
MOD_RES                    20
                           note = Aminoisobutyric acid
VARIANT                    24
                           note = any amino acid
source                     1..39
                           mol_type = protein
                           organism = synthetic construct
SEQUENCE: 21
YXEGTYTNDY SIYLDKXAAX EFVXWLIAGG PSSGAPPPS                              39

SEQ ID NO: 22              moltype = AA  length = 39
FEATURE                    Location/Qualifiers
REGION                     1..39
                           note = Description of Artificial Sequence: Synthetic
                            polypeptide
MOD_RES                    2
                           note = Aminoisobutyric acid
VARIANT                    14
                           note = any amino acid
MOD_RES                    20
                           note = Aminoisobutyric acid
VARIANT                    21
                           note = any amino acid
source                     1..39
                           mol_type = protein
                           organism = synthetic construct
SEQUENCE: 22
YXEGTYTSDY SIYXDKQAAX XFVNWLIAGG PSSGAPPPS                              39

SEQ ID NO: 23              moltype = AA  length = 39
FEATURE                    Location/Qualifiers
```

```
REGION                  1..39
                        note = Description of Artificial Sequence: Synthetic
                         polypeptide
source                  1..39
                        mol_type = protein
                        organism = synthetic construct
SEQUENCE: 23
HGEGTFTSDL SKQMEEEAVR LFIEWLKNGG PSSGAPPPS                              39

SEQ ID NO: 24           moltype = AA   length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 24
HDEFERHAEG TFTSDVSSYL EGQAAKEFIA WLVKGR                                 36

SEQ ID NO: 25           moltype = AA   length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 25
HADGSFSDEM NTILDNLAAR DFINWLIQTK ITDR                                   34

SEQ ID NO: 26           moltype = AA   length = 42
FEATURE                 Location/Qualifiers
REGION                  1..42
                        note = Description of Artificial Sequence: Synthetic
                         polypeptide
source                  1..42
                        mol_type = protein
                        organism = synthetic construct
SEQUENCE: 26
YAEGTFISDY SIAMDKIHQQ DFVNWLLAQK GKKNDWKHNI TQ                          42

SEQ ID NO: 27           moltype = AA   length = 39
FEATURE                 Location/Qualifiers
REGION                  1..39
                        note = Description of Artificial Sequence: Synthetic
                         polypeptide
MOD_RES                 2
                        note = Aminoisobutyric acid
MOD_RES                 13
                        note = Aminoisobutyric acid
source                  1..39
                        mol_type = protein
                        organism = synthetic construct
SEQUENCE: 27
YXEGTFTSDY SIXLDKIAQK AFVQWLIAGG PSSGAPPPS                              39

SEQ ID NO: 28           moltype = AA   length = 39
FEATURE                 Location/Qualifiers
REGION                  1..39
                        note = Description of Artificial Sequence: Synthetic
                         polypeptide
MOD_RES                 2
                        note = Aminoisobutyric acid
MOD_RES                 20
                        note = Aminoisobutyric acid
source                  1..39
                        mol_type = protein
                        organism = synthetic construct
SEQUENCE: 28
YXEGTFTSDY SIYLDKQAAX EFVNWLLAGG PSSGAPPPS                              39

SEQ ID NO: 29           moltype = AA   length = 39
FEATURE                 Location/Qualifiers
REGION                  1..39
                        note = Description of Artificial Sequence: Synthetic
                         polypeptide
MOD_RES                 2
                        note = Aminoisobutyric acid
```

```
MOD_RES                 20
                        note = Aminoisobutyric acid
VARIANT                 23
                        note = any amino acid
VARIANT                 27
                        note = any amino acid
source                  1..39
                        mol_type = protein
                        organism = synthetic construct
SEQUENCE: 29
YXEGTFTSDY SIYKDKQAAX KFXNWLXAGG PSSGAPPPS                              39

SEQ ID NO: 30           moltype = AA  length = 39
FEATURE                 Location/Qualifiers
REGION                  1..39
                        note = Description of Artificial Sequence: Synthetic
                         polypeptide
MOD_RES                 2
                        note = Aminoisobutyric acid
VARIANT                 14
                        note = any amino acid
VARIANT                 17
                        note = any amino acid
MOD_RES                 20
                        note = Aminoisobutyric acid
VARIANT                 21
                        note = any amino acid
source                  1..39
                        mol_type = protein
                        organism = synthetic construct
VARIANT                 24
                        note = any amino acid
SEQUENCE: 30
YXEGTFTSDY SIYXDKXAAX XFVXWLIAGG PSSGAPPPS                              39

SEQ ID NO: 31           moltype = AA  length = 39
FEATURE                 Location/Qualifiers
REGION                  1..39
                        note = Description of Artificial Sequence: Synthetic
                         polypeptide
MOD_RES                 2
                        note = Aminoisobutyric acid
MOD_RES                 20
                        note = Aminoisobutyric acid
source                  1..39
                        mol_type = protein
                        organism = synthetic construct
SEQUENCE: 31
YXEGTFTSDY SIYLDKQAAX EFVNWLLAGG PSSGAPPPS                              39

SEQ ID NO: 32           moltype = AA  length = 39
FEATURE                 Location/Qualifiers
REGION                  1..39
                        note = Description of Artificial Sequence: Synthetic
                         polypeptide
MOD_RES                 2
                        note = Aminoisobutyric acid
MOD_RES                 20
                        note = Aminoisobutyric acid
source                  1..39
                        mol_type = protein
                        organism = synthetic construct
SEQUENCE: 32
YXEGTFTSDY SIYLDKKAAX EFVKWLLAGG PSSGAPPPS                              39

SEQ ID NO: 33           moltype = AA  length = 39
FEATURE                 Location/Qualifiers
REGION                  1..39
                        note = Description of Artificial Sequence: Synthetic
                         polypeptide
MOD_RES                 2
                        note = Aminoisobutyric acid
MOD_RES                 20
                        note = Aminoisobutyric acid
source                  1..39
                        mol_type = protein
                        organism = synthetic construct
SEQUENCE: 33
YXEGTFTSDY SIYKDKQAAX KFVNWLLAGG PSSGAPPPS                              39
```

```
SEQ ID NO: 34          moltype = AA   length = 39
FEATURE                Location/Qualifiers
REGION                 1..39
                       note = Description of Artificial Sequence: Synthetic
                        polypeptide
MOD_RES                2
                       note = Aminoisobutyric acid
MOD_RES                20
                       note = Aminoisobutyric acid
source                 1..39
                       mol_type = protein
                       organism = synthetic construct
SEQUENCE: 34
YXEGTFTSDY SIYKDKQAAX KFKNWLKAGG PSSGAPPPS                              39

SEQ ID NO: 35          moltype = AA   length = 39
FEATURE                Location/Qualifiers
REGION                 1..39
                       note = Description of Artificial Sequence: Synthetic
                        polypeptide
MOD_RES                2
                       note = Aminoisobutyric acid
MOD_RES                20
                       note = Aminoisobutyric acid
source                 1..39
                       mol_type = protein
                       organism = synthetic construct
SEQUENCE: 35
YXEGTFTSDY SIYLDKKAQX AFVKWLIAQG PSSGAPPPS                              39

SEQ ID NO: 36          moltype = AA   length = 39
FEATURE                Location/Qualifiers
REGION                 1..39
                       note = Description of Artificial Sequence: Synthetic
                        polypeptide
MOD_RES                2
                       note = Aminoisobutyric acid
MOD_RES                20
                       note = Aminoisobutyric acid
source                 1..39
                       mol_type = protein
                       organism = synthetic construct
SEQUENCE: 36
YXEGTFHSDY DIYKDKQAAX KFVQWLLAGG PSSGAPPPS                              39

SEQ ID NO: 37          moltype = AA   length = 39
FEATURE                Location/Qualifiers
REGION                 1..39
                       note = Description of Artificial Sequence: Synthetic
                        polypeptide
MOD_RES                2
                       note = Aminoisobutyric acid
MOD_RES                20
                       note = Neuroleucine
source                 1..39
                       mol_type = protein
                       organism = synthetic construct
SEQUENCE: 37
YXEGTFHSDY DIYKDKQAAX KFVAWLLAGG PSSGAPPPS                              39

SEQ ID NO: 38          moltype = AA   length = 39
FEATURE                Location/Qualifiers
REGION                 1..39
                       note = Description of Artificial Sequence: Synthetic
                        polypeptide
MOD_RES                2
                       note = Aminoisobutyric acid
MOD_RES                8
                       note = D-Serine
MOD_RES                11
                       note = D-Serine
MOD_RES                20
                       note = Neuroleucine
source                 1..39
                       mol_type = protein
                       organism = synthetic construct
SEQUENCE: 38
YXEGTFTSDY SIYKDKQAAX KFVAWLLAGG PSSGAPPPS                              39
```

```
SEQ ID NO: 39          moltype = AA   length = 39
FEATURE                Location/Qualifiers
REGION                 1..39
                       note = Description of Artificial Sequence: Synthetic
                        polypeptide
MOD_RES                2
                       note = Aminoisobutyric acid
MOD_RES                20
                       note = Aminoisobutyric acid
source                 1..39
                       mol_type = protein
                       organism = synthetic construct
SEQUENCE: 39
YXEGTFTSDY SIYKDKQAAX KFVNWLLAGG PSSGAPPPS                               39

SEQ ID NO: 40          moltype = AA   length = 39
FEATURE                Location/Qualifiers
REGION                 1..39
                       note = Description of Artificial Sequence: Synthetic
                        polypeptide
MOD_RES                2
                       note = Aminoisobutyric acid
MOD_RES                20
                       note = Aminoisobutyric acid
source                 1..39
                       mol_type = protein
                       organism = synthetic construct
SEQUENCE: 40
YXEGTFTSDY SIYKDKQAAX KFVNWLLAGG PSSGAPPPS                               39

SEQ ID NO: 41          moltype = AA   length = 39
FEATURE                Location/Qualifiers
REGION                 1..39
                       note = Description of Artificial Sequence: Synthetic
                        polypeptide
MOD_RES                2
                       note = Aminoisobutyric acid
MOD_RES                20
                       note = Aminoisobutyric acid
source                 1..39
                       mol_type = protein
                       organism = synthetic construct
SEQUENCE: 41
YXEGTFTSDY SIYKDKQAAX KFVNWLLAGG PSSGAPPPS                               39

SEQ ID NO: 42          moltype = AA   length = 39
FEATURE                Location/Qualifiers
REGION                 1..39
                       note = Description of Artificial Sequence: Synthetic
                        polypeptide
MOD_RES                2
                       note = Aminoisobutyric acid
MOD_RES                20
                       note = Aminoisobutyric acid
source                 1..39
                       mol_type = protein
                       organism = synthetic construct
SEQUENCE: 42
YXEGTFTSDY SIYLDKKAAX EFVKWLLAGG PSSGAPPPS                               39

SEQ ID NO: 43          moltype = AA   length = 39
FEATURE                Location/Qualifiers
REGION                 1..39
                       note = Description of Artificial Sequence: Synthetic
                        polypeptide
MOD_RES                2
                       note = Aminoisobutyric acid
MOD_RES                20
                       note = Aminoisobutyric acid
source                 1..39
                       mol_type = protein
                       organism = synthetic construct
SEQUENCE: 43
YXEGTFHSDY DIYKDKQAAX KFVQWLLAGG PSSGAPPPS                               39

SEQ ID NO: 44          moltype = AA   length = 39
FEATURE                Location/Qualifiers
```

```
REGION                   1..39
                         note = Description of Artificial Sequence: Synthetic
                          polypeptide
MOD_RES                  2
                         note = Aminoisobutyric acid
MOD_RES                  20
                         note = Neuroleucine
source                   1..39
                         mol_type = protein
                         organism = synthetic construct
SEQUENCE: 44
YXEGTFHSDY DIYKDKQAAX KFVAWLLAGG PSSGAPPPS                                   39

SEQ ID NO: 45            moltype = AA  length = 39
FEATURE                  Location/Qualifiers
REGION                   1..39
                         note = Description of Artificial Sequence: Synthetic
                          polypeptide
MOD_RES                  2
                         note = Aminoisobutyric acid
MOD_RES                  8
                         note = D-Serine
MOD_RES                  11
                         note = D-Serine
MOD_RES                  20
                         note = Neuroleucine
source                   1..39
                         mol_type = protein
                         organism = synthetic construct
SEQUENCE: 45
YXEGTFTSDY SIYKDKQAAX KFVAWLLAGG PSSGAPPPS                                   39

SEQ ID NO: 46            moltype = AA  length = 39
FEATURE                  Location/Qualifiers
REGION                   1..39
                         note = Description of Artificial Sequence: Synthetic
                          polypeptide
MOD_RES                  2
                         note = Aminoisobutyric acid
MOD_RES                  20
                         note = Aminoisobutyric acid
source                   1..39
                         mol_type = protein
                         organism = synthetic construct
SEQUENCE: 46
YXEGTFHSDY DIYKDKQAAX KFVQWLLAGG PSSGAPPPS                                   39

SEQ ID NO: 47            moltype = AA  length = 39
FEATURE                  Location/Qualifiers
REGION                   1..39
                         note = Description of Artificial Sequence: Synthetic
                          polypeptide
MOD_RES                  2
                         note = Aminoisobutyric acid
MOD_RES                  20
                         note = Neuroleucine
source                   1..39
                         mol_type = protein
                         organism = synthetic construct
SEQUENCE: 47
YXEGTFHSDY DIYKDKQAAX KFVAWLLAGG PSSGAPPPS                                   39

SEQ ID NO: 48            moltype = AA  length = 39
FEATURE                  Location/Qualifiers
REGION                   1..39
                         note = Description of Artificial Sequence: Synthetic
                          polypeptide
MOD_RES                  2
                         note = Aminoisobutyric acid
MOD_RES                  8
                         note = D-Serine
MOD_RES                  11
                         note = D-Serine
MOD_RES                  20
                         note = Neuroleucine
source                   1..39
                         mol_type = protein
                         organism = synthetic construct
```

```
SEQUENCE: 48
YXEGTFTSDY SIYKDKQAAX KFVAWLLAGG PSSGAPPPS                              39

SEQ ID NO: 49           moltype = AA  length = 39
FEATURE                 Location/Qualifiers
REGION                  1..39
                        note = Description of Artificial Sequence: Synthetic
                         polypeptide
MOD_RES                 2
                        note = Aminoisobutyric acid
MOD_RES                 20
                        note = Aminoisobutyric acid
source                  1..39
                        mol_type = protein
                        organism = synthetic construct
SEQUENCE: 49
YXEGTFTSDY SIYCDKQAAX CFVNWLLAGG PSSGAPPPS                              39

SEQ ID NO: 50           moltype = AA  length = 39
FEATURE                 Location/Qualifiers
REGION                  1..39
                        note = Description of Artificial Sequence: Synthetic
                         polypeptide
MOD_RES                 2
                        note = Aminoisobutyric acid
MOD_RES                 20
                        note = Aminoisobutyric acid
source                  1..39
                        mol_type = protein
                        organism = synthetic construct
SEQUENCE: 50
YXEGTFTSDY SIYCDKQAAX CFVNWLLAGG PSSGAPPPS                              39

SEQ ID NO: 51           moltype = AA  length = 39
FEATURE                 Location/Qualifiers
REGION                  1..39
                        note = Description of Artificial Sequence: Synthetic
                         polypeptide
MOD_RES                 2
                        note = Aminoisobutyric acid
MOD_RES                 20
                        note = Aminoisobutyric acid
source                  1..39
                        mol_type = protein
                        organism = synthetic construct
SEQUENCE: 51
YXEGTFTSDY SIYCDKQAAX CFVNWLIAGG PSSGAPPPS                              39

SEQ ID NO: 52           moltype = AA  length = 39
FEATURE                 Location/Qualifiers
REGION                  1..39
                        note = Description of Artificial Sequence: Synthetic
                         polypeptide
MOD_RES                 2
                        note = Aminoisobutyric acid
MOD_RES                 20
                        note = Aminoisobutyric acid
source                  1..39
                        mol_type = protein
                        organism = synthetic construct
SEQUENCE: 52
YXEGTFTSDY SIYCDKQAAX CFVNWLIAGG PSSGAPPPS                              39

SEQ ID NO: 53           moltype = AA  length = 39
FEATURE                 Location/Qualifiers
REGION                  1..39
                        note = Description of Artificial Sequence: Synthetic
                         polypeptide
MOD_RES                 2
                        note = Aminoisobutyric acid
MOD_RES                 20
                        note = Aminoisobutyric acid
source                  1..39
                        mol_type = protein
                        organism = synthetic construct
SEQUENCE: 53
YXEGTFISDV SIYCDKQAAX CFVNWLIAGG PSSGAPPPS                              39
```

```
SEQ ID NO: 54          moltype = AA   length = 39
FEATURE                Location/Qualifiers
REGION                 1..39
                       note = Description of Artificial Sequence: Synthetic
                       polypeptide
MOD_RES                2
                       note = Aminoisobutyric acid
MOD_RES                20
                       note = Aminoisobutyric acid
source                 1..39
                       mol_type = protein
                       organism = synthetic construct
SEQUENCE: 54
YXEGTFISDV SIYCDKQAAX CFVNWLIAGG PSSGAPPPS                        39

SEQ ID NO: 55          moltype = AA   length = 39
FEATURE                Location/Qualifiers
REGION                 1..39
                       note = Description of Artificial Sequence: Synthetic
                       polypeptide
MOD_RES                2
                       note = Aminoisobutyric acid
MOD_RES                20
                       note = Aminoisobutyric acid
source                 1..39
                       mol_type = protein
                       organism = synthetic construct
SEQUENCE: 55
YXEGTFTSDY SIYLDKCAAX EFVCWLLAGG PSSGAPPPS                        39

SEQ ID NO: 56          moltype = AA   length = 39
FEATURE                Location/Qualifiers
REGION                 1..39
                       note = Description of Artificial Sequence: Synthetic
                       polypeptide
MOD_RES                2
                       note = Aminoisobutyric acid
MOD_RES                20
                       note = Aminoisobutyric acid
source                 1..39
                       mol_type = protein
                       organism = synthetic construct
SEQUENCE: 56
YXEGTFTSDY SIYLDKCAAX EFVCWLLAGG PSSGAPPPS                        39

SEQ ID NO: 57          moltype = AA   length = 39
FEATURE                Location/Qualifiers
REGION                 1..39
                       note = Description of Artificial Sequence: Synthetic
                       polypeptide
MOD_RES                2
                       note = Aminoisobutyric acid
MOD_RES                20
                       note = Aminoisobutyric acid
source                 1..39
                       mol_type = protein
                       organism = synthetic construct
SEQUENCE: 57
YXEGTFTSDY SIYLDKCAQX AFVCWLIAQG PSSGAPPPS                        39

SEQ ID NO: 58          moltype = AA   length = 39
FEATURE                Location/Qualifiers
REGION                 1..39
                       note = Description of Artificial Sequence: Synthetic
                       polypeptide
MOD_RES                2
                       note = Aminoisobutyric acid
MOD_RES                20
                       note = Aminoisobutyric acid
source                 1..39
                       mol_type = protein
                       organism = synthetic construct
SEQUENCE: 58
YXEGTYTSDY SIYCDKQAAX CFVNWLIAGG PSSGAPPPS                        39

SEQ ID NO: 59          moltype = AA   length = 39
FEATURE                Location/Qualifiers
```

```
REGION                  1..39
                        note = Description of Artificial Sequence: Synthetic
                         polypeptide
MOD_RES                 2
                        note = Aminoisobutyric acid
MOD_RES                 20
                        note = Aminoisobutyric acid
source                  1..39
                        mol_type = protein
                        organism = synthetic construct
SEQUENCE: 59
YXEGTYTSDY SIYLDKCAAX EFVCWLIAGG PSSGAPPPS                                    39

SEQ ID NO: 60           moltype = AA  length = 39
FEATURE                 Location/Qualifiers
REGION                  1..39
                        note = Description of Artificial Sequence: Synthetic
                         polypeptide
MOD_RES                 2
                        note = Aminoisobutyric acid
MOD_RES                 20
                        note = Aminoisobutyric acid
source                  1..39
                        mol_type = protein
                        organism = synthetic construct
SEQUENCE: 60
YXEGTYTNDY SIYLDKCAAX EFVCWLIAGG PSSGAPPPS                                    39

SEQ ID NO: 61           moltype = AA  length = 39
FEATURE                 Location/Qualifiers
REGION                  1..39
                        note = Description of Artificial Sequence: Synthetic
                         polypeptide
MOD_RES                 2
                        note = Aminoisobutyric acid
MOD_RES                 20
                        note = Aminoisobutyric acid
source                  1..39
                        mol_type = protein
                        organism = synthetic construct
SEQUENCE: 61
YXEGTFTSDY SIYLDKCAAX EFVCWLIAGG PSSGAPPPS                                    39

SEQ ID NO: 62           moltype = AA  length = 39
FEATURE                 Location/Qualifiers
REGION                  1..39
                        note = Description of Artificial Sequence: Synthetic
                         polypeptide
MOD_RES                 2
                        note = Aminoisobutyric acid
MOD_RES                 20
                        note = Aminoisobutyric acid
source                  1..39
                        mol_type = protein
                        organism = synthetic construct
SEQUENCE: 62
YXEGTFTSDY SIYKDKQAAX KFVNWLLAGG PSSGAPPPS                                    39
```

LONG-ACTING DUAL GIP/GLP-1 PEPTIDE CONJUGATES AND METHODS OF USE

CROSS-REFERENCE

This application is a continuation of International Application No. PCT/CN2022/097662 filed Jun. 8, 2022, which claims the benefit of U.S. Provisional Application Ser. No. 63/208,952 filed Jun. 9, 2021, both of which are incorporated by reference herein in its entirety.

SEQUENCE LISTING

The instant application contains a Sequence Listing which has been submitted electronically in XML format and is hereby incorporated by reference in its entirety. Said XML copy, created on Aug. 7, 2023, is named 36271-714_301_SL.xml and is 162,675 bytes in size.

BACKGROUND OF THE INVENTION

The development of therapeutic agents is often hampered by short half-lives. The biological half-life of an agent is the time it takes for the agent to lose half of its pharmacologic, physiologic, or radiologic activity. As a result, patients are often administered higher dosages of a therapeutic agent more frequently, which can lead to reduced compliance, higher costs and greater risk of side effects. Accordingly, there is a need for generation of therapeutic agents with extended half-lives.

SUMMARY OF THE INVENTION

Disclosed herein is a peptide conjugate comprising:
a) a peptide and
b) a staple attached to the peptide at a first amino acid and a second amino acid;
wherein the staple is of Formula (I):

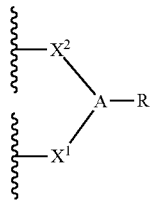

Formula (I)

wherein
A is —N—;
$X^1$ and $X^2$ are a bond, —C(=O)—, -alkylene-C(=O)—, —C(=O)-alkylene-, -alkylene-C(=O)NR$^3$—, -alkylene-NR$^3$C(=O)—, —C(=O)NR$^3$-alkylene-, —NR$^3$C(=O)-alkylene-, -alkylene-C(=O)NR$^3$-alkylene-, or -alkylene-NR$^3$C(=O)-alkylene-;
wherein $X^1$ is attached to the first amino acid of the peptide, $X^2$ is attached to the second amino acid of the peptide, and $X^1$ and $X^2$ are identical;
R is hydrogen or -(L)$_s$-Y;
each L is independently —(CR$^1$R$^2$)$_v$—, -alkylene-O—, —O-alkylene-, —C(=O)-alkylene-, -alkylene-C(=O)—, —NR$^3$-alkylene-, -alkylene-NR$^3$—, —S-alkylene-, -alkylene-S—, —S(=O)-alkylene-, -alkylene-S(=O)—, —S(=O)$_2$-alkylene, -alkylene-S(=O)$_2$—, —C(=O)—, —C(=O)NR$^3$—, —NR$^3$C(=O)—, —NR$^3$C(=O)NR$^3$—, —NR$^3$C(=O)NR$^3$-alkylene-, —NR$^3$C(=O)-alkylene-NR$^3$—, -alkylene-C(=O)NR$^3$—, —C(=O)NR$^3$-alkylene-, -alkylene-NR$^3$C(=O)—, or —NR$^3$C(=O)-alkylene-;
v is 2-20;
each $R^1$ or $R^2$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;
or $R^1$ and $R^2$ are taken together to form a $C_1$-$C_6$ cycloalkyl or $C_1$-$C_6$ heterocycloalkyl;
each $R^3$ is independently hydrogen, —S(=O)R$^b$, —S(=O)$_2$R$^a$, —S(=O)$_2$NR$^c$R$^d$, —C(=O)R$^b$, —CO$_2$R$^a$, —C(=O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;
Y is hydrogen, $C_1$-$C_6$ alkyl, —CO$_2$H, —CO$_2$($C_1$-$C_6$ alkyl), —CO$_2$NH$_2$, —CO$_2$N(alkyl)$_2$, or —CO$_2$NH(alkyl);
s is 0-20;
R$^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;
R$^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$; and
each R$^c$ and R$^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;
or R$^c$ and R$^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —NH$_2$.

Also provided herein is a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61.

Also provided herein is a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 1-61. Also provided herein is a peptide comprising a sequence at least 95% identical to SEQ ID NO. 6 (YAibEGT-FTSDY-SIYLD-KX1AAAib-EFVX2W-LI-AGG-PSSGA-PPPS).

Also provided herein is a peptide comprising SEQ ID NO: 6 (YAibEGT-FTSDY-SIYLD-KX1AAAib-EFVX2W-LI-AGG-PSSGA-PPPS), or a peptide having 1 amino acid substitution, deletion, or insertion, or any combination thereof, as compared to SEQ ID NO: 6 (YAibEGT-FTSDY-SIYLD-KX1AAAib-EFVX2W-LIAGG-PSSGA-PPPS).

In some embodiments, the peptide comprises a sequence at least 98% identical to SEQ ID NO. 6. In some embodiments, the peptide comprises SEQ ID NO. 6. In some embodiments, the peptide comprises X1 and/or X2. In some embodiments, the peptide comprises X1, wherein X1 is a cysteine or lysine. In some embodiments, the peptide comprises X2, wherein X2 is a cysteine or lysine. In some embodiments, the peptide comprises X1 and X2, wherein X1 is cysteine and X2 is cysteine.

Also provided herein are peptide conjugates comprising any peptide herein, and a staple.

Also provided herein are peptide conjugates comprising a peptide at least 79% identical to SEQ ID NO: 6 (YAibEGT-FTSDY-SIYLD-KX1AAAib-EFVX2W-LIAGG-PSSGA-PPPS), and a staple.

In some embodiments, the peptide comprises X1 and/or X2 of SEQ ID NO: 6, and the staple is attached at the X1 and/or X2. In some embodiments, the peptide conjugate further comprising a fatty acid and/or half life extending moiety.

In some embodiments, the staple is attached to the peptide at a first amino acid and a second amino acid; wherein the staple is of Formula (I):

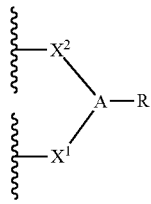

Formula (I)

wherein
A is —N—;
$X^1$ and $X^2$ are a bond, —C(=O)—, -alkylene-C(=O)—, —C(=O)-alkylene-, -alkylene-C(=O)NR$^3$—, -alkylene-NR$^3$C(=O)—, —C(=O)NR$^3$-alkylene-, —NR$^3$C(=O)-alkylene-, -alkylene-C(=O)NR$^3$-alkylene-, or -alkylene-NR$^3$C(=O)-alkylene-;
wherein $X^1$ is attached to the first amino acid of the peptide, $X^2$ is attached to the second amino acid of the peptide, and $X^1$ and $X^2$ are identical;
R is hydrogen or -(L)$_s$-Y;
each L is independently —(CR$^1$R$^2$)$_v$—, -alkylene-O—, —O-alkylene-, —C(=O)-alkylene-, -alkylene-C(=O)—, —NR$^3$-alkylene-, -alkylene-NR$^3$—, —S-alkylene-, -alkylene-S—, —S(=O)-alkylene-, -alkylene-S(=O)—, —S(=O)$_2$-alkylene, -alkylene-S(=O)$_2$—, —C(=O)—, —C(=O)NR$^3$—, —NR$^3$C(=O)—, —NR$^3$C(=O)NR$^3$—, —NR$^3$C(=O)NR$^3$-alkylene-, —NR$^3$C(=O)-alkylene-NR$^3$—, -alkylene-C(=O)NR$^3$—, —C(=O)NR$^3$-alkylene-, -alkylene-NR$^3$C(=O)—, or —NR$^3$C(=O)-alkylene-;
v is 2-20;
each $R^1$ or $R^2$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;
or $R^1$ and $R^2$ are taken together to form a $C_1$-$C_6$ cycloalkyl or $C_1$-$C_6$ heterocycloalkyl; each $R^3$ is independently hydrogen, —S(=O)R$^b$, —S(=O)$_2$R$^a$, —S(=O)$_2$NR$^c$R$^d$, —C(=O)R$^b$, —CO$_2$R$^a$, —C(=O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;
Y is hydrogen, $C_1$-$C_6$ alkyl, —CO$_2$H, —CO$_2$($C_1$-$C_6$ alkyl), —CO$_2$NH$_2$, —CO$_2$N(alkyl)$_2$, or —CO$_2$NH(alkyl);
s is 0-20;
$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;
$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$; and each R$^c$ and R$^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —NH$_2$, and wherein optionally the peptide comprises X1 and X2, and the first amino acid is X1 and the second amino acid is X2.

In some embodiments, the first amino acid and the second amino acid are independently a sulfydryl containing amino acid. In some embodiments, the first amino acid and the second amino acid are independently selected from cysteine, homocysteine, 2-amino-5-mercaptopentanoic acid, and 2-amino-6-mercaptohexanoic acid. In some embodiments, the first amino acid and second amino acids are cysteines. In some embodiments, the first amino acid and the second amino acid are independently an amine-containing amino acid. In some embodiments, the amine-containing amino acid is selected from lysine, ornithine, diaminobutyric acid, diaminopropionic acid and homolysine. In some embodiments, the first amino acid and the second amino acids are lysines. In some embodiments, the first amino acid has a position i in the peptide and the second amino acid has a position i+n in the peptide, wherein n is 4-16. In some embodiments, the peptide modulates a GLP-1 receptor. In some embodiments, the peptide binds to a GLP-1 receptor. In some embodiments, the peptide modulates a GIP receptor. In some embodiments, the peptide binds to a GIP receptor. In some embodiments, the peptide is a GLP-1 receptor agonist. In some embodiments, the peptide is a GIP receptor agonist. In some embodiments, the peptide is a dual GLP-1 receptor and GIP receptor agonist. In some embodiments, the peptide is resistant to proteolysis by a gastrointestinal protease. In some embodiments, the half-life of the peptide conjugate is at least about 2-fold greater than the half-life of an unmodified form of the peptide. In some embodiments, the binding affinity of the peptide conjugate is within about 5-20% of the binding affinity of an unmodified form of the peptide.

In some embodiments, $X^1$ and $X^2$ are —C(=O)—. In some embodiments, $X^1$ and $X^2$ are -alkylene-C(=O)— or —C(=O)alkylene-. In some embodiments, $X^1$ and $X^2$ are —CH$_2$—C(=O)— or —C(=O)—CH$_2$—. In some embodiments, $X^1$ and $X^2$ are -alkylene-C(=O)NR$^3$— or —C(=O)NR$^3$-alkylene-. In some embodiments, $X^1$ and $X^2$ are —CH$_2$—C(=O)NR$^3$— or —C(=O)NR$^3$—CH$_2$—. In some embodiments, $X^1$ and $X^2$ are -alkylene-C(=O)NR$^3$-alkylene- or -alkylene-NR$^3$C(=O)-alkylene-. In some embodiments, $X^1$ and $X^2$ are —CH$_2$—C(=O)NR$^3$—CH$_2$CH$_2$— or —CH$_2$—NR$^3$C(=O)—CH$_2$CH$_2$—. In some embodiments, $X^1$ and $X^2$ are —CH$_2$—C(=O)NH—CH$_2$CH$_2$— or —CH$_2$—NHC(=O)—CH$_2$CH$_2$—. In some embodiments, >A-R has the following structure:

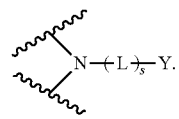

In some embodiments, s is 1-15. In some embodiments, s is 1-10. In some embodiments, s is 5-15. In some embodiments, s is 5-10. In some embodiments, Y is hydrogen or —CO$_2$H. In some embodiments, each L is independently —(CR$^1$R$^2$)$_v$—, -alkylene-O—, —C(=O)—, —C(=O)NR$^3$—, —NR$^3$C(=O)—, -alkylene-C(=O)NR$^3$—, or -alkylene-NR$^3$C(=O)—; and v is 2-20.

In some embodiments, the peptide conjugate comprises:

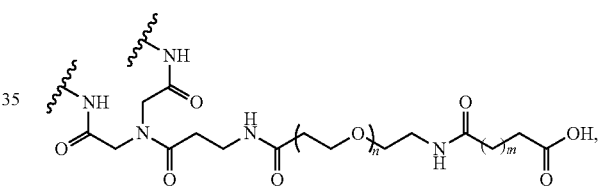

wherein n is 1-4 and m is 6-20.

In some embodiments, n is 3 and m is 15.

In some embodiments, the peptide conjugate comprises:

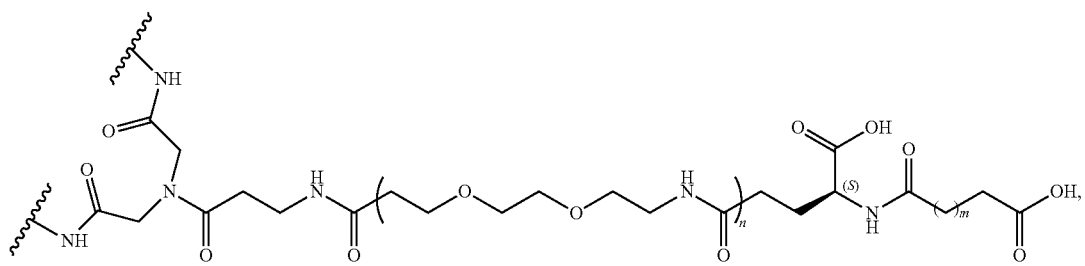

wherein n is 1-4 and m is 6-20.

In some embodiments, n is 2 and m is 15.

In some embodiments, n is 2 and m is 17.

In some embodiments, the peptide conjugate comprises:
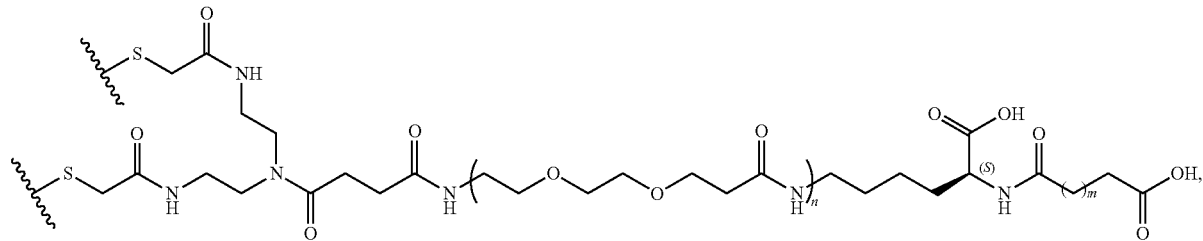
wherein n is 1-4 and m is 6-20.
In some embodiments, n is 2 and m is 15.
In some embodiments, n is 2 and m is 17.
In some embodiments, n is 2 and m is 13.
In some embodiments, the peptide conjugate comprises:
L5A(S)
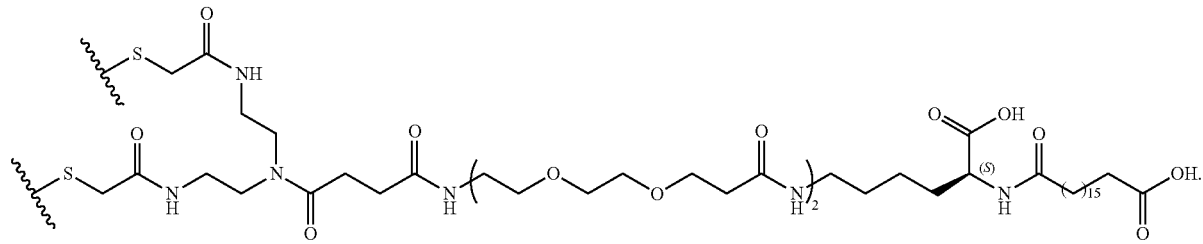
In some embodiments, the peptide conjugate comprises:
L5A
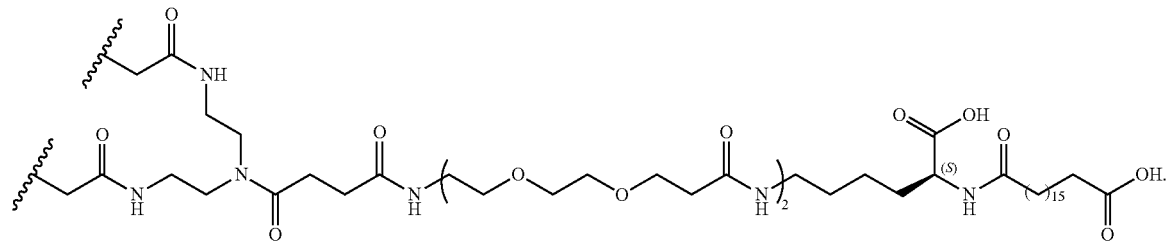
In some embodiments, the peptide conjugate comprises:
C20L5A
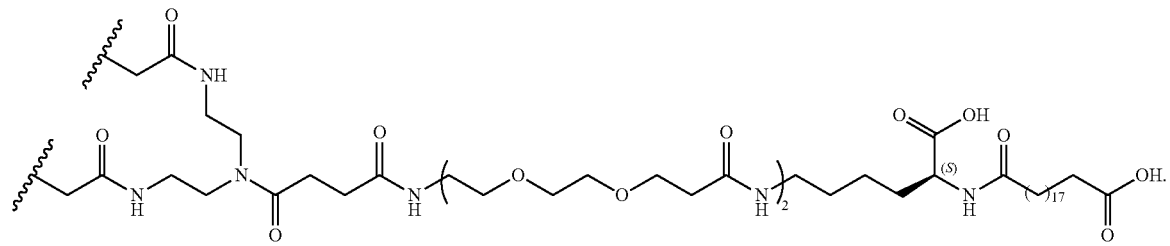

In some embodiments, the peptide conjugate comprises: C16L5A

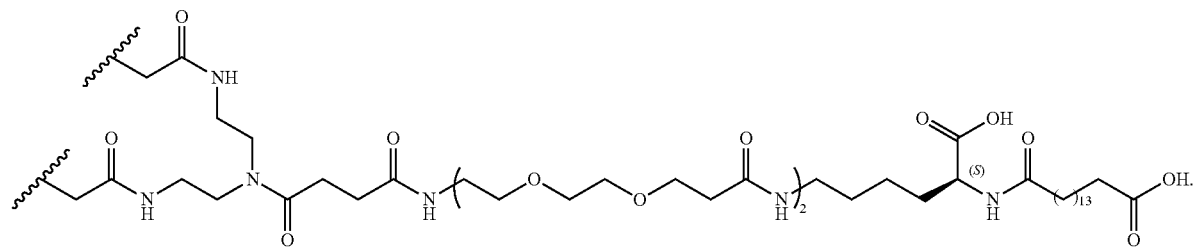

In some embodiments, the peptide conjugate comprises: K4

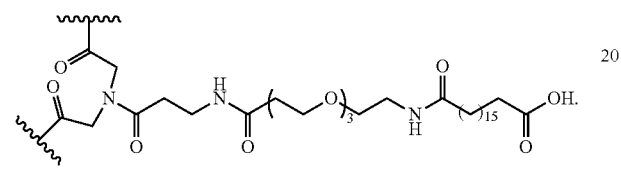

In some embodiments, the peptide conjugate comprises: K5

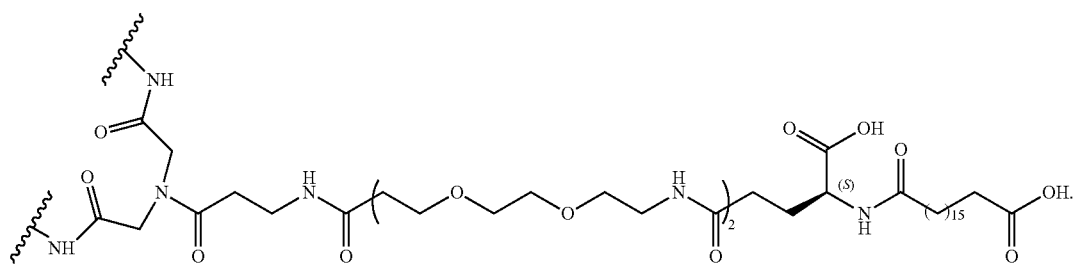

In some embodiments, the peptide conjugate comprises: C20K5

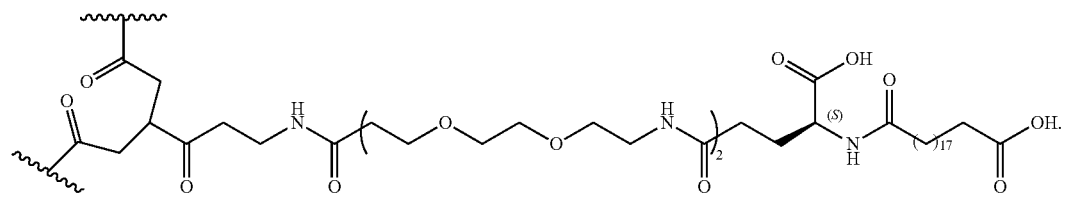

Also provided herein is a pharmaceutical composition comprising the peptide or peptide conjugate described herein and a pharmaceutically acceptable excipient.

Also provided herein is a method for treating a disease or condition in a subject in need thereof, the method comprising administering to the subject a composition comprising a therapeutically effective amount of a peptide or peptide conjugate described herein. The peptide or peptide conjugate may be administered about once every week, or about once every two weeks.

In some embodiments, the disease or condition is diabetes or obesity. In some embodiments, the diabetes is Type 1 diabetes mellitus, Type 2 diabetes mellitus, gestational diabetes, neonatal diabetes, maturity onset diabetes of the young, or latent autoimmune diabetes in adults, or any combination thereof. In some embodiments, the disease or condition is non-alcoholic fatty liver disease (NAFLD), nonalcoholic steatohepatitis (NASH), or cardiovascular disease. In some embodiments, the disease or condition is short bowel syndrome (SBS). In some embodiments, the disease or condition is inflammatory bowel disease (IBD), inflammatory bowel syndrome (IBS), or psoriasis. In some embodiments, the disease or condition is Crohn's disease or ulcerative colitis. In some embodiments, the disease or condition is Alzheimer's disease, Parkinson's disease or Huntington's disease.

In some embodiments, the method further comprises administering to the subject one or more additional therapeutic agents. In some embodiments, the one or more additional therapeutic agents comprises an incretin hormone or a derivative thereof. In some embodiments, the incretin hormone or derivative thereof is selected from GLP-1, exendin-4, glucagon (GCG), glucose-dependent insulinotropic polypeptide (GIP), oxyntomodulin, and combinations thereof.

In some embodiments, the peptide conjugate is administered about once every 7 days. In some embodiments, the peptide conjugate is administered about once every 14 days. In some embodiments, the peptide conjugate is administered about once a month. In some embodiments, the peptide conjugate is administered about once every two months. In some embodiments, the peptide conjugate is administered about once every three months.

BRIEF DESCRIPTION OF FIGURES

FIG. 16 also shows a graph of AUC calculations from this experiment.

DETAILED DESCRIPTION OF THE INVENTION

Figure 1A:
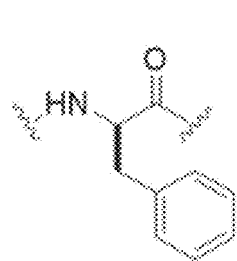
FIG. 1A and FIG. 1B display example components of a peptide, such as amino acids.
Figure 1A:
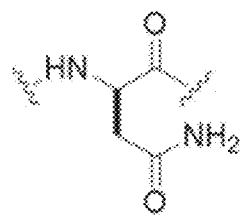
Figure 1A:
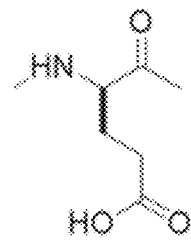
Figure 1A:
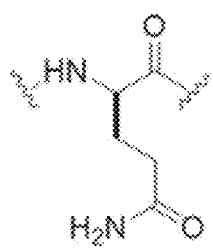
Figure 1A:
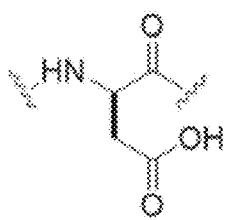
Figure 1A:
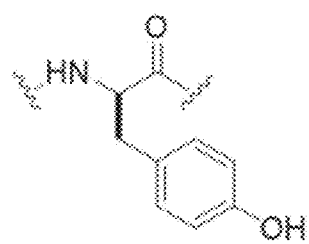
Figure 1A:
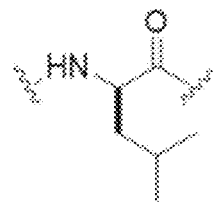
Figure 1A:
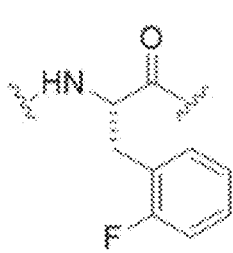
Figure 1A:
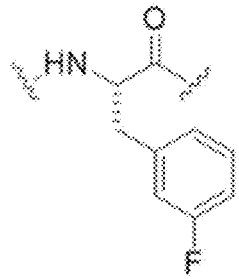
Figure 1A:
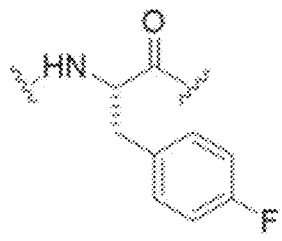
Figure 1A:
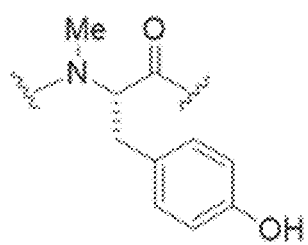
Figure 1A:
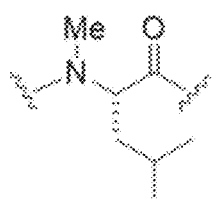
Figure 1A:
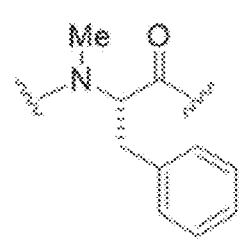

G protein-coupled receptors (GPCRs) are membrane-bound proteins that have seven transmembrane domains linked by three intracellular and three extracellular loops. Their ligand-binding sites are highly specialized so that each receptor responds only to a limited variety of chemicals which bind with high affinity. Examples of GPCR ligands are peptides, proteins, lipid-derived molecules, small organic compounds and ions. GPCRs have been of long-standing interest as pharmaceutical drug targets, as they are involved in a plethora of pathophysiological processes, including the regulation of neuronal excitability, metabolism, reproduction, hormonal homeostasis, and behavior. It is estimated that around 34% of all Food and Drug Administration (FDA) approved drugs target 108 members of the GPCR family. GPCRs are generally classified into multiple superfamilies. Family B GPCRs, or the so-called secretin receptor family, are a small but structurally and functionally diverse set of receptors. These proteins are vital to many physiological functions and serve as key drug targets for several human diseases such as type 2 diabetes mellitus (T2DM), migraine, osteoporosis, depression, and anxiety. Members of this family include receptors for polypeptide hormones of 27-141 residues in length. Nine of these receptors are targeted by ligands that are structurally related to one another, examples of which include glucagon-like peptides (GLP-1 and GLP-2), glucagon, glucose-dependent insulinotropic polypeptide (GIP), vasoactive intestinal peptide (VIP), pituitary adenylate cyclase-activating polypeptide (PACAP) and growth hormone-releasing hormone (GHRH).

Glucagon-like peptide 1 (GLP-1) is a naturally-occurring incretin hormone released into the circulation by the L cells of the gut in response to ingested nutrients. By binding to its cognate receptor (GLP-1R) GLP-1 is able to promote insulin secretion while suppressing glucagon secretion, but only when glucose levels are raised, thus offering the potential to lower plasma glucose levels while reducing the risk of hypoglycemia. Furthermore, GLP-1 decreases the rate of gastric emptying, and reduces appetite, thus resulting in weight loss.

GLP-1 receptor agonists (GLP-1RAs) represent a unique approach to the treatment of diabetes, with benefits beyond glucose control, including favorable effects on body weight, blood pressure, cholesterol levels, and beta-cell function. Two short-acting (exenatide and liraglutide; once- or twice-daily administration) and three long-acting (albiglutide, dulaglutide, and exenatide LAR; weekly administration) GLP-1RAs are currently approved in the United States. In particular, exenatide, a GLP-1 analog originally isolated from the saliva of the Gila monster, has a half-life of 30 min after i.v. administration and a half-life of 2-3 h after s.c. administration in humans. These drugs mimic the effects of the naturally occurring incretin hormone GLP-1 by activating GLP-1 receptors in the pancreas, which leads to enhanced insulin release and reduced glucagon release in a glucose-dependent manner—with a consequently low risk of hypoglycemia. The effects of these GLP-1RAs on GLP-1 receptors in the CNS and the gastrointestinal tract also lead to reduced appetite and delayed glucose absorption, with concomitant weight loss. Given their limited oral bioavailability, these GLP-1RAs are currently given as an s.c. injection. In some aspects, provided herein are GLP-1RAs connected to a fatty-acid derived side-chain staple to increase half-life.

Incretin-based peptides are effective therapeutics for treating type 2 diabetes mellitus (T2DM). Oxyntomodulin (OXM), a dual agonist of GLP-1R and GCGR, has shown superior weight loss and glucose lowering effects, compared to single GLP-1R agonists. To overcome the short half-life and rapid renal clearance of OXM, which limit its therapeutic potential, both lipid and PEG modified OXM analogs have been reported. However, these approaches often result in reduced potency or PEG-associated toxicity. In certain embodiments, provided herein are GLP-1R and GCGR dual agonists having increased plasma stability and higher potency in activating both GLP-1R and GCGR.

GIP is also characterized as an incretin that stimulates insulin secretion in a glucose-dependent manner. A GIP and GLP-1 receptor dual agonist has been shown to reduce fasting serum glucose compared to placebo and to reduce body weight. This dual agonist, LY3298176, is administered once-weekly subcutaneously. In certain embodiments, further provided herein are GIPR and GLP-1R dual agonists comprising a stapled feature to increase serum stability and half-life.

Provided herein are peptides and peptide conjugates comprising a therapeutic peptide stapled to a molecule, such as a half-life extending molecule.

In certain embodiments, the stapled peptides comprise incretin peptides or incretin peptide mimetics. Incretin peptides generally bind to their cognate receptors in an α-helical conformation, therefore certain embodiments herein provide for modifications that stabilize the α-helix, which in some cases may increase binding affinity to their receptors. Moreover, proteolytic stability may also be enhanced in a helical rather than an extended conformation. In some aspects, provided herein are such conjugated peptides having increased circulatory half-life and potency toward their cognate receptors.

In some aspects, described herein is a peptide engineering strategy used to generate stapled long-acting peptide analogs with comparable potency as native peptides and significantly enhanced pharmacokinetic properties.

Peptides

In one aspect, provided herein are peptides and peptide conjugates comprising a peptide that modulates the GLP-1 receptor and/or the GIP receptor. In some embodiments, the peptide modulates both the GLP-1 receptor and the GIP receptor. In some embodiments, a peptide that modulates the GLP-1 receptor is a GLP-1 receptor agonist. In some embodiments, a peptide that modulates the GIP receptor is a GIP receptor agonist.

The binding affinity of the peptide conjugate as described herein may be within about 5% of the binding affinity of an unmodified form of the peptide to a receptor (e.g., GLP-1 and/or GIP receptor). The binding affinity of the peptide conjugate as described herein may be within about 10% of the binding affinity of an unmodified form of the peptide. The binding affinity of the peptide conjugate as described herein may be within about 15% of the binding affinity of an unmodified form of the peptide. The binding affinity of the peptide conjugate as described herein may be within about 20% of the binding affinity of an unmodified form of the peptide.

The peptide may comprise one or more sulfhydryl containing amino acid residues. The one or more sulfhydryl containing amino acid residues may be used for connecting a staple. The one or more sulfhydryl containing amino acid residues may be used for connecting a HEM (half-life extending molecule). The one or more sulfhydryl containing amino acid residues may be naturally occurring in the peptide. The one or more sulfhydryl containing amino acid residues may be inserted into the peptide. The one or more sulfhydryl containing amino acid residues may replace one or more amino acid residues in the peptide. Methods for amino acid substitution and/or insertion are known in the art.

The peptide may comprise one or more amine containing residues. Non-limiting examples of amine containing residues include lysine, ornithine, diaminobutyric acid, diaminopropionic acid and homolysine. The one or more amine containing residues may be used for connecting a staple. The one or more one or more amine containing residues may be used for connecting a HEM. The one or more one or more amine containing residues may be naturally occurring in the peptide. The one or more one or more amine containing residues may be inserted into the peptide. The one or more one or more amine containing residues may replace one or more amino acid residues in the peptide.

The peptide may comprise at least a portion of a wild-type peptide comprising one or more amino acid mutations. The one or more amino acid mutations may comprise a deletion, substitution, addition or a combination thereof. The one or more amino acid mutations may comprise adding one or more amino acid residues to a wild-type peptide. The one or more amino acid mutations may comprise deletion of one or more amino acid residues of the wild-type peptide. The one or more amino acid mutations may comprise substitution of one or more amino acid residues of the wild-type peptide. The one or more amino acid mutations may comprise substituting one or more amino acid residues of the wild-type peptide with one or more cysteine, lysine or other sulfhydryl or amine containing residues. The one or more amino acid mutations may comprise substituting one or more amino acid residues of the wild-type peptide with one or more D-amino acid residues. The one or more amino acid residues of the wild-type peptide may comprise one or more alanines, methionines, arginines, serines, threonines, and tyrosines.

The peptide may be modified with, for example, acetylation, phosphorylation, and methylation. The peptide modification may comprise a chemical modification. Peptide modifications may occur on the N-terminus of the peptide. Peptide modifications may comprise acetyling the amino group at the N-terminus of the peptide. Alternatively, or additionally, peptide modifications may occur on the C-terminus of the peptide. Peptide modifications may occur at one or more internal amino acids of the peptide. Peptide modifications may comprise replacing the carboxyl group at the C-terminus of the peptide. Peptide modifications may comprise modifying the carboxyl group at the C-terminus of the peptide. The carboxyl group at the C-terminus of the peptide may be modified to produce an amide group. The carboxyl group at the C-terminus of the peptide may be modified to produce an amine group.

In some embodiments, the peptide may be a modified peptide with a D-serine in place of L-serine. In some embodiments, the peptide may be a modified with an aminoisobutyric acid [Aib] in place of L-serine. In some embodiments, the peptide may be a modified peptide with a neuroleucine [Nle] in place of leucine (Leu). In some embodiments, the peptide comprises aMeF (alpha-methyl Phe). In some embodiments, the peptide comprises 4Pal (4-pyridyl-Ala). In some embodiments, the peptide comprises aMeL (alpha-methyl Leu). In some embodiments, the peptide comprises Orn (ornithine). In some embodiments, the peptide comprises aMeY (alpha-methyl tyrosine).

Figure 1B:
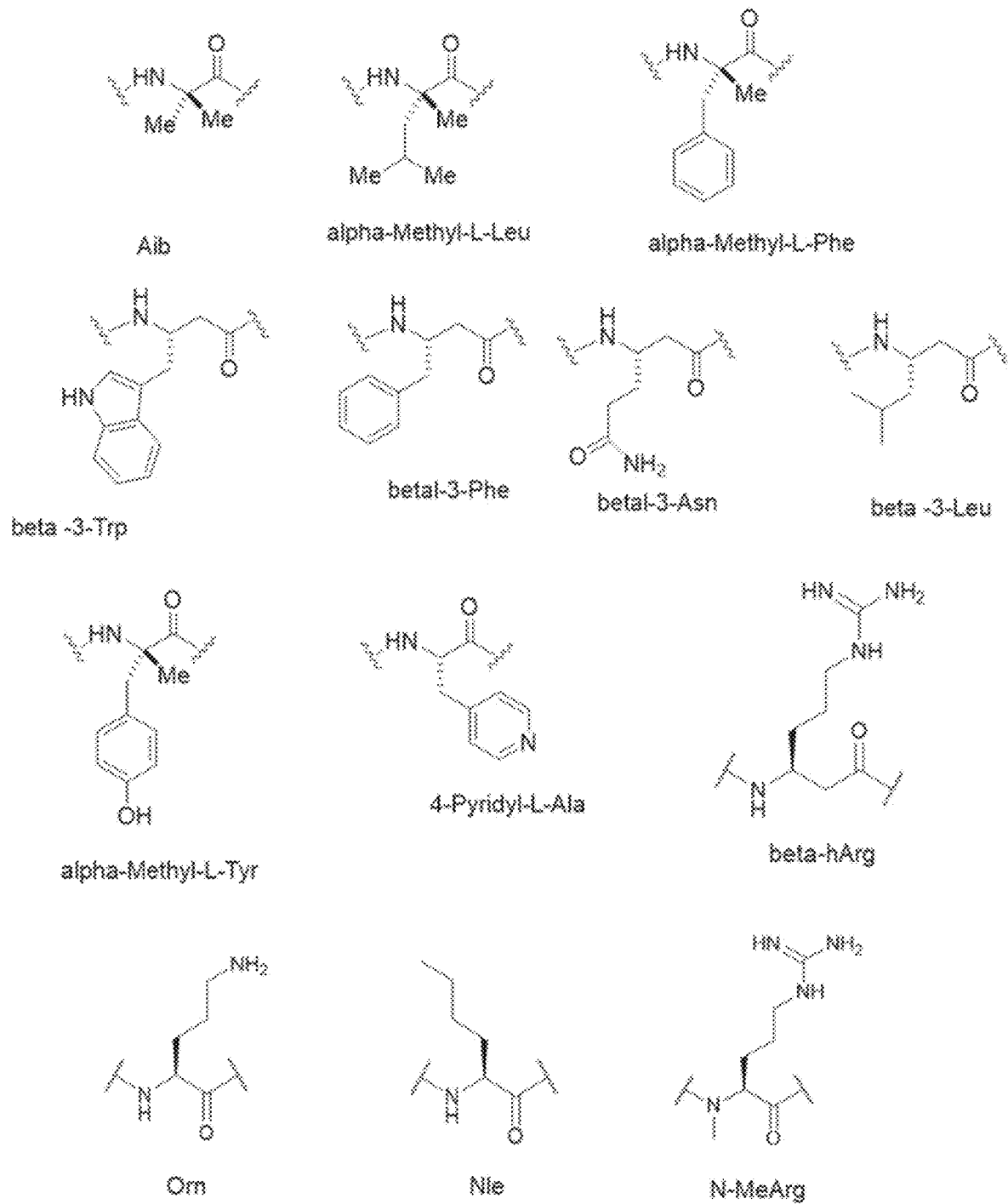

In some embodiments, the peptide comprises one or more of the following amino acids: N-methyl-Phe, D-Phe, alpha-methyl-Phe, Phe (2-F), Phe (3-F), Phe (4-F), 4-Pyridyl-Ala, Aib, N-methyl-Leu, D-Leu, alpha-methyl-Leu, beta-3-Leu, beta-3-Phe, beta-3-Asn, beta-3-Trp, D-Asn, D-Glu, D-Gln, D-Asp. In some embodiments, the peptide comprises an amino acid of FIGS. 1A-1B.

In some embodiments, the peptide comprises a sequence of any one of SEQ ID NOs: 1-61. In some cases, the peptide comprises a sequence at least about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to any one of SEQ ID NOs: 1-61. In some cases, the peptide comprises a sequence at least about 90% identical to any one of SEQ ID NOs: 1-61. In some cases, the peptide comprises a sequence at least about 95% identical to any one of SEQ ID NOs: 1-61. In some cases, the peptide comprises a sequence at least about 99% identical to any one of SEQ ID NOs: 1-61. In some cases, the peptide comprises an amino acid sequence having up to about 1, 2, 3, 4, or 5 amino acid insertions, deletions, modifications, or substitutions as compared to any one of SEQ ID NOS: 1-61.

Non-limiting examples of peptides are shown in Table 1. X refers to any natural or unnatural amino acid. Lower case letters refer to D-amino acids (e.g., "s" is D-serine). In some cases, an X comprises a sulfydryl containing amino acid. In some cases, an X comprises an amine-containing amino acid. In some cases, an X is Lys. In some cases, an X is a Cys. In some cases, a first X of the peptide is an amine-containing amino acid and a second X of the peptide is a sulfydryl containing amino acid. In some cases, a second X of the peptide is an amine-containing amino acid and a first X of the peptide is a sulfydryl containing amino acid. In some embodiments, a peptide is resistant to a GI protease. In some cases, a GI protease resistant peptide comprises SEQ ID NO: 7. In some cases, a GI protease resistant peptide comprises SEQ ID NO: 9. In some cases, a GI protease resistant peptide comprises SEQ ID NO: 6. In some embodiments, the peptide comprises SEQ ID NO: 6, and the first X is a cysteine and the second X is a cysteine.

TABLE 1

Peptide SEQ ID

| SEQ ID NO. | Sequence |
|---|---|
| 1 | YAibEGT-FTSDY-SIYXD-KQAAAib-XFVNW-LLAGG-PSSGA-PPPS-NH2 |
| 2 | YAibEGT-FHSDY-DIYXD-KQAAAib-XFVQW-LLAGG-PSSGA-PPPS-NH2 |
| 3 | YAibEGT-FHSDY-DIYXD-KQAANle-XFVAW-LLAGG-PSSGA-PPPS-NH2 |

TABLE 1-continued

Peptide SEQ ID

| SEQ ID NO. | Sequence |
|---|---|
| 4 | YAibEGT-FTsDY-SIYXD-KQAANle-XFVAW-LLAGG-PSSGA-PPPS-NH2 |
| 5 | YAibEGT-FTSDY-SIYXD-KQAAAib-XFVNW-LIAGG-PSSGA-PPPS-NH2 |
| 6 | YAibEGT-FTSDY-SIYLD-KXAAAib-EFVXW-LIAGG-PSSGA-PPPS-NH2 |
| 30 | YAibEGT-FTSDY-SIYXD-KXAAAib-XFVXW-LIAGG-PSSGA-PPPS-NH2 |
| 7 | YAibEGT-aa6TSDaa10-SIaa13LD-aa16XAAAib-EFVXaa25-LIaa33GG-PSSGA-PPPS-NH2<br>aa6: alpha-methyl Phe, N-methyl Phe, D-Phe, beta3-Phe, alpha-methyl Phe, alpha-methyl Phe (2-F), alpha-methyl Phe (3-F), and alpha-methyl (4-F), Phe (2-F), Phe (3-F), or Phe (4-F)<br>aa10: alpha-methyl Tyr, N-methyl Tyr, D-Tyr, beta3-Tyr, 4-Pyr-Ala, Phe (2-F), Phe (3-F), or Phe (4-F)<br>aa13: alpha-methyl Leu, N-methyl Leu, D-Leu, beta3-Leu, Leu, Val, Ile, Aib, alpha-methyl Tyr, N-methyl Tyr, D-Tyr, beta3-Tyr, 4-Pyr-Ala, Phe (2-F), Phe (3-F), or Phe (4-F)<br>aa16: L-Orn, alpha-methyl Lys, N-methyl Lys, D-Lys, or beta3-Lys<br>aa25: alpha-methyl Trp, N-methyl Trp, D-Trp, beta3-Trp, alpha-methyl Tyr, or Aib<br>aa33: A or E |
| 8 | YAibEGT-aa6TSDaa10-SIaa13LD-aa16XAAAib-EFVXaa25-LIaa33GG-PSSGA-PPPS-NH2 |
| 9 | YAibEGT-aa6TSDaa10-SIaa13XD-aa16QAAAib-XFVaa24aa25-LIaa33GG-PSSGA-PPPS-NH2<br>aa6: alpha-methyl Phe, N-methyl Phe, D-Phe, beta3-Phe, alpha-methyl Phe (2-F), alpha-methyl Phe (3-F), and alpha-methyl (4-F), Phe (2-F), Phe (3-F), or Phe (4-F)<br>aa10: alpha-methyl Tyr, N-methyl Tyr, D-Tyr, beta3-Tyr, 4-Pyr-Ala, Phe (2-F), Phe (3-F), Phe (4-F), or 4-pyridyl-Ala<br>aa13: alpha-methyl Leu, N-methyl Leu, D-Leu, beta3-Leu, Val, Ile, or Aib<br>aa16: alpha-methyl Leu, N-methyl Leu, D-Leu, beta3-Leu, Val, Ile, or Aib<br>aa24: alpha-methyl Asn, N-methyl Asn, beta3-Asn, Aib, D-Asn, D-Asp, D-Glu, or D-Gln<br>aa25: alpha-methyl Trp, N-methyl Trp, D-Trp, beta3-Trp, alpha-methyl Tyr, or Aib<br>aa33: A or E |
| 10 | Yaa2EGT-FTSDY-SIaa13LD-KXAAaa20-EFVXW-LIAGG-PSSGA-PPPS-NH2<br>aa2: Gly, Val, Leu, Ile, or Aib<br>aa13: alpha-methyl Leu, N-methyl Leu, D-Leu, beta3-Leu, Leu, Val, Ile, Aib, alpha-methyl Tyr, N-methyl Tyr, D-Tyr, beta3-Tyr, 4-Pyr-Ala, Phe (2-F), Phe (3-F), or Phe (4-F)<br>aa20: Gly, Val, Leu, Ile, or Aib |
| 11 | Yaa2EGT-FTSDY-SIaa13LD-KXAAaa20-EFVXW-LIA-NH2<br>aa2: Gly, Val, Leu, Ile, or Aib<br>aa13: alpha-methyl Leu, N-methyl Leu, D-Leu, beta3-Leu, Leu, Val, Ile, Aib, alpha-methyl Tyr, N-methyl Tyr, D-Tyr, beta3-Tyr, 4-Pyr-Ala, Phe (2-F), Phe (3-F), Phe (4-F)<br>aa20: Gly, Val, Leu, Ile, or Aib |
| 12 | Yaa2EGT-FTSDY-SIaa13XD-KQAAaa20-XFVNW-LIAGG-PSSGA-PPPS-NH2<br>aa2: Gly, Val, Leu, Ile, or Aib<br>aa13: alpha-methyl Leu, N-methyl Leu, D-Leu, beta3-Leu, Leu, Val, Ile, Aib, alpha-methyl Tyr, N-methyl Tyr, D-Tyr, beta3-Tyr, 4-Pyr-Ala, Phe (2-F), Phe (3-F), or Phe (4-F)<br>aa20: Gly, Val, Leu, Ile, or Aib |
| 13 | Yaa2EGT-FTSDV-SIaa13XD-KQAAaa20-XFVNW-LIA-NH2<br>aa2: Gly, Val, Leu, Ile, or Aib<br>aa13: alpha-methyl Leu, N-methyl Leu, D-Leu, beta3-Leu, Leu, Val, Ile, Aib, alpha-methyl Tyr, N-methyl Tyr, D-Tyr, beta3-Tyr, 4-Pyr-Ala, Phe (2-F), Phe (3-F), or Phe (4-F)<br>aa20: Gly, Val, Leu, Ile, or Aib |

TABLE 1-continued

Peptide SEQ ID

| SEQ ID NO. | Sequence |
|---|---|
| 14 | YAibEGT-aMeFTSD-4Pal-SIaMeLLD-OrnXAAAib-EFVXaMeY-LIAGG-PSSGA-PPPS-NH2 |
| 15 | YAibEGT-aMeFTSD-4Pal-SIaMeLXD-OrnQAAAib-XFV(D-Glu)aMeY-LIAGG-PSSGA-PPPS-NH2 |
| 16 | YAibEGT-FTSDY-SIYXD-KQAAAib-XFVQW-LLAGG-PSSGA-PPPS-NH2 |
| 17 | YAibEGT-FISDV-SIYXD-KQAAAib-XFVNW-LIAGG-PSSGA-PPPS-NH2 |
| 18 | YAibEGT-FTSDY-SIYLD-KXAAAib-EFVXW-LLAGG-PSSGA-PPPS-NH2 |
| 19 | YAibEGT-FTSDY-SIYLD-KXAQAib-AFVXW-LIAQG-PSSGA-PPPS-NH2 |
| 20 | YAibEGT-YTSDY-SIYLD-KXAAAib-EFVXW-LIAGG-PSSGA-PPPS-NH2 |
| 21 | YAibEGT-YTNDY-SIYLD-KXAAAib-EFVXW-LIAGG-PSSGA-PPPS-NH2 |
| 22 | YAibEGT-YTSDY-SIYXD-KQAAAib-XFVNW-LIAGG-PSSGA-PPPS-NH2 |
| 23 | HGEGT-FTSDL-SKQME-EEAVR-LFIEW-LKNGG-PSSGA-PPPS-NH2 (extendin) |
| 24 | HDEFE-RHAEG-TFTSD-VSSYL-EGQAA-KEFIA-WLVKG-R-NH2 (GLP1) |
| 25 | HADGS-FSDEM-NTILD-NLAAR-DFINW-LIQTK-ITDR (GLP2) |
| 26 | YAEGT-FISDY-SIAMD-KIHQQ-DFVNW-LLAQK-GKKNDWKHNITQ-NH2 (GIP) |
| 27 | YAibEGT-FTSDY-SIAibLD-KIAQK-AFVQW-LIAGG-PSSGA-PPPS-NH2 |
| 28 | YAibEGT-FTSDY-SIYLD-KQAAAib-EFVNW-LLAGG-PSSGA-PPPS |
| 29 | YAibEGT-FTSDY-SIYKD-KQAAAib-KFXNW-LXAGG-PSSGA-PPPS |

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61. In some aspects, provided is a peptide or peptide conjugate comprising the first 28 amino acids of any one of SEQ ID NOs: 1-61.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 1-61. In some aspects, provided is a peptide or peptide conjugate comprising the peptide comprises any one of SEQ ID NOs: 1-61.

In various embodiments, each X of any one of SEQ ID NOS: 1-61 is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 1. In some aspects, provided is a peptide or peptide conjugate comprising the first 28 amino acids of SEQ ID NO: 1. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1. In some aspects, provided is a peptide or peptide conjugate comprising SEQ ID NO: 1. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 2. In some aspects, provided is a peptide or peptide conjugate comprising the first 28 amino acids of SEQ ID NO: 2. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2. In some aspects, provided is a peptide or peptide conjugate comprising SEQ ID NO: 2. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 3. In some aspects, provided is a peptide or peptide conjugate comprising the first 28 amino acids of SEQ ID NO: 3. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3. In some aspects, provided is a peptide or peptide conjugate comprising SEQ ID NO: 3. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 4. In some aspects, provided is a peptide or peptide conjugate comprising the first 28 amino acids of SEQ ID NO: 4. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 4. In some aspects, provided is a peptide or peptide conjugate comprising SEQ ID NO: 4. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 5. In some aspects, provided is a peptide or peptide conjugate comprising the first 28 amino acids of SEQ ID NO: 5. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 5. In some aspects, provided is a peptide or peptide conjugate comprising SEQ ID NO: 5. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 6. In some aspects, provided is a peptide or peptide conjugate comprising the first 28 amino acids of SEQ ID NO: 6. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 6. In some aspects, provided is a peptide or peptide conjugate comprising SEQ ID NO: 6. In various embodiments, each X is independently selected from a sulfhydryl-containing amino acid and an amine-containing amino acid. In some cases, an X is a cysteine. In some cases, an X is a lysine. In some cases, the first X is a cysteine and the second X is a cysteine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 7. In some aspects, provided is a peptide or peptide conjugate comprising the first 28 amino acids of SEQ ID NO: 7. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7. In some aspects, provided is a peptide or peptide conjugate comprising SEQ ID NO: 7. In various embodiments, each X is independently selected from a sulfhydryl-containing amino acid and an amine-containing amino acid. In some cases, an X is a cysteine. In some cases, an X is a lysine. In some cases, aa6 is alpha-methyl Phe, N-methyl Phe, D-Phe, beta3-Phe, alpha-methyl Phe, alpha-methyl Phe (2-F), alpha-methyl Phe (3-F), and alpha-methyl (4-F), Phe (2-F), Phe (3-F), or Phe (4-F). In some cases, aa10 is alpha-methyl Tyr, N-methyl Tyr, D-Tyr, beta3-Tyr, 4-Pyr-Ala, Phe (2-F), Phe (3-F), or Phe (4-F). In some cases, aa13 is alpha-methyl Leu, N-methyl Leu, D-Leu, beta3-Leu, Leu, Val, Ile, Aib, alpha-methyl Tyr, N-methyl Tyr, D-Tyr, beta3-Tyr, 4-Pyr-Ala, Phe (2-F), Phe (3-F), or Phe (4-F). In some cases, aa16 is L-Orn, alpha-methyl Lys, N-methyl Lys, D-Lys, or beta3-Lys. In some cases, aa25 is alpha-methyl Trp, N-methyl Trp, D-Trp, beta3-Trp, alpha-methyl Tyr, or Aib. In some cases, aa33 is A or E.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 8. In some aspects, provided is a peptide or peptide conjugate comprising the first 28 amino acids of SEQ ID NO: 8. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8. In some aspects, provided is a peptide or peptide conjugate comprising SEQ ID NO: 8. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 9. In some aspects, provided is a peptide or peptide conjugate comprising the first 28 amino acids of SEQ ID NO: 9. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9. In some aspects, provided is a peptide or peptide conjugate comprising SEQ ID NO: 9. In various embodiments, each X is independently selected from a sulfhydryl-containing amino acid and an amine-containing amino acid. In some cases, an X is a cysteine. In some cases, an X is a lysine. In some cases, aa6 is alpha-methyl Phe, N-methyl Phe, D-Phe, beta3-Phe, alpha-methyl Phe (2-F), alpha-methyl Phe (3-F), and alpha-methyl (4-F), Phe (2-F), Phe (3-F), or Phe (4-F). In some cases, aa10 is alpha-methyl Tyr, N-methyl Tyr, D-Tyr, beta3-Tyr, 4-Pyr-Ala, Phe (2-F), Phe (3-F), Phe (4-F), or 4-pyridyl-Ala. In some cases, aa13 is alpha-methyl Leu, N-methyl Leu, D-Leu, beta3-Leu, Val, Ile, or Aib. In some cases, aa16 is alpha-methyl Leu, N-methyl Leu, D-Leu, beta3-Leu, Val, Ile, or Aib. In some cases, aa24 is alpha-methyl Asn, N-methyl Asn, beta3-Asn, Aib, D-Asn, D-Asp, D-Glu, or D-Gln. In some cases, aa25 is alpha-methyl Trp, N-methyl Trp, D-Trp, beta3-Trp, alpha-methyl Tyr, or Aib. In some cases, aa33 is A or E.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 10. In some aspects, provided is a peptide or peptide conjugate comprising the first 28 amino acids of SEQ ID NO: 10. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 10. In some aspects, provided is a peptide or peptide conjugate comprising SEQ ID NO: 10. In various embodiments, each X is independently selected from a sulfhydryl-containing amino acid and an amine-containing amino acid. In some cases, an X is a cysteine. In some cases, an X is a lysine. In some cases, aa2 is Gly, Val, Leu, Ile, or Aib. In some cases, aa20 is Gly, Val, Leu, Ile, or Aib. In some cases, aa13 is alpha-methyl Leu, N-methyl Leu, D-Leu, beta3-Leu, Leu, Val, Ile, Aib, alpha-methyl Tyr, N-methyl Tyr, D-Tyr, beta3-Tyr, 4-Pyr-Ala, Phe (2-F), Phe (3-F), or Phe (4-F).

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 11. In some aspects, provided is a peptide or peptide conjugate comprising the first 28 amino acids of SEQ ID NO: 11. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 11. In some aspects, provided is a peptide or peptide conjugate comprising SEQ ID NO: 11. In various embodiments, each X is independently selected from a sulfhydryl-containing amino acid and an amine-containing amino acid. In some cases, an X is a cysteine. In some cases, an X is a lysine. In some cases, aa2 is Gly, Val, Leu, Ile, or Aib. In some cases, aa20 is Gly, Val, Leu, Ile, or Aib. In some cases, aa13 is alpha-methyl Leu, N-methyl Leu, D-Leu, beta3-Leu, Leu, Val, Ile, Aib, alpha-methyl Tyr, N-methyl Tyr, D-Tyr, beta3-Tyr, 4-Pyr-Ala, Phe (2-F), Phe (3-F), or Phe (4-F).

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 12. In some aspects, provided is a peptide or peptide conjugate comprising the first 28 amino acids of SEQ ID NO: 12. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 12. In some aspects, provided is a peptide or peptide conjugate comprising SEQ ID NO: 12. In various embodiments, each X is independently selected from a sulfhydryl-containing amino acid and an amine-containing amino acid. In some cases, an X is a cysteine. In some cases, an X is a lysine. In some cases, aa2 is Gly, Val, Leu, Ile, or Aib. In some cases, aa20 is Gly, Val, Leu, Ile, or Aib. In some cases, aa13 is alpha-methyl Leu, N-methyl Leu, D-Leu, beta3-Leu, Leu, Val, Ile, Aib, alpha-methyl Tyr, N-methyl Tyr, D-Tyr, beta3-Tyr, 4-Pyr-Ala, Phe (2-F), Phe (3-F), or Phe (4-F).

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 13. In some aspects, provided is a peptide or peptide conjugate comprising the first 28 amino acids of SEQ ID NO: 13. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 13. In some aspects, provided is a peptide or peptide conjugate comprising SEQ ID NO: 13. In various embodiments, each X is independently selected from a sulfhydryl-containing amino acid and an amine-containing amino acid. In some cases, an X is a cysteine. In some cases, an X is a lysine. In some cases, aa2 is Gly, Val, Leu, Ile, or Aib. In some cases, aa20 is Gly, Val, Leu, Ile, or Aib. In some cases, aa13 is alpha-methyl Leu, N-methyl Leu, D-Leu, beta3-Leu, Leu, Val, Ile, Aib, alpha-methyl Tyr, N-methyl Tyr, D-Tyr, beta3-Tyr, 4-Pyr-Ala, Phe (2-F), Phe (3-F), or Phe (4-F).

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 14. In some aspects, provided is a peptide or peptide conjugate comprising the first 28 amino acids of SEQ ID NO: 14. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 14. In some aspects, provided is a peptide or peptide conjugate comprising SEQ ID NO: 14. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 15. In some aspects, provided is a peptide or peptide conjugate comprising the first 28 amino acids of SEQ ID NO: 15. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 15. In some aspects, provided is a peptide or peptide conjugate comprising SEQ ID NO: 15. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 16. In some aspects, provided is a peptide or peptide conjugate comprising the first 28 amino acids of SEQ ID NO: 16. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 16. In some aspects, provided is a peptide or peptide conjugate comprising SEQ ID NO: 16. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 17. In some aspects, provided is a peptide or peptide conjugate comprising the first 28 amino acids of SEQ ID NO: 17. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 17. In some aspects, provided is a peptide or peptide conjugate comprising SEQ ID NO: 17. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 18. In some aspects, provided is a peptide or peptide conjugate comprising the first 28 amino acids of SEQ ID NO: 18. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 18. In some aspects, provided is a peptide or peptide conjugate comprising SEQ ID NO: 18. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 19. In some aspects, provided is a peptide or peptide conjugate comprising the first 28 amino acids of SEQ ID NO: 19. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 19. In some aspects, provided is a peptide or peptide conjugate comprising SEQ ID NO: 19. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 20. In some aspects, provided is a peptide or peptide conjugate comprising the first 28 amino acids of SEQ ID NO: 20. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 20. In some aspects, provided is a peptide or peptide conjugate comprising SEQ ID NO: 20. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 21. In some aspects, provided is a peptide or peptide conjugate comprising the first 28 amino acids of SEQ ID NO: 21. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 21. In some aspects, provided is a peptide or peptide conjugate comprising SEQ ID NO: 21. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 22. In some aspects, provided is a peptide or peptide conjugate comprising the first 28 amino acids of SEQ ID NO: 22. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 22. In some aspects, provided is a peptide or peptide conjugate comprising SEQ ID NO: 22. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 23. In some aspects, provided is a peptide or peptide conjugate comprising the first 28 amino acids of SEQ ID NO: 23. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 23. In some aspects, provided is a peptide or peptide conjugate comprising SEQ ID NO: 23. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 24. In some aspects, provided is a peptide or peptide conjugate comprising the first 28 amino acids of SEQ ID NO: 24. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 24. In some aspects, provided is a peptide or peptide conjugate comprising SEQ ID NO: 24. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 25. In some aspects, provided is a peptide or peptide conjugate comprising the first 28 amino acids of SEQ ID NO: 25. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 25. In some aspects, provided is a peptide or peptide conjugate comprising SEQ ID NO: 25. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 26. In some aspects, provided is a peptide or peptide conjugate comprising the first 28 amino acids of SEQ ID NO: 26. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 26. In some aspects, provided is a peptide or peptide conjugate comprising SEQ ID NO: 26. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 27. In some aspects, provided is a peptide or peptide conjugate comprising the first 28 amino acids of SEQ ID NO: 27. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 27. In some aspects, provided is a peptide or peptide conjugate comprising SEQ ID NO: 27. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 28. In some aspects, provided is a peptide or peptide conjugate comprising the first 28 amino acids of SEQ ID NO: 28. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 28. In some aspects, provided is a peptide or peptide conjugate comprising SEQ ID NO: 28. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 29. In some aspects, provided is a peptide or peptide conjugate comprising the first 28 amino acids of SEQ ID NO: 29. In some aspects, provided is a peptide or peptide conjugate comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 29. In some aspects, provided is a peptide or peptide conjugate comprising SEQ ID NO: 29. In various embodiments, each X is independently selected from a sulfhydryl-containing amino acid and an amine-containing amino acid. In some cases, an X is a cysteine. In some cases, an X is a lysine.

In some aspects, provided is a peptide or peptide conjugate comprising a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 30. In some aspects, provided is a peptide or peptide conjugate comprising the first 28 amino acids of SEQ ID NO: 30. In some aspects, provided is a peptide or peptide conjugate comprising a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 30. In some aspects, provided is a peptide or peptide conjugate comprising SEQ ID NO: 30. In various embodiments, each X is independently selected from a sulfhydryl-containing amino acid and an amine-containing amino acid. In some cases, an X is a cysteine. In some cases, an X is a lysine.

Staples

Disclosed herein are peptide conjugates comprising a staple.

In some embodiments, the staple attached to the peptide is of Formula (I):

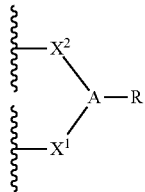

Formula (I)

wherein
A is an optionally substituted alkylene, optionally substituted arylene, optionally substituted heteroarylene, optionally substituted —$NR^3$-alkylene-$NR^3$—, or —N—;

$X^1$ and $X^2$ are independently a bond, —C(=O)—, -alkylene-C(=O)—, —C(=O)-alkylene-, -alkylene-C(=O)$NR^3$—, -alkylene-$NR^3$C(=O)—, —C(=O)$NR^3$-alkylene-, —$NR^3$C(=O)-alkylene-, -alkylene-C(=O)$NR^3$-alkylene-, or -alkylene-$NR^3$C(=O)-alkylene-;

wherein $X^1$ is attached to a first amino acid of the peptide, and $X^2$ is attached to a second amino acid of the peptide;

R is hydrogen or -(L)$_s$-Y;

each L is independently —$(CR^1R^2)_v$—, -alkylene-O—, —O-alkylene-, —C(=O)-alkylene-, -alkylene-C(=O)—, —$NR^3$-alkylene-, -alkylene-$NR^3$—, —S-alkylene-, -alkylene-S—, —S(=O)-alkylene-, -alkylene-S(=O)—, —S(=O)$_2$-alkylene, -alkylene-S(=O)$_2$—, —C(=O)—, —C(=O)$NR^3$—, —$NR^3$C(=O)—, —$NR^3$C(=O)$NR^3$—, —$NR^3$C(=O)$NR^3$-alkylene-, —$NR^3$C(=O)-alkylene-$NR^3$—, -alkylene-C(=O)$NR^3$—, —C(=O)$NR^3$-alkylene-, -alkylene-$NR^3$C(=O)—, or —$NR^3$C(=O)-alkylene-;

v is 2-20;

each $R^1$ or $R^2$ is independently hydrogen, halogen, —CN, —$OR^a$, —$SR^a$, —S(=O)$R^b$, —$NO_2$, —$NR^cR^d$, —S(=O)$_2R^a$, —$NR^a$S(=O)$_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^a$C(=O)$NR^cR^d$, —$NR^a$C(=O)$R^b$, —$NR^a$C(=O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^b$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, —$NR^cR^d$, or $R^1$ and $R^2$ are taken together to form a $C_1$-$C_6$ cycloalkyl or $C_1$-$C_6$ heterocycloalkyl;

each $R^3$ is independently hydrogen, —S(=O)$R^b$, —S(=O)$_2R^a$, —S(=O)$_2NR^cR^d$, —C(=O)$R^b$, —$CO_2R^a$, —C(=O)$NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

Y is hydrogen, $C_1$-$C_6$ alkyl, —$CO_2$H, —$CO_2(C_1$-$C_6$ alkyl), —$CO_2NH_2$, —$CO_2$N(alkyl)$_2$, or —$CO_2$NH(alkyl); and s is 0-20;

$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —$NH_2$.

In some embodiments, the staple attached to the peptide is of Formula (I):

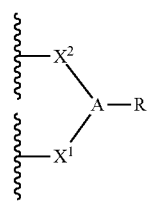

Formula (I)

wherein
A is —N—;

$X^1$ and $X^2$ are a bond, —C(=O)—, -alkylene-C(=O)—, —C(=O)-alkylene-, -alkylene-C(=O)$NR^3$—, -alkylene-$NR^3$C(=O)—, —C(=O)$NR^3$-alkylene-, —$NR^3$C(=O)-alkylene-, -alkylene-C(=O)$NR^3$-alkylene-, or -alkylene-$NR^3$C(=O)-alkylene-;

wherein $X^1$ is attached to a first amino acid of the peptide, $X^2$ is attached to a second amino acid of the peptide, and $X^1$ and $X^2$ are identical;

R is hydrogen or -(L)$_s$-Y;

each L is independently —$(CR^1R^2)_v$—, -alkylene-O—, —O-alkylene-, —C(=O)-alkylene-, -alkylene-C(=O)—, —$NR^3$-alkylene-, -alkylene-$NR^3$—, —S-alkylene-, -alkylene-S—, —S(=O)-alkylene-, -alkylene-S(=O)—, —S(=O)$_2$-alkylene, -alkylene-S(=O)$_2$—, —C(=O)—, —C(=O)$NR^3$—, —$NR^3$C(=O)—, —$NR^3$C(=O)$NR^3$—, —$NR^3$C(=O)$NR^3$-alkylene-, —$NR^3$C(=O)-alkylene-$NR^3$—, -alkylene- —C(=O)NR³—, —C(=O)NR³-alkylene-, -alkylene-NR³C(=O)—, or —NR³C(=O)-alkylene-;

v is 2-20;

each R¹ or R² is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

or R¹ and R² are taken together to form a C$_1$-C$_6$ cycloalkyl or C$_1$-C$_6$ heterocycloalkyl;

each R³ is independently hydrogen, —S(=O)R$^b$, —S(=O)$_2$R$^a$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

Y is hydrogen, C$_1$-C$_6$ alkyl, —CO$_2$H, —CO$_2$(C$_1$-C$_6$ alkyl), —CO$_2$NH$_2$, —CO$_2$N(alkyl)$_2$, or —CO$_2$NH(alkyl);

s is 0-20;

R$^a$ is hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

R$^b$ is C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$; and each R$^c$ and R$^d$ is independently hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

or R$^c$ and R$^d$, together with the nitrogen atom to which they are attached, form a heterocycloalkyl or heteroaryl; wherein the heterocycloalkyl and heteroaryl is optionally substituted with one, two, or three of halogen, C$_1$-C$_6$ alkyl, C$_1$-C$_6$ haloalkyl, —OH, —OMe, or —NH$_2$.

In some embodiments, A is optionally substituted alkylene. In some embodiments, A is —(CH$_2$)$_t$—, wherein t is 1-12. In some embodiments, A is —(CH$_2$)$_t$—, wherein t is 1-10. In some embodiments, A is —(CH$_2$)$_t$—, wherein t is 1-8. In some embodiments, A is —(CH$_2$)$_t$—, wherein t is 1-6. In some embodiments, A is —(CH$_2$)$_t$—, wherein t is 1-4.

In some embodiments, A is optionally substituted arylene. In some embodiments, A is arylene optionally substituted with halogen, alkyl, or haloalkyl. In some embodiments, A is unsubstituted arylene.

In some embodiments, A is —NR³-alkylene-NR³—. In some embodiments, A is —N—.

In some embodiments, X¹ and X² are identical. In some embodiments, X¹ and X² are different.

In some embodiments, X¹ and X² are —C(=O)—. In some embodiments, X¹ and X² are independently -alkylene-C(=O)— or —C(=O)alkylene-. In some embodiments, X¹ and X² are independently —CH$_2$—C(=O)— or —C(=O)—CH$_2$—. In some embodiments, X¹ and X² are independently -alkylene-C(=O)NR³— or —C(=O)NR³-alkylene-. In some embodiments, X¹ and X² are independently —CH$_2$—C(=O)NR³— or —C(=O)NR³—CH$_2$—. In some embodiments, X¹ and X² are independently -alkylene-C(=O)NR³-alkylene- or -alkylene-NR³C(=O)-alkylene-. In some embodiments, X¹ and X² are independently —CH$_2$—C(=O)NR³—CH$_2$CH$_2$— or —CH$_2$—NR³C(=O)—CH$_2$CH$_2$—. In some embodiments, X¹ and X² are independently —CH$_2$—C(=O)NH—CH$_2$CH$_2$— or —CH$_2$—NHC(=O)—CH$_2$CH$_2$—.

In some embodiments, each R³ is independently hydrogen or C$_1$-C$_6$ alkyl. In some embodiments, each R³ is hydrogen.

In some embodiments, >A-R has the following structure:

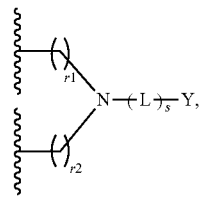

wherein r1 and r2 are each independently 0-4.

In some embodiments, r1 and r2 are each independently 0-2. In some embodiments, r1 and r2 are each 0. In some embodiments, r1 and r2 are each 1. In some embodiments, r1 and r2 are each 3. In some embodiments, r1 and r2 are each 2.

In some embodiments, >A-R has the following structure:

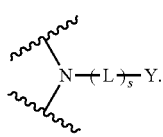

In some embodiments, >A-R has the following structure:

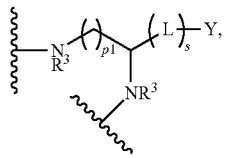

wherein p1 is 1-5.

In some embodiments, p1 is 1-3. In some embodiments, p1 is 1-2. In some embodiments, p1 is 1. In some embodiments, p1 is 2. In some embodiments, p1 is 3. In some embodiments, p1 is 4. In some embodiments, p1 is 5.

In some embodiments, >A-R has the following structure:

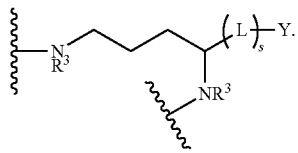

In some embodiments, >A-R has the following structure:

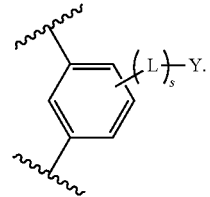

In some embodiments, s is 1-15. In some embodiments, s is 1-10. In some embodiments, s is 5-15. In some embodiments, s is 5-10. In some embodiments, s is 5-20.

In some embodiments, Y is hydrogen or —$CO_2H$. In some embodiments, Y is hydrogen. In some embodiments, Y is —$CO_2H$.

In some embodiments, each L is independently —$(CR^1R^2)_v$—, -alkylene-O—, —C(=O)—, —C(=O)NR$^3$—, —NR$^3$C(=O)—, -alkylene-C(=O)NR$^3$—, or -alkylene-NR$^3$C(=O)—; and v is 2-20.

In some embodiments, each L is independently —$(CR^1R^2)_v$—, -alkylene-O—, —C(=O)—, —C(=O)NR$^3$—, —NR$^3$C(=O)—, -alkylene-C(=O)NR$^3$—, or -alkylene-NR$^3$C(=O)—; and v is 2-16.

In some embodiments, v is 2-16. In some embodiments, v is 2-5. In some embodiments, v is 5-16. In some embodiments, v is 5 or 16. In some embodiments, v is 2 or 16.

In some embodiments, each $R^1$ or $R^2$ is independently hydrogen, halogen, —CN, —OR$^a$, —NR$^c$R$^d$, —C(=O)R$^b$, —$CO_2R^a$, —C(=O)NR$^c$R$^d$, or $C_1$-$C_6$ alkyl.

In some embodiments, each $R^1$ or $R^2$ is independently hydrogen, halogen, —$CO_2R^a$, —C(=O)NR$^c$R$^d$, or $C_1$-$C_6$ alkyl. In some embodiments, each $R^1$ or $R^2$ is independently hydrogen, —$CO_2R^a$, or —C(=O)NR$^c$R$^d$. In some embodiments, each $R^1$ or $R^2$ is independently hydrogen or —$CO_2R^a$.

In some embodiments, the staple is

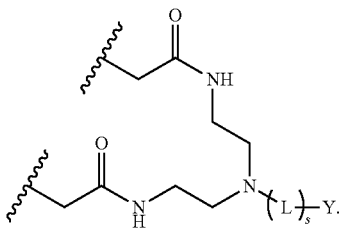

In some embodiments, the staple attached to the peptide is

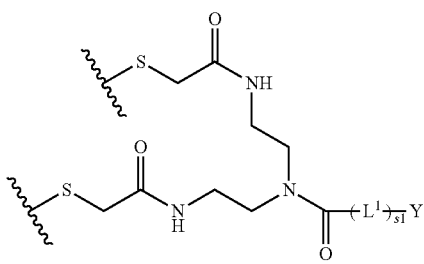

wherein each $L^1$ is independently —$(CR^1R^2)_v$—, -alkylene-O—, —O-alkylene-, —C(=O)NR$^3$—, —NR$^3$C(=O)—, -alkylene-C(=O)NR$^3$—, or -alkylene-NR$^3$C(=O)—; v is 2-20; and s1 is 1-15.

In some embodiments, the staple attached to the peptide is

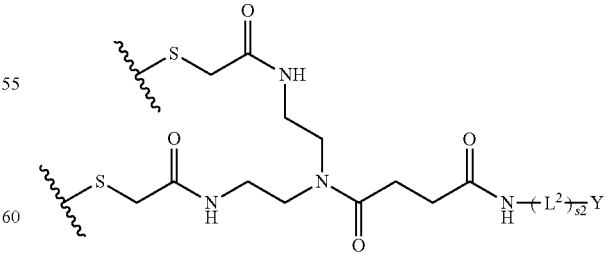

wherein each $L^2$ is independently —$(CR^1R^2)_v$—, -alkylene-O—, —O-alkylene-, —C(=O)NR$^3$—, —NR$^3$C(=O)—, -alkylene-C(=O)NR$^3$—, or -alkylene-NR$^3$C(=O)—; v is 2-20; and s2 is 1-15.

In some embodiments, the staple attached to the peptide is

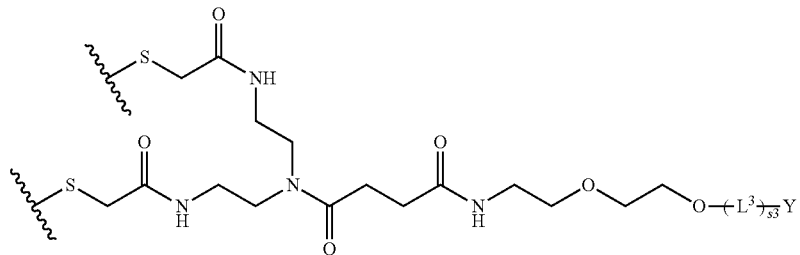

15 wherein each $L^3$ is independently $-(CR^1R^2)_v-$, -alkylene-O—, —O-alkylene-, —C(=O)NR$^3$—, —NR$^3$C(=O)—, -alkylene-C(=O)NR$^3$—, or -alkylene-NR$^3$C(=O)—; v is 2-20; and s3 is 1-15.

In some embodiments, the staple attached to the peptide is

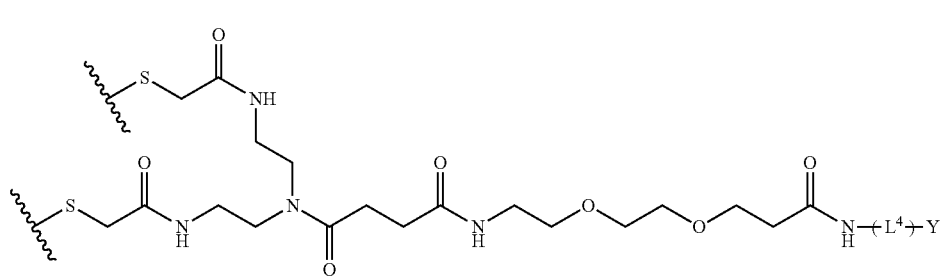

s4 wherein each $L^4$ is independently $-(CR^1R^2)_v-$, -alkylene-O—, —O-alkylene-, —C(=O)NR$^3$—, —NR$^3$C(=O)—, -alkylene-C(=O)NR$^3$—, or -alkylene-NR$^3$C(=O)—; v is 2-20; and s4 is 1-15.

In some embodiments, the staple attached to the peptide is

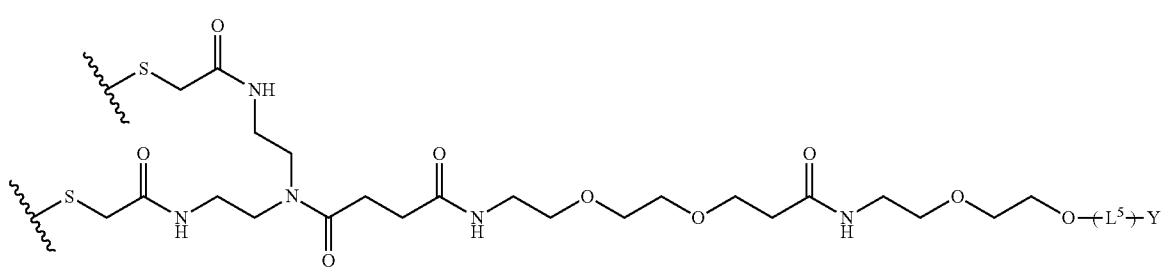

s5 wherein each $L^5$ is independently $-(CR^1R^2)_v-$, —C(=O)NR$^3$—, —NR$^3$C(=O)—, -alkylene-C(=O)NR$^3$—, or -alkylene-NR$^3$C(=O)—; v is 2-20; and s5 is 1-10.

In some embodiments, the staple attached to the peptide is

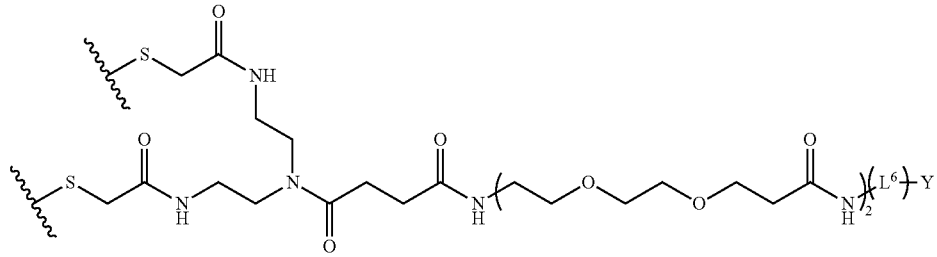

s6 wherein each $L^6$ is independently —$(CR^1R^2)_v$—, —C(=O)NR$^3$—, —NR$^3$C(=O)—, -alkylene-C(=O)NR$^3$—, or -alkylene-NR$^3$C(=O)—; v is 2-20; and s6 is 1-5.

In some embodiments, the staple attached to the peptide is

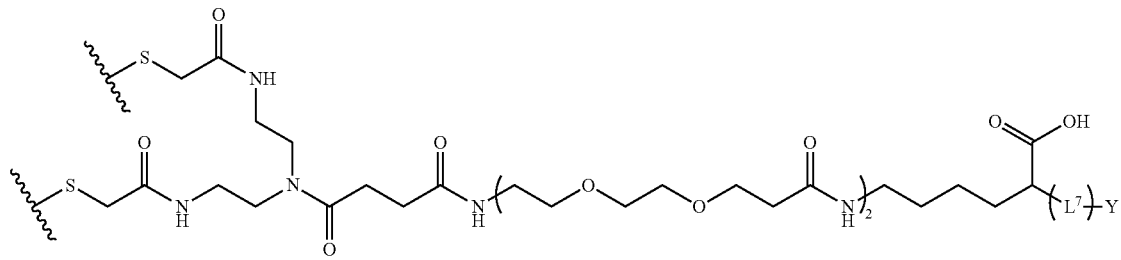

s7 wherein each $L^7$ is independently —$(CR^1R^2)_v$—, —C(=O)NR$^3$—, or —NR$^3$C(=O)—; v is 2-20; and s7 is 1-5.

In some embodiments, the staple attached to the peptide is

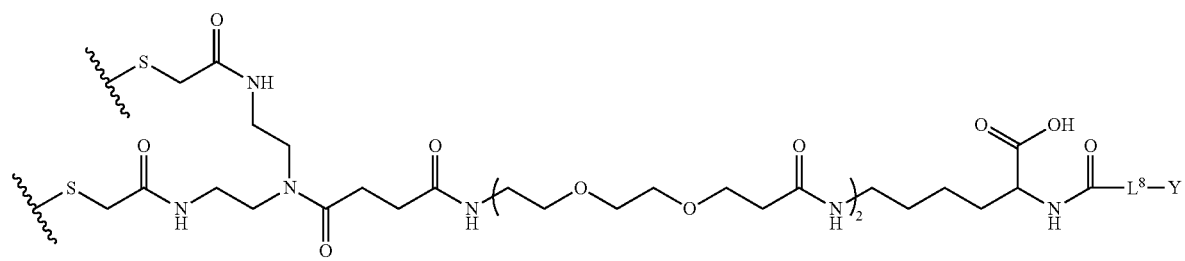

wherein $L^8$ is —$(CR^1R^2)_v$— and v is 10-20.

In some embodiments, the staple attached to the peptide is

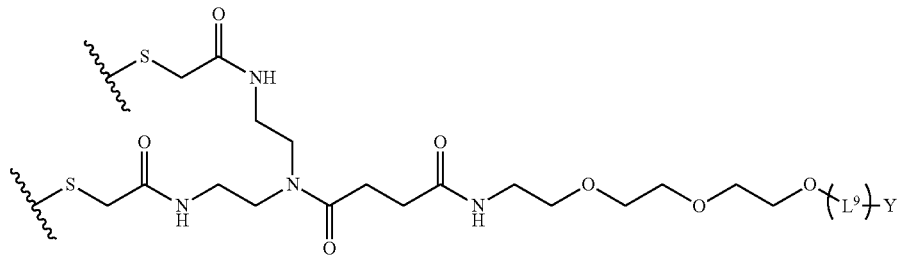

wherein each $L^9$ is independently —$(CR^1R^2)_v$—, —C(=O)NR$^3$—, —NR$^3$C(=O)—, -alkylene-C(=O)NR$^3$—, or -alkylene-NR$^3$C(=O)—; v is 2-20; and s9 is 1-5.

In some embodiments, the staple attached to the peptide is

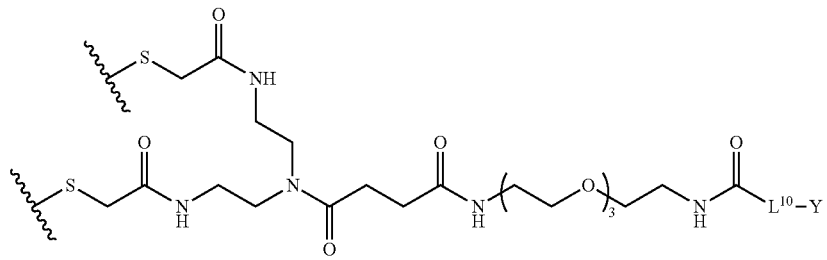

wherein $L^{10}$ is —$(CR^1R^2)_v$— and v is 10-20.

In some embodiments, the staple attached to the peptide is

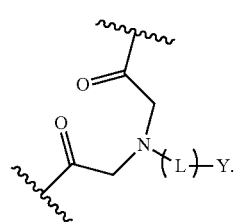

In some embodiments, the staple attached to the peptide is

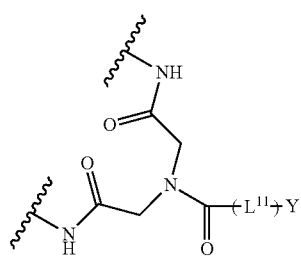

wherein each $L^{11}$ is independently —$(CR^1R^2)_v$—, -alkylene-O—, —O-alkylene-, —C(=O)NR$^3$—, —NR$^3$C(=O)—, -alkylene-C(=O)NR$^3$—, or -alkylene-NR$^3$C(=O)—; v is 2-20; and s12 is 1-15.

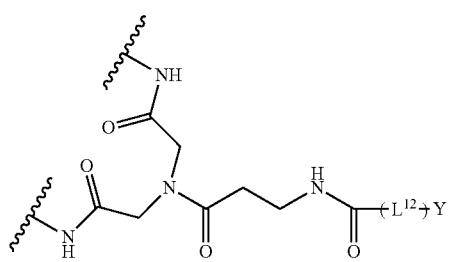

In some embodiments, the staple attached to the peptide is

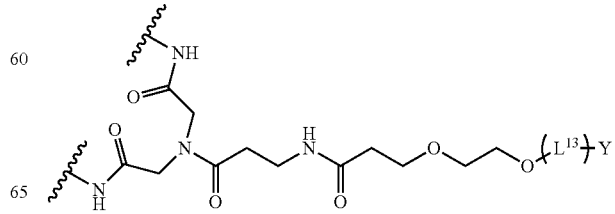

wherein each $L^{13}$ is independently —$(CR^1R^2)_v$—, -alkylene-O—, —O-alkylene-, —C(=O)NR$^3$—, —NR$^3$C(=O)—, -alkylene-C(=O)NR$^3$—, or -alkylene-NR$^3$C(=O)—; v is 2-20; and s13 is 1-15.

In some embodiments, the staple attached to the peptide is

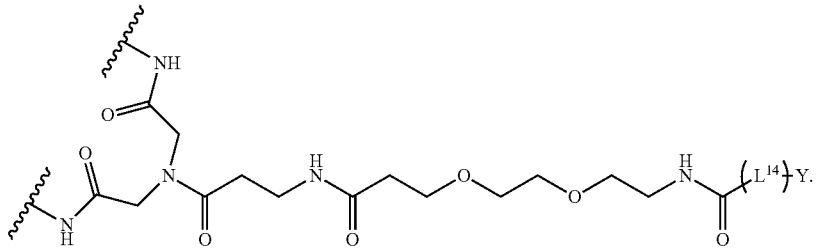

s14 wherein each $L^{14}$ is independently —$(CR^1R^2)_v$—, -alkylene-O—, —O-alkylene-, —C(=O)NR$^3$—, —NR$^3$C(=O)—, -alkylene-C(=O)NR$^3$—, or -alkylene-NR$^3$C(=O)—; v is 2-20; and s14 is 1-15.

In some embodiments, the staple attached to the peptide is

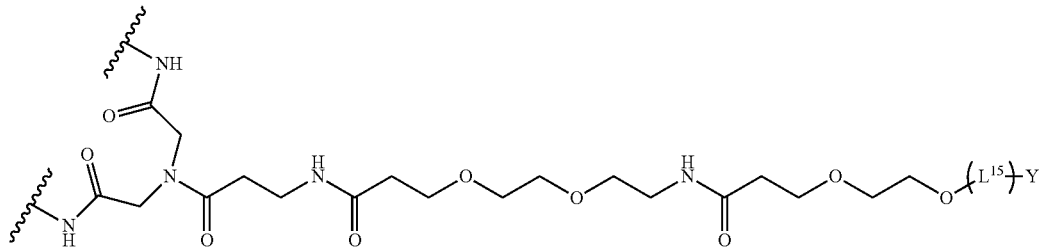

s15 wherein each $L^{15}$ is independently —$(CR^1R^2)_v$—, —C(=O)NR$^3$—, —NR$^3$C(=O)—, -alkylene-C(=O)NR$^3$—, or -alkylene-NR$^3$C(=O)—; v is 2-20; and s15 is 1-10.

In some embodiments, the staple attached to the peptide is

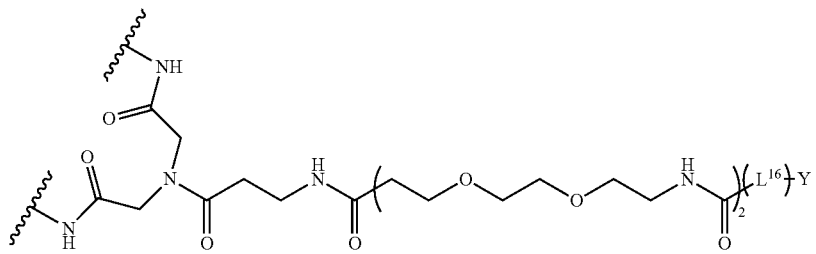

s16 wherein each $L^{16}$ is independently —$(CR^1R^2)_v$—, —C(=O)NR$^3$—, or —NR$^3$C(=O)—; v is 2-20; and s16 is 1-5.

In some embodiments, the staple attached to the peptide is

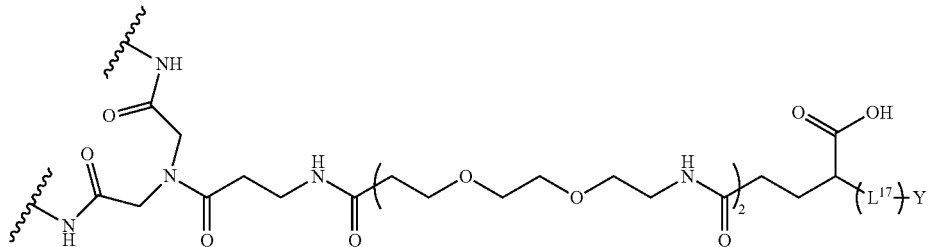

s17 wherein each $L^{17}$ is independently —$(CR^1R^2)_v$—, —C(=O)NR$^3$—, or —NR$^3$C(=O)—; v is 2-20; and s17 is 1-5.

In some embodiments, the staple attached to the peptide is

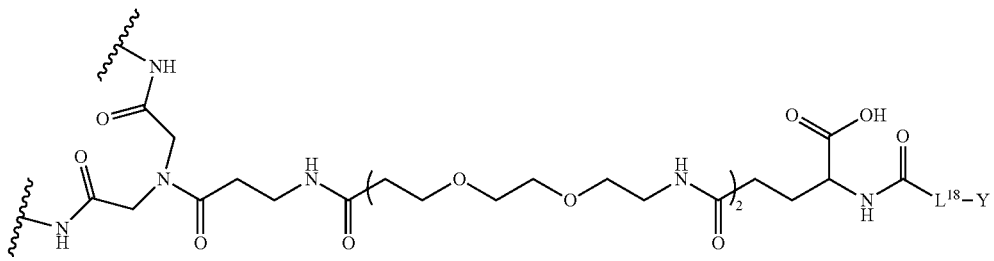

wherein $L^{18}$ is —$(CR^1R^2)_v$— and v is 10-20.

In some embodiments, the staple attached to the peptide is

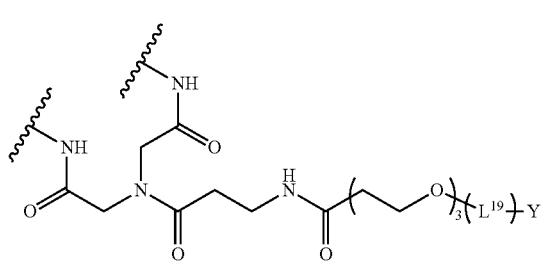

s19 wherein each $L^{19}$ is independently —$(CR^1R^2)_v$—, —C(=O)NR$^3$—, —NR$^3$C(=O)—, -alkylene-C(=O)NR$^3$—, or -alkylene-NR$^3$C(=O)—; v is 2-20; and s19 is 1-5.

In some embodiments, the staple attached to the peptide is

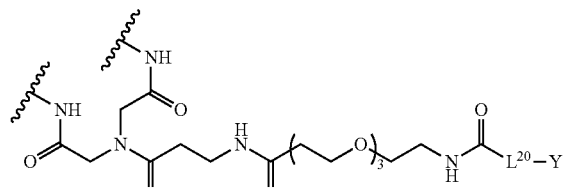

wherein $L^{20}$ is —$(CR^1R^2)_v$— and v is 10-20.

In some embodiments, the staple attached to the peptide is:
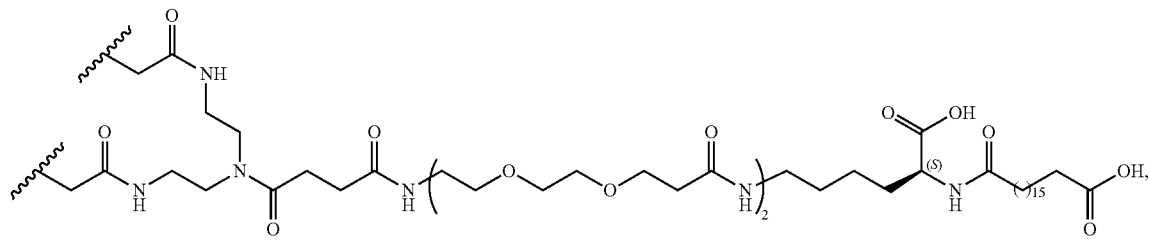
(L5A)
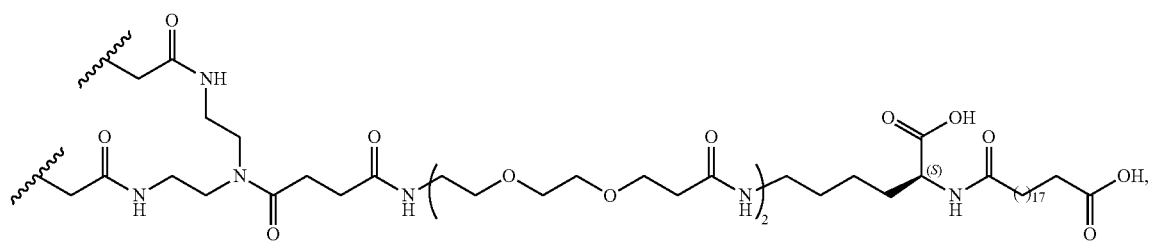
(C20L5A)
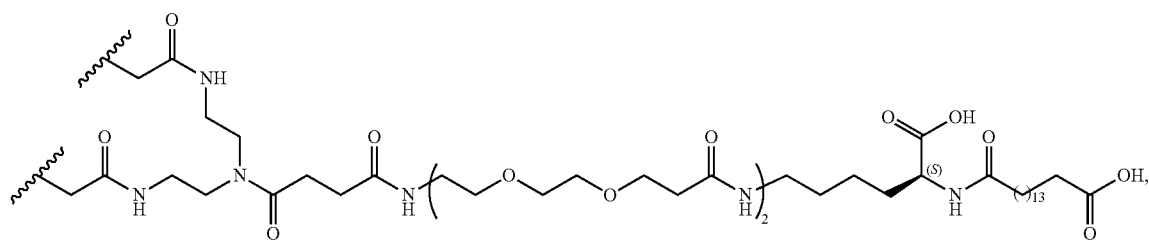
(C16L5A)
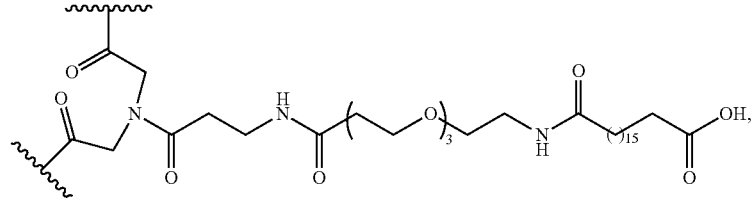
(K4)
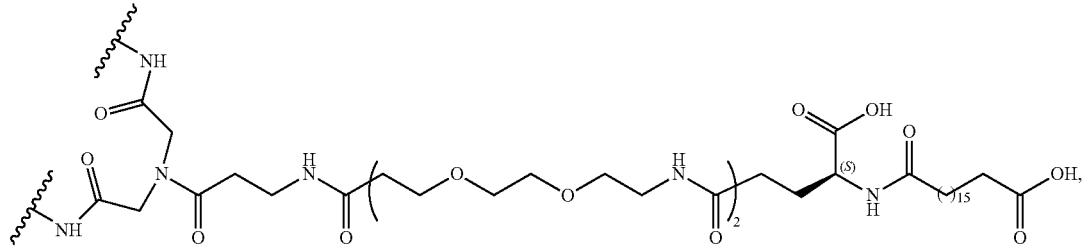
(K5)
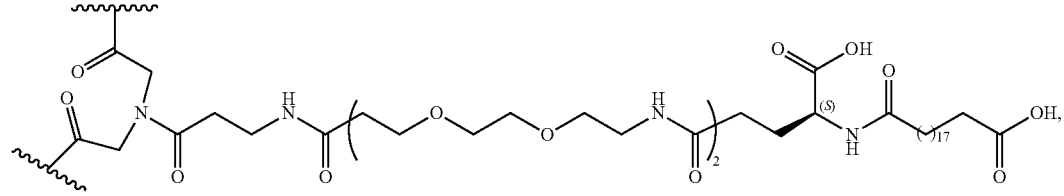
(C20K5)

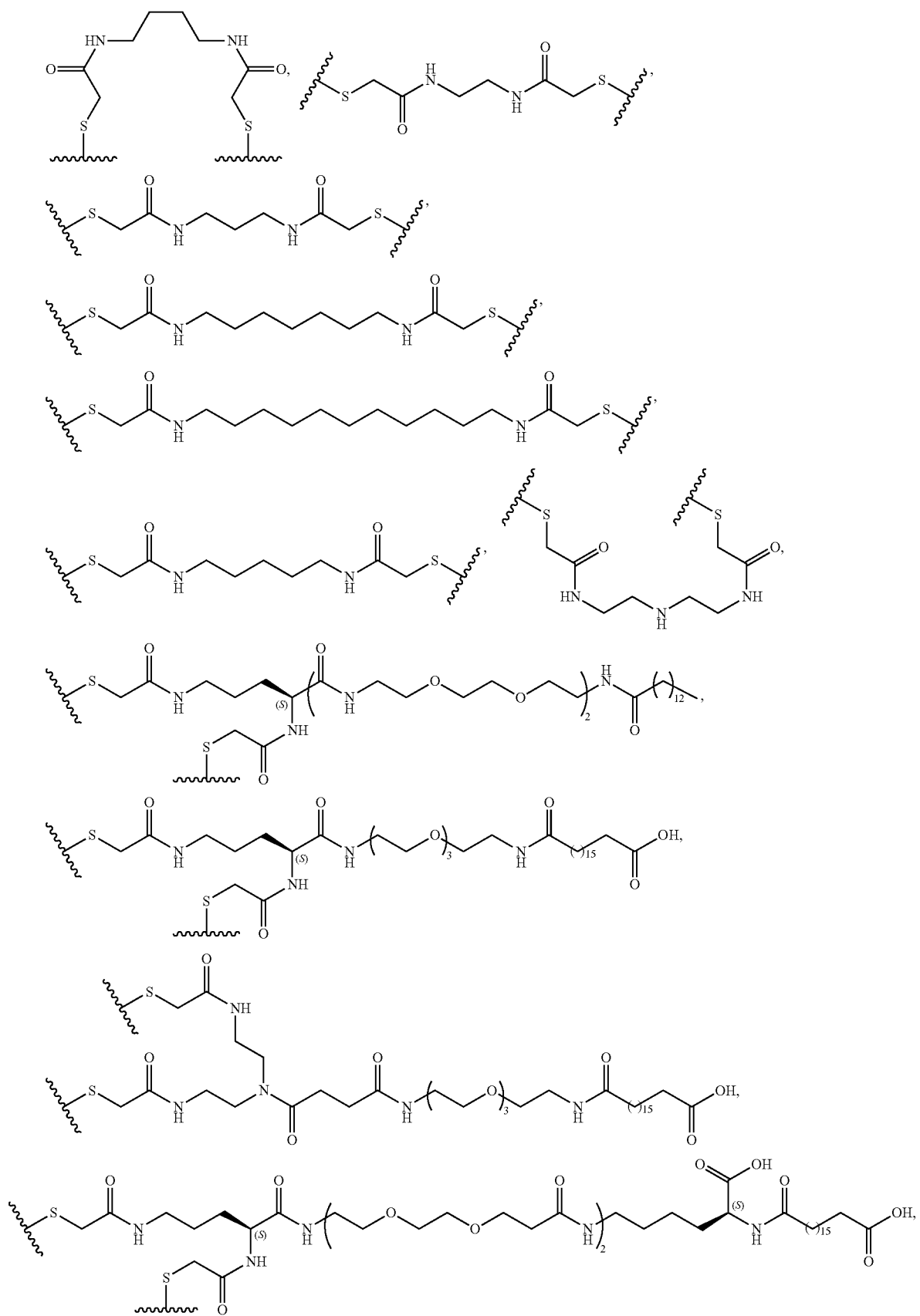

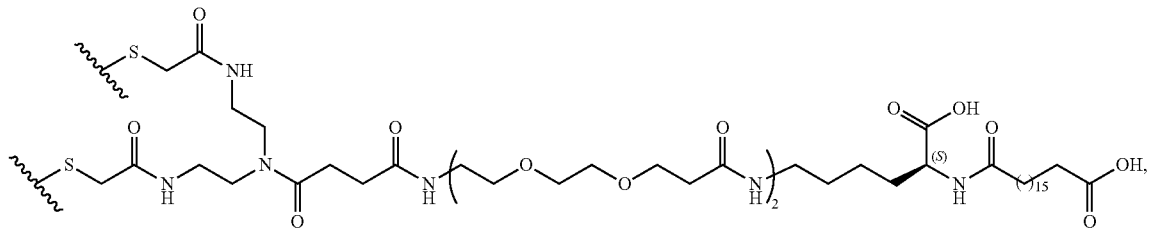
(L5A(S))
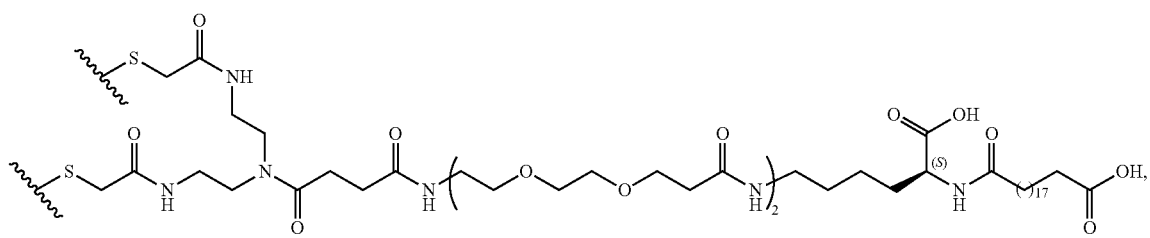
(C20L5A(S))
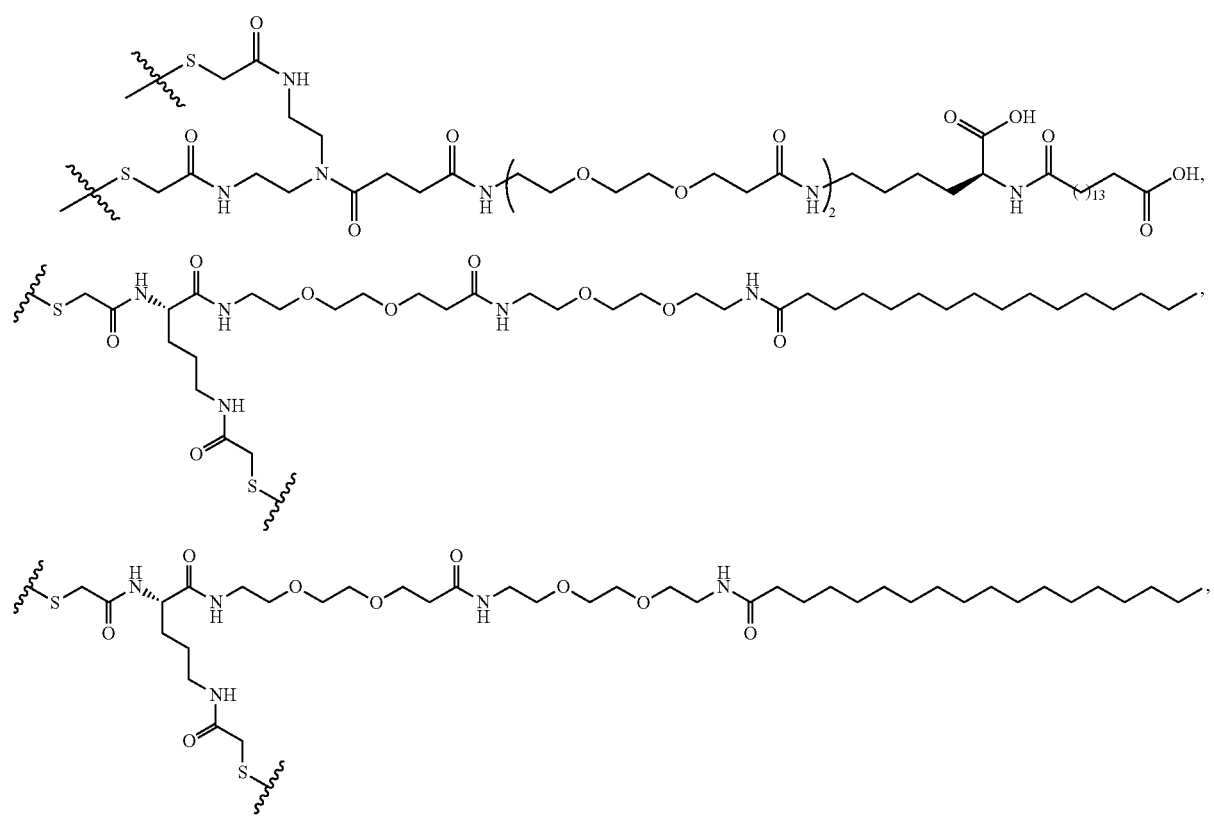
(C16L5A(S))
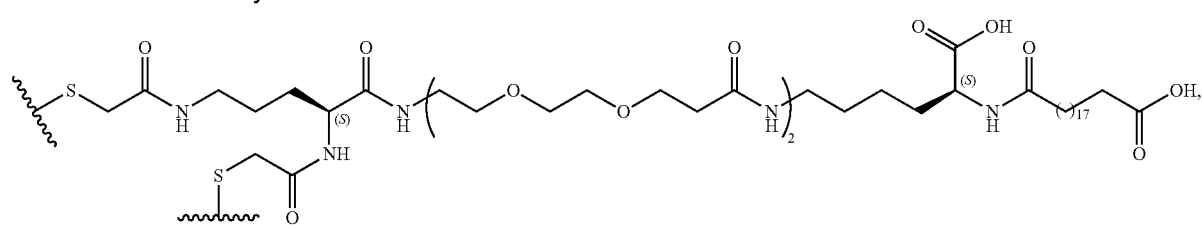

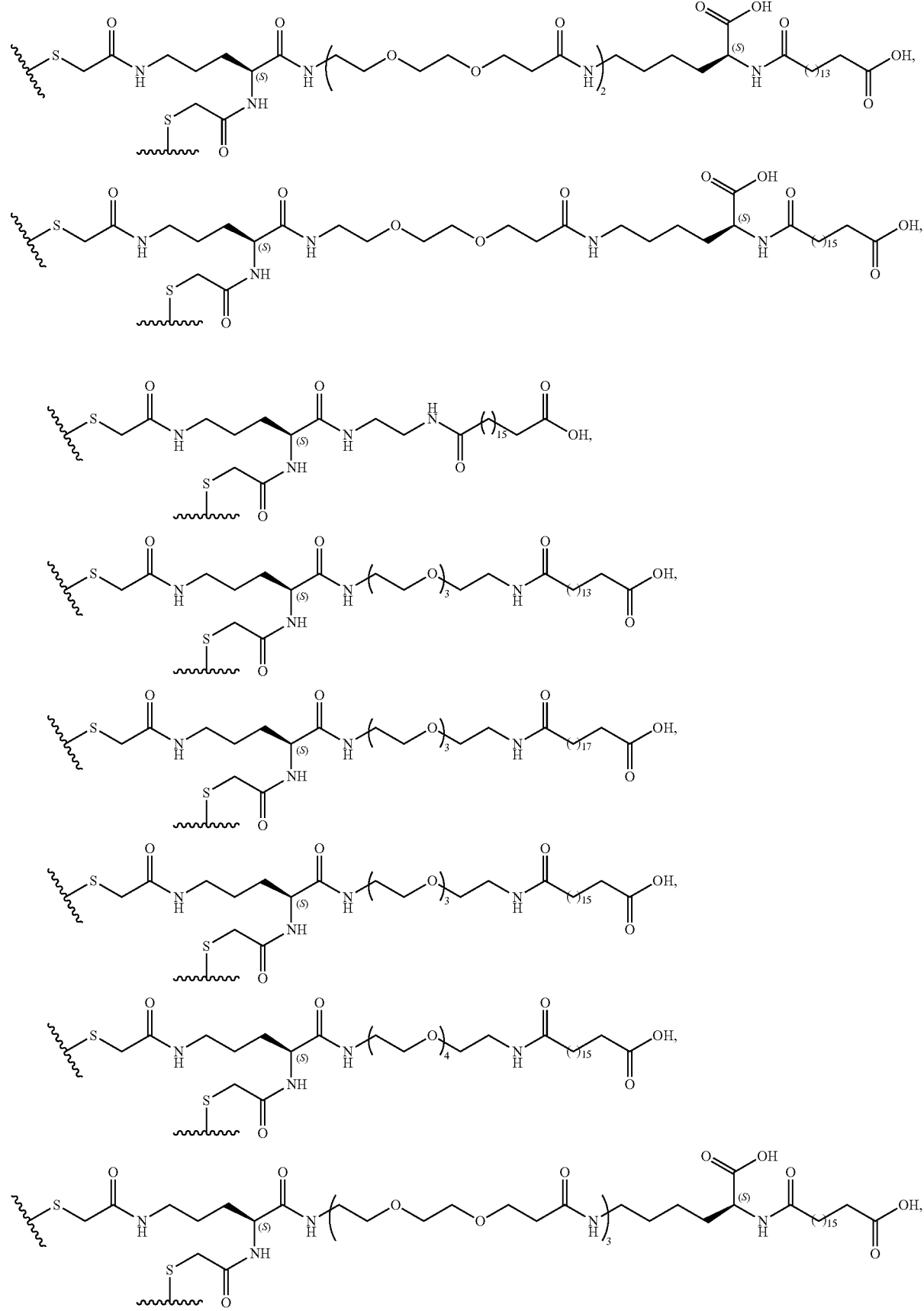

-continued
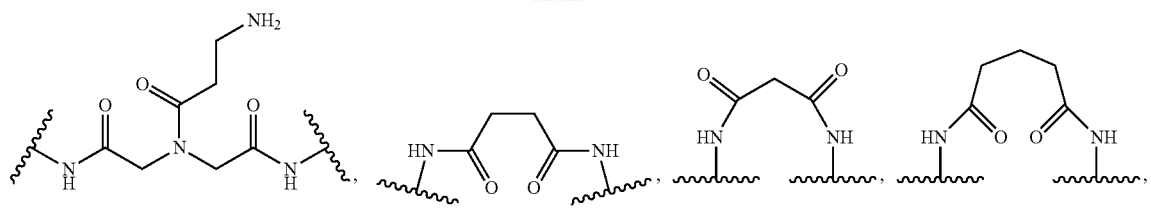
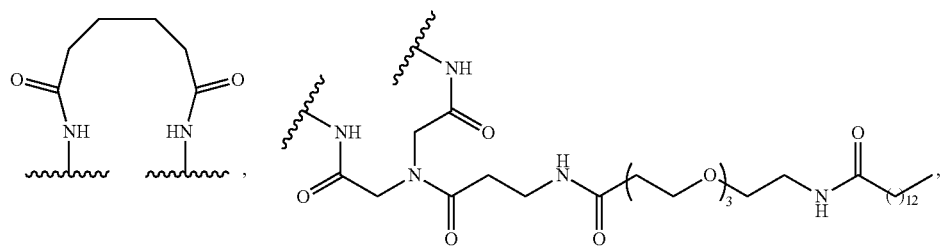
(K4(NH))
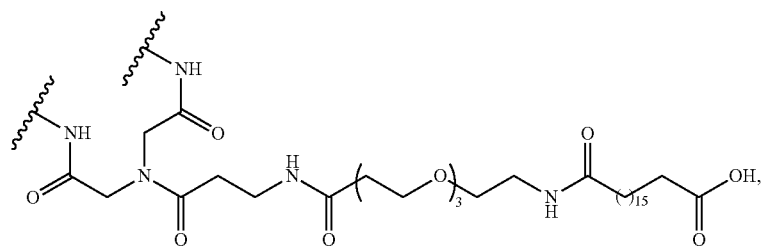
(K5(NH))
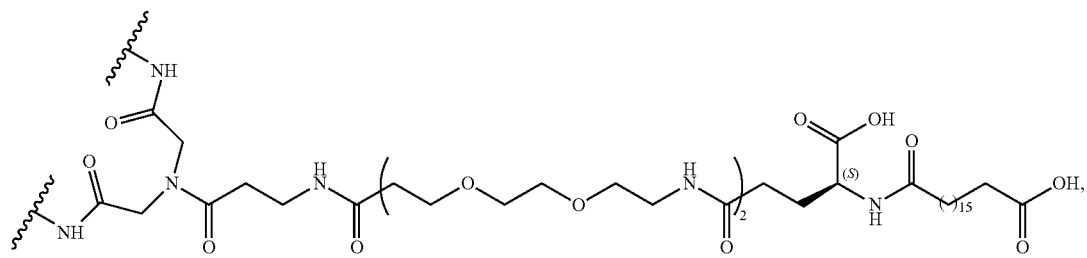
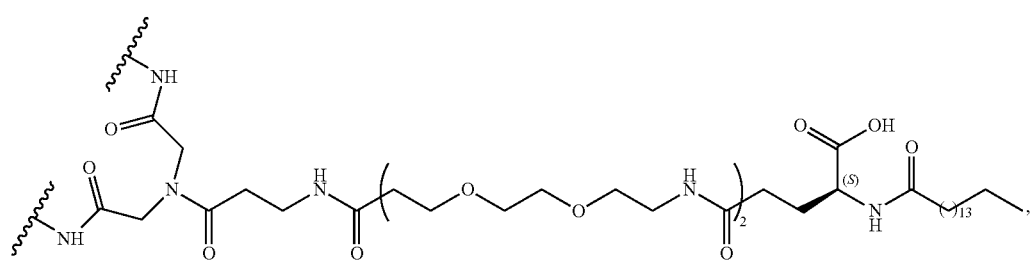
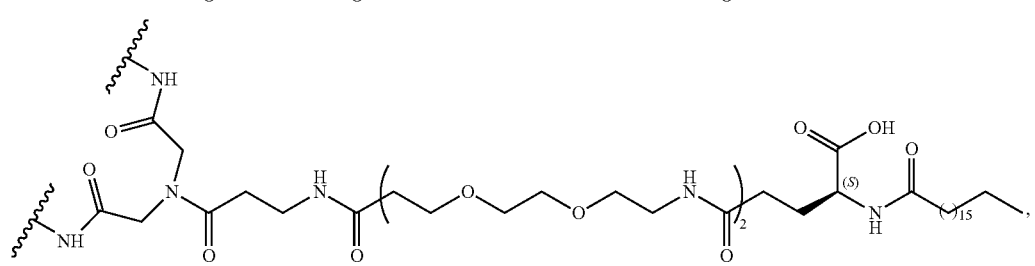

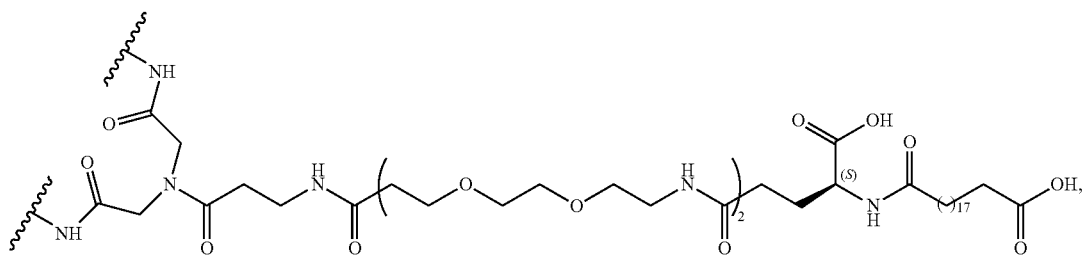
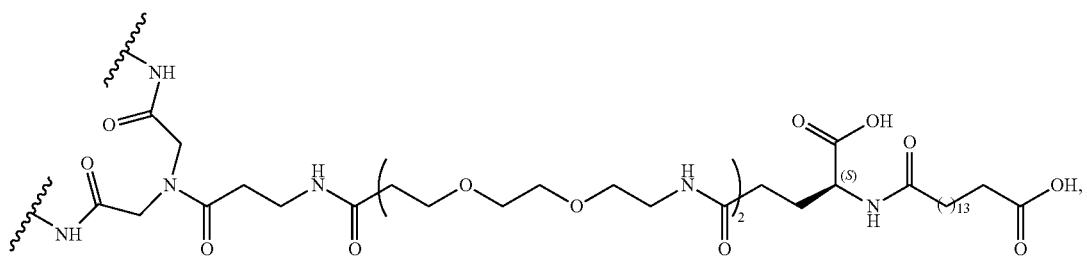
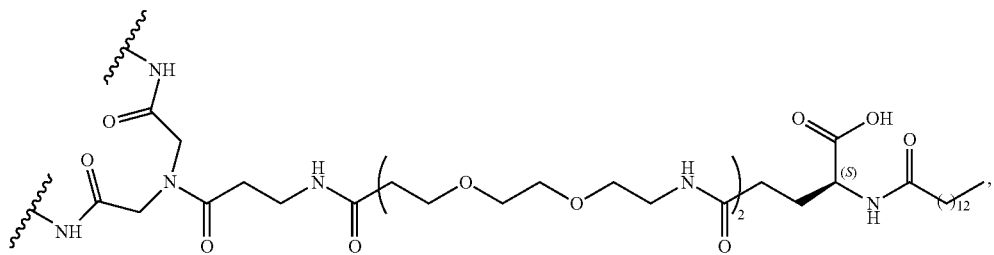
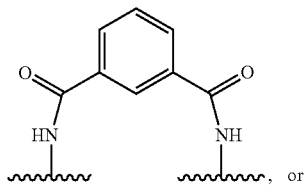, or
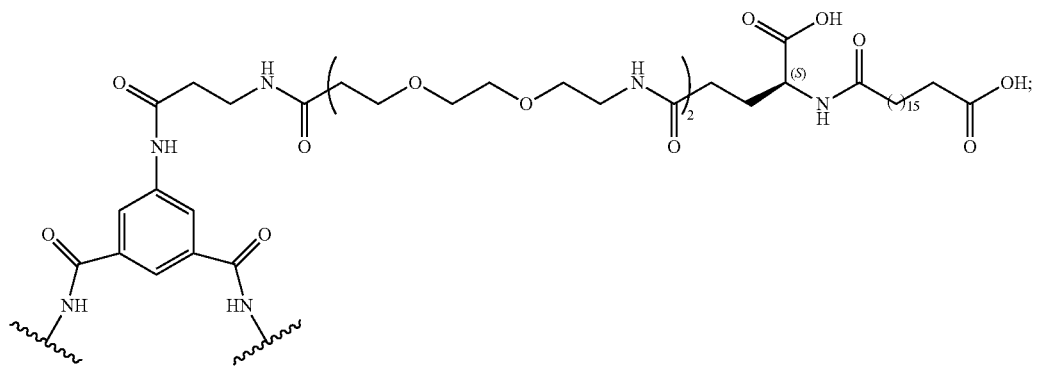
the "⸺S" being part of a cysteine, homocysteine, 2-amino-5-mercaptopentanoic acid, or 2-amino-6-mercaptohexanoic acid residue and the "⸺NH" being part of a lysine, ornithine, diaminobutyric acid, diaminopropionic acid, or homolysine residue.

In some embodiments, the staple attached to the peptide is:

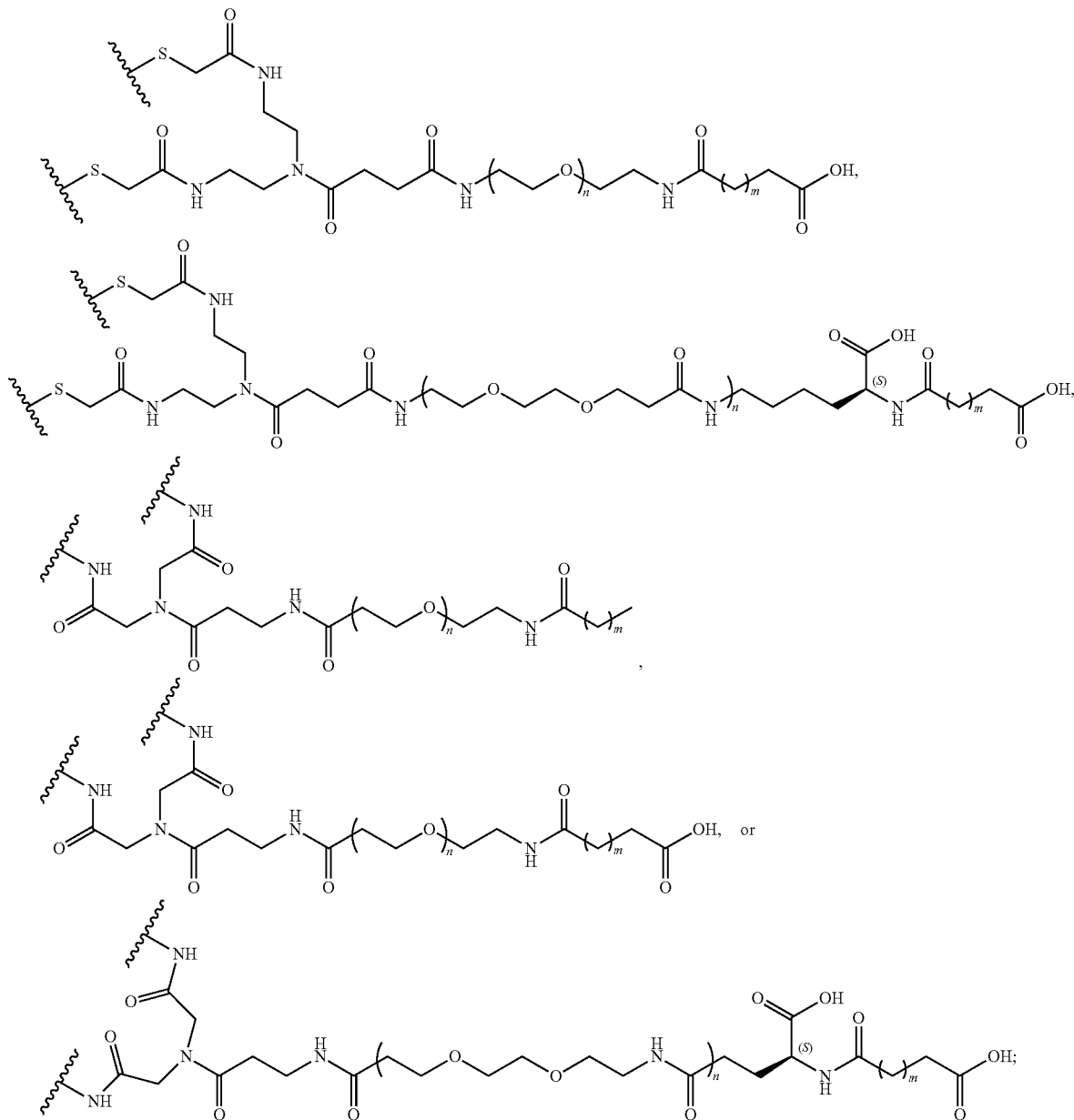

wherein n is 1-4 and m is 6-20; the "⌁-S" being part of a cysteine, homocysteine, 2-amino-5-mercaptopentanoic acid, or 2-amino-6-mercaptohexanoic acid residue and the "⌁-NH" being part of a lysine, ornithine, diaminobutyric acid, diaminopropionic acid, or homolysine residue. In some embodiments, n is 1 and m is 6. In some embodiments, n is 1 and m is 7. In some embodiments, n is 1 and m is 8. In some embodiments, n is 1 and m is 9. In some embodiments, n is 1 and m is 10. In some embodiments, n is 1 and m is 11. In some embodiments, n is 1 and m is 12. In some embodiments, n is 1 and m is 13. In some embodiments, n is 1 and m is 14. In some embodiments, n is 1 and m is 15. In some embodiments, n is 1 and m is 16. In some embodiments, n is 1 and m is 17. In some embodiments, n is 1 and m is 18. In some embodiments, n is 1 and m is 19. In some embodiments, n is 1 and m is 20. In some embodiments, n is 2 and m is 6. In some embodiments, n is 2 and m is 7. In some embodiments, n is 2 and m is 8. In some embodiments, n is 2 and m is 9. In some embodiments, n is 2 and m is 10. In some embodiments, n is 2 and m is 11. In some embodiments, n is 2 and m is 12. In some embodiments, n is 2 and m is 13. In some embodiments, n is 2 and m is 14. In some embodiments, n is 2 and m is 15. In some embodiments, n is 2 and m is 16. In some embodiments, n is 2 and m is 17. In some embodiments, n is 2 and m is 18. In some embodiments, n is 2 and m is 19. In some embodiments, n is 2 and m is 20. In some embodiments, n is 3 and m is 6. In some embodiments, n is 3 and m is 7. In some embodiments, n is 3 and m is 8. In some embodiments, n is 3 and m is 9. In some embodiments, n is 3 and m is 10. In some embodiments, n is 3 and m is 11. In some embodiments, n is 3 and m is 12. In some embodiments, n is 3 and m is 13. In some embodiments, n is 3 and m is 14. In some embodiments, n is 3 and m is 15. In some embodiments, n is 3 and m is 16. In some embodiments, n is 3 and m is 17. In some embodiments, n is 3 and m is 18. In some embodiments, n is 3 and m is 19. In some embodiments, n is 3 and m is 20. In some embodiments, n is 4 and m is 6. In some embodiments, n is 4 and m is 7. In some embodiments, n is 4 and m is 8. In some embodiments, n is 4 and m is 9. In some embodiments, n is 4 and m is 10. In some embodiments, n is 4 and m is 11. In some embodiments, n is 4 and m is 12. In some embodiments, n is 4 and m is 13. In some embodiments, n is 4 and m is 14. In some embodiments, n is 4 and m is 15. In some embodiments, n is 4 and m is 16. In some embodiments, n is 4 and m is 17. In some embodiments, n is 4 and m is 18. In some embodiments, n is 4 and m is 19. In some embodiments, n is 4 and m is 20.

In some embodiments, the staple attached to the peptide is:

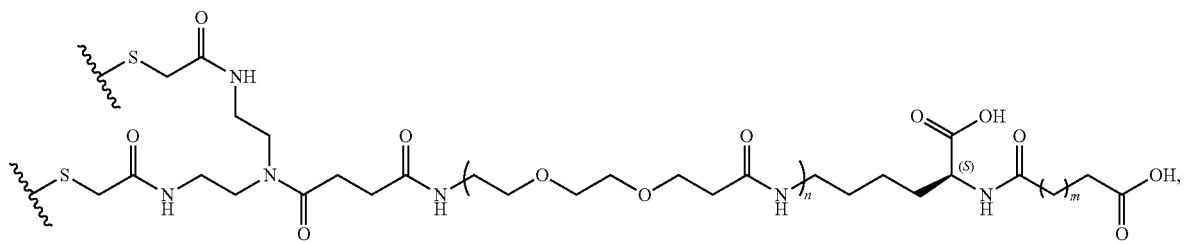

wherein n is 1-4 and m is 6-20; the "⌐-S" being part of a cysteine, homocysteine, 2-amino-5-mercaptopentanoic acid, or 2-amino-6-mercaptohexanoic acid residue and the "⌐-NH" being part of a lysine, ornithine, diaminobutyric acid, diaminopropionic acid, or homolysine residue. In some embodiments, n is 1 and m is 6. In some embodiments, n is 1 and m is 7. In some embodiments, n is 1 and m is 8. In some embodiments, n is 1 and m is 9. In some embodiments, n is 1 and m is 10. In some embodiments, n is 1 and m is 11. In some embodiments, n is 1 and m is 12. In some embodiments, n is 1 and m is 13. In some embodiments, n is 1 and m is 14. In some embodiments, n is 1 and m is 15. In some embodiments, n is 1 and m is 16. In some embodiments, n is 1 and m is 17. In some embodiments, n is 1 and m is 18. In some embodiments, n is 1 and m is 19. In some embodiments, n is 1 and m is 20. In some embodiments, n is 2 and m is 6. In some embodiments, n is 2 and m is 7. In some embodiments, n is 2 and m is 8. In some embodiments, n is 2 and m is 9. In some embodiments, n is 2 and m is 10. In some embodiments, n is 2 and m is 11. In some embodiments, n is 2 and m is 12. In some embodiments, n is 2 and m is 13. In some embodiments, n is 2 and m is 14. In some embodiments, n is 2 and m is 15. In some embodiments, n is 2 and m is 16. In some embodiments, n is 2 and m is 17. In some embodiments, n is 2 and m is 18. In some embodiments, n is 2 and m is 19. In some embodiments, n is 2 and m is 20. In some embodiments, n is 3 and m is 6. In some embodiments, n is 3 and m is 7. In some embodiments, n is 3 and m is 8. In some embodiments, n is 3 and m is 9. In some embodiments, n is 3 and m is 10. In some embodiments, n is 3 and m is 11. In some embodiments, n is 3 and m is 12. In some embodiments, n is 3 and m is 13. In some embodiments, n is 3 and m is 14. In some embodiments, n is 3 and m is 15. In some embodiments, n is 3 and m is 16. In some embodiments, n is 3 and m is 17. In some embodiments, n is 3 and m is 18. In some embodiments, n is 3 and m is 19. In some embodiments, n is 3 and m is 20. In some embodiments, n is 4 and m is 6. In some embodiments, n is 4 and m is 7. In some embodiments, n is 4 and m is 8. In some embodiments, n is 4 and m is 9. In some embodiments, n is 4 and m is 10. In some embodiments, n is 4 and m is 11. In some embodiments, n is 4 and m is 12. In some embodiments, n is 4 and m is 13. In some embodiments, n is 4 and m is 14. In some embodiments, n is 4 and m is 15. In some embodiments, n is 4 and m is 16. In some embodiments, n is 4 and m is 17. In some embodiments, n is 4 and m is 18. In some embodiments, n is 4 and m is 19. In some embodiments, n is 4 and m is 20.

In some embodiments, the staple attached to the peptide is:

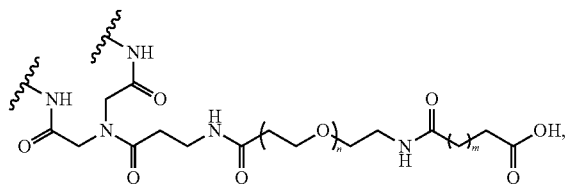

wherein n is 1-4 and m is 6-20; the "⌐-S" being part of a cysteine, homocysteine, 2-amino-5-mercaptopentanoic acid, or 2-amino-6-mercaptohexanoic acid residue and the "⌐-NH" being part of a lysine, ornithine, diaminobutyric acid, diaminopropionic acid, or homolysine residue. In some embodiments, n is 1 and m is 6. In some embodiments, n is 1 and m is 7. In some embodiments, n is 1 and m is 8. In some embodiments, n is 1 and m is 9. In some embodiments, n is 1 and m is 10. In some embodiments, n is 1 and m is 11. In some embodiments, n is 1 and m is 12. In some embodiments, n is 1 and m is 13. In some embodiments, n is 1 and m is 14. In some embodiments, n is 1 and m is 15. In some embodiments, n is 1 and m is 16. In some embodiments, n is 1 and m is 17. In some embodiments, n is 1 and m is 18. In some embodiments, n is 1 and m is 19. In some embodiments, n is 1 and m is 20. In some embodiments, n is 2 and m is 6. In some embodiments, n is 2 and m is 7. In some embodiments, n is 2 and m is 8. In some embodiments, n is 2 and m is 9. In some embodiments, n is 2 and m is 10. In some embodiments, n is 2 and m is 11. In some embodiments, n is 2 and m is 12. In some embodiments, n is 2 and m is 13. In some embodiments, n is 2 and m is 14. In some embodiments, n is 2 and m is 15. In some embodiments, n is 2 and m is 16. In some embodiments, n is 2 and m is 17. In some embodiments, n is 2 and m is 18. In some embodiments, n is 2 and m is 19. In some embodiments, n is 2 and m is 20. In some embodiments, n is 3 and m is 6. In some embodiments, n is 3 and m is 7. In some embodiments, n is 3 and m is 8. In some embodiments, n is 3 and m is 9. In some embodiments, n is 3 and m is 10. In some embodiments, n is 3 and m is 11. In some embodiments, n is 3 and m is 12. In some embodiments, n is 3 and m is 13. In some embodiments, n is 3 and m is 14. In some embodiments, n is 3 and m is 15. In some embodiments, n is 3 and m is 16. In some embodiments, n is 3 and m is 17. In some embodiments, n is 3 and m is 18. In some embodiments, n is 3 and m is 19. In some embodiments, n is 3 and m is 20. In some embodiments, n is 4 and m is 6. In some embodiments, n is 4 and m is 7. In some embodiments, n is 4 and m is 8. In some embodiments, n is 4 and m is 9. In some embodiments, n is 4 and m is 10. In some embodiments, n is 4 and m is 11. In some embodiments, n is 4 and m is 12. In some embodiments, n is 4 and m is 13. In some embodiments, n is 4 and m is 14. In some embodiments, n is 4 and m is 15. In some embodiments, n is 4 and m is 16. In some embodiments, n is 4 and m is 17. In some embodiments, n is 4 and m is 18. In some embodiments, n is 4 and m is 19. In some embodiments, n is 4 and m is 20.

In some embodiments, the staple attached to the peptide is:

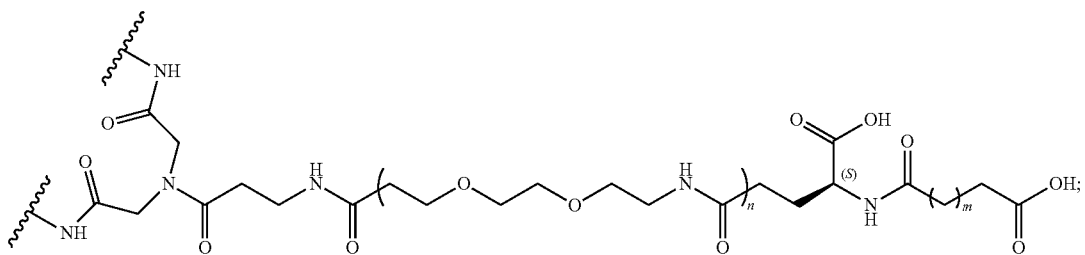

wherein n is 1-4 and m is 6-20; the "ʔ-S" being part of a cysteine, homocysteine, 2-amino-5-mercaptopentanoic acid, or 2-amino-6-mercaptohexanoic acid residue and the "ʔ-NH" being part of a lysine, ornithine, diaminobutyric acid, diaminopropionic acid, or homolysine residue. In some embodiments, n is 1 and m is 6. In some embodiments, n is 1 and m is 7. In some embodiments, n is 1 and m is 8. In some embodiments, n is 1 and m is 9. In some embodiments, n is 1 and m is 10. In some embodiments, n is 1 and m is 11. In some embodiments, n is 1 and m is 12. In some embodiments, n is 1 and m is 13. In some embodiments, n is 1 and m is 14. In some embodiments, n is 1 and m is 15. In some embodiments, n is 1 and m is 16. In some embodiments, n is 1 and m is 17. In some embodiments, n is 1 and m is 18. In some embodiments, n is 1 and m is 19. In some embodiments, n is 1 and m is 20. In some embodiments, n is 2 and m is 6. In some embodiments, n is 2 and m is 7. In some embodiments, n is 2 and m is 8. In some embodiments, n is 2 and m is 9. In some embodiments, n is 2 and m is 10. In some embodiments, n is 2 and m is 11. In some embodiments, n is 2 and m is 12. In some embodiments, n is 2 and m is 13. In some embodiments, n is 2 and m is 14. In some embodiments, n is 2 and m is 15. In some embodiments, n is 2 and m is 16. In some embodiments, n is 2 and m is 17. In some embodiments, n is 2 and m is 18. In some embodiments, n is 2 and m is 19. In some embodiments, n is 2 and m is 20. In some embodiments, n is 3 and m is 6. In some embodiments, n is 3 and m is 7. In some embodiments, n is 3 and in is 8. In some embodiments, n is 3 and m is 9. In some embodiments, n is 3 and m is 10. In some embodiments, n is 3 and m is 11. In some embodiments, n is 3 and m is 12. In some embodiments, n is 3 and m is 13. In some embodiments, n is 3 and m is 14. In some embodiments, n is 3 and m is 15. In some embodiments, n is 3 and m is 16. In some embodiments, n is 3 and m is 17. In some embodiments, n is 3 and m is 18. In some embodiments, n is 3 and m is 19. In some embodiments, n is 3 and m is 20. In some embodiments, n is 4 and m is 6. In some embodiments, n is 4 and m is 7. In some embodiments, n is 4 and m is 8. In some embodiments, n is 4 and m is 9. In some embodiments, n is 4 and m is 10. In some embodiments, n is 4 and m is 11. In some embodiments, n is 4 and m is 12. In some embodiments, n is 4 and m is 13. In some embodiments, n is 4 and m is 14. In some embodiments, n is 4 and m is 15. In some embodiments, n is 4 and m is 16. In some embodiments, n is 4 and m is 17. In some embodiments, n is 4 and m is 18. In some embodiments, n is 4 and m is 19. In some embodiments, n is 4 and m is 20.

In some embodiments, the staple attached to the peptide is:

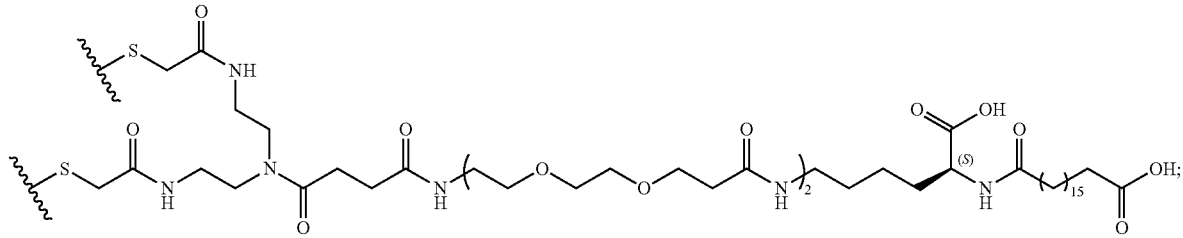

(L5A(S))

the "⸹-S" being part of a cysteine, homocysteine, 2-amino-5-mercaptopentanoic acid, or 2-amino-6-mercaptohexanoic acid residue.

In some embodiments, the staple attached to the peptide is:

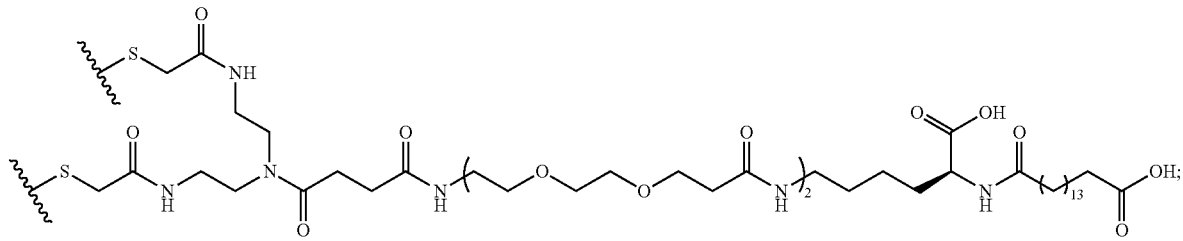

(C16L5A(S))

the "⸹-S" being part of a cysteine, homocysteine, 2-amino-5-mercaptopentanoic acid, or 2-amino-6-mercaptohexanoic acid residue.

In some embodiments, the staple attached to the peptide is:

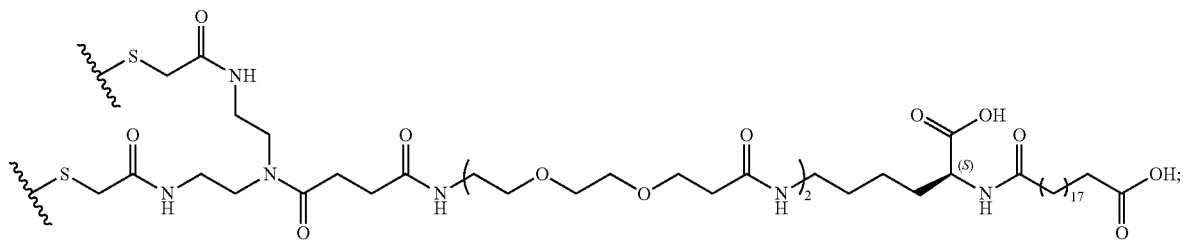

(C20L5A(S))

the "⸹-S" being part of a cysteine, homocysteine, 2-amino-5-mercaptopentanoic acid, or 2-amino-6-mercaptohexanoic acid residue.

In some embodiments, the staple attached to the peptide is:

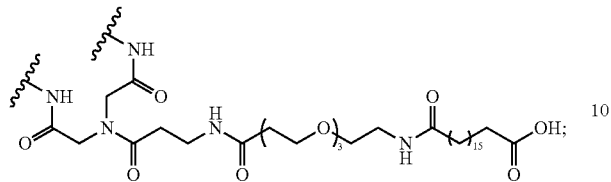

(K4(NH))

the "ξ-NH" being part of a lysine, ornithine, diaminobutyric acid, diaminopropionic acid, or homolysine residue.

In some embodiments, the staple attached to the peptide is:

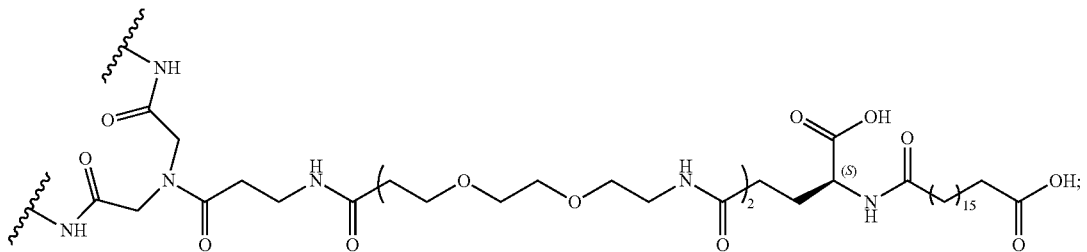

(K5(NH))

the "ξ-NH" being part of a lysine, ornithine, diaminobutyric acid, diaminopropionic acid, or homolysine residue.

In some embodiments, the staple attached to the peptide is:

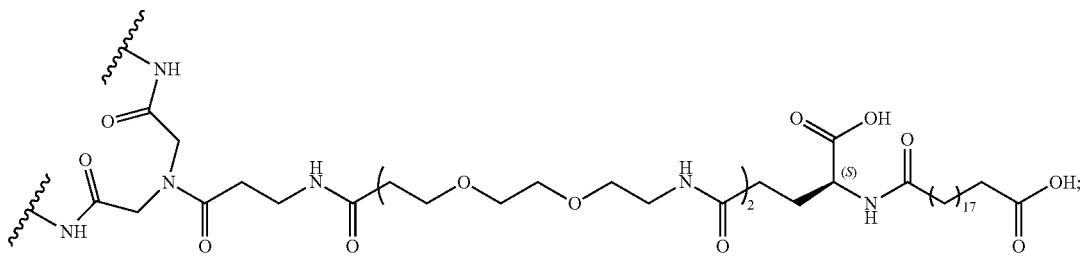

(C2K5(NH))

the "ξ-NH" being part of a lysine, ornithine, diaminobutyric acid, diaminopropionic acid, or homolysine residue.

In some embodiments, the staple attached to the peptide is:

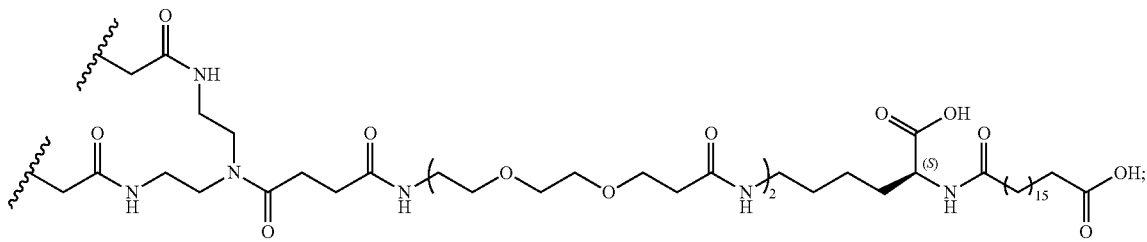

(L5A)

wherein each "⌇-" is connected to an amino acid of the peptide. For instance, the amino acid is a cysteine, homocysteine, 2-amino-5-mercaptopentanoic acid, 2-amino-6-mercaptohexanoic acid, lysine, ornithine, diaminobutyric acid, diaminopropionic acid, or homolysine residue of the peptide.

In some embodiments, the staple attached to the peptide is:

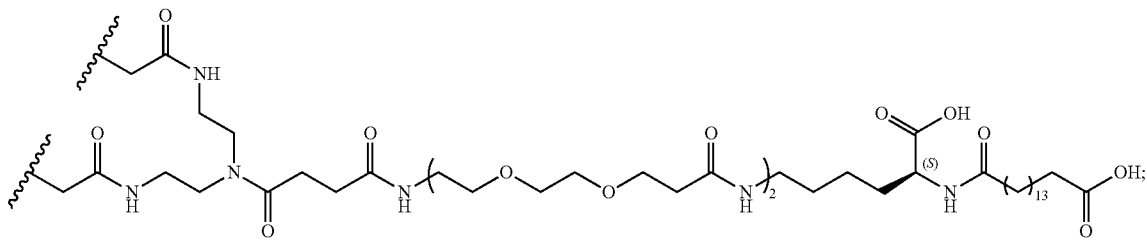

(C16L5A)

wherein each "⌇-" is connected to an amino acid of the peptide. For instance, the amino acid is a cysteine, homocysteine, 2-amino-5-mercaptopentanoic acid, 2-amino-6-mercaptohexanoic acid, lysine, ornithine, diaminobutyric acid, diaminopropionic acid, or homolysine residue of the peptide.

In some embodiments, the staple attached to the peptide is:

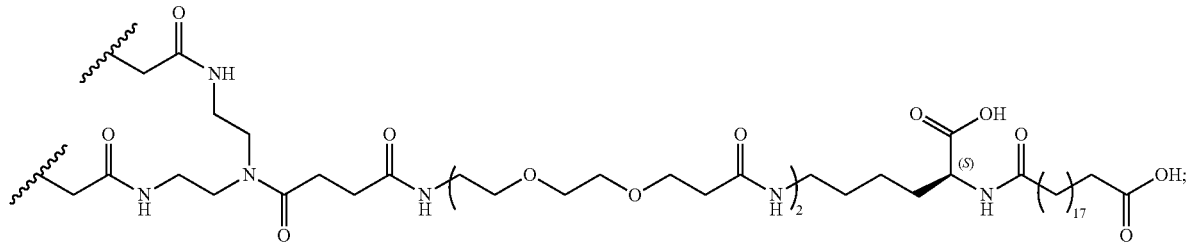

(C20L5A)

wherein each "⌇-" is connected to an amino acid of the peptide. For instance, the amino acid is a cysteine, homocysteine, 2-amino-5-mercaptopentanoic acid, 2-amino-6-mercaptohexanoic acid, lysine, ornithine, diaminobutyric acid, diaminopropionic acid, or homolysine residue of the peptide.

In some embodiments, the staple attached to the peptide is:

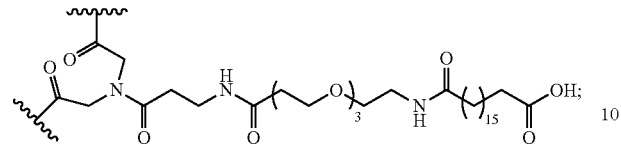
(K4)

wherein each "ξ-" is connected to an amino acid of the peptide. For instance, the amino acid is a cysteine, homocysteine, 2-amino-5-mercaptopentanoic acid, 2-amino-6-mercaptohexanoic acid, lysine, ornithine, diaminobutyric acid, diaminopropionic acid, or homolysine residue of the peptide.

In some embodiments, the staple attached to the peptide is:

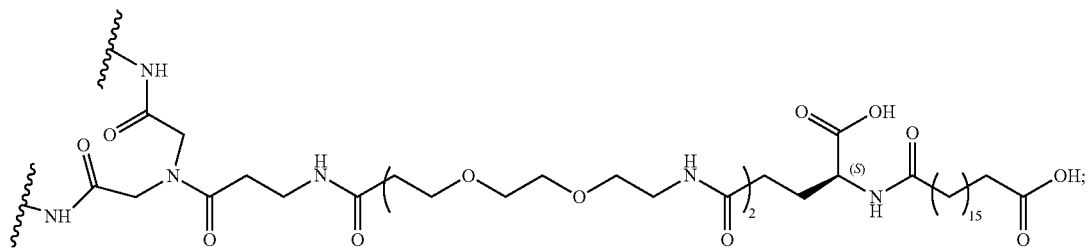
(K5)

wherein each "ξ-" is connected to an amino acid of the peptide. For instance, the amino acid is a cysteine, homocysteine, 2-amino-5-mercaptopentanoic acid, 2-amino-6-mercaptohexanoic acid, lysine, ornithine, diaminobutyric acid, diaminopropionic acid, or homolysine residue of the peptide.

In some embodiments, the staple attached to the peptide is:

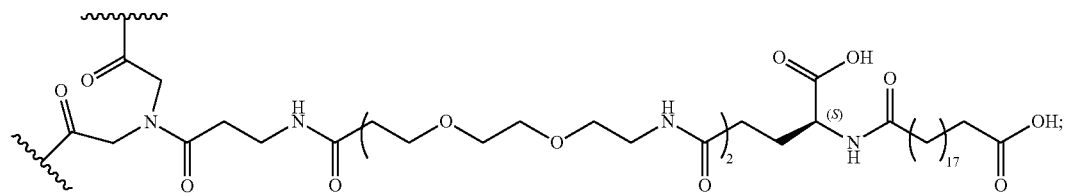
(C20K5)

wherein each "ξ-" is connected to an amino acid of the peptide. For instance, the amino acid is a cysteine, homocysteine, 2-amino-5-mercaptopentanoic acid, 2-amino-6-mercaptohexanoic acid, lysine, ornithine, diaminobutyric acid, diaminopropionic acid, or homolysine residue of the peptide.

In some embodiments, the staple attached to the peptide is:

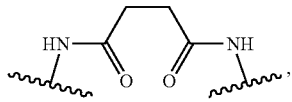

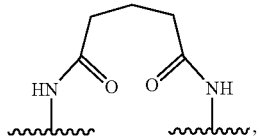

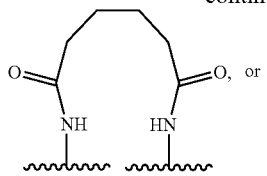

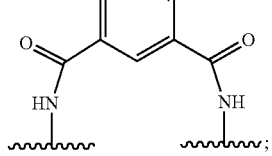

the "⟋-NH" being part of a lysine, ornithine, diaminobutyric acid, diaminopropionic acid, or homolysine residue.

In some embodiments, the staple attached to the peptide is:

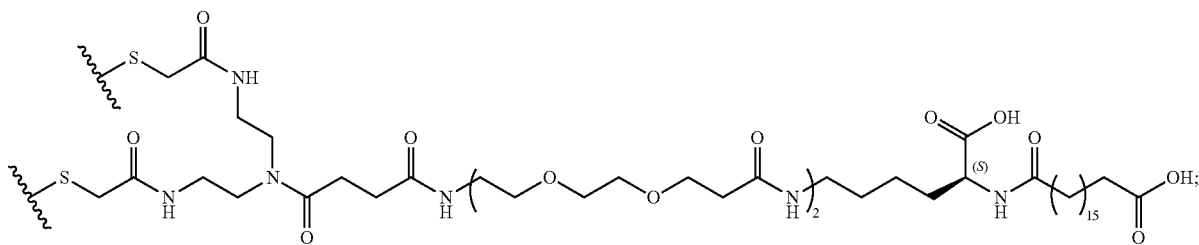

the "⟋-S" being part of a cysteine, homocysteine, 2-amino-5-mercaptopentanoic acid, or 2-amino-6-mercaptohexanoic acid residue.

In some embodiments, the staple attached to the peptide is:

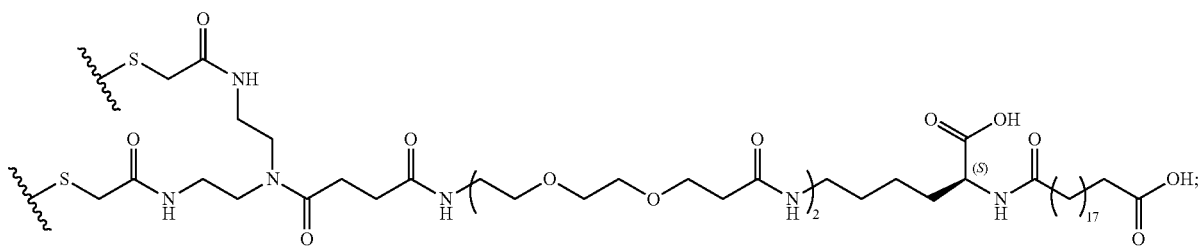

the "⟋-S" being part of a cysteine, homocysteine, 2-amino-5-mercaptopentanoic acid, or 2-amino-6-mercaptohexanoic acid residue.

In some embodiments, the staple attached to the peptide is:

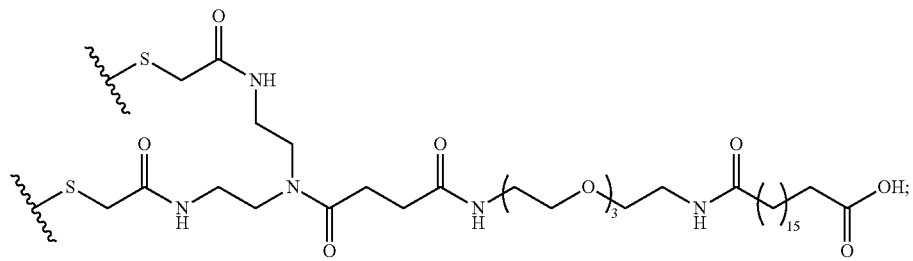

the "ξ-S" being part of a cysteine, homocysteine, 2-amino-5-mercaptopentanoic acid, or 2-amino-6-mercaptohexanoic acid residue.

In some embodiments, the staple attached to the peptide is:

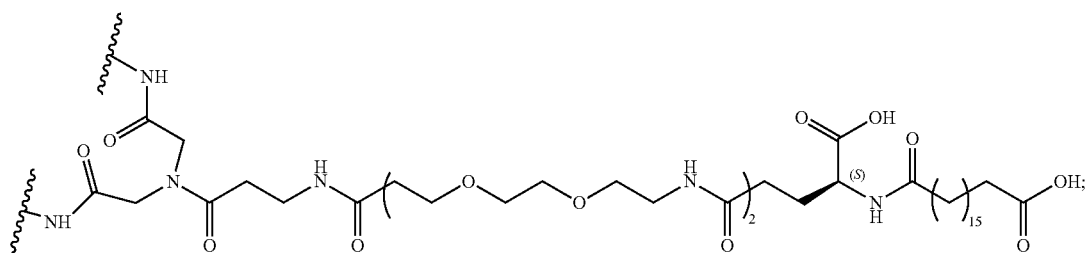

the "ξ-NH" being part of a lysine, ornithine, diaminobutyric acid, diaminopropionic acid, or homolysine residue.

In some embodiments, the staple attached to the peptide is:

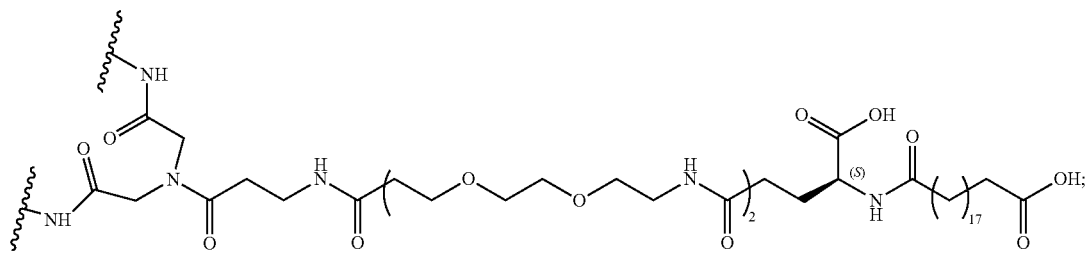

the "ξ-NH" being part of a lysine, ornithine, diaminobutyric acid, diaminopropionic acid, or homolysine residue.

In some embodiments, the staple attached to the peptide is:

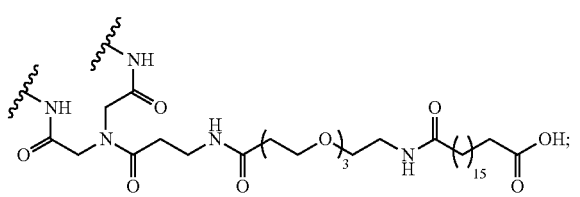

the "ξ-NH" being part of a lysine, ornithine, diaminobutyric acid, diaminopropionic acid, or homolysine residue.

In some embodiments, the staple attached to the peptide comprises Linker L1, Linker L2, or Linker L3:

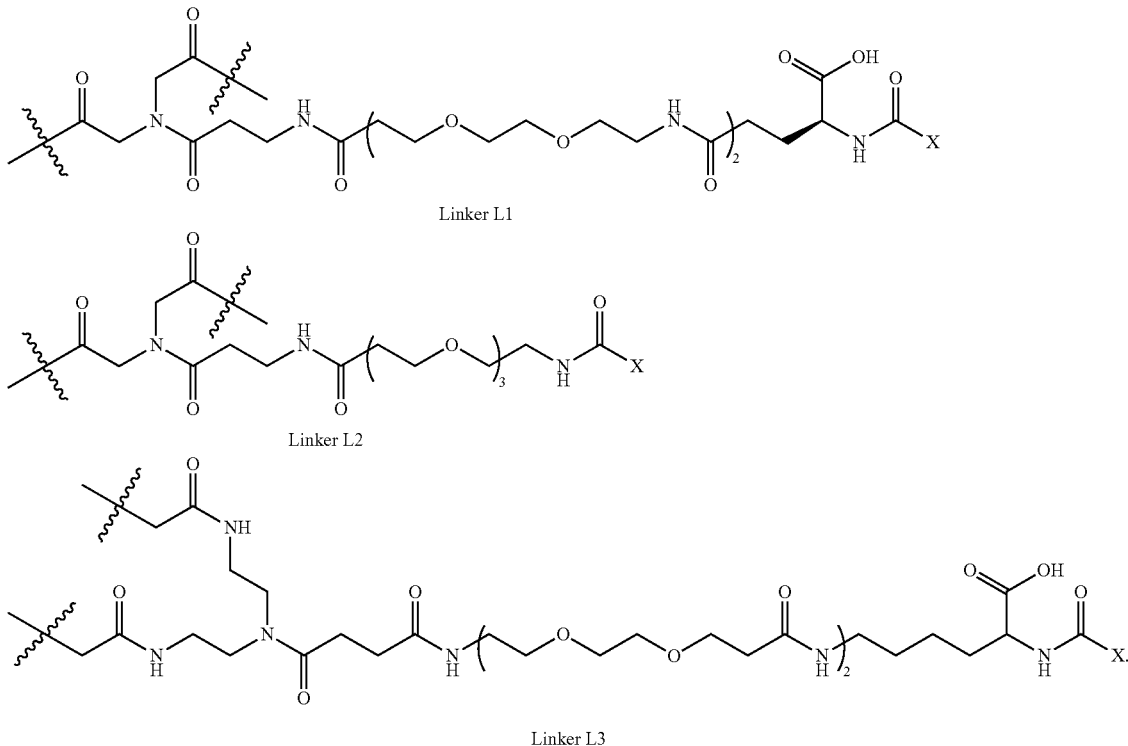

Linker L1

Linker L2

Linker L3

In some embodiments, X independently comprises C14, C14 diacid, C16, C16 diacid, C18, C18 diacid, C20 or C20 diacid. In some embodiments, X comprises Propionic acid (CH3CH2COOH, C3:0). In some embodiments, X comprises Butyric acid (Butanoic acid, CH3(CH2)2COOH, C4:0). In some embodiments, X is Valeric acid (Pentanoic acid, CH3(CH2)3COOH, C5:0). In some embodiments, X comprises Caproic acid (Hexanoic acid, CH3(CH2)4COOH, C6:0). In some embodiments, X comprises Enanthic acid (Heptanoic acid, CH3(CH2)5COOH, C7:00. In some embodiments, X comprises Caprylic acid (Octanoic acid, CH3(CH2)6COOH, C8:0). In some embodiments, X comprises Pelargonic acid (Nonanoic acid, CH3(CH2)7COOH, C9:0). In some embodiments, X comprises Capric acid (Decanoic acid, CH3(CH2)8COOH, C10:0). In some embodiments, X comprises Undecylic acid (Undecanoic acid, CH3(CH2)9COOH, C11:0). In some embodiments, X comprises Lauric acid (Dodecanoic acid, CH3(CH2)10COOH, C12:0). In some embodiments, X comprises Tridecylic acid (Tridecanoic acid, CH3(CH2)11COOH, C13:0). In some embodiments, X comprises Myristic acid (Tetradecanoic acid, CH3(CH2)12COOH, C14:0). In some embodiments, X comprises Pentadecylic acid (Pentadecanoic acid, CH3(CH2)13COOH, C15:0). In some embodiments, X comprises Palmitic acid (Hexadecanoic acid, CH3(CH2)14COOH, C16:0). In some embodiments, X comprises Margaric acid (Heptadecanoic acid, CH3(CH2)15C00H, C17:0). In some embodiments, X comprises Stearic acid (Octadecanoic acid, CH3(CH2)16COOH, C18:0). In some embodiments, X comprises Nonadecylic acid (Nonadecanoic acid, CH3(CH2)17COOH, C19:0). In some embodiments, X comprises Arachidic acid (Eicosanoic acid, CH3(CH2)18C00H, C20:0). In some embodiments, X comprises Heneicosylic acid (Heneicosanoic acid, CH3(CH2)19COOH, C21:0). In some embodiments, X comprises Behenic acid (Docosanoic acid, CH3(CH2)20COOH, C22:0). In some embodiments, X comprises Tricosylic acid (Tricosanoic acid, CH3(CH2)21COOH, C23:0). In some embodiments, X comprises Lignoceric acid (Tetracosanoic acid, CH3(CH2)22COOH, C24:0). In some embodiments, X comprises Pentacosylic acid (Pentacosanoic acid, CH3(CH2)23COOH, C25:0).

Half-Life Extending Moiety (HEM)

Disclosed herein are peptide conjugates comprising a HEM.

In some embodiments, the HEM attached to the peptide is of Formula (II):

$$-X^3\text{-}(L)_s\text{-}Y \qquad \text{Formula (II)}$$

wherein $X^3$ is a bond, —C(=O)—, -alkylene-C(=O)—, —C(=O)-alkylene-, -alkylene-C(=O)NR$^3$—, -alkylene-NR$^3$C(=O)—, —C(=O)NR$^3$-alkylene-, —NR$^3$C(=O)-alkylene-, -alkylene-C(=O)NR$^3$-alkylene-, or -alkylene-NR$^3$C(=O)-alkylene-;

wherein $X^3$ is attached to a first amino acid of the peptide;

each L is independently —(CR$^1$R$^2$)$_v$—, -alkylene-O—, —O-alkylene-, —C(=O)-alkylene-, -alkylene-C(=O)—, —NR$^3$-alkylene-, -alkylene-NR$^3$—, —S-alkylene-, -alkylene-S—, —S(=O)-alkylene-, -alkylene-S(=O)—, —S(=O)$_2$-alkylene, -alkylene-S(=O)$_2$—, —C(=O)—, —C(=O)NR$^3$—, —NR$^3$C(=O)—, —NR$^3$C(=O)NR$^3$—, —NR$^3$C(=O)NR$^3$-alkylene-, —NR$^3$C(=O)-alkylene-NR$^3$—, -alkylene- C(=O)NR³—, —C(=O)NR³-alkylene-, -alkylene-NR³C(=O)—, or —NR³C(=O)-alkylene-;
v is 2-20;
each R¹ or R² is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, —NR$^c$R$^d$,
or R¹ and R² are taken together to form a C$_1$-C$_6$ cycloalkyl or C$_1$-C$_6$ heterocycloalkyl;
each R³ is independently hydrogen, —S(=O)R$^b$, —S(=O)$_2$R$^a$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;
Y is hydrogen, C$_1$-C$_6$ alkyl, —CO$_2$H, —CO$_2$(C$_1$-C$_6$ alkyl), —CO$_2$NH$_2$, —CO$_2$N(alkyl)$_2$, or —CO$_2$NH(alkyl); and
s is 0-20;
R$^a$ is hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;
R$^b$ is C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;
each R$^c$ and R$^d$ is independently hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;
or R$^c$ and R$^d$, together with the nitrogen atom to which they are attached, form a heterocycloalkyl or heteroaryl; wherein the heterocycloalkyl and heteroaryl is optionally substituted with one, two, or three of halogen, C$_1$-C$_6$ alkyl, C$_1$-C$_6$ haloalkyl, —OH, —OMe, or —NH$_2$.

In some embodiments, X³ is a bond.
In some embodiments, X³ is -alkylene-C(=O)— or —C(=O)alkylene-. In some embodiments, X³ is —CH$_2$—C(=O)— or —C(=O)—CH$_2$—. In some embodiments, X³ is -alkylene-C(=O)NR³— or —C(=O)NR³— alkylene-. In some embodiments, X³ is —CH$_2$—C(=O)NR³— or —C(=O)NR³—CH$_2$—. In some embodiments, X³ is -alkylene-C(=O)NR³-alkylene- or -alkylene-NR³C(=O)-alkylene-. In some embodiments, X³ is —CH$_2$—C(=O)NR³—CH$_2$CH$_2$— or —CH$_2$—NR³C(=O)—CH$_2$CH$_2$—. In some embodiments, X³ is —CH$_2$—C(=O)NH—CH$_2$CH$_2$— or —CH$_2$—NHC(=O)—CH$_2$CH$_2$—.

In some embodiments, each R³ is independently hydrogen or C$_1$-C$_6$ alkyl. In some embodiments, each R³ is hydrogen.

In some embodiments, s is 1-15. In some embodiments, s is 1-10. In some embodiments, s is 5-15. In some embodiments, s is 5-10. In some embodiments, s is 5-20.

In some embodiments, Y is hydrogen or —CO$_2$H. In some embodiments, Y is hydrogen. In some embodiments, Y is —CO$_2$H.

In some embodiments, each L is independently —(CR¹R²)$_v$—, -alkylene-O—, —C(=O)—, —C(=O)NR³—, —NR³C(=O)—, -alkylene-C(=O)NR³—, or -alkylene-NR³C(=O)—; and v is 2-20.

In some embodiments, each L is independently —(CR¹R²)$_v$—, -alkylene-O—, —C(=O)—, —C(=O)NR³—, —NR³C(=O)—, -alkylene-C(=O)NR³—, or -alkylene-NR³C(=O)—; and v is 2-16.

In some embodiments, v is 2-16. In some embodiments, v is 2-5. In some embodiments, v is 5-16. In some embodiments, v is 5 or 16. In some embodiments, v is 2 or 16.

In some embodiments, each R¹ or R² is independently hydrogen, halogen, —CN, —OR$^a$, —NR$^c$R$^d$, —C(=O)R$^b$, —CO$_2$R$^a$, —C(=O)NR$^c$R$^d$, or C$_1$-C$_6$ alkyl.

In some embodiments, each R¹ or R² is independently hydrogen, halogen, —CO$_2$R$^a$, —C(=O)NR$^c$R$^d$, or C$_1$-C$_6$ alkyl. In some embodiments, each R¹ or R² is independently hydrogen, —CO$_2$R$^a$, or —C(=O)NR$^c$R$^d$. In some embodiments, each R¹ or R² is independently hydrogen or —CO$_2$R$^a$.

In some embodiments, the HEM attached to the peptide is:

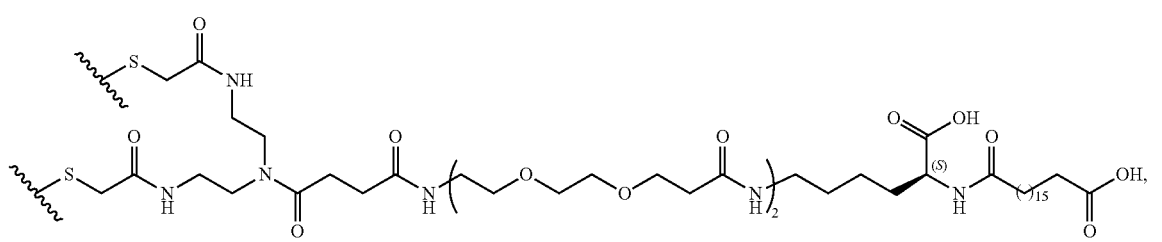

(L5A(S))

-continued
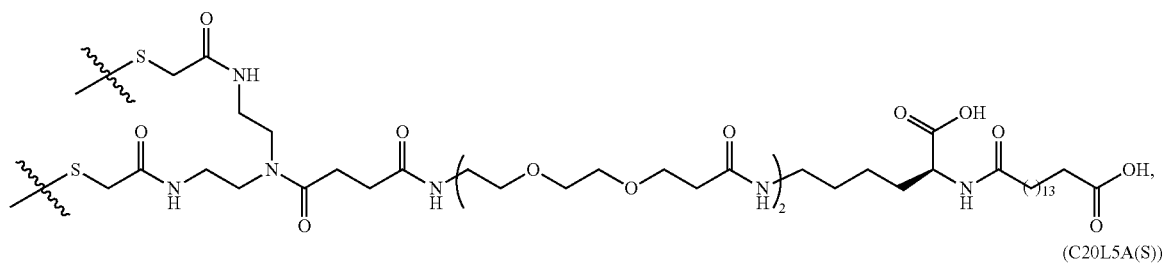
(C16L5A(S))
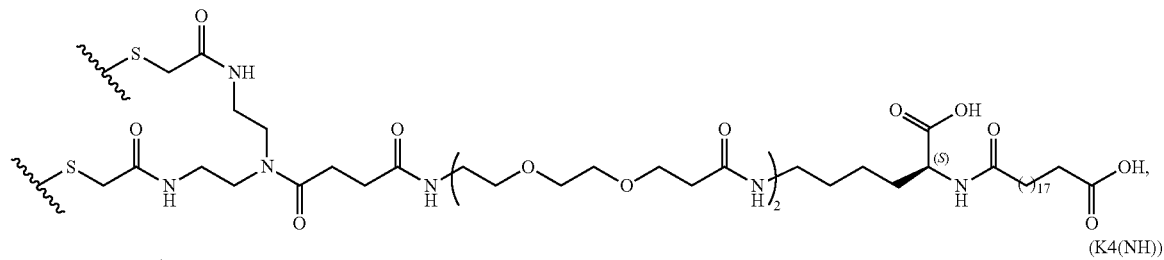
(C20L5A(S))
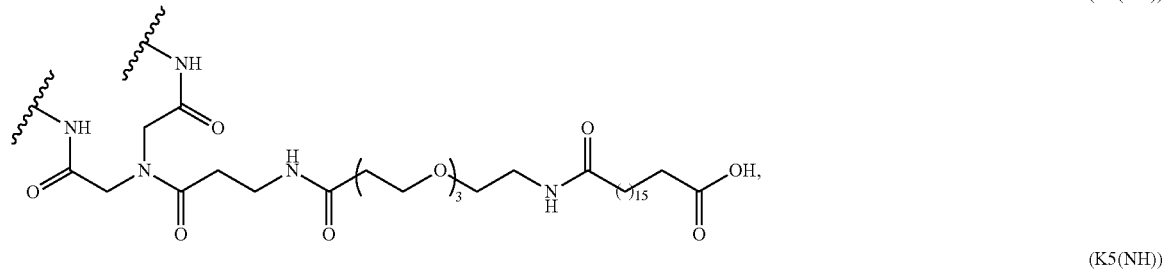
(K4(NH))
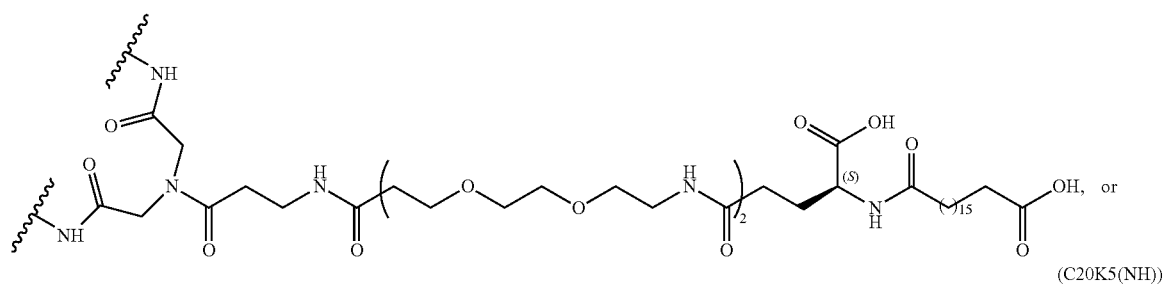
(K5(NH))
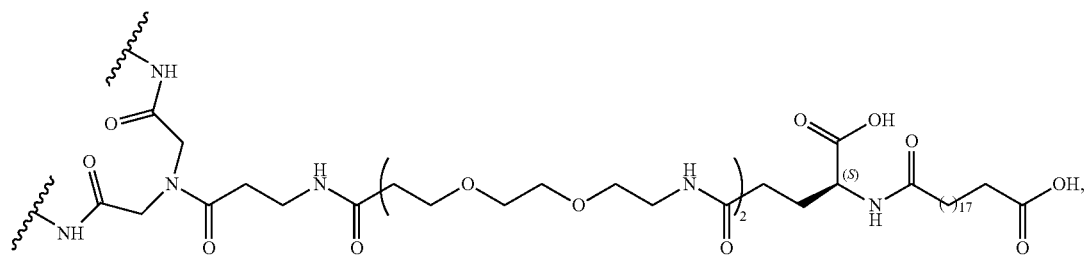
(C20K5(NH))
the "⸹-S" being part of a cysteine, homocysteine, 2-amino-5-mercaptopentanoic acid, or 2-amino-6-mercaptohexanoic acid residue, and the "⸹-NH" being part of a lysine, ornithine, diaminobutyric acid, diaminopropionic acid, or homolysine residue.

In some embodiments, the HEM attached to the peptide is:

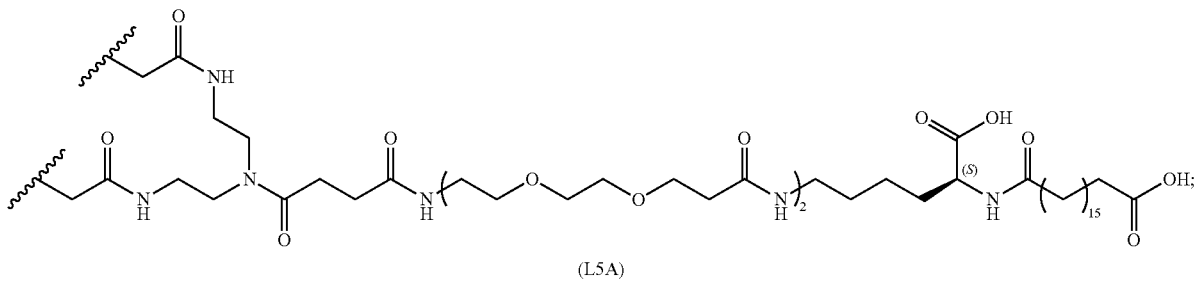

(L5A)

wherein each "ξ-" is connected to an amino acid of the peptide. For instance, the amino acid is a cysteine, homocysteine, 2-amino-5-mercaptopentanoic acid, 2-amino-6-mercaptohexanoic acid, lysine, ornithine, diaminobutyric acid, diaminopropionic acid, or homolysine residue of the peptide.

In some embodiments, the HEM attached to the peptide is:

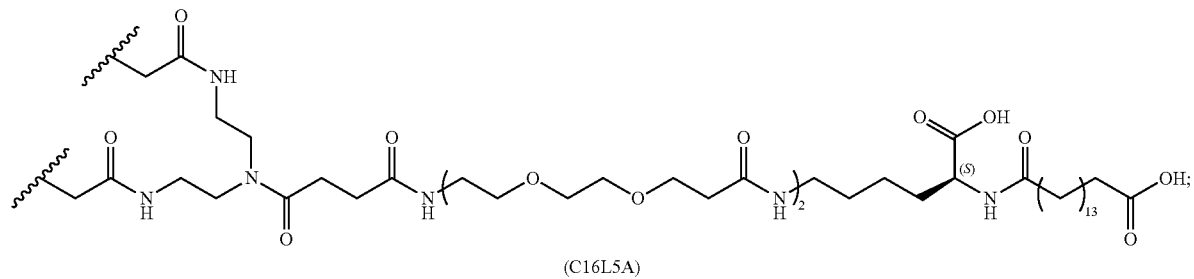

(C16L5A)

wherein each "ξ-" is connected to an amino acid of the peptide. For instance, the amino acid is a cysteine, homocysteine, 2-amino-5-mercaptopentanoic acid, 2-amino-6-mercaptohexanoic acid, lysine, ornithine, diaminobutyric acid, diaminopropionic acid, or homolysine residue of the peptide.

In some embodiments, the HEM attached to the peptide is:

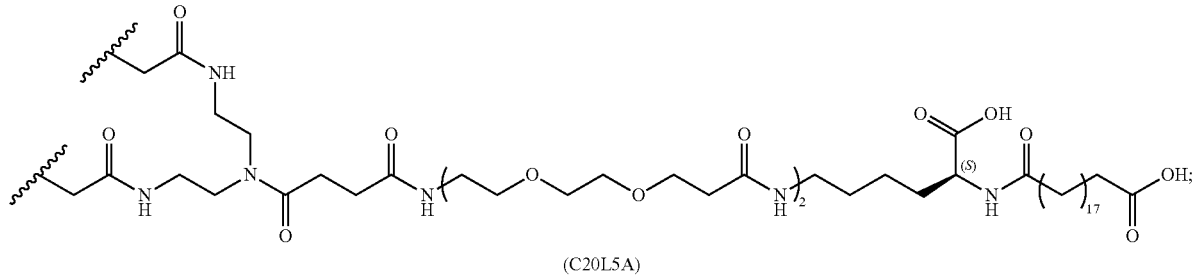

(C20L5A)

wherein each "ξ-" is connected to an amino acid of the peptide. For instance, the amino acid is a cysteine, homocysteine, 2-amino-5-mercaptopentanoic acid, 2-amino-6-mercaptohexanoic acid, lysine, ornithine, diaminobutyric acid, diaminopropionic acid, or homolysine residue of the peptide.

In some embodiments, the HEM attached to the peptide is:

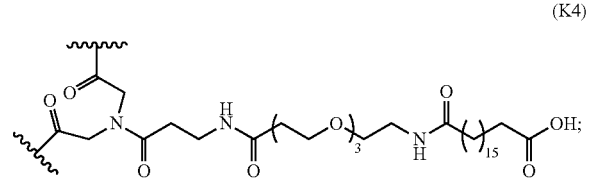
(K4)

wherein each "ξ-" is connected to an amino acid of the peptide. For instance, the amino acid is a cysteine, homocysteine, 2-amino-5-mercaptopentanoic acid, 2-amino-6-mercaptohexanoic acid, lysine, ornithine, diaminobutyric acid, diaminopropionic acid, or homolysine residue of the peptide.

In some embodiments, the HEM attached to the peptide is:

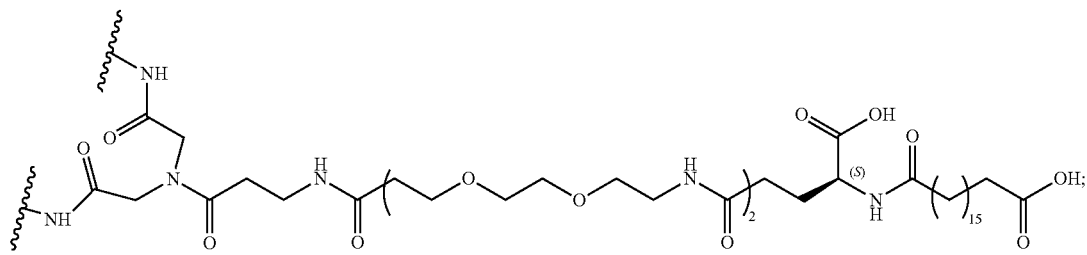
(K5)

wherein each "ξ-" is connected to an amino acid of the peptide. For instance, the amino acid is a cysteine, homocysteine, 2-amino-5-mercaptopentanoic acid, 2-amino-6-mercaptohexanoic acid, lysine, ornithine, diaminobutyric acid, diaminopropionic acid, or homolysine residue of the peptide.

In some embodiments, the HEM attached to the peptide is:

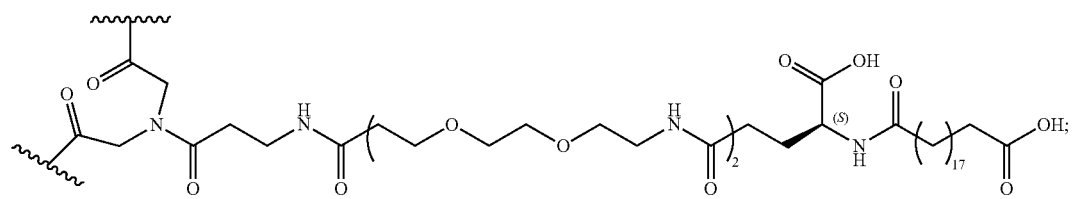
(C20K5)

wherein each "ξ-" is connected to an amino acid of the peptide. For instance, the amino acid is a cysteine, homocysteine, 2-amino-5-mercaptopentanoic acid, 2-amino-6-mercaptohexanoic acid, lysine, ornithine, diaminobutyric acid, diaminopropionic acid, or homolysine residue of the peptide.

Peptide Conjugates with a Staple

In one aspect, disclosed herein are peptide conjugates comprising: a peptide and a staple attached to the peptide at a first amino acid and a second amino acid.

In some embodiments, the peptide conjugates comprise (a) a peptide that modulates a GIP-1R receptor; and (b) a staple attached to the peptide at a first amino acid and a second amino acid.

In some embodiments, the peptide conjugates comprise (a) a peptide that binds to a GLP-1 receptor; and (b) a staple attached to the peptide at a first amino acid and a second amino acid.

In some embodiments, the peptide conjugates comprise (a) a peptide that modulates a GIP receptor; and (b) a staple attached to the peptide at a first amino acid and a second amino acid.

In some embodiments, the peptide conjugates comprise (a) a peptide that binds a GIP receptor; and (b) a staple attached to the peptide at a first amino acid and a second amino acid.

Non-limiting examples of amino acids for use in conjugation include cysteine, homocysteine, 2-amino-5-mercaptopentanoic acid, 2-amino-6-mercaptohexanoic acid, lysine, ornithine, diaminobutyric acid, diaminopropionic acid, homolysine, other sulfhydryl containing amino acids, or other amine containing amino acids. In some embodiments, the two amino acids connected by a staple are about or at least about 3, 4, 5, 6, 7, 8, 9, 10, 11, 12, 13, 14, 15, 16, or more amino acids apart. For example, the first amino acid has position i, and the second amino acid has position i+7, i+11, i+13, i+15, or i+16. For example, the first amino acid has a position i in the peptide and the second amino acid has a position i+n in the peptide, wherein n is 4-16. In some embodiments, the first amino acid is at the 14 position and the second amino acid is at the 21 position in the peptide. In some embodiments, the first amino acid is at the 17 position and the second amino acid is at the 24 position in the peptide.

For example, the first amino acid has a position i in the peptide and the second amino acid has a position i+4 in the peptide. For example, the first amino acid has a position i in the peptide and the second amino acid has a position i+5 in the peptide. For example, the first amino acid has a position i in the peptide and the second amino acid has a position i+6 in the peptide. For example, the first amino acid has a position i in the peptide and the second amino acid has a position i+7 in the peptide. For example, the first amino acid has a position i in the peptide and the second amino acid has a position i+8 in the peptide. For example, the first amino acid has a position i in the peptide and the second amino acid has a position i+9 in the peptide. For example, the first amino acid has a position i in the peptide and the second amino acid has a position i+10 in the peptide. For example, the first amino acid has a position i in the peptide and the second amino acid has a position i+11 in the peptide. For example, the first amino acid has a position i in the peptide and the second amino acid has a position i+12 in the peptide. For example, the first amino acid has a position i in the peptide and the second amino acid has a position i+13 in the peptide. For example, the first amino acid has a position i in the peptide and the second amino acid has a position i+14 in the peptide. For example, the first amino acid has a position i in the peptide and the second amino acid has a position i+15 in the peptide. For example, the first amino acid has a position i in the peptide and the second amino acid has a position i+16 in the peptide.

In some embodiments, the first amino acid and the second amino acid are independently selected from the group consisting of an amine-containing amino acid and a sulfhydryl-containing amino acid.

In some embodiments, the first amino acid and second amino acid is independently selected from cysteine, homocysteine, 2-amino-5-mercaptopentanoic acid, and 2-amino-6-mercaptohexanoic acid. In some embodiments, the first amino acid and second amino acid are cysteines.

In some embodiments, the first amino acid and second amino acid is independently selected from lysine, ornithine, diaminobutyric acid, diaminopropionic acid and homolysine.

In some embodiments, the first amino acid and second amino acid are lysines.

In some embodiments, the first amino acid and second amino acid are ornithines.

In some embodiments, the peptide conjugate further comprises a half-life extending molecule attached to a sulfhydryl containing amino acid or an amine-containing amino acid residue in the peptide.

In some embodiments, the amine-containing amino acid is selected from lysine, ornithine, diaminobutyric acid, diaminopropionic acid, and homolysine.

In some embodiments, the amine-containing amino acid is lysine.

In some embodiments, the sulfhydryl-containing amino acid is selected from cysteine, homocysteine, 2-amino-5-mercaptopentanoic acid, and 2-amino-6-mercaptohexanoic acid.

In some embodiments, the sulfhydryl-containing amino acid is cysteine.

In some embodiments, the peptide comprises a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61. In some embodiments, the peptide comprises a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 1-61. As a non-limiting example, the peptide comprises a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 6.

Peptide Conjugates

In one aspect, disclosed herein are peptide conjugates comprising: a peptide and a staple. The staple and/or peptide may comprise a half-life extending moiety (HEM).

In some embodiments, the peptide conjugates comprise (a) a peptide that modulates a GIP-1R receptor; and (b) a half-life extending moiety (HEM) attached to the peptide at a first amino acid.

In some embodiments, the peptide conjugates comprise (a) a peptide that binds to a GLP-1 receptor; and (b) a half-life extending moiety (HEM) attached to the peptide at a first amino acid.

In some embodiments, the peptide conjugates comprise (a) a peptide that modulates a GIP receptor; and (b) a half-life extending moiety (HEM) attached to the peptide at a first amino acid.

In some embodiments, the peptide conjugates comprise (a) a peptide that binds a GIP receptor; and (b) a half-life extending moiety (HEM) attached to the peptide at a first amino acid.

Non-limiting examples of amino acids for use in conjugation include cysteine, homocysteine, 2-amino-5-mercaptopentanoic acid, 2-amino-6-mercaptohexanoic acid, lysine, ornithine, diaminobutyric acid, diaminopropionic acid, homolysine, other sulfhydryl containing amino acids, or other amine containing amino acids. In some embodiments, the first amino acid is selected from the group consisting of an amine-containing amino acid and a sulfhydryl-containing amino acid. In some embodiments, the first amino acid is selected from cysteine, homocysteine, 2-amino-5-mercaptopentanoic acid, and 2-amino-6-mercaptohexanoic acid. In some embodiments, the first amino acid is cysteine. In some embodiments, the first amino acid is selected from lysine, ornithine, diaminobutyric acid, diaminopropionic acid and homolysine. In some embodiments, the first amino acid is lysine. In some embodiments, the first amino acid is ornithine. In some embodiments, the peptide conjugate further comprises a second half-life extending moiety attached to a sulfhydryl containing amino acid or an amine-containing amino acid residue in the peptide. In some embodiments, the amine-containing amino acid is selected from lysine, ornithine, diaminobutyric acid, diaminopropionic acid, and homolysine. In some embodiments, the amine-containing amino acid is lysine. In some embodiments, the sulfhydryl-containing amino acid is selected from cysteine, homocysteine, 2-amino-5-mercaptopentanoic acid, and 2-amino-6-mercaptohexanoic acid. In some embodiments, the sulfhydryl-containing amino acid is cysteine.

The peptide may modulate and/or bind to: a GLP-1 receptor, a GIP receptor, or a GLP-1 receptor and GIP receptor. In exemplary cases, the peptide comprises two amino acids connected by a staple. Non-limiting examples of amino acids for use in conjugation include cysteine, homocysteine, 2-amino-5-mercaptopentanoic acid, 2-amino-6-mercaptohexanoic acid, or other sulfhydryl containing amino acids. The two amino acids may be about or at least about 3, 4, 5, 6, 7, 8, 9, 10, 11, 12, 13, 14, or more amino acids apart. For example, the first amino acid has position i, and the second amino acid has position i+7, i+11, i+13, i+15, or i+16. For example, the first amino acid has a position i in the peptide and the second amino acid has a position i+n in the peptide, wherein n is 4-16. For example, the first amino acid has a position i in the peptide and the second amino acid has a position i+7 in the peptide. For example, the first amino acid has a position i in the peptide and the second amino acid has a position i+11 in the peptide. For example, the first amino acid has a position i in the peptide and the second amino acid has a position i+15 in the peptide. For example, the first amino acid has a position i in the peptide and the second amino acid has a position i+16 in the peptide.

In some embodiments, the first amino acid and the second amino acid are independently selected from sulfhydryl-containing amino acids.

In some embodiments, the first amino acid and second amino acid is independently selected from cysteine, homocysteine, 2-amino-5-mercaptopentanoic acid, and 2-amino-6-mercaptohexanoic acid. In some embodiments, the first amino acid and second amino acid are cysteines.

In some embodiments, a peptide herein is conjugated to a structure of Table 2.

TABLE 2

Example Structures

| Ex | ID | Structure |
|----|-----|-----------|
| 1 | FA2 | 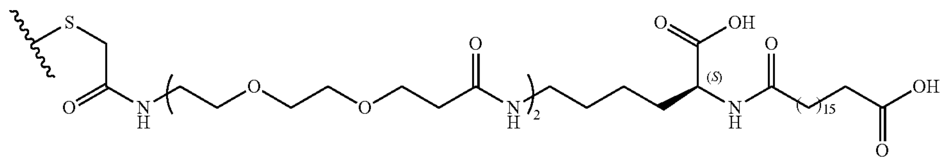 |
| 2 | L1 | 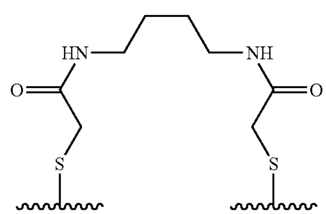 [SMILES: *SCC(=O)NCCCCNC(=O)CS*] |
| 3 | L1B | 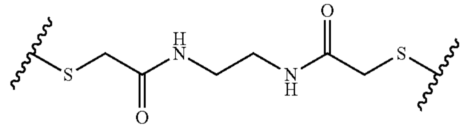 [SMILES: *SCC(=O)NCCNC(=O)CS*] |
| 4 | L1C | 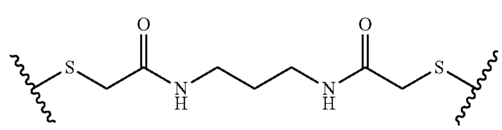 [SMILES: *SCC(=O)NCCCNC(=O)CS*] |
| 5 | L1D | 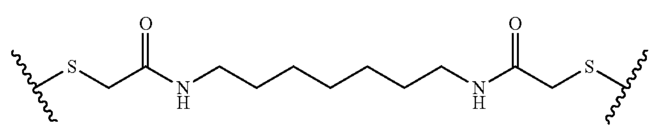 [SMILES: *SCC(=O)NCCCCCCCNC(=O)CS*] |
| 6 | L1E | 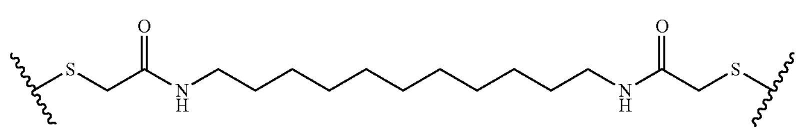 [SMILES: *SCC(=O)NCCCCCCCCCCCNC(=O)CS*] |
| 7 | L1F | 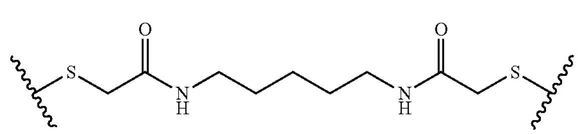 [SMILES: *SCC(=O)NCCCCCNC(=O)CS*] |
| 8 | L1G | 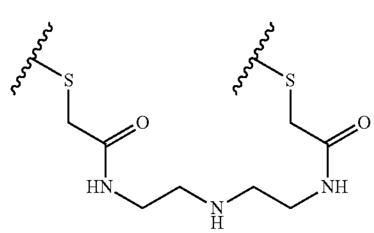 [SMILES: *SCC(=O)NCCNCCNC(=O)CS*] |

TABLE 2-continued
Example Structures
| Ex | ID | Structure |
|---|---|---|
|  | L2 | 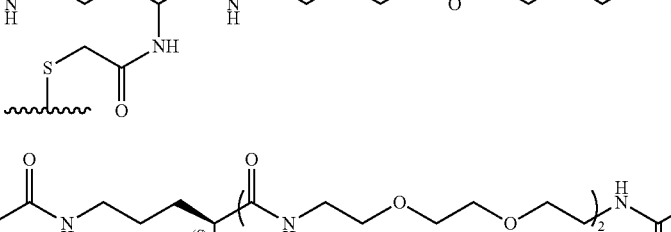 |
| 9 | L3 | 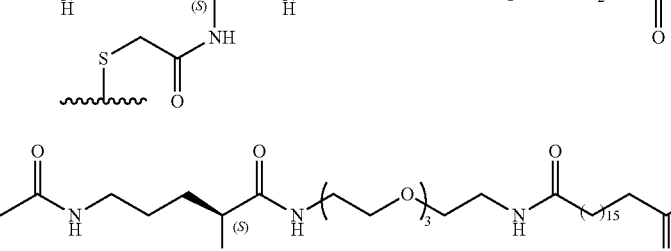 |
| 10 | L4 | 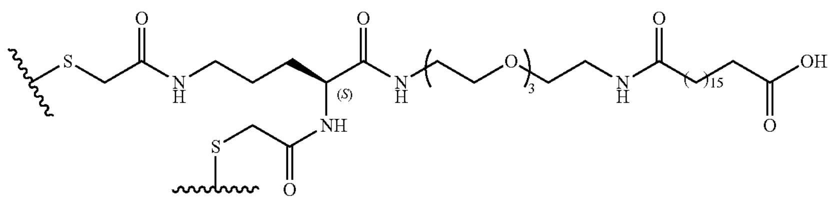 |
| 11 | L4A | 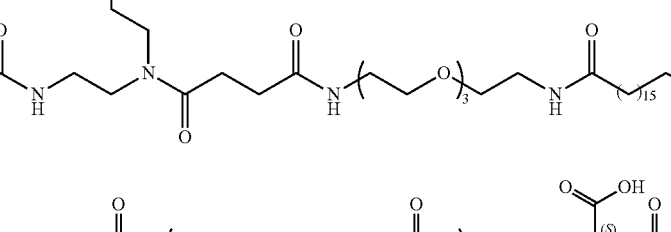 |
| 12 | L5 | 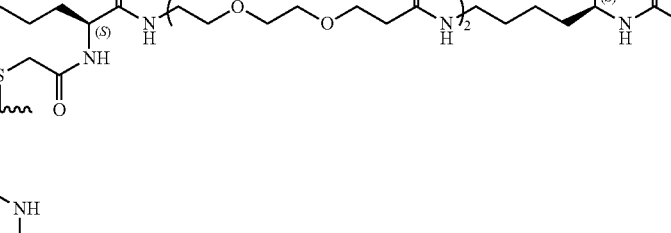 |
| 13 | L5A(S) | 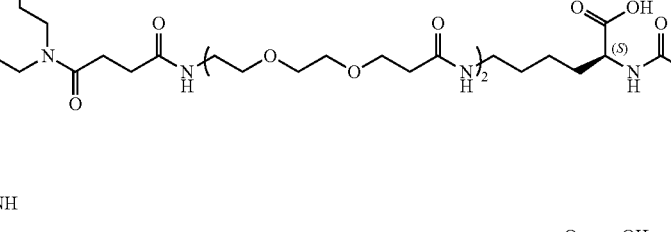 |
|  | L5A | 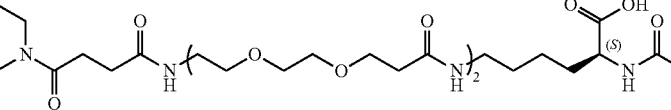 |

TABLE 2-continued
Example Structures
| Ex | ID | Structure |
|---|---|---|
| 13 | C20L5A(S) | 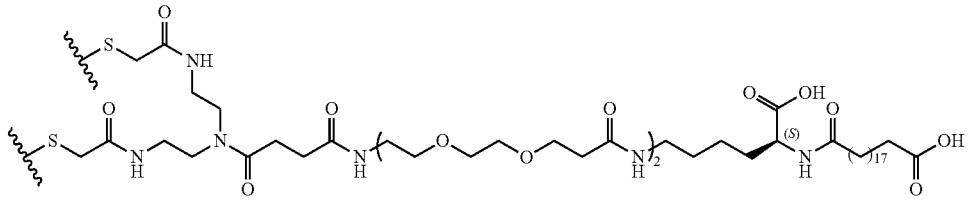 |
|  | C20L5A | 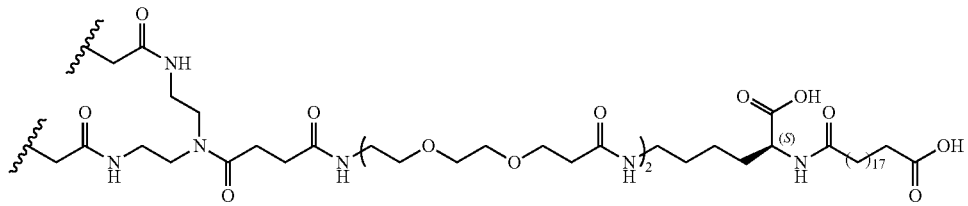 |
|  | C16L5A(S) | 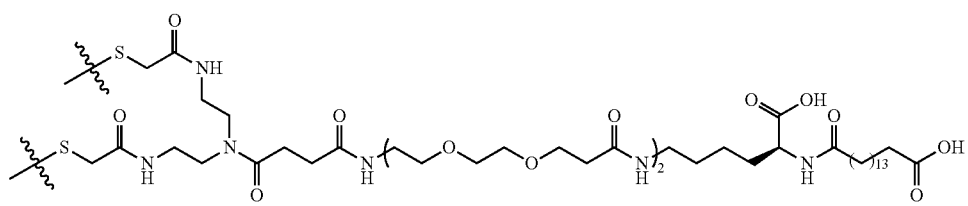 |
|  | C16L5A | 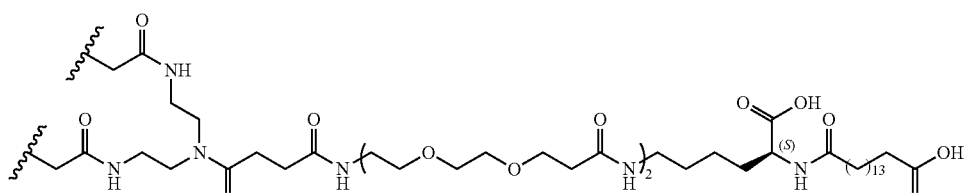 |
| 14 | L6 | 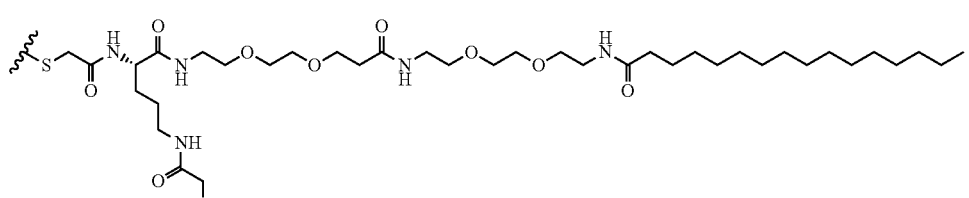 |
| 15 | L7 | 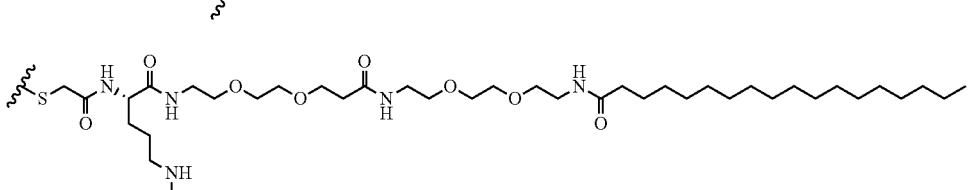 |
| 16 | L8 | 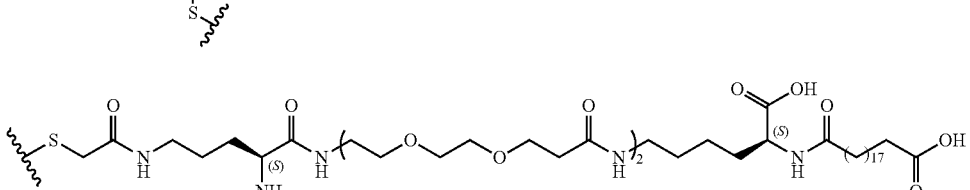 |

TABLE 2-continued
Example Structures
| Ex | ID | Structure |
|---|---|---|
| 17 | L9 | 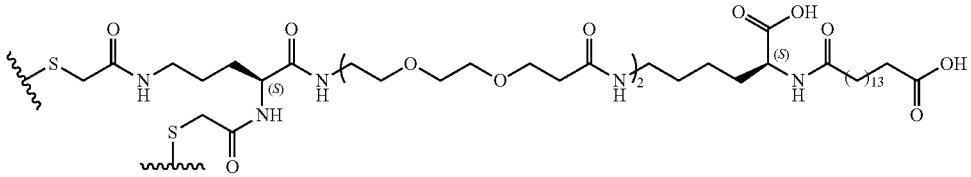 |
| 18 | L12 | 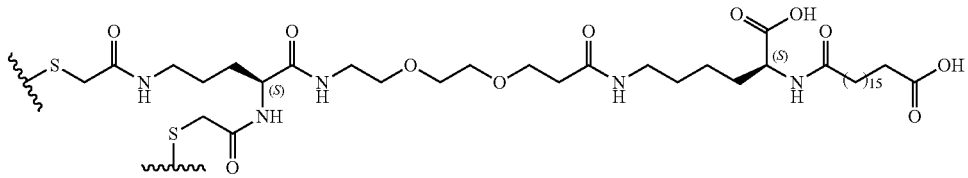 |
|  | L13 | 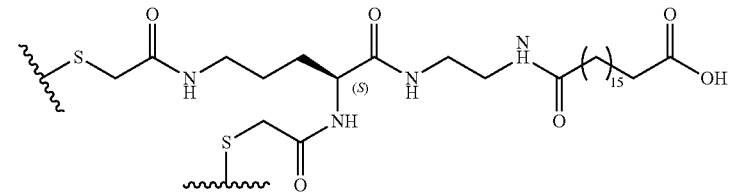 |
| 19 | L14 | 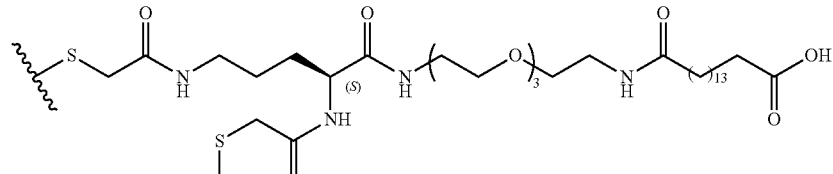 |
| 20 | L15 | 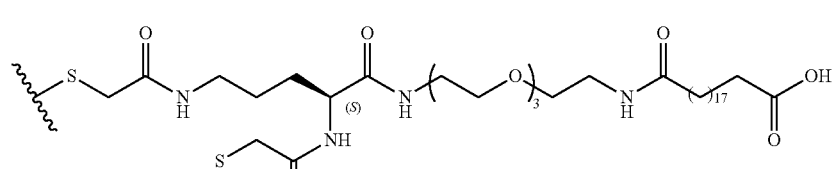 |
| 21 | L16 | 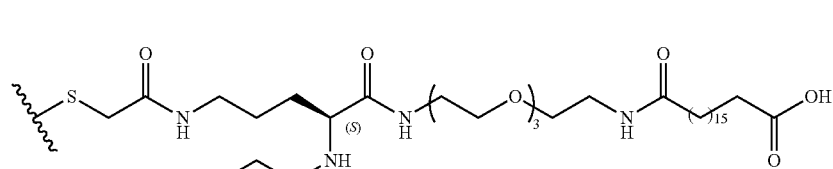 |
| 22 | L17 | 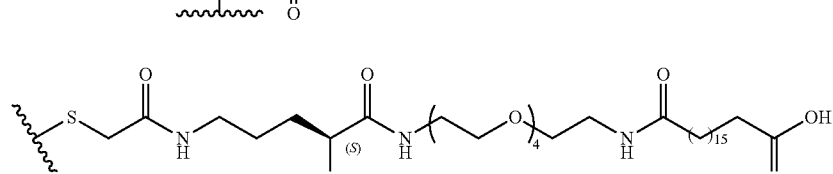 |

TABLE 2-continued

Example Structures

| Ex | ID | Structure |
|----|-----|-----------|
| 23 | L18 | 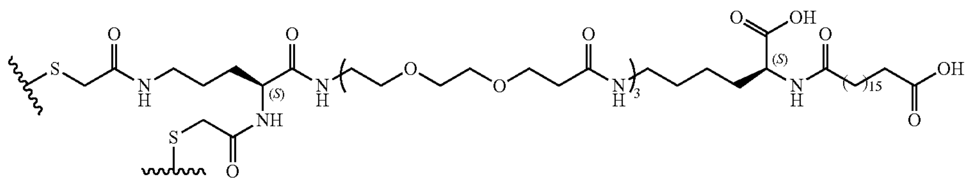 |
|    | L19 | |
|    | K0  | |
|    | K1  | |
|    | K1C | |
|    | K1F | |
|    | K1H | |
|    | K3  | |

TABLE 2-continued

Example Structures

| Ex | ID | Structure |
|----|----|-----------|
| | K4(NH) | |
| | K4 | |
| | K5(NH) | |
| | K5 | |
| | C20K5(NH) | |
| | C20K5 | |
| | K6 | |

TABLE 2-continued

Example Structures

| Ex | ID | Structure |
|----|----|-----------|
| | K7 | |
| | K8 | |
| | K9 | |
| | K20 | |
| | A1 | |
| | A5 | |

The "⸹-S" being part of a cysteine, homocysteine, 2-amino-5-mercaptopentanoic acid, or 2-amino-6-mercaptohexanoic acid residue, and the "⸹-N" being part of a lysine, ornithine, diaminobutyric acid, diaminopropionic acid, or homolysine residue. Each "⸹-" of L5A, C20L5A, C16L5A, K4, K5, and C20K5 is connected to an amino acid of the peptide. For instance, the amino acid is a cysteine, homocysteine, 2-amino-5-mercaptopentanoic acid, 2-amino-6-mercaptohexanoic acid, lysine, ornithine, diaminobutyric acid, diaminopropionic acid, or homolysine residue of the peptide In some embodiments, the peptide comprises a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61. In some embodiments, the peptide comprises a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 1-61.

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61; and
b) a staple comprising Linker L1 attached to the peptide at a first amino acid and a second amino acid.

In some embodiments, a peptide conjugate comprises:
a) a peptide comprising the first 28 amino acids of any one of SEQ ID NOs: 1-61; and
b) a staple comprising Linker L1 attached to the peptide at a first amino acid and a second amino acid.

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61; and
b) a staple comprising Linker L1 attached to the peptide at a first amino acid and a second amino acid.

In some embodiments, a peptide conjugate comprises:
a) a peptide comprising any one of SEQ ID NOs: 1-61; and
b) a staple comprising Linker L1 attached to the peptide at a first amino acid and a second amino acid.

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61; and
b) a staple comprising Linker L2 attached to the peptide at a first amino acid and a second amino acid.

In some embodiments, a peptide conjugate comprises:
a) a peptide comprising the first 28 amino acids of any one of SEQ ID NOs: 1-61; and
b) a staple comprising Linker L2 attached to the peptide at a first amino acid and a second amino acid.

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61; and
b) a staple comprising Linker L2 attached to the peptide at a first amino acid and a second amino acid.

In some embodiments, a peptide conjugate comprises:
a) a peptide comprising any one of SEQ ID NOs: 1-61; and
b) a staple comprising Linker L2 attached to the peptide at a first amino acid and a second amino acid.

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61; and
b) a staple comprising Linker L3 attached to the peptide at a first amino acid and a second amino acid.

In some embodiments, a peptide conjugate comprises:
a) a peptide comprising the first 28 amino acids of any one of SEQ ID NOs: 1-61; and
b) a staple comprising Linker L3 attached to the peptide at a first amino acid and a second amino acid.

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61; and
b) a staple comprising Linker L3 attached to the peptide at a first amino acid and a second amino acid.

In some embodiments, a peptide conjugate comprises:
a) a peptide comprising any one of SEQ ID NOs: 1-61; and
b) a staple comprising Linker L3 attached to the peptide at a first amino acid and a second amino acid.

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61; and
b) a staple comprising

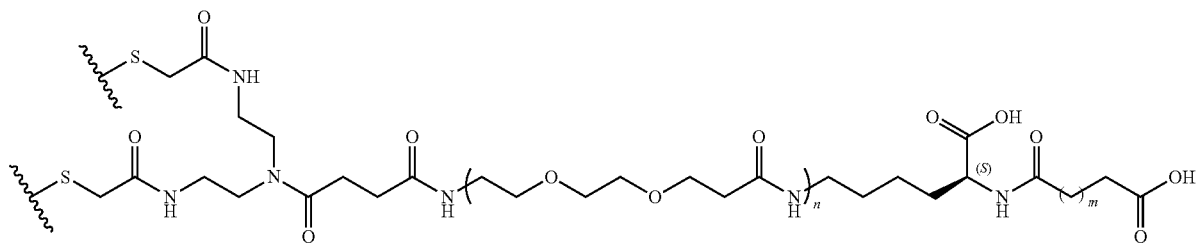

attached to the peptide at a first amino acid and a second amino acid. In some cases, n is 1-4 and m is 6-20. For example, n is 2 and m is 15, n is 2 and m is 17, or n is 2 and m is 13.

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61; and
b) a staple comprising

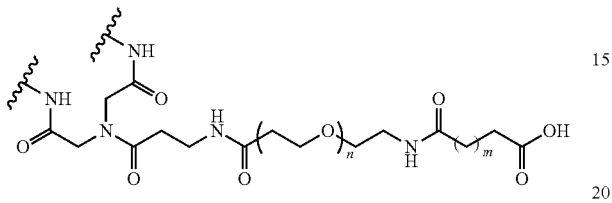

attached to the peptide at a first amino acid and a second amino acid. In some cases, n is 1-4 and m is 6-20. For example, n is 3 and m is 15.

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61; and
b) a staple comprising

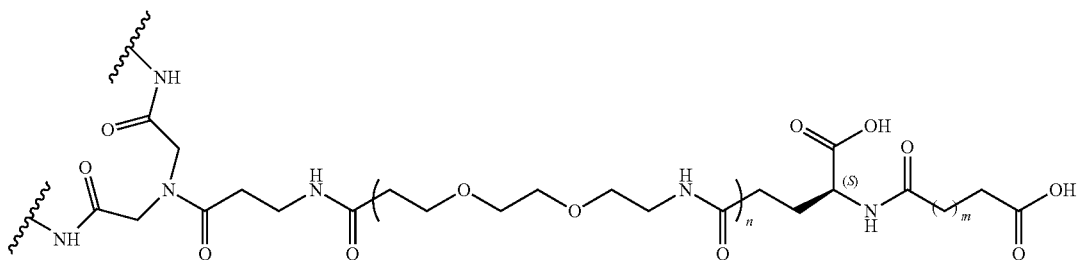

attached to the peptide at a first amino acid and a second amino acid. In some cases, n is 1-4 and m is 6-20. For example, n is 2 and m is 15, or n is 2 and m is 17.

In some embodiments, a peptide conjugate comprises:
a) a peptide comprising the first 28 amino acids of any one of SEQ ID NOs: 1-61; and
b) a staple comprising

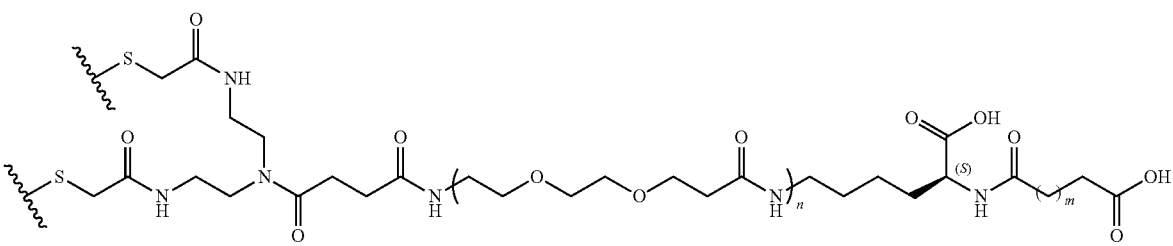

attached to the peptide at a first amino acid and a second amino acid. In some cases, n is 1-4 and m is 6-20. For example, n is 2 and m is 15, n is 2 and m is 17, or n is 2 and m is 13.

In some embodiments, a peptide conjugate comprises:
a) a peptide comprising the first 28 amino acids of any one of SEQ ID NOs: 1-61; and
b) a staple comprising

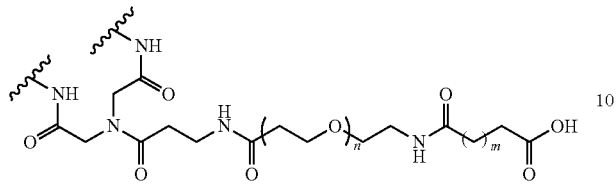

attached to the peptide at a first amino acid and a second amino acid. In some cases, n is 1-4 and m is 6-20. For example, n is 3 and m is 15.

In some embodiments, a peptide conjugate comprises:
a) a peptide comprising the first 28 amino acids of any one of SEQ ID NOs: 1-61; and
b) a staple comprising

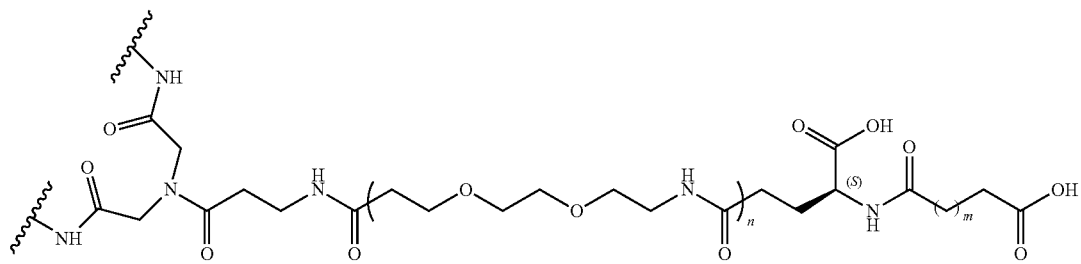

attached to the peptide at a first amino acid and a second amino acid. In some cases, n is 1-4 and m is 6-20. For example, n is 2 and m is 15, or n is 2 and m is 17.

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 1-61; and
b) a staple comprising

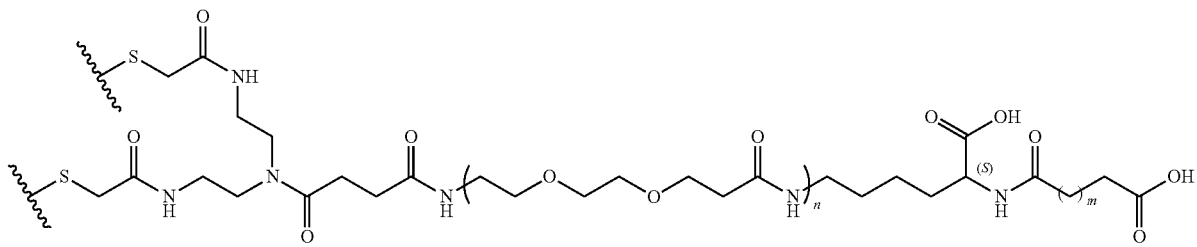

attached to the peptide at a first amino acid and a second amino acid. In some cases, n is 1-4 and m is 6-20. For example, n is 2 and m is 15, n is 2 and m is 17, or n is 2 and m is 13.

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 1-61; and
b) a staple comprising

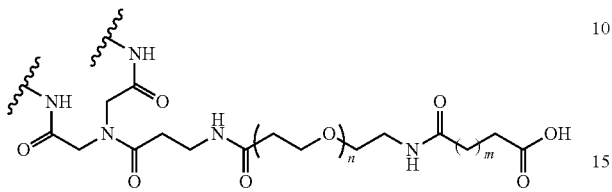

attached to the peptide at a first amino acid and a second amino acid. In some cases, n is 1-4 and m is 6-20. For example, n is 3 and m is 15.

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 1-61; and
b) a staple comprising

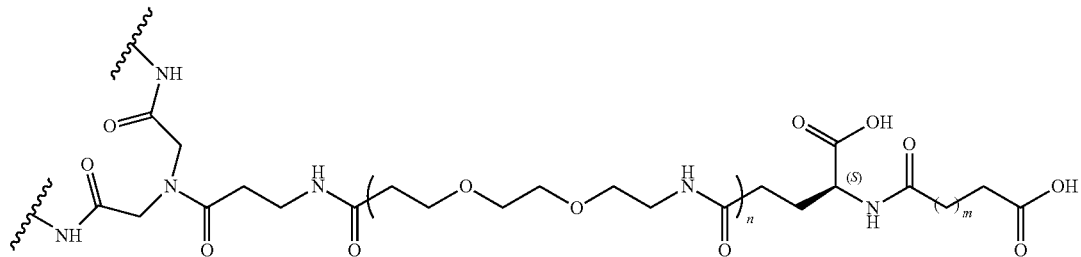

attached to the peptide at a first amino acid and a second amino acid. In some cases, n is 1-4 and m is 6-20. For example, n is 2 and m is 15, or n is 2 and m is 17.

In some embodiments, a peptide conjugate comprises:
a) a peptide comprising the peptide comprises any one of SEQ ID NOs: 1-61; and
b) a staple comprising

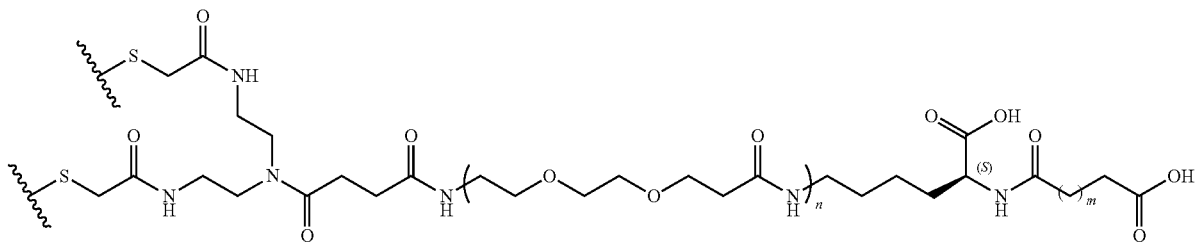

attached to the peptide at a first amino acid and a second amino acid. In some cases, n is 1-4 and m is 6-20. For example, n is 2 and m is 15, n is 2 and m is 17, or n is 2 and m is 13.

In some embodiments, a peptide conjugate comprises:
a) a peptide comprising the peptide comprises any one of SEQ ID NOs: 1-61; and
b) a staple comprising

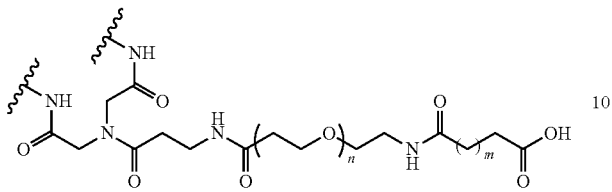

attached to the peptide at a first amino acid and a second amino acid. In some cases, n is 1-4 and m is 6-20. For example, n is 3 and m is 15.

In some embodiments, a peptide conjugate comprises:
a) a peptide comprising the peptide comprises any one of SEQ ID NOs: 1-61; and
b) a staple comprising

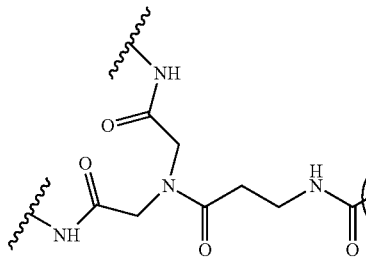

attached to the peptide at a first amino acid and a second amino acid. In some cases, n is 1-4 and m is 6-20. For example, n is 2 and m is 15, or n is 2 and m is 17.

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61; and
b) a staple comprising L5A attached to the peptide at a first amino acid and a second amino acid. In some cases, the L5A is L5A(S).

In some embodiments, a peptide conjugate comprises:
a) a peptide comprising the first 28 amino acids of any one of SEQ ID NOs: 1-61; and
b) a staple comprising L5A attached to the peptide at a first amino acid and a second amino acid. In some cases, the L5A is L5A(S).

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61; and
b) a staple comprising L5A attached to the peptide at a first amino acid and a second amino acid. In some cases, the L5A is L5A(S).

In some embodiments, a peptide conjugate comprises:
a) a peptide comprising any one of SEQ ID NOs: 1-61; and
b) a staple comprising L5A attached to the peptide at a first amino acid and a second amino acid. In some cases, the L5A is L5A(S).

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61; and
b) a staple comprising C16L5A attached to the peptide at a first amino acid and a second amino acid. In some cases, the C16L5A is C16L5A(S).

In some embodiments, a peptide conjugate comprises:
a) a peptide comprising the first 28 amino acids of any one of SEQ ID NOs: 1-61; and
b) a staple comprising C16L5A attached to the peptide at a first amino acid and a second amino acid. In some cases, the C16L5A is C16L5A(S).

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61; and
b) a staple comprising C16L5A attached to the peptide at a first amino acid and a second amino acid. In some cases, the C16L5A is C16L5A(S).

In some embodiments, a peptide conjugate comprises:
a) a peptide comprising any one of SEQ ID NOs: 1-61; and
b) a staple comprising C16L5A attached to the peptide at a first amino acid and a second amino acid. In some cases, the C16L5A is C16L5A(S).

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61; and
b) a staple comprising C20L5A attached to the peptide at a first amino acid and a second amino acid. In some cases, the C20L5A is C20L5A(S).

In some embodiments, a peptide conjugate comprises:
a) a peptide comprising the first 28 amino acids of any one of SEQ ID NOs: 1-61; and
b) a staple comprising C20L5A attached to the peptide at a first amino acid and a second amino acid. In some cases, the C20L5A is C20L5A(S).

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61; and
b) a staple comprising C20L5A attached to the peptide at a first amino acid and a second amino acid. In some cases, the C20L5A is C20L5A(S).

In some embodiments, a peptide conjugate comprises:
a) a peptide comprising any one of SEQ ID NOs: 1-61; and
b) a staple comprising C20L5A attached to the peptide at a first amino acid and a second amino acid. In some cases, the C20L5A is C20L5A(S).

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61; and
b) a staple comprising K4 attached to the peptide at a first amino acid and a second amino acid. In some cases, the K4 is K4(NH).

In some embodiments, a peptide conjugate comprises:
a) a peptide comprising the first 28 amino acids of any one of SEQ ID NOs: 1-61; and
b) a staple comprising K4 attached to the peptide at a first amino acid and a second amino acid. In some cases, the K4 is K4(NH).

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61; and
b) a staple comprising K4 attached to the peptide at a first amino acid and a second amino acid. In some cases, the K4 is K4(NH).

In some embodiments, a peptide conjugate comprises:
a) a peptide comprising any one of SEQ ID NOs: 1-61; and
b) a staple comprising K4 attached to the peptide at a first amino acid and a second amino acid. In some cases, the K4 is K4(NH).

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61; and
b) a staple comprising K5 attached to the peptide at a first amino acid and a second amino acid. In some cases, the K5 is K5(NH).

In some embodiments, a peptide conjugate comprises:
a) a peptide comprising the first 28 amino acids of any one of SEQ ID NOs: 1-61; and
b) a staple comprising K5 attached to the peptide at a first amino acid and a second amino acid. In some cases, the K5 is K5(NH).

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61; and
b) a staple comprising K5 attached to the peptide at a first amino acid and a second amino acid. In some cases, the K5 is K5(NH).

In some embodiments, a peptide conjugate comprises:
a) a peptide comprising any one of SEQ ID NOs: 1-61; and
b) a staple comprising K5 attached to the peptide at a first amino acid and a second amino acid. In some cases, the K5 is K5(NH).

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61; and
b) a staple comprising C20K5 attached to the peptide at a first amino acid and a second amino acid. In some cases, the C20K5 is C20K5(NH).

In some embodiments, a peptide conjugate comprises:
a) a peptide comprising the first 28 amino acids of any one of SEQ ID NOs: 1-61; and
b) a staple comprising C20K5 attached to the peptide at a first amino acid and a second amino acid. In some cases, the C20K5 is C20K5(NH).

In some embodiments, a peptide conjugate comprises:
a) a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61; and
b) a staple comprising C20K5 attached to the peptide at a first amino acid and a second amino acid. In some cases, the C20K5 is C20K5(NH).

In some embodiments, a peptide conjugate comprises:
a) a peptide comprising any one of SEQ ID NOs: 1-61; and
b) a staple comprising C20K5 attached to the peptide at a first amino acid and a second amino acid. In some cases, the C20K5 is C20K5(NH).

In some embodiments, a peptide conjugate described herein is as shown in Table 3.

TABLE 3

Peptide Conjugates

| Conjugate | Sequence | Con-jugation position | Staple | Calc mass [M + 4H]$^{4+}$ | Mass found |
|---|---|---|---|---|---|
| mCMD307 (2050-K4) | YAibEGT-FTSDY-SIYXD-KQAAAib-XFVNW-LLAGG-PSSGA-PPPS-NH2 (where each X is K) (SEQ ID NO: 39) | 14, 21 | K4 | 1197.86 | 1197.87 |
| mCLZ715 | YAibEGT-FTSDY-SIYXD-KQAAAib-XFVNW-LLAGG-PSSGA-PPPS-NH2 (where each X is K) (SEQ ID NO: 40) | 14, 21 | K5 | 1259.14 | 1258.9 |

TABLE 3-continued

Peptide Conjugates

| Conjugate | Sequence | Conjugation position | Staple | Calc mass [M + 4H]$^{4+}$ | Mass found |
|---|---|---|---|---|---|
| mCMD307 C20K5 ZA-39- C20K5 | YAibEGT-FTSDY-SIYXD-KQAAAib-XFVNW-LLAGG-PSSGA-PPPS-NH2 (where each X is K) (SEQ ID NO: 41) | 14, 21 | C20K5 | 1265.91 | 1266.41 |
| mCLZ715- C20K5 ZA-40-/ C20K5 | YAibEGT-FTSDY-SIYLD-KXAAAib-EFVXW-LLAGG-PSSGA-PPPS-NH2 (where each X is K) (SEQ ID NO: 42) | 17, 24 | C20K5 | 1265.91 | 1266.42 |
| mCMG681K4 | YAibEGT-FHSDY-DIYXD-KQAAAib-XFVQW-LLAGG-PSSGA-PPPS-NH2 (where each X is K) (SEQ ID NO: 43) | 14, 21 | K4 | 1217.87 | 1217.96 |
| mCMG679K4 | YAibEGT-FHSDY-DIYXD-KQAANle-XFVAW-LLAGG-PSSGA-PPPS-NH2 (where each X is K) (SEQ ID NO: 44) | 14, 21 | K4 | 1210.62 | 1210.94 |
| mCMG683K4 | YAibEGT-FTsDY-SIYXD-KQAANle-XFVAW-LLAGG-PSSGA-PPPS-NH2 (where each X is K) (SEQ ID NO: 45) | 14, 21 | K4 | 1194.37 | 1194.70 |
| mCMG682K5 | YAibEGT-FHSDY-DIYXD-KQAAAib-XFVQW-LLAGG-PSSGA-PPPS-NH2 (where each X is K) (SEQ ID NO: 46) | 14, 21 | K5 | 1278.89 | 1279.32 |
| mCMG680K5 | YAibEGT-FHSDY-DIYXD-KQAANle-XFVAW-LLAGG-PSSGA-PPPS-NH2 (where each X is K) (SEQ ID NO: 47) | 14, 21 | K5 | 1271.65 | 1271.73 |
| mCMG684K5 | YAibEGT-FTsDY-SIYXD-KQAANle-XFVAW-LLAGG-PSSGA-PPPS-NH2 (where each X is K) (SEQ ID NO: 48) | 14, 21 | K5 | 1255.65 | 1255.99 |
| mCMC759 (C(14-21)- L5A) | YAibEGT-FTSDY-SIYXD-KQAAAib-XFVNW-LLAGG-PSSGA-PPPS-NH2 (where each X is C) (SEQ ID NO: 49) | 14, 21 | L5A | 1274.88 | 1275.13 |
| C(14-21)- C20L5A | YAibEGT-FTSDY-SIYXD-KQAAAib-XFVNW-LLAGG-PSSGA-PPPS-NH2 (where each X is C) (SEQ ID NO: 50) | 14, 21 | C20L5A | 1281.89 | |
| 27I, C(14-21)-L5A | YAibEGT-FTSDY-SIYXD-KQAAAib-XFVNW-LIAGG-PSSGA-PPPS-NH2 (where each X is C) (SEQ ID NO: 51) | 14, 21 | L5A | 1274.88 | |
| mCMV266 (27I, C(14-21)- C20L5A) | YAibEGT-FTSDY-SIYXD-KQAAAib-XFVNW-LIAGG-PSSGA-PPPS-NH2 (where each X is C) (SEQ ID NO: 52) | 14, 21 | C20L5A | 1281.89 | 1282.20 |

TABLE 3-continued

Peptide Conjugates

| Conjugate | Sequence | Conjugation position | Staple | Calc mass [M + 4H]$^{4+}$ | Mass found |
|---|---|---|---|---|---|
| 71, 10V, 27I, C(14-21)-L5A | YAibEGT-FISDV-SIYXD-KQAAAib-XFVNW-LIAGG-PSSGA-PPPS-NH2 (where each X is C) (SEQ ID NO: 53) | 14, 21 | L5A | 1261.89 | |
| 71, 10V, 27I, C(14-21)-C20L5A | YAibEGT-FISDV-SIYXD-KQAAAib-XFVNW-LIAGG-PSSGA-PPPS-NH2 (where each X is C) (SEQ ID NO: 54) | 14, 21 | C20L5A | 1268.90 | |
| C(17-24)-L5A | YAibEGT-FTSDY-SIYLD-KXAAAib-EFVXW-LLAGG-PSSGA-PPPS-NH2 (where each X is C) (SEQ ID NO: 55) | 17, 24 | L5A | 1275.13 | |
| C(17-24)-C20L5A | YAibEGT-FTSDY-SIYLD-KXAAAib-EFVXW-LLAGG-PSSGA-PPPS-NH2 (where each X is C) (SEQ ID NO: 56) | 17, 24 | C20L5A | 1282.14 | |
| 19Q, 21A, 27I, 29Q, C(17-24)-C20L5A | YAibEGT-FTSDY-SIYLD-KXAQAib-AFVXW-LIAQG-PSSGA-PPPS-NH2 (where each X is C) (SEQ ID NO: | 17, 24 | C20L5A | 1299.40 | |
| 6Y, 27I, C(14-21)-C20L5A | YAibEGT-YTSDY-SIYXD-KQAAAib-XFVNW-LIAGG-PSSGA-PPPS-NH2 (where each X is C) (SEQ ID NO: 58) | 14, 21 | C20L5A | 1285.64 | |
| 6Y, 27I, C(17-24)-C20L5A | YAibEGT-YTSDY-SIYLD-KXAAAib-EFVXW-LIAGG-PSSGA-PPPS-NH2 (where each X is C) (SEQ ID NO: 59) | 17, 24 | C20L5A | 1285.89 | |
| 6Y, 8N, 27I, C(17-24)-C20L5A | YAibEGT-YTNDY-SIYLD-KXAAAib-EFVXW-LIAGG-PSSGA-PPPS-NH2 (where each X is C) (SEQ ID NO: 60) | 17, 24 | C20L5A | 1292.64 | |
| mCMV268 (27I, C(17-24)-C20L5A) | YAibEGT-FTSDY-SIYLD-KXAAAib-EFVXW-LIAGG-PSSGA-PPPS-NH2 (where each X is C) (SEQ ID NO: 61) | 17, 24 | C20L5A | 1282.14 | 1282.20 |
| mCMZ370 (C(14-21)-L5A(S)) | YAibEGT-FTSDY-SIYXD-KQAAAib-XFVNW-LIAGG-PSSGA-PPPS-NH2 (where each X is C) (SEQ ID NO: 52) | 14, 21 | L5A(S) | | |
| mCMZ371 (C(17-24)-L5A(S)) | YAibEGT-FTSDY-SIYLD-KXAAAib-EFVXW-LIAGG-PSSGA-PPPS-NH2 (where each X is C) (SEQ ID NO: 61) | 17, 24 | L5A(S) | | |

An example peptide conjugate is shown below, where the —NH— is part of the Lys (K) in the peptide. The example below discloses SEQ ID NO: 62.

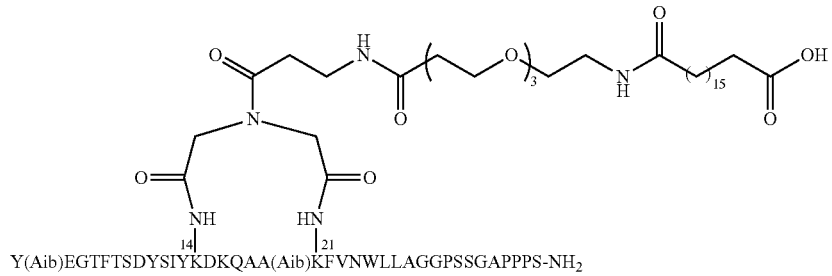

Y(Aib)EGTFTSDYSIYKDKQAA(Aib)KFVNWLLAGGPSSGAPPPS-NH₂

Another example peptide conjugate is shown below.

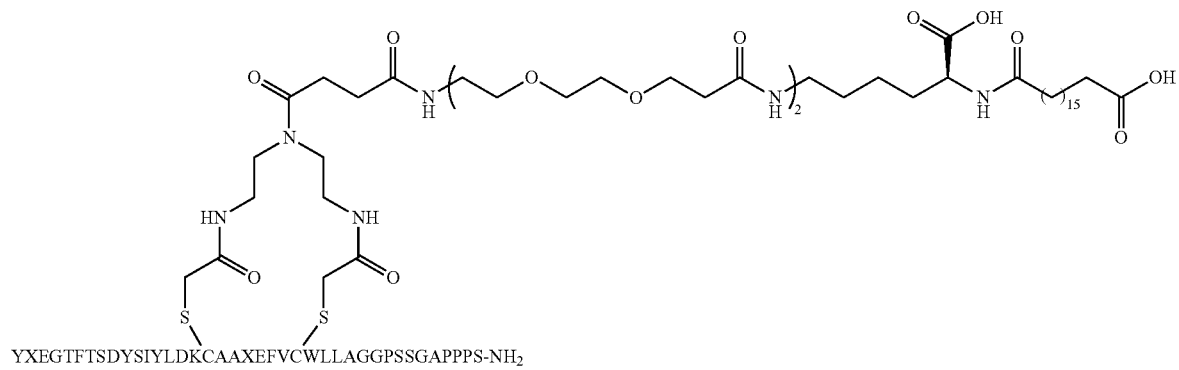

YXEGTFTSDYSIYLDKCAAXEFVCWLLAGGPSSGAPPPS-NH₂

X = Aib

A further example peptide conjugate is shown below.

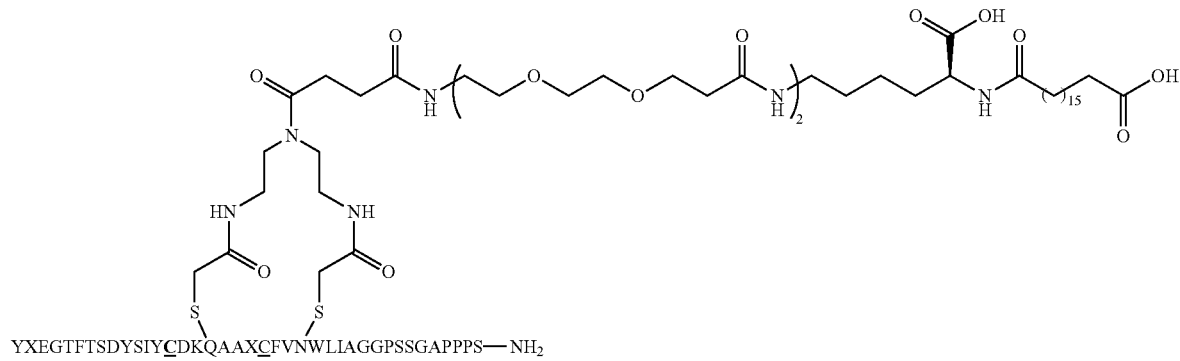

YXEGTFTSDYSIYCDKQAAXCFVNWLIAGGPSSGAPPPS—NH₂ mCMZ370

X = Aib

Non-Limiting Example Peptide and Peptide Conjugate Embodiments

1. A peptide conjugate comprising:
   a) a peptide; and
   b) a staple attached to the peptide at a first amino acid and a second amino acid;
   wherein the staple is of Formula (I):

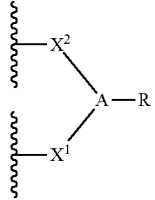

Formula (I)

wherein
   A is —N—;
   $X^1$ and $X^2$ are a bond, —C(=O)—, -alkylene-C(=O)—, —C(=O)-alkylene-, -alkylene-C(=O)NR$^3$—, -alkylene-NR$^3$C(=O)—, —C(=O)NR$^3$-alkylene-, —NR$^3$C(=O)-alkylene-, -alkylene-C(=O)NR$^3$—alkylene-, or -alkylene-NR$^3$C(=O)-alkylene-;
   wherein $X^1$ is attached to the first amino acid of the peptide, $X^2$ is attached to the second amino acid of the peptide, and $X^1$ and $X^2$ are identical;
   R is hydrogen or -(L)$_s$-Y;
   each L is independently —(CR$^1$R$^2$)$_v$—, -alkylene-O—, —O-alkylene-, —C(=O)-alkylene-, -alkylene-C(=O)—, —NR$^3$-alkylene-, -alkylene-NR$^3$—, —S-alkylene-, -alkylene-S—, —S(=O)-alkylene-, -alkylene-S(=O)—, —S(=O)$_2$-alkylene, -alkylene-S(=O)$_2$—, —C(=O)—, —C(=O)NR$^3$—, —NR$^3$C(=O)—, —NR$^3$C(=O)NR$^3$—, —NR$^3$C(=O)NR$^3$-alkylene-, —NR$^3$C(=O)-alkylene-NR$^3$—, -alkylene-C(=O)NR$^3$—, —C(=O)NR$^3$-alkylene-, -alkylene-NR$^3$C(=O)—, or —NR$^3$C(=O)-alkylene-;
   v is 2-20;
   each $R^1$ or $R^2$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;
   or $R^1$ and $R^2$ are taken together to form a $C_1$-$C_6$ cycloalkyl or $C_1$-$C_6$ heterocycloalkyl;
   each $R^3$ is independently hydrogen, —S(=O)R$^b$, —S(=O)$_2$R$^a$, —S(=O)$_2$NR$^c$R$^d$, —C(=O)R$^b$, —CO$_2$R$^a$, —C(=O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;
   Y is hydrogen, $C_1$-$C_6$ alkyl, —CO$_2$H, —CO$_2$($C_1$-$C_6$ alkyl), —CO$_2$NH$_2$, —CO$_2$N(alkyl)$_2$, or —CO$_2$NH(alkyl);
   s is 0-20;
   $R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;
   $R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$; and
   each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;
   or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —NH$_2$.

2. The peptide conjugate of embodiment 1, wherein the first amino acid and the second amino acid are independently a sulfydryl containing amino acid.

3. The peptide conjugate of embodiment 1 or embodiment 2, wherein the first amino acid and the second amino acid are independently selected from cysteine, homocysteine, 2-amino-5-mercaptopentanoic acid, and 2-amino-6-mercaptohexanoic acid.

4. The peptide conjugate of any one of embodiments 1-3, wherein the first amino acid and second amino acids are cysteines.

5. The peptide conjugate of embodiment 1, wherein the first amino acid and the second amino acid are independently an amine-containing amino acid.

6. The peptide conjugate of embodiment 5, wherein the amine-containing amino acid is selected from lysine, ornithine, diaminobutyric acid, diaminopropionic acid and homolysine.

7. The peptide conjugate of embodiment 5 or 6, wherein the first amino acid and the second amino acids are lysines.

8. The peptide conjugate of any one of embodiments 1-7, wherein the first amino acid has a position i in the peptide and the second amino acid has a position i+n in the peptide, wherein n is 4-16.

9. The peptide conjugate of any one of embodiments 1-7, wherein the first amino acid has a position i in the peptide and the second amino acid has a position i+4 in the peptide.

10. The peptide conjugate of any one of embodiments 1-7, wherein the first amino acid has a position i in the peptide and the second amino acid has a position i+7 in the peptide.
11. The peptide conjugate of any one of embodiments 1-7, wherein the first amino acid has a position i in the peptide and the second amino acid has a position i+11 in the peptide.
12. The peptide conjugate of any one of embodiments 1-7, wherein the first amino acid has a position i in the peptide and the second amino acid has a position i+15 in the peptide.
13. The peptide conjugate of any one of embodiments 1-7, wherein the first amino acid has a position i in the peptide and the second amino acid has a position i+16 in the peptide.
14. The peptide conjugate of any one of embodiments 1-13, wherein the peptide modulates a GLP-1 receptor.
15. The peptide conjugate of any one of embodiments 1-14, wherein the peptide binds to a GLP-1 receptor.
16. The peptide conjugate of any one of embodiments 1-15, wherein the peptide modulates a GIP receptor.
17. The peptide conjugate of any one of embodiments 1-16, wherein the peptide binds to a GIP receptor.
18. The peptide conjugate of any one of embodiments 1-17, wherein the peptide is a GLP-1 receptor agonist.
19. The peptide conjugate of any one of embodiments 1-18, wherein the peptide is a GIP receptor agonist.
20. The peptide conjugate of any one of embodiments 1-19, wherein the peptide is a dual GLP-1 receptor and GIP receptor agonist.
21. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61.
22. The peptide conjugate of any one of embodiments 1-20, wherein the peptide comprises the first 28 amino acids of any one of SEQ ID NOs: 1-61.
23. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 1-61.
24. The peptide conjugate of any one of embodiments 1-20, wherein the peptide comprises any one of SEQ ID NOs: 1-61.
25. The peptide conjugate of any one of embodiments 21-24, wherein each X is independently selected from a sulfhydryl-containing amino acid and an amine-containing amino acid.
26. The peptide conjugate of any one of embodiments 21-25, wherein each X is a cysteine.
27. The peptide conjugate of any one of embodiments 21-25, wherein each X is a lysine.
28. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 1.
29. The peptide conjugate of any one of embodiments 1-20, wherein the peptide comprises the first 28 amino acids of SEQ ID NO: 1.
30. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1.
31. The peptide conjugate of any one of embodiments 1-20, wherein the peptide comprises SEQ ID NO: 1.
32. The peptide conjugate of any one of embodiments 28-31, wherein each X is independently selected from a sulfhydryl-containing amino acid and an amine-containing amino acid.
33. The peptide conjugate of any one of embodiments 28-31, wherein each X is a cysteine.
34. The peptide conjugate of any one of embodiments 28-31, wherein each X is a lysine.
35. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 2.
36. The peptide conjugate of any one of embodiments 1-20, wherein the peptide comprises the first 28 amino acids of SEQ ID NO: 2.
37. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2.
38. The peptide conjugate of any one of embodiments 1-20, wherein the peptide comprises SEQ ID NO: 2.
39. The peptide conjugate of any one of embodiments 35-38, wherein each X is independently selected from a sulfhydryl-containing amino acid and an amine-containing amino acid.
40. The peptide conjugate of any one of embodiments 35-38, wherein each X is a cysteine.
41. The peptide conjugate of any one of embodiments 35-38, wherein each X is a lysine.
42. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 3.
43. The peptide conjugate of any one of embodiments 1-20, wherein the peptide comprises the first 28 amino acids of SEQ ID NO: 3.
44. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3.
45. The peptide conjugate of any one of embodiments 1-20, wherein the peptide comprises SEQ ID NO: 3.
46. The peptide conjugate of any one of embodiments 42-45, wherein each X is independently selected from a sulfhydryl-containing amino acid and an amine-containing amino acid.
47. The peptide conjugate of any one of embodiments 42-45, wherein each X is a cysteine.
48. The peptide conjugate of any one of embodiments 42-45, wherein each X is a lysine.
49. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 4.
50. The peptide conjugate of any one of embodiments 1-20, wherein the peptide comprises the first 28 amino acids of SEQ ID NO: 4.
51. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 4.
52. The peptide conjugate of any one of embodiments 1-20, wherein the peptide comprises SEQ ID NO: 4.

53. The peptide conjugate of any one of embodiments 49-52, wherein each X is independently selected from a sulfhydryl-containing amino acid and an amine-containing amino acid.
54. The peptide conjugate of any one of embodiments 49-52, wherein each X is a cysteine.
55. The peptide conjugate of any one of embodiments 49-52, wherein each X is a lysine.
56. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 5.
57. The peptide conjugate of any one of embodiments 1-20, wherein the peptide comprises the first 28 amino acids of SEQ ID NO: 5.
58. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 5.
59. The peptide conjugate of any one of embodiments 1-20, wherein the peptide comprises SEQ ID NO: 5.
60. The peptide conjugate of any one of embodiments 56-59, wherein each X is independently selected from a sulfhydryl-containing amino acid and an amine-containing amino acid.
61. The peptide conjugate of any one of embodiments 56-59, wherein each X is a cysteine.
62. The peptide conjugate of any one of embodiments 56-59, wherein each X is a lysine.
63. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 6.
64. The peptide conjugate of any one of embodiments 1-20, wherein the peptide comprises the first 28 amino acids of SEQ ID NO: 6.
65. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 6.
66. The peptide conjugate of any one of embodiments 1-20, wherein the peptide comprises SEQ ID NO: 6.
67. The peptide conjugate of any one of embodiments 63-66, wherein each X is independently selected from a sulfhydryl-containing amino acid and an amine-containing amino acid.
68. The peptide conjugate of any one of embodiments 63-66, wherein each X is a cysteine.
69. The peptide conjugate of any one of embodiments 63-66, wherein each X is a lysine.
70. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 7.
71. The peptide conjugate of any one of embodiments 1-20, wherein the peptide comprises the first 28 amino acids of SEQ ID NO: 7.
72. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7.
73. The peptide conjugate of any one of embodiments 1-20, wherein the peptide comprises SEQ ID NO: 7.
74. The peptide conjugate of any one of embodiments 70-73, wherein each X is independently selected from a sulfhydryl-containing amino acid and an amine-containing amino acid.
75. The peptide conjugate of any one of embodiments 70-73, wherein each X is a cysteine.
76. The peptide conjugate of any one of embodiments 70-73, wherein each X is a lysine.
77. The peptide conjugate of any one of embodiments 70-76, wherein aa6 is alpha-methyl Phe, N-methyl Phe, D-Phe, beta3-Phe, alpha-methyl Phe, alpha-methyl Phe (2-F), alpha-methyl Phe (3-F), and alpha-methyl (4-F), Phe (2-F), Phe (3-F), or Phe (4-F).
78. The peptide conjugate of any one of embodiments 70-77, wherein aa10 is alpha-methyl Tyr, N-methyl Tyr, D-Tyr, beta3-Tyr, 4-Pyr-Ala, Phe (2-F), Phe (3-F), or Phe (4-F).
79. The peptide conjugate of any one of embodiments 70-78, wherein aa13 is alpha-methyl Leu, N-methyl Leu, D-Leu, beta3-Leu, Leu, Val, Ile, Aib, alpha-methyl Tyr, N-methyl Tyr, D-Tyr, beta3-Tyr, 4-Pyr-Ala, Phe (2-F), Phe (3-F), or Phe (4-F).
80. The peptide conjugate of any one of embodiments 70-79, wherein aa16 is L-Orn, alpha-methyl Lys, N-methyl Lys, D-Lys, or beta3-Lys.
81. The peptide conjugate of any one of embodiments 70-80, wherein aa25 is alpha-methyl Trp, N-methyl Trp, D-Trp, beta3-Trp, alpha-methyl Tyr, or Aib.
82. The peptide conjugate of any one of embodiments 70-81, wherein aa33 is A or E.
83. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 8.
84. The peptide conjugate of any one of embodiments 1-20, wherein the peptide comprises the first 28 amino acids of SEQ ID NO: 8.
85. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8.
86. The peptide conjugate of any one of embodiments 1-20, wherein the peptide comprises SEQ ID NO: 8.
87. The peptide conjugate of any one of embodiments 83-86, wherein each X is independently selected from a sulfhydryl-containing amino acid and an amine-containing amino acid.
88. The peptide conjugate of any one of embodiments 83-86, wherein each X is a cysteine.
89. The peptide conjugate of any one of embodiments 83-86, wherein each X is a lysine.
90. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 9.
91. The peptide conjugate of any one of embodiments 1-20, wherein the peptide comprises the first 28 amino acids of SEQ ID NO: 9.
92. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9.
93. The peptide conjugate of any one of embodiments 1-20, wherein the peptide comprises SEQ ID NO: 9.

94. The peptide conjugate of any one of embodiments 90-93, wherein each X is independently selected from a sulfhydryl-containing amino acid and an amine-containing amino acid.

95. The peptide conjugate of any one of embodiments 90-93, wherein each X is a cysteine.

96. The peptide conjugate of any one of embodiments 90-93, wherein each X is a lysine.

97. The peptide conjugate of any one of embodiments 90-96, wherein aa6 is alpha-methyl Phe, N-methyl Phe, D-Phe, beta3-Phe, alpha-methyl Phe (2-F), alpha-methyl Phe (3-F), and alpha-methyl (4-F), Phe (2-F), Phe (3-F), or Phe (4-F).

98. The peptide conjugate of any one of embodiments 90-97, wherein aa10 is alpha-methyl Tyr, N-methyl Tyr, D-Tyr, beta3-Tyr, 4-Pyr-Ala, Phe (2-F), Phe (3-F), Phe (4-F), or 4-pyridyl-Ala.

99. The peptide conjugate of any one of embodiments 90-98, wherein aa13 is alpha-methyl Leu, N-methyl Leu, D-Leu, beta3-Leu, Val, Ile, or Aib.

100. The peptide conjugate of any one of embodiments 90-99, wherein aa16 is alpha-methyl Leu, N-methyl Leu, D-Leu, beta3-Leu, Val, Ile, or Aib.

101. The peptide conjugate of any one of embodiments 90-100, wherein aa24 is alpha-methyl Asn, N-methyl Asn, beta3-Asn, Aib, D-Asn, D-Asp, D-Glu, or D-Gln 102. The peptide conjugate of any one of embodiments 90-101, wherein aa25 is alpha-methyl Trp, N-methyl Trp, D-Trp, beta3-Trp, alpha-methyl Tyr, or Aib.

103. The peptide conjugate of any one of embodiments 90-102, wherein aa33 is A or E.

104. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 10.

105. The peptide conjugate of any one of embodiments 1-20, wherein the peptide comprises the first 28 amino acids of SEQ ID NO: 10.

106. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 10.

107. The peptide conjugate of any one of embodiments 1-20, wherein the peptide comprises SEQ ID NO: 10.

108. The peptide conjugate of any one of embodiments 104-107, wherein each X is independently selected from a sulfhydryl-containing amino acid and an amine-containing amino acid.

109. The peptide conjugate of any one of embodiments 104-107, wherein each X is a cysteine.

110. The peptide conjugate of any one of embodiments 104-107, wherein each X is a lysine.

111. The peptide conjugate of any one of embodiments 104-110, wherein aa2 is Gly, Val, Leu, Ile, or Aib.

112. The peptide conjugate of any one of embodiments 104-111, wherein aa20 is Gly, Val, Leu, Ile, or Aib.

113. The peptide conjugate of any one of embodiments 104-112, wherein aa13 is alpha-methyl Leu, N-methyl Leu, D-Leu, beta3-Leu, Leu, Val, Ile, Aib, alpha-methyl Tyr, N-methyl Tyr, D-Tyr, beta3-Tyr, 4-Pyr-Ala, Phe (2-F), Phe (3-F), or Phe (4-F).

114. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 11.

115. The peptide conjugate of any one of embodiments 1-20, wherein the peptide comprises the first 28 amino acids of SEQ ID NO: 11.

116. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 11.

117. The peptide conjugate of any one of embodiments 1-20, wherein the peptide comprises SEQ ID NO: 11.

118. The peptide conjugate of any one of embodiments 114-117, wherein each X is independently selected from a sulfhydryl-containing amino acid and an amine-containing amino acid.

119. The peptide conjugate of any one of embodiments 114-117, wherein each X is a cysteine.

120. The peptide conjugate of any one of embodiments 114-117, wherein each X is a lysine.

121. The peptide conjugate of any one of embodiments 114-120, wherein aa2 is Gly, Val, Leu, Ile, or Aib.

122. The peptide conjugate of any one of embodiments 114-121, wherein aa20 is Gly, Val, Leu, Ile, or Aib.

123. The peptide conjugate of any one of embodiments 114-122, wherein aa13 is alpha-methyl Leu, N-methyl Leu, D-Leu, beta3-Leu, Leu, Val, Ile, Aib, alpha-methyl Tyr, N-methyl Tyr, D-Tyr, beta3-Tyr, 4-Pyr-Ala, Phe (2-F), Phe (3-F), or Phe (4-F).

124. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 12.

125. The peptide conjugate of any one of embodiments 1-20, wherein the peptide comprises the first 28 amino acids of SEQ ID NO: 12.

126. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 12.

127. The peptide conjugate of any one of embodiments 1-20, wherein the peptide comprises SEQ ID NO: 12.

128. The peptide conjugate of any one of embodiments 124-127, wherein each X is independently selected from a sulfhydryl-containing amino acid and an amine-containing amino acid.

129. The peptide conjugate of any one of embodiments 124-127, wherein each X is a cysteine.

130. The peptide conjugate of any one of embodiments 124-127, wherein each X is a lysine.

131. The peptide conjugate of any one of embodiments 124-130, wherein aa2 is Gly, Val, Leu, Ile, or Aib.

132. The peptide conjugate of any one of embodiments 124-131, wherein aa20 is Gly, Val, Leu, Ile, or Aib.

133. The peptide conjugate of any one of embodiments 124-132, wherein aa13 is alpha-methyl Leu, N-methyl Leu, D-Leu, beta3-Leu, Leu, Val, Ile, Aib, alpha-methyl Tyr, N-methyl Tyr, D-Tyr, beta3-Tyr, 4-Pyr-Ala, Phe (2-F), Phe (3-F), or Phe (4-F).

134. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 13.

135. The peptide conjugate of any one of embodiments 1-20, wherein the peptide comprises the first 28 amino acids of SEQ ID NO: 13.

136. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 13.

137. The peptide conjugate of any one of embodiments 1-20, wherein the peptide comprises SEQ ID NO: 13.

138. The peptide conjugate of any one of embodiments 134-137, wherein each X is independently selected from a sulfhydryl-containing amino acid and an amine-containing amino acid.

139. The peptide conjugate of any one of embodiments 134-137, wherein each X is a cysteine.

140. The peptide conjugate of any one of embodiments 134-137, wherein each X is a lysine.

141. The peptide conjugate of any one of embodiments 134-140, wherein aa2 is Gly, Val, Leu, Ile, or Aib.

142. The peptide conjugate of any one of embodiments 134-141, wherein aa20 is Gly, Val, Leu, Ile, or Aib.

143. The peptide conjugate of any one of embodiments 134-142, wherein aa13 is alpha-methyl Leu, N-methyl Leu, D-Leu, beta3-Leu, Leu, Val, Ile, Aib, alpha-methyl Tyr, N-methyl Tyr, D-Tyr, beta3-Tyr, 4-Pyr-Ala, Phe (2-F), Phe (3-F), or Phe (4-F).

144. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 14.

145. The peptide conjugate of any one of embodiments 1-20, wherein the peptide comprises the first 28 amino acids of SEQ ID NO: 14.

146. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 14.

147. The peptide conjugate of any one of embodiments 1-20, wherein the peptide comprises SEQ ID NO: 14.

148. The peptide conjugate of any one of embodiments 144-147, wherein each X is independently selected from a sulfhydryl-containing amino acid and an amine-containing amino acid.

149. The peptide conjugate of any one of embodiments 144-147, wherein each X is a cysteine.

150. The peptide conjugate of any one of embodiments 144-147, wherein each X is a lysine.

151. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 15.

152. The peptide conjugate of any one of embodiments 1-20, wherein the peptide comprises the first 28 amino acids of SEQ ID NO: 15.

153. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 15.

154. The peptide conjugate of any one of embodiments 1-20, wherein the peptide comprises SEQ ID NO: 15.

155. The peptide conjugate of any one of embodiments 151-154, wherein each X is independently selected from a sulfhydryl-containing amino acid and an amine-containing amino acid.

156. The peptide conjugate of any one of embodiments 151-154, wherein each X is a cysteine.

157. The peptide conjugate of any one of embodiments 151-154, wherein each X is a lysine.

158. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 16.

159. The peptide conjugate of any one of embodiments 1-20, wherein the peptide comprises the first 28 amino acids of SEQ ID NO: 16.

160. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 16.

161. The peptide conjugate of any one of embodiments 1-20, wherein the peptide comprises SEQ ID NO: 16.

162. The peptide conjugate of any one of embodiments 158-161, wherein each X is independently selected from a sulfhydryl-containing amino acid and an amine-containing amino acid.

163. The peptide conjugate of any one of embodiments 158-161, wherein each X is a cysteine.

164. The peptide conjugate of any one of embodiments 158-161, wherein each X is a lysine.

165. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 17.

166. The peptide conjugate of any one of embodiments 1-20, wherein the peptide comprises the first 28 amino acids of SEQ ID NO: 17.

167. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 17.

168. The peptide conjugate of any one of embodiments 1-20, wherein the peptide comprises SEQ ID NO: 17.

169. The peptide conjugate of any one of embodiments 165-168, wherein each X is independently selected from a sulfhydryl-containing amino acid and an amine-containing amino acid.

170. The peptide conjugate of any one of embodiments 165-168, wherein each X is a cysteine.

171. The peptide conjugate of any one of embodiments 165-168, wherein each X is a lysine.

172. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 18.

173. The peptide conjugate of any one of embodiments 1-20, wherein the peptide comprises the first 28 amino acids of SEQ ID NO: 18.

174. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 18.

175. The peptide conjugate of any one of embodiments 1-20, wherein the peptide comprises SEQ ID NO: 18.

176. The peptide conjugate of any one of embodiments 172-175, wherein each X is independently selected from a sulfhydryl-containing amino acid and an amine-containing amino acid.

177. The peptide conjugate of any one of embodiments 172-175, wherein each X is a cysteine.

178. The peptide conjugate of any one of embodiments 172-175, wherein each X is a lysine.

179. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 19.

180. The peptide conjugate of any one of embodiments 1-20, wherein the peptide comprises the first 28 amino acids of SEQ ID NO: 19.

181. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 19.

182. The peptide conjugate of any one of embodiments 1-20, wherein the peptide comprises SEQ ID NO: 19.

183. The peptide conjugate of any one of embodiments 179-182, wherein each X is independently selected from a sulfhydryl-containing amino acid and an amine-containing amino acid.

184. The peptide conjugate of any one of embodiments 179-182, wherein each X is a cysteine.

185. The peptide conjugate of any one of embodiments 179-182, wherein each X is a lysine.

186. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 20.

187. The peptide conjugate of any one of embodiments 1-20, wherein the peptide comprises the first 28 amino acids of SEQ ID NO: 20.

188. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 20.

189. The peptide conjugate of any one of embodiments 1-20, wherein the peptide comprises SEQ ID NO: 20.

190. The peptide conjugate of any one of embodiments 186-189, wherein each X is independently selected from a sulfhydryl-containing amino acid and an amine-containing amino acid.

191. The peptide conjugate of any one of embodiments 186-189, wherein each X is a cysteine.

192. The peptide conjugate of any one of embodiments 186-189, wherein each X is a lysine.

193. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 21.

194. The peptide conjugate of any one of embodiments 1-20, wherein the peptide comprises the first 28 amino acids of SEQ ID NO: 21.

195. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 21.

196. The peptide conjugate of any one of embodiments 1-20, wherein the peptide comprises SEQ ID NO: 21.

197. The peptide conjugate of any one of embodiments 193-196, wherein each X is independently selected from a sulfhydryl-containing amino acid and an amine-containing amino acid.

198. The peptide conjugate of any one of embodiments 193-196, wherein each X is a cysteine.

199. The peptide conjugate of any one of embodiments 193-196, wherein each X is a lysine.

200. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 22.

201. The peptide conjugate of any one of embodiments 1-20, wherein the peptide comprises the first 28 amino acids of SEQ ID NO: 22.

202. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 22.

203. The peptide conjugate of any one of embodiments 1-20, wherein the peptide comprises SEQ ID NO: 22.

204. The peptide conjugate of any one of embodiments 200-203, wherein each X is independently selected from a sulfhydryl-containing amino acid and an amine-containing amino acid.

205. The peptide conjugate of any one of embodiments 200-203, wherein each X is a cysteine.

206. The peptide conjugate of any one of embodiments 200-203, wherein each X is a lysine.

207. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 23.

208. The peptide conjugate of any one of embodiments 1-20, wherein the peptide comprises the first 28 amino acids of SEQ ID NO: 23.

209. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 23.

210. The peptide conjugate of any one of embodiments 1-20, wherein the peptide comprises SEQ ID NO: 23.

211. The peptide conjugate of any one of embodiments 207-210, wherein each X is independently selected from a sulfhydryl-containing amino acid and an amine-containing amino acid.

212. The peptide conjugate of any one of embodiments 207-210, wherein each X is a cysteine.

213. The peptide conjugate of any one of embodiments 207-210, wherein each X is a lysine.

214. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 24.

215. The peptide conjugate of any one of embodiments 1-20, wherein the peptide comprises the first 28 amino acids of SEQ ID NO: 24.

216. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 24.

217. The peptide conjugate of any one of embodiments 1-20, wherein the peptide comprises SEQ ID NO: 24.

218. The peptide conjugate of any one of embodiments 214-217, wherein each X is independently selected from a sulfhydryl-containing amino acid and an amine-containing amino acid.

219. The peptide conjugate of any one of embodiments 214-217, wherein each X is a cysteine.

220. The peptide conjugate of any one of embodiments 214-217, wherein each X is a lysine.

221. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 25.

222. The peptide conjugate of any one of embodiments 1-20, wherein the peptide comprises the first 28 amino acids of SEQ ID NO: 25.

223. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 25.

224. The peptide conjugate of any one of embodiments 1-20, wherein the peptide comprises SEQ ID NO: 25.

225. The peptide conjugate of any one of embodiments 221-224, wherein each X is independently selected from a sulfhydryl-containing amino acid and an amine-containing amino acid.

226. The peptide conjugate of any one of embodiments 221-224, wherein each X is a cysteine.

227. The peptide conjugate of any one of embodiments 221-224, wherein each X is a lysine.

228. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 26.

229. The peptide conjugate of any one of embodiments 1-20, wherein the peptide comprises the first 28 amino acids of SEQ ID NO: 26.

230. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 26.

231. The peptide conjugate of any one of embodiments 1-20, wherein the peptide comprises SEQ ID NO: 26.

232. The peptide conjugate of any one of embodiments 228-231, wherein each X is independently selected from a sulfhydryl-containing amino acid and an amine-containing amino acid.

233. The peptide conjugate of any one of embodiments 228-231, wherein each X is a cysteine.

234. The peptide conjugate of any one of embodiments 228-231, wherein each X is a lysine.

235. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 27.

236. The peptide conjugate of any one of embodiments 1-20, wherein the peptide comprises the first 28 amino acids of SEQ ID NO: 27.

237. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 27.

238. The peptide conjugate of any one of embodiments 1-20, wherein the peptide comprises SEQ ID NO: 27.

239. The peptide conjugate of any one of embodiments 235-238, wherein each X is independently selected from a sulfhydryl-containing amino acid and an amine-containing amino acid.

240. The peptide conjugate of any one of embodiments 235-238, wherein each X is a cysteine.

241. The peptide conjugate of any one of embodiments 235-238, wherein each X is a lysine.

242. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 28.

243. The peptide conjugate of any one of embodiments 1-20, wherein the peptide comprises the first 28 amino acids of SEQ ID NO: 28.

244. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 28.

245. The peptide conjugate of any one of embodiments 1-20, wherein the peptide comprises SEQ ID NO: 28.

246. The peptide conjugate of any one of embodiments 242-245, wherein each X is independently selected from a sulfhydryl-containing amino acid and an amine-containing amino acid.

247. The peptide conjugate of any one of embodiments 242-245, wherein each X is a cysteine.

248. The peptide conjugate of any one of embodiments 242-245, wherein each X is a lysine.

249. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 29.

250. The peptide conjugate of any one of embodiments 1-20, wherein the peptide comprises the first 28 amino acids of SEQ ID NO: 29.

251. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 29.

252. The peptide conjugate of any one of embodiments 1-20, wherein the peptide comprises SEQ ID NO: 29.

253. The peptide conjugate of any one of embodiments 249-252, wherein each X is independently selected from a sulfhydryl-containing amino acid and an amine-containing amino acid.

254. The peptide conjugate of any one of embodiments 249-252, wherein each X is a cysteine.

255. The peptide conjugate of any one of embodiments 249-252, wherein each X is a lysine.

256. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 30.

257. The peptide conjugate of any one of embodiments 1-20, wherein the peptide comprises the first 28 amino acids of SEQ ID NO: 30.
258. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 30.
259. The peptide conjugate of any one of embodiments 1-20, wherein the peptide comprises SEQ ID NO: 30.
260. The peptide conjugate of any one of embodiments 256-259, wherein each X is independently selected from a sulfhydryl-containing amino acid and an amine-containing amino acid.
261. The peptide conjugate of any one of embodiments 256-259, wherein each X is a cysteine.
262. The peptide conjugate of any one of embodiments 256-259, wherein each X is a lysine.
263. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOS: 31-61.
264. The peptide conjugate of any one of embodiments 1-20, wherein the peptide comprises the first 28 amino acids of any one of SEQ ID NOS: 31-61.
265. The peptide conjugate of any one of embodiments 1-20, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOS: 31-61.
266. The peptide conjugate of any one of embodiments 1-20, wherein the peptide comprises any one of SEQ ID NOS: 31-61.
267. The peptide conjugate of any one of embodiments 263-266, wherein each X is independently selected from a sulfhydryl-containing amino acid and an amine-containing amino acid.
268. The peptide conjugate of any one of embodiments 263-266, wherein each X is a cysteine.
269. The peptide conjugate of any one of embodiments 263-266, wherein each X is a lysine.
270. The peptide conjugate of any one of embodiments 1-269, wherein the peptide is resistant to proteolysis by a gastrointestinal protease.
271. The peptide conjugate of any one of embodiments 1-270, wherein the half-life of the peptide conjugate is at least about 2-fold greater than the half-life of an unmodified form of the peptide.
272. The peptide conjugate of any one of embodiments 1-270, wherein the half-life of the peptide conjugate is at least about 5-fold greater than the half-life of an unmodified form of the peptide.
273. The peptide conjugate of any one of embodiments 1-270, wherein the half-life of the peptide conjugate is at least about 10-fold greater than the half-life of an unmodified form of the peptide.
274. The peptide conjugate of any one of embodiments 1-273, wherein the binding affinity of the peptide conjugate is within about 5% of the binding affinity of an unmodified form of the peptide.
275. The peptide conjugate of any one of embodiments 1-273, wherein the binding affinity of the peptide conjugate is within about 10% of the binding affinity of an unmodified form of the peptide.
276. The peptide conjugate of any one of embodiments 1-273, wherein the binding affinity of the peptide conjugate is within about 15% of the binding affinity of an unmodified form of the peptide.
277. The peptide conjugate of any one of embodiments 1-273, wherein the binding affinity of the peptide conjugate is within about 20% of the binding affinity of an unmodified form of the peptide.
278. The peptide conjugate of any one of embodiments 1-277, wherein $X^1$ and $X^2$ are —C(=O)—.
279. The peptide conjugate of any one of embodiments 1-277, wherein $X^1$ and $X^2$ are -alkylene-C(=O)— or —C(=O)alkylene-.
280. The peptide conjugate of any one of embodiments 1-277, wherein $X^1$ and $X^2$ are —CH$_2$—C(=O)— or —C(=O)—CH$_2$—.
281. The peptide conjugate of any one of embodiments 1-277, wherein $X^1$ and $X^2$ are -alkylene-C(=O)NR$^3$— or —C(=O)NR$^3$-alkylene-.
282. The peptide conjugate of any one of embodiments 1-277, wherein $X^1$ and $X^2$ are —CH$_2$—C(=O)NR$^3$— or —C(=O)NR$^3$—CH$_2$—.
283. The peptide conjugate of any one of embodiments 1-277, wherein $X^1$ and $X^2$ are -alkylene-C(=O)NR$^3$-alkylene- or -alkylene-NR$^3$C(=O)-alkylene-.
284. The peptide conjugate of any one of embodiments 1-277, wherein $X^1$ and $X^2$ are —CH$_2$—C(=O)NR$^3$—CH$_2$CH$_2$— or —CH$_2$—NR$^3$C(=O)—CH$_2$CH$_2$—.
285. The peptide conjugate of any one of embodiments 1-277, wherein $X^1$ and $X^2$ are —CH$_2$—C(=O)NH—CH$_2$CH$_2$— or —CH$_2$—NHC(=O)—CH$_2$CH$_2$—.
286. The peptide conjugate of any one of embodiments 1-285, wherein >A-R has the following structure:

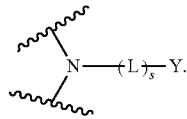

287. The peptide conjugate of any one of embodiments 1-286, wherein s is 1-15.
288. The peptide conjugate of any one of embodiments 1-287, wherein s is 1-10.
289. The peptide conjugate of any one of embodiments 1-288, wherein s is 5-15.
290. The peptide conjugate of any one of embodiments 1-289, wherein s is 5-10.
291. The peptide conjugate of any one of embodiments 1-290, wherein Y is hydrogen or —CO$_2$H.
292. The peptide conjugate of any one of embodiments 1-291, wherein each L is independently —(CR$^1$R$^2$)$_v$—, -alkylene-O—, —C(=O)—, —C(=O)NR$^3$—, —NR$^3$C(=O)—, -alkylene-C(=O)NR$^3$—, or -alkylene-NR$^3$C(=O)—; and v is 2-20.
293. The peptide conjugate of any one of embodiments 1-277, wherein the peptide conjugate comprises:

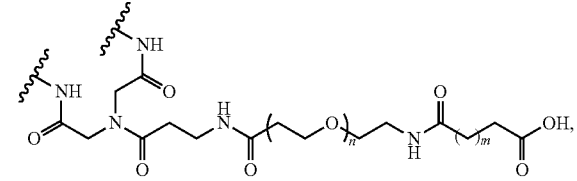

wherein n is 1-4 and m is 6-20.
294. The peptide conjugate of embodiment 293, wherein n is 3 and m is 15.
295. The peptide conjugate of any one of embodiments 1-277, wherein the peptide conjugate comprises:

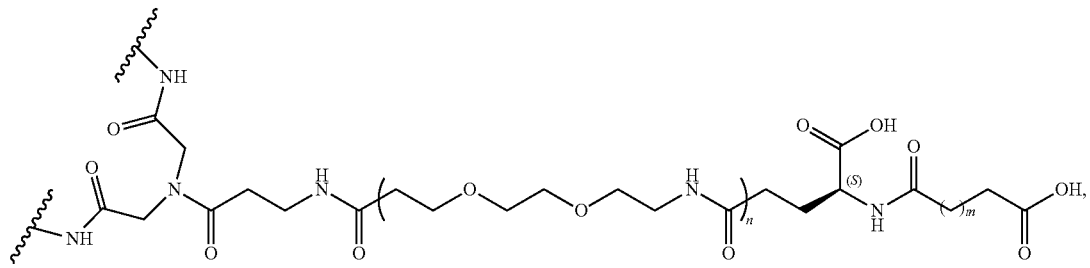

wherein n is 1-4 and m is 6-20.
296. The peptide conjugate of embodiment 295, wherein n is 2 and m is 15.
297. The peptide conjugate of embodiment 295, wherein n is 2 and m is 17.
298. The peptide conjugate of any one of embodiments 1-277, wherein the peptide conjugate comprises:

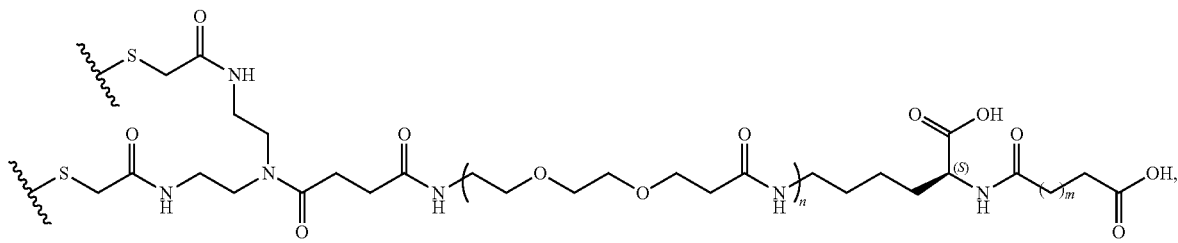

wherein n is 1-4 and m is 6-20.
299. The peptide conjugate of embodiment 298, wherein n is 2 and m is 15.
300. The peptide conjugate of embodiment 298, wherein n is 2 and m is 17.
301. The peptide conjugate of embodiment 298, wherein n is 2 and m is 13.
302. The peptide conjugate of any one of embodiments 1-277, wherein the peptide conjugate comprises: L5A

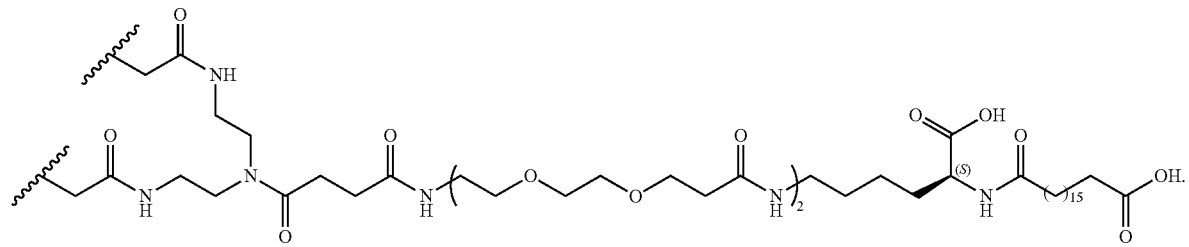

303. The peptide conjugate of any one of embodiments 1-277, wherein the peptide conjugate comprises: C20L5A

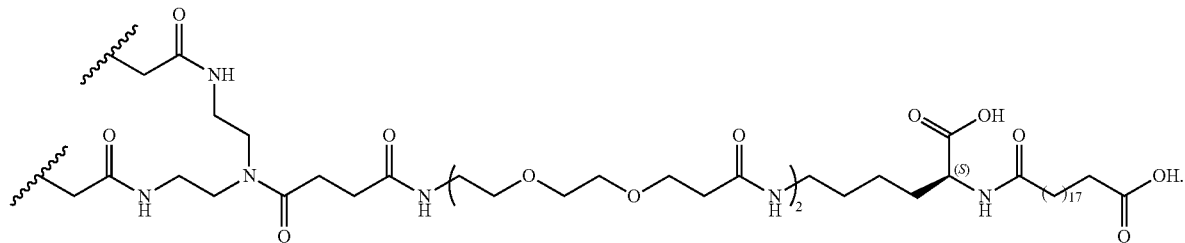

304. The peptide conjugate of ofany one of embodiments 1-277, wherein the peptide conjugate comprises: C16L5A

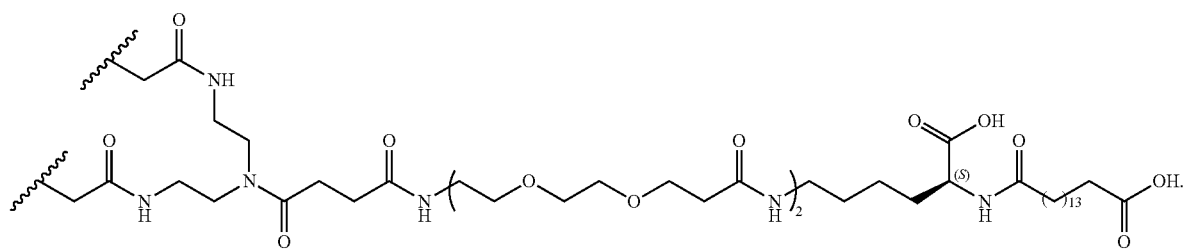

305. The peptide conjugate of any one of embodiments 1-277, wherein the peptide conjugate comprises: K4

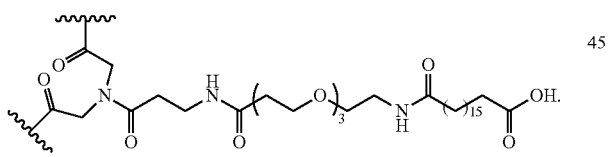

306. The peptide conjugate of any one of embodiments 1-277, wherein the peptide conjugate comprises: K5

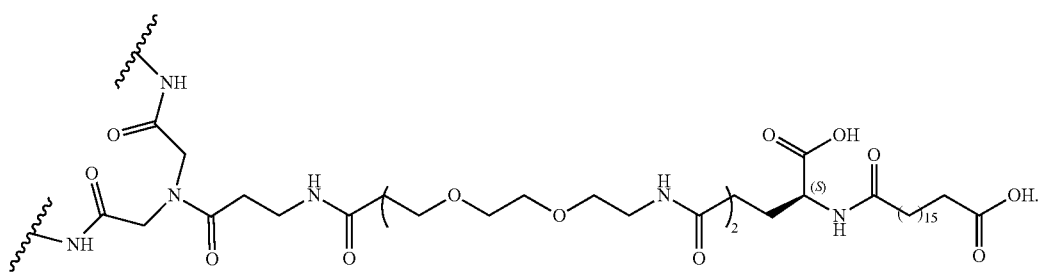

307. The peptide conjugate of any one of embodiments 1-277, wherein the peptide conjugate comprises: C20K5

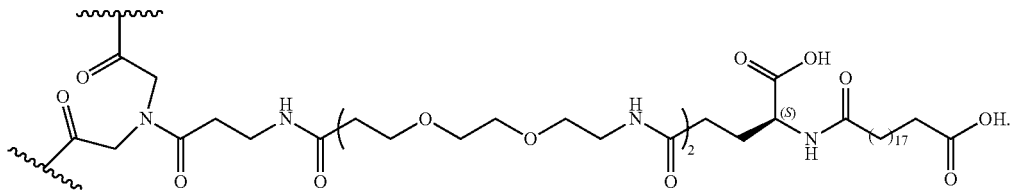

308. A peptide conjugate comprising mCMD307 (Table 3).
309. A peptide conjugate comprising: mCMV266 (Table 3).
310. A peptide conjugate comprising: mCMV268 (Table 3).
311. A peptide conjugate comprising any molecule of Table 3.
312. A peptide conjugate comprising:
  a) a peptide, and
  b) a staple attached to the peptide at a first amino acid and a second amino acid.
313. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOs: 1-61.
314. The peptide conjugate of embodiment 312, wherein the peptide comprises the first 28 amino acids of any one of SEQ ID NOs: 1-61.
315. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 1-61.
316. The peptide conjugate of embodiment 312, wherein the peptide comprises any one of SEQ ID NOs: 1-61.
317. The peptide conjugate of any one of embodiments 313-316, wherein each X is independently selected from a sulfhydryl-containing amino acid and an amine-containing amino acid.
318. The peptide conjugate of any one of embodiments 313-316, wherein each X is a cysteine.
319. The peptide conjugate of any one of embodiments 313-316, wherein each X is a lysine.
320. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 1.
321. The peptide conjugate of embodiment 312, wherein the peptide comprises the first 28 amino acids of SEQ ID NO: 1.
322. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1.
323. The peptide conjugate of embodiment 312, wherein the peptide comprises SEQ ID NO: 1.
324. The peptide conjugate of any one of embodiments 320-323, wherein each X is independently selected from a sulfhydryl-containing amino acid and an amine-containing amino acid.
325. The peptide conjugate of any one of embodiments 320-323, wherein each X is a cysteine.
326. The peptide conjugate of any one of embodiments 320-323, wherein each X is a lysine.
327. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 2.
328. The peptide conjugate of embodiment 312, wherein the peptide comprises the first 28 amino acids of SEQ ID NO: 2.
329. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2.
330. The peptide conjugate of embodiment 312, wherein the peptide comprises SEQ ID NO: 2.
331. The peptide conjugate of any one of embodiments 327-330, wherein each X is independently selected from a sulfhydryl-containing amino acid and an amine-containing amino acid.
332. The peptide conjugate of any one of embodiments 327-330, wherein each X is a cysteine.
333. The peptide conjugate of any one of embodiments 327-330, wherein each X is a lysine.
334. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 3.
335. The peptide conjugate of embodiment 312, wherein the peptide comprises the first 28 amino acids of SEQ ID NO: 3.
336. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3.
337. The peptide conjugate of embodiment 312, wherein the peptide comprises SEQ ID NO: 3.
338. The peptide conjugate of any one of embodiments 334-337, wherein each X is independently selected from a sulfhydryl-containing amino acid and an amine-containing amino acid.
339. The peptide conjugate of any one of embodiments 334-337, wherein each X is a cysteine.
340. The peptide conjugate of any one of embodiments 334-337, wherein each X is a lysine.
341. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 4.
342. The peptide conjugate of embodiment 312, wherein the peptide comprises the first 28 amino acids of SEQ ID NO: 4.

343. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 4.

344. The peptide conjugate of embodiment 312, wherein the peptide comprises SEQ ID NO: 4.

345. The peptide conjugate of any one of embodiments 341-344, wherein each X is independently selected from a sulfhydryl-containing amino acid and an amine-containing amino acid.

346. The peptide conjugate of any one of embodiments 341-344, wherein each X is a cysteine.

347. The peptide conjugate of any one of embodiments 341-344, wherein each X is a lysine.

348. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 5.

349. The peptide conjugate of embodiment 312, wherein the peptide comprises the first 28 amino acids of SEQ ID NO: 5.

350. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 5.

351. The peptide conjugate of embodiment 312, wherein the peptide comprises SEQ ID NO: 5.

352. The peptide conjugate of any one of embodiments 348-351, wherein each X is independently selected from a sulfhydryl-containing amino acid and an amine-containing amino acid.

353. The peptide conjugate of any one of embodiments 348-351, wherein each X is a cysteine.

354. The peptide conjugate of any one of embodiments 348-351, wherein each X is a lysine.

355. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 6.

356. The peptide conjugate of embodiment 312, wherein the peptide comprises the first 28 amino acids of SEQ ID NO: 6.

357. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 6.

358. The peptide conjugate of embodiment 312, wherein the peptide comprises SEQ ID NO: 6.

359. The peptide conjugate of any one of embodiments 355-358, wherein each X is independently selected from a sulfhydryl-containing amino acid and an amine-containing amino acid.

360. The peptide conjugate of any one of embodiments 355-358, wherein each X is a cysteine.

361. The peptide conjugate of any one of embodiments 355-358, wherein each X is a lysine.

362. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 7.

363. The peptide conjugate of embodiment 312, wherein the peptide comprises the first 28 amino acids of SEQ ID NO: 7.

364. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7.

365. The peptide conjugate of embodiment 312, wherein the peptide comprises SEQ ID NO: 7.

366. The peptide conjugate of any one of embodiments 362-365, wherein each X is independently selected from a sulfhydryl-containing amino acid and an amine-containing amino acid.

367. The peptide conjugate of any one of embodiments 362-365, wherein each X is a cysteine.

368. The peptide conjugate of any one of embodiments 362-365, wherein each X is a lysine.

369. The peptide conjugate of any one of embodiments 362-368, wherein aa6 is alpha-methyl Phe, N-methyl Phe, D-Phe, beta3-Phe, alpha-methyl Phe, alpha-methyl Phe (2-F), alpha-methyl Phe (3-F), and alpha-methyl (4-F), Phe (2-F), Phe (3-F), or Phe (4-F).

370. The peptide conjugate of any one of embodiments 362-369, wherein aa10 is alpha-methyl Tyr, N-methyl Tyr, D-Tyr, beta3-Tyr, 4-Pyr-Ala, Phe (2-F), Phe (3-F), or Phe (4-F).

371. The peptide conjugate of any one of embodiments 362-370, wherein aa13 is alpha-methyl Leu, N-methyl Leu, D-Leu, beta3-Leu, Leu, Val, Ile, Aib, alpha-methyl Tyr, N-methyl Tyr, D-Tyr, beta3-Tyr, 4-Pyr-Ala, Phe (2-F), Phe (3-F), or Phe (4-F).

372. The peptide conjugate of any one of embodiments 362-371, wherein aa16 is L-Orn, alpha-methyl Lys, N-methyl Lys, D-Lys, or beta3-Lys.

373. The peptide conjugate of any one of embodiments 362-372, wherein aa25 is alpha-methyl Trp, N-methyl Trp, D-Trp, beta3-Trp, alpha-methyl Tyr, or Aib.

374. The peptide conjugate of any one of embodiments 362-373, wherein aa33 is A or E.

375. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 8.

376. The peptide conjugate of embodiment 312, wherein the peptide comprises the first 28 amino acids of SEQ ID NO: 8.

377. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8.

378. The peptide conjugate of embodiment 312, wherein the peptide comprises SEQ ID NO: 8.

379. The peptide conjugate of any one of embodiments 375-378, wherein each X is independently selected from a sulfhydryl-containing amino acid and an amine-containing amino acid.

380. The peptide conjugate of any one of embodiments 375-378, wherein each X is a cysteine.

381. The peptide conjugate of any one of embodiments 375-378, wherein each X is a lysine.

382. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 9.

383. The peptide conjugate of embodiment 312, wherein the peptide comprises the first 28 amino acids of SEQ ID NO: 9.

384. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9.

385. The peptide conjugate of embodiment 312, wherein the peptide comprises SEQ ID NO: 9.

386. The peptide conjugate of any one of embodiments 382-385, wherein each X is independently selected from a sulfhydryl-containing amino acid and an amine-containing amino acid.

387. The peptide conjugate of any one of embodiments 382-385, wherein each X is a cysteine.

388. The peptide conjugate of any one of embodiments 382-385, wherein each X is a lysine.

389. The peptide conjugate of any one of embodiments 382-388, wherein aa6 is alpha-methyl Phe, N-methyl Phe, D-Phe, beta3-Phe, alpha-methyl Phe (2-F), alpha-methyl Phe (3-F), and alpha-methyl (4-F), Phe (2-F), Phe (3-F), or Phe (4-F).

390. The peptide conjugate of any one of embodiments 382-389, wherein aa10 is alpha-methyl Tyr, N-methyl Tyr, D-Tyr, beta3-Tyr, 4-Pyr-Ala, Phe (2-F), Phe (3-F), Phe (4-F), or 4-pyridyl-Ala.

391. The peptide conjugate of any one of embodiments 382-390, wherein aa13 is alpha-methyl Leu, N-methyl Leu, D-Leu, beta3-Leu, Val, Ile, or Aib.

392. The peptide conjugate of any one of embodiments 382-391, wherein aa16 is alpha-methyl Leu, N-methyl Leu, D-Leu, beta3-Leu, Val, Ile, or Aib.

393. The peptide conjugate of any one of embodiments 382-392, wherein aa24 is alpha-methyl Asn, N-methyl Asn, beta3-Asn, Aib, D-Asn, D-Asp, D-Glu, or D-Gln 394. The peptide conjugate of any one of embodiments 382-393, wherein aa25 is alpha-methyl Trp, N-methyl Trp, D-Trp, beta3-Trp, alpha-methyl Tyr, or Aib.

395. The peptide conjugate of any one of embodiments 382-394, wherein aa33 is A or E.

396. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 10.

397. The peptide conjugate of embodiment 312, wherein the peptide comprises the first 28 amino acids of SEQ ID NO: 10.

398. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 10.

399. The peptide conjugate of embodiment 312, wherein the peptide comprises SEQ ID NO: 10.

400. The peptide conjugate of any one of embodiments 396-399, wherein each X is independently selected from a sulfhydryl-containing amino acid and an amine-containing amino acid.

401. The peptide conjugate of any one of embodiments 396-399, wherein each X is a cysteine.

402. The peptide conjugate of any one of embodiments 396-399, wherein each X is a lysine.

403. The peptide conjugate of any one of embodiments 396-402, wherein aa2 is Gly, Val, Leu, Ile, or Aib.

404. The peptide conjugate of any one of embodiments 396-403, wherein aa20 is Gly, Val, Leu, Ile, or Aib.

405. The peptide conjugate of any one of embodiments 396-404, wherein aa13 is alpha-methyl Leu, N-methyl Leu, D-Leu, beta3-Leu, Leu, Val, Ile, Aib, alpha-methyl Tyr, N-methyl Tyr, D-Tyr, beta3-Tyr, 4-Pyr-Ala, Phe (2-F), Phe (3-F), or Phe (4-F).

406. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 11.

407. The peptide conjugate of embodiment 312, wherein the peptide comprises the first 28 amino acids of SEQ ID NO: 11.

408. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 11.

409. The peptide conjugate of embodiment 312, wherein the peptide comprises SEQ ID NO: 11.

410. The peptide conjugate of any one of embodiments 406409, wherein each X is independently selected from a sulfhydryl-containing amino acid and an amine-containing amino acid.

411. The peptide conjugate of any one of embodiments 406-409, wherein each X is a cysteine.

412. The peptide conjugate of any one of embodiments 406-409, wherein each X is a lysine.

413. The peptide conjugate of any one of embodiments 406-412, wherein aa2 is Gly, Val, Leu, Ile, or Aib.

414. The peptide conjugate of any one of embodiments 406413, wherein aa20 is Gly, Val, Leu, Ile, or Aib.

415. The peptide conjugate of any one of embodiments 406414, wherein aa13 is alpha-methyl Leu, N-methyl Leu, D-Leu, beta3-Leu, Leu, Val, Ile, Aib, alpha-methyl Tyr, N-methyl Tyr, D-Tyr, beta3-Tyr, 4-Pyr-Ala, Phe (2-F), Phe (3-F), or Phe (4-F).

416. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 12.

417. The peptide conjugate of embodiment 312, wherein the peptide comprises the first 28 amino acids of SEQ ID NO: 12.

418. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 12.

419. The peptide conjugate of embodiment 312, wherein the peptide comprises SEQ ID NO: 12.

420. The peptide conjugate of any one of embodiments 416-419, wherein each X is independently selected from a sulfhydryl-containing amino acid and an amine-containing amino acid.

421. The peptide conjugate of any one of embodiments 416-419, wherein each X is a cysteine.

422. The peptide conjugate of any one of embodiments 416-419, wherein each X is a lysine.

423. The peptide conjugate of any one of embodiments 416-422, wherein aa2 is Gly, Val, Leu, Ile, or Aib.

424. The peptide conjugate of any one of embodiments 416-423, wherein aa20 is Gly, Val, Leu, Ile, or Aib.

425. The peptide conjugate of any one of embodiments 416-424, wherein aa13 is alpha-methyl Leu, N-methyl Leu, D-Leu, beta3-Leu, Leu, Val, Ile, Aib, alpha-methyl Tyr, N-methyl Tyr, D-Tyr, beta3-Tyr, 4-Pyr-Ala, Phe (2-F), Phe (3-F), or Phe (4-F).

426. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 13.

427. The peptide conjugate of embodiment 312, wherein the peptide comprises the first 28 amino acids of SEQ ID NO: 13.

428. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 13.

429. The peptide conjugate of embodiment 312, wherein the peptide comprises SEQ ID NO: 13.

430. The peptide conjugate of any one of embodiments 426-429, wherein each X is independently selected from a sulfhydryl-containing amino acid and an amine-containing amino acid.

431. The peptide conjugate of any one of embodiments 426-429, wherein each X is a cysteine.

432. The peptide conjugate of any one of embodiments 426-429, wherein each X is a lysine.

433. The peptide conjugate of any one of embodiments 426-432, wherein aa2 is Gly, Val, Leu, Ile, or Aib.

434. The peptide conjugate of any one of embodiments 426-433, wherein aa20 is Gly, Val, Leu, Ile, or Aib.

435. The peptide conjugate of any one of embodiments 426-434, wherein aa13 is alpha-methyl Leu, N-methyl Leu, D-Leu, beta3-Leu, Leu, Val, Ile, Aib, alpha-methyl Tyr, N-methyl Tyr, D-Tyr, beta3-Tyr, 4-Pyr-Ala, Phe (2-F), Phe (3-F), or Phe (4-F).

436. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 14.

437. The peptide conjugate of embodiment 312, wherein the peptide comprises the first 28 amino acids of SEQ ID NO: 14.

438. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 14.

439. The peptide conjugate of embodiment 312, wherein the peptide comprises SEQ ID NO: 14.

440. The peptide conjugate of any one of embodiments 436-439, wherein each X is independently selected from a sulfhydryl-containing amino acid and an amine-containing amino acid.

441. The peptide conjugate of any one of embodiments 436-439, wherein each X is a cysteine.

442. The peptide conjugate of any one of embodiments 436-439, wherein each X is a lysine.

443. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 15.

444. The peptide conjugate of embodiment 312, wherein the peptide comprises the first 28 amino acids of SEQ ID NO: 15.

445. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 15.

446. The peptide conjugate of embodiment 312, wherein the peptide comprises SEQ ID NO: 15.

447. The peptide conjugate of any one of embodiments 443-446, wherein each X is independently selected from a sulfhydryl-containing amino acid and an amine-containing amino acid.

448. The peptide conjugate of any one of embodiments 443-446, wherein each X is a cysteine.

449. The peptide conjugate of any one of embodiments 443-446, wherein each X is a lysine.

450. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 16.

451. The peptide conjugate of embodiment 312, wherein the peptide comprises the first 28 amino acids of SEQ ID NO: 16.

452. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 16.

453. The peptide conjugate of embodiment 312, wherein the peptide comprises SEQ ID NO: 16.

454. The peptide conjugate of any one of embodiments 450-453, wherein each X is independently selected from a sulfhydryl-containing amino acid and an amine-containing amino acid.

455. The peptide conjugate of any one of embodiments 450-453, wherein each X is a cysteine.

456. The peptide conjugate of any one of embodiments 450-453, wherein each X is a lysine.

457. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 17.

458. The peptide conjugate of embodiment 312, wherein the peptide comprises the first 28 amino acids of SEQ ID NO: 17.

459. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 17.

460. The peptide conjugate of embodiment 312, wherein the peptide comprises SEQ ID NO: 17.

461. The peptide conjugate of any one of embodiments 457460, wherein each X is independently selected from a sulfhydryl-containing amino acid and an amine-containing amino acid.

462. The peptide conjugate of any one of embodiments 457-460, wherein each X is a cysteine.

463. The peptide conjugate of any one of embodiments 457460, wherein each X is a lysine.

464. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 18.

465. The peptide conjugate of embodiment 312, wherein the peptide comprises the first 28 amino acids of SEQ ID NO: 18.

466. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 18.

467. The peptide conjugate of embodiment 312, wherein the peptide comprises SEQ ID NO: 18.

468. The peptide conjugate of any one of embodiments 464-467, wherein each X is independently selected from a sulfhydryl-containing amino acid and an amine-containing amino acid.

469. The peptide conjugate of any one of embodiments 464467, wherein each X is a cysteine.

470. The peptide conjugate of any one of embodiments 464-467, wherein each X is a lysine.

471. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 19.

472. The peptide conjugate of embodiment 312, wherein the peptide comprises the first 28 amino acids of SEQ ID NO: 19.

473. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 19.

474. The peptide conjugate of embodiment 312, wherein the peptide comprises SEQ ID NO: 19.

475. The peptide conjugate of any one of embodiments 471-474, wherein each X is independently selected from a sulfhydryl-containing amino acid and an amine-containing amino acid.

476. The peptide conjugate of any one of embodiments 471-474, wherein each X is a cysteine.

477. The peptide conjugate of any one of embodiments 471-474, wherein each X is a lysine.

478. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 20.

479. The peptide conjugate of embodiment 312, wherein the peptide comprises the first 28 amino acids of SEQ ID NO: 20.

480. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 20.

481. The peptide conjugate of embodiment 312, wherein the peptide comprises SEQ ID NO: 20.

482. The peptide conjugate of any one of embodiments 478-481, wherein each X is independently selected from a sulfhydryl-containing amino acid and an amine-containing amino acid.

483. The peptide conjugate of any one of embodiments 478-481, wherein each X is a cysteine.

484. The peptide conjugate of any one of embodiments 478-481, wherein each X is a lysine.

485. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 21.

486. The peptide conjugate of embodiment 312, wherein the peptide comprises the first 28 amino acids of SEQ ID NO: 21.

487. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 21.

488. The peptide conjugate of embodiment 312, wherein the peptide comprises SEQ ID NO: 21.

489. The peptide conjugate of any one of embodiments 485-488, wherein each X is independently selected from a sulfhydryl-containing amino acid and an amine-containing amino acid.

490. The peptide conjugate of any one of embodiments 485-488, wherein each X is a cysteine.

491. The peptide conjugate of any one of embodiments 485488, wherein each X is a lysine.

492. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 22.

493. The peptide conjugate of embodiment 312, wherein the peptide comprises the first 28 amino acids of SEQ ID NO: 22.

494. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 22.

495. The peptide conjugate of embodiment 312, wherein the peptide comprises SEQ ID NO: 22.

496. The peptide conjugate of any one of embodiments 492-495, wherein each X is independently selected from a sulfhydryl-containing amino acid and an amine-containing amino acid.

497. The peptide conjugate of any one of embodiments 492-495, wherein each X is a cysteine.

498. The peptide conjugate of any one of embodiments 492-495, wherein each X is a lysine.

499. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 23.

500. The peptide conjugate of embodiment 312, wherein the peptide comprises the first 28 amino acids of SEQ ID NO: 23.

501. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 23.

502. The peptide conjugate of embodiment 312, wherein the peptide comprises SEQ ID NO: 23.

503. The peptide conjugate of any one of embodiments 499-502, wherein each X is independently selected from a sulfhydryl-containing amino acid and an amine-containing amino acid.

504. The peptide conjugate of any one of embodiments 499-502, wherein each X is a cysteine.

505. The peptide conjugate of any one of embodiments 499-502, wherein each X is a lysine.

506. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 24.

507. The peptide conjugate of embodiment 312, wherein the peptide comprises the first 28 amino acids of SEQ ID NO: 24.

508. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 24.

509. The peptide conjugate of embodiment 312, wherein the peptide comprises SEQ ID NO: 24.

510. The peptide conjugate of any one of embodiments 506-509, wherein each X is independently selected from a sulfhydryl-containing amino acid and an amine-containing amino acid.

511. The peptide conjugate of any one of embodiments 506-509, wherein each X is a cysteine.

512. The peptide conjugate of any one of embodiments 506-509, wherein each X is a lysine.

513. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 25.

514. The peptide conjugate of embodiment 312, wherein the peptide comprises the first 28 amino acids of SEQ ID NO: 25.

515. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 25.

516. The peptide conjugate of embodiment 312, wherein the peptide comprises SEQ ID NO: 25.

517. The peptide conjugate of any one of embodiments 513-516, wherein each X is independently selected from a sulfhydryl-containing amino acid and an amine-containing amino acid.

518. The peptide conjugate of any one of embodiments 513-516, wherein each X is a cysteine.

519. The peptide conjugate of any one of embodiments 513-516, wherein each X is a lysine.

520. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 26.

521. The peptide conjugate of embodiment 312, wherein the peptide comprises the first 28 amino acids of SEQ ID NO: 26.

522. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 26.

523. The peptide conjugate of embodiment 312, wherein the peptide comprises SEQ ID NO: 26.

524. The peptide conjugate of any one of embodiments 520-523, wherein each X is independently selected from a sulfhydryl-containing amino acid and an amine-containing amino acid.

525. The peptide conjugate of any one of embodiments 520-523, wherein each X is a cysteine.

526. The peptide conjugate of any one of embodiments 520-523, wherein each X is a lysine.

527. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 27.

528. The peptide conjugate of embodiment 312, wherein the peptide comprises the first 28 amino acids of SEQ ID NO: 27.

529. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 27.

530. The peptide conjugate of embodiment 312, wherein the peptide comprises SEQ ID NO: 27.

531. The peptide conjugate of any one of embodiments 527-530, wherein each X is independently selected from a sulfhydryl-containing amino acid and an amine-containing amino acid.

532. The peptide conjugate of any one of embodiments 527-530, wherein each X is a cysteine.

533. The peptide conjugate of any one of embodiments 527-530, wherein each X is a lysine.

534. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 28.

535. The peptide conjugate of embodiment 312, wherein the peptide comprises the first 28 amino acids of SEQ ID NO: 28.

536. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 28.

537. The peptide conjugate of embodiment 312, wherein the peptide comprises SEQ ID NO: 28.

538. The peptide conjugate of any one of embodiments 534-537, wherein each X is independently selected from a sulfhydryl-containing amino acid and an amine-containing amino acid.

539. The peptide conjugate of any one of embodiments 534-537, wherein each X is a cysteine.

540. The peptide conjugate of any one of embodiments 534-537, wherein each X is a lysine.

541. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 29.

542. The peptide conjugate of embodiment 312, wherein the peptide comprises the first 28 amino acids of SEQ ID NO: 29.

543. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 29.

544. The peptide conjugate of embodiment 312, wherein the peptide comprises SEQ ID NO: 29.

545. The peptide conjugate of any one of embodiments 541-544, wherein each X is independently selected from a sulfhydryl-containing amino acid and an amine-containing amino acid.

546. The peptide conjugate of any one of embodiments 541-544, wherein each X is a cysteine.

547. The peptide conjugate of any one of embodiments 541-544, wherein each X is a lysine.

548. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of SEQ ID NO: 30.

549. The peptide conjugate of embodiment 312, wherein the peptide comprises the first 28 amino acids of SEQ ID NO: 30.

550. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 30.

551. The peptide conjugate of embodiment 312, wherein the peptide comprises SEQ ID NO: 30.

552. The peptide conjugate of any one of embodiments 548-551, wherein each X is independently selected from a sulfhydryl-containing amino acid and an amine-containing amino acid.

553. The peptide conjugate of any one of embodiments 548-551, wherein each X is a cysteine.

554. The peptide conjugate of any one of embodiments 548-551, wherein each X is a lysine.

555. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to the first 28 amino acids of any one of SEQ ID NOS: 31-61.

556. The peptide conjugate of embodiment 312, wherein the peptide comprises the first 28 amino acids of any one of SEQ ID NOS: 31-61.

557. The peptide conjugate of embodiment 312, wherein the peptide comprises a sequence about or at least about 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOS: 31-61.

558. The peptide conjugate of embodiment 312, wherein the peptide comprises any one of SEQ ID NOS: 31-61.

559. The peptide conjugate of any one of embodiments 555-558, wherein each X is independently selected from a sulfhydryl-containing amino acid and an amine-containing amino acid.

560. The peptide conjugate of any one of embodiments 555-558, wherein each X is a cysteine.

561. The peptide conjugate of any one of embodiments 555-558, wherein each X is a lysine.

562. The peptide conjugate of any one of embodiments 312-561, wherein the peptide is resistant to proteolysis by a gastrointestinal protease.

563. The peptide conjugate of any one of embodiments 312-562, wherein the first amino acid and the second amino acid are independently an amine-containing amino acid or a sulfhydryl-containing amino acid.

564. The peptide conjugate of any one of embodiments 312-562, wherein the first amino acid and second amino acid are independently selected from cysteine, homocysteine, 2-amino-5-mercaptopentanoic acid, and 2-amino-6-mercaptohexanoic acid.

565. The peptide conjugate of any one of embodiments 312-562, wherein the first amino acid and second amino acid are each cysteines.

566. The peptide conjugate of any one of embodiments 312-562, wherein the first amino acid and second amino acid is independently selected from lysine, ornithine, diaminobutyric acid, diaminopropionic acid and homolysine.

567. The peptide conjugate of any one of embodiments 312-562, wherein the first amino acid and second amino acid are each lysines.

568. The peptide conjugate of any one of embodiments 312-562 further comprising a half-life extending molecule attached to a sulfhydryl containing amino acid.

569. The peptide conjugate of any one of embodiments 312-562 further comprising a half-life extending molecule attached to an amine-containing amino acid residue in the peptide.

570. The peptide conjugate of embodiment 569, wherein the amine-containing amino acid is selected from lysine, ornithine, diaminobutyric acid, diaminopropionic acid and homolysine.

571. The peptide conjugate of embodiment 569, wherein the amine-containing amino acid is lysine.

572. The peptide conjugate of embodiment 568, wherein the sulfhydryl-containing amino acid is selected from cysteine, homocysteine, 2-amino-5-mercaptopentanoic acid, and 2-amino-6-mercaptohexanoic acid.

573. The peptide conjugate of embodiment 568, wherein the sulfhydryl-containing amino acid is cysteine.

574. The peptide conjugate of any one of embodiments 312-573, wherein the first amino acid has a position i in the peptide and the second amino acid has a position i+n in the peptide, wherein n is 4-16.

575. The peptide conjugate of any one of embodiments 312-573, wherein the first amino acid has a position i in the peptide and the second amino acid has a position i+7 in the peptide.

576. The peptide conjugate of any one of embodiments 312-573, wherein the half-life of the peptide conjugate is at least about 2-fold greater than the half-life of an unmodified form of the peptide.

577. The peptide conjugate of any one of embodiments 312-573, wherein the half-life of the peptide conjugate is at least about 5-fold greater than the half-life of an unmodified form of the peptide.

578. The peptide conjugate of any one of embodiments 312-573, wherein the half-life of the peptide conjugate is at least about 10-fold greater than the half-life of an unmodified form of the peptide.

579. The peptide conjugate of any one of embodiments 312-578, wherein the binding affinity of the peptide conjugate is within about 5% of the binding affinity of an unmodified form of the peptide.

580. The peptide conjugate of any one of embodiments 312-578, wherein the binding affinity of the peptide conjugate is within about 10% of the binding affinity of an unmodified form of the peptide.

581. The peptide conjugate of any one of embodiments 312-578, wherein the binding affinity of the peptide conjugate is within about 15% of the binding affinity of an unmodified form of the peptide.

582. The peptide conjugate of any one of embodiments 312-578, wherein the binding affinity of the peptide conjugate is within about 20% of the binding affinity of an unmodified form of the peptide.

583. The peptide conjugate of any one of embodiments 312-582, wherein the staple is of Formula (I):

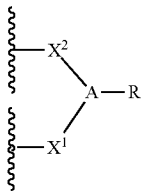

Formula (I)

wherein

A is an optionally substituted alkylene, optionally substituted arylene, optionally substituted heteroarylene, optionally substituted —NR$^3$-alkylene-NR$^3$—, or —N—;

$X^1$ and $X^2$ are independently a bond, —C(=O)—, -alkylene-C(=O)—, —C(=O)-alkylene-, -alkylene-C(=O)NR$^3$—, -alkylene-NR$^3$C(=O)—, —C(=O)NR$^3$-alkylene-, —NR$^3$C(=O)-alkylene-, -alkylene-C(=O)NR$^3$-alkylene-, or -alkylene-NR$^3$C(=O)-alkylene-;

wherein $X^1$ is attached to a first amino acid of the peptide, and $X^2$ is attached to a second amino acid of the peptide;

R is hydrogen or -(L)$_s$-Y;

each L is independently —(CR$^1$R$^2$)$_v$—, -alkylene-O—, —O-alkylene-, —C(=O)-alkylene-, -alkylene-C(=O)—, —NR$^3$-alkylene-, -alkylene-NR$^3$—, —S-alkylene-, -alkylene-S—, —S(=O)-alkylene-, -alkylene-S(=O)—, —S(=O)$_2$-alkylene, -alkylene-S(=O)$_2$—, —C(=O)—, —C(=O)NR$^3$—, —NR$^3$C(=O)—, —NR$^3$C(=O)NR$^3$—, —NR$^3$C(=O)NR$^3$-alkylene-, —NR$^3$C(=O)-alkylene-NR$^3$—, -alkylene-C(=O)NR$^3$—, —C(=O)NR$^3$-alkylene-, -alkylene-NR$^3$C(=O)—, or —NR$^3$C(=O)-alkylene-;

v is 2-20;

each R$^1$ or R$^2$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, —NR$^c$R$^d$, or R$^1$ and R$^2$ are taken together to form a C$_1$-C$_6$ cycloalkyl or C$_1$-C$_6$ heterocycloalkyl;

each R$^3$ is independently hydrogen, —S(=O)R$^b$, —S(=O)$_2$R$^a$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

Y is hydrogen, C$_1$-C$_6$ alkyl, —CO$_2$H, —CO$_2$(C$_1$-C$_6$ alkyl), —CO$_2$NH$_2$, —CO$_2$N(alkyl)$_2$, or —CO$_2$NH(alkyl); and s is 0-20;

R$^a$ is hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

R$^b$ is C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

each R$^c$ and R$^d$ is independently hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

or R$^c$ and R$^d$, together with the nitrogen atom to which they are attached, form a heterocycloalkyl or heteroaryl; wherein the heterocycloalkyl and heteroaryl is optionally substituted with one, two, or three of halogen, C$_1$-C$_6$ alkyl, C$_1$-C$_6$ haloalkyl, —OH, —OMe, or —NH$_2$.

584. The peptide conjugate of embodiment 583, wherein A is optionally substituted alkylene.

585. The peptide conjugate of embodiment 583 or 584, wherein A is —(CH$_2$)$_t$—, wherein t is 1-12.

586. The peptide conjugate of embodiment 583, wherein A is optionally substituted arylene.

587. The peptide conjugate of embodiment 583, wherein A is —NR$^3$-alkylene-NR$^3$—.

588. The peptide conjugate of embodiment 583, wherein A is —N—.

589. The peptide conjugate of any one of embodiments 583-588, wherein $X^1$ and $X^2$ are identical.

590. The peptide conjugate of any one of embodiments 583-588, wherein $X^1$ and $X^2$ are different.

591. The peptide conjugate of any one of embodiments 583-588, wherein $X^1$ and $X^2$ are —C(=O)—.

592. The peptide conjugate of any one of embodiments 583-588, wherein $X^1$ and $X^2$ are independently -alkylene-C(=O)— or —C(=O)alkylene-.

593. The peptide conjugate of any one of embodiments 583-588, wherein $X^1$ and $X^2$ are independently —CH$_2$—C(=O)— or —C(=O)—CH$_2$—.

594. The peptide conjugate of any one of embodiments 583-588, wherein $X^1$ and $X^2$ are independently -alkylene-C(=O)NR$^3$— or —C(=O)NR$^3$-alkylene-.

595. The peptide conjugate of any one of embodiments 583-588, wherein $X^1$ and $X^2$ are independently —CH$_2$—C(=O)NR$^3$— or —C(=O)NR$^3$—CH$_2$—.

596. The peptide conjugate of any one of embodiments 583-588, wherein $X^1$ and $X^2$ are independently -alkylene-C(=O)NR$^3$-alkylene- or -alkylene-NR$^3$C(=O)-alkylene-.

597. The peptide conjugate of any one of embodiments 583-588, wherein $X^1$ and $X^2$ are independently —CH$_2$—C(=O)NR$^3$—CH$_2$CH$_2$— or —CH$_2$—NR$^3$C(=O)—CH$_2$CH$_2$—.

598. The peptide conjugate of any one of embodiments 583-588, wherein $X^1$ and $X^2$ are independently —CH$_2$—C(=O)NH—CH$_2$CH$_2$— or —CH$_2$—NHC(=O)—CH$_2$CH$_2$—.

599. The peptide conjugate of any one of embodiments 583-598, wherein >A-R has the following structure:

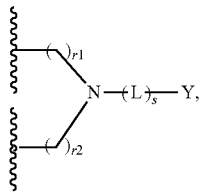

wherein r1 and r2 are each independently 0-4.

600. The peptide conjugate of any one of embodiments 583-599, wherein >A-R has the following structure:

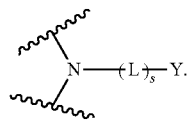

601. The peptide conjugate of any one of embodiments 583-600, wherein >A-R has the following structure:

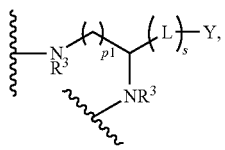

wherein p1 is 1-5.

602. The peptide conjugate of any one of embodiments 583-598 or 601, wherein >A-R has the following structure:

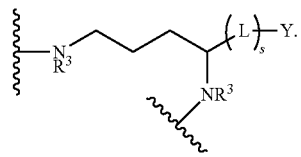

603. The peptide conjugate of any one of embodiments 583-598, wherein >A-R has the following structure:

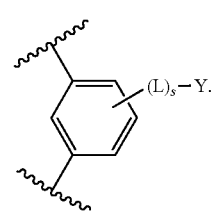

604. The peptide conjugate of any one of embodiments 583-603, wherein s is 1-15.

605. The peptide conjugate of any one of embodiments 583-603, wherein s is 1-10.

606. The peptide conjugate of any one of embodiments 583-603, wherein s is 5-15.

607. The peptide conjugate of any one of embodiments 583-603, wherein s is 5-10.

608. The peptide conjugate of any one of embodiments 583-607, wherein Y is hydrogen or —CO$_2$H.

609. The peptide conjugate of any one of embodiments 583-608, wherein each L is independently —(CR$^1$R$^2$)$_v$—, -alkylene-O—, —C(=O)—, —C(=O)NR$^3$—, —NR$^3$C(=O)—, -alkylene-C(=O)NR$^3$—, or -alkylene-NR$^3$C(=O)—; and v is 2-20.

610. The peptide conjugate of any one of embodiments 312-582, wherein the staple comprises Linker L1, Linker L2, or Linker L3:

Linker L1

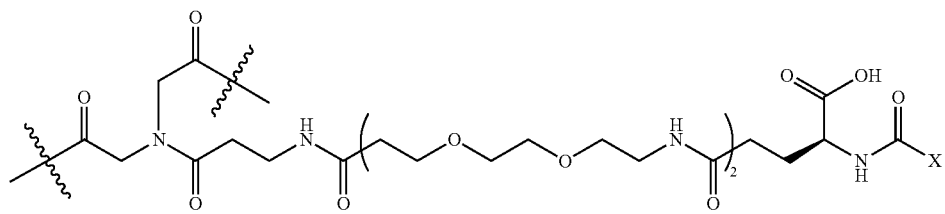

Linker L2

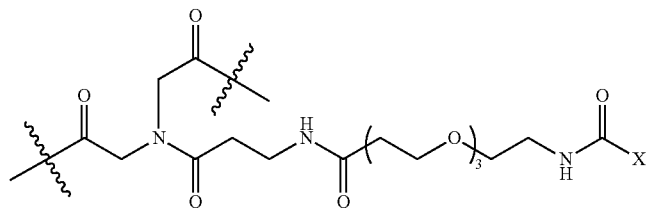

Linker L3

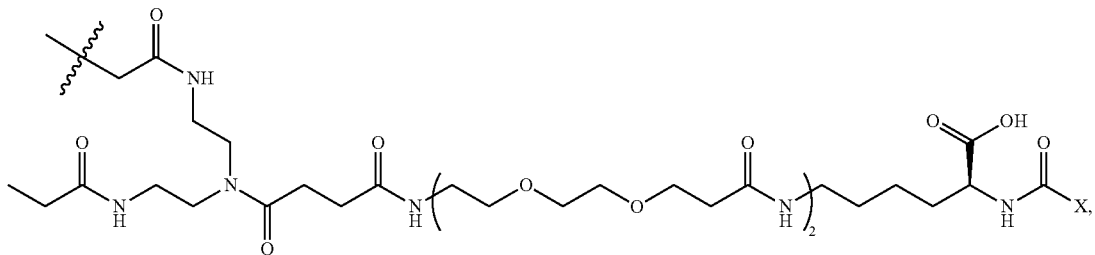

wherein X comprises a fatty acid.
611. The peptide conjugate of embodiment 610, wherein the fatty acid comprises a chain of about 10 to about 22 carbon atoms.
612. The peptide conjugate of embodiment 610, wherein the fatty acid comprises propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, or pentacosylic acid.
613. The peptide conjugate of any one of embodiments 610-612, comprising the Linker L1.
614. The peptide conjugate of any one of embodiments 610-612, comprising the Linker L2.
615. The peptide conjugate of any one of embodiments 610-612, comprising the Linker L3.
616. The peptide conjugate of any one of embodiments 312-582, wherein the peptide conjugate comprises:

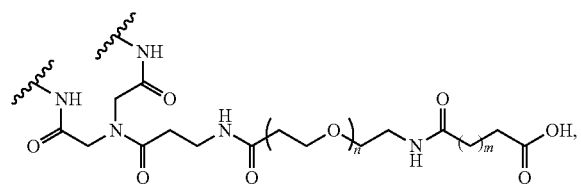

wherein n is 1-4 and m is 6-20.
617. The peptide conjugate of embodiment 616, wherein n is 3 and m is 15.
618. The peptide conjugate of any one of embodiments 312-582, wherein the peptide conjugate comprises:

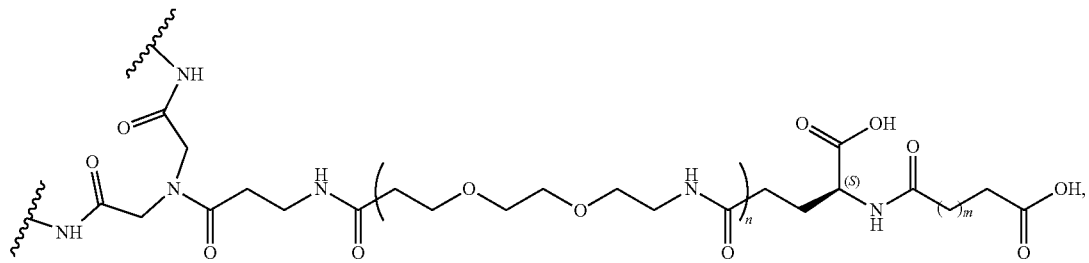

wherein n is 1-4 and m is 6-20.
619. The peptide conjugate of embodiment 618, wherein n is 2 and m is 15.
620. The peptide conjugate of embodiment 618, wherein n is 2 and m is 17.
621. The peptide conjugate of any one of embodiments 312-582, wherein the peptide conjugate comprises:

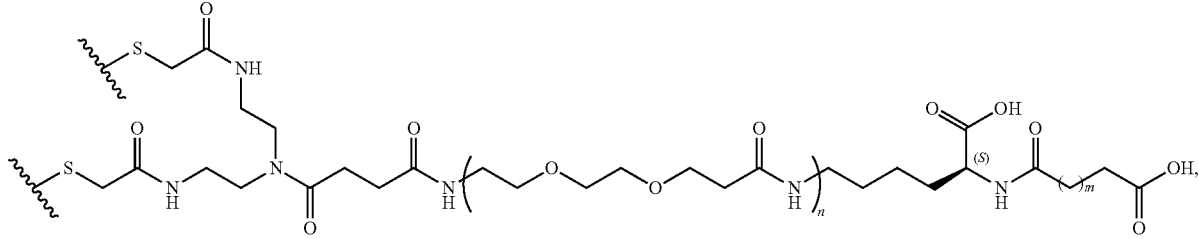

wherein n is 1-4 and m is 6-20.

622. The peptide conjugate of embodiment 621, wherein n is 2 and m is 15.

623. The peptide conjugate of embodiment 621, wherein n is 2 and m is 17.

624. The peptide conjugate of embodiment 621, wherein n is 2 and m is 13.

625. The peptide conjugate of any one of embodiments 312-582, wherein the peptide conjugate comprises: L5A

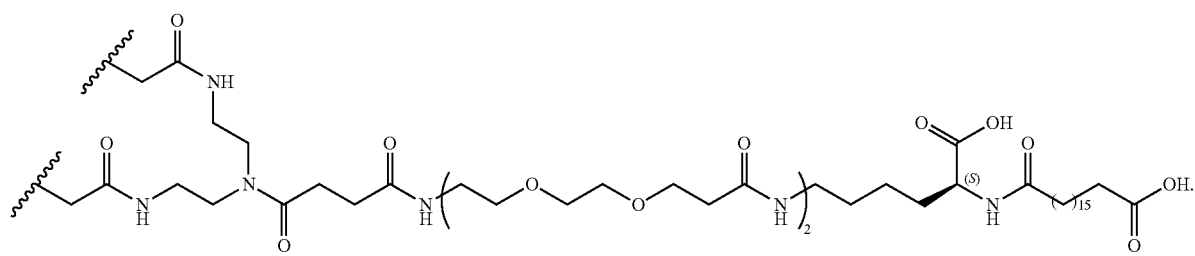

626. The peptide conjugate of any one of embodiments 312-582, wherein the peptide conjugate comprises: C20L5A

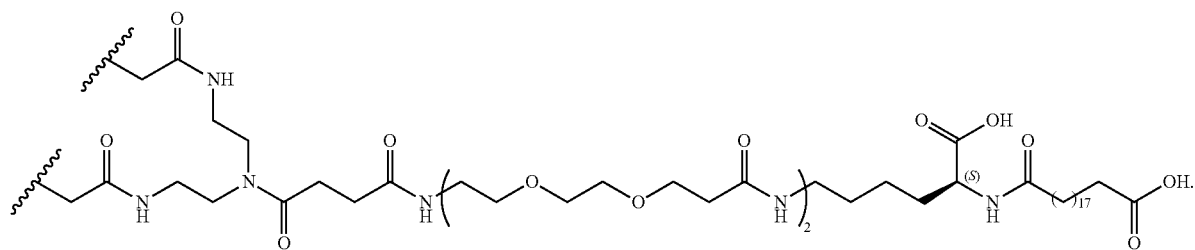

627. The peptide conjugate of ofany one of embodiments 312-582, wherein the peptide conjugate comprises: C16L5A

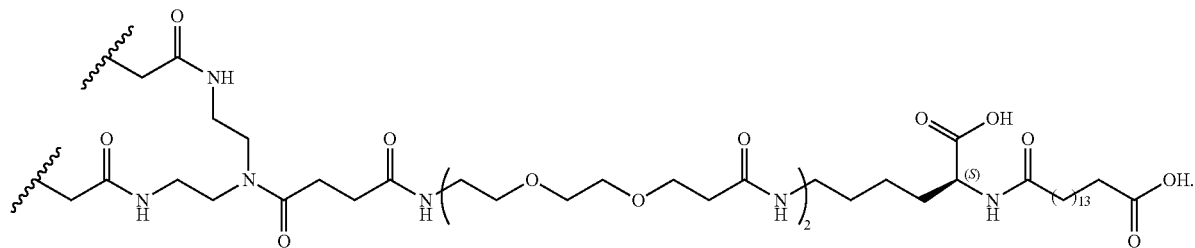

628. The peptide conjugate of any one of embodiments 312-582, wherein the peptide conjugate comprises: K4

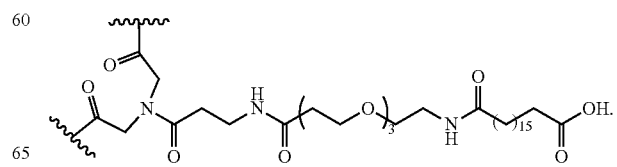

629. The peptide conjugate of any one of embodiments 312-582, wherein the peptide conjugate comprises: K5

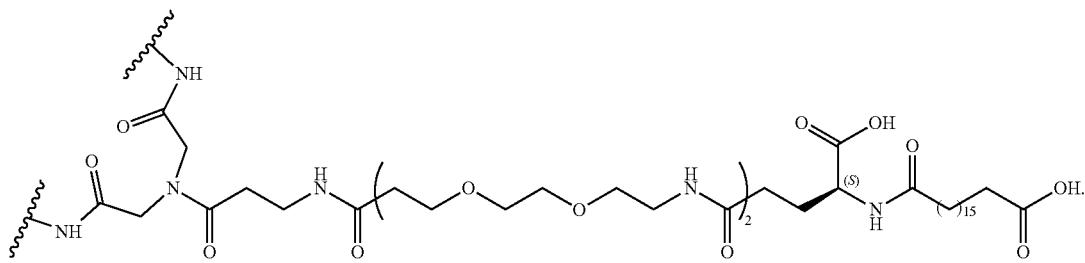

630. The peptide conjugate of any one of embodiments 312-582, wherein the peptide conjugate comprises: C20K5

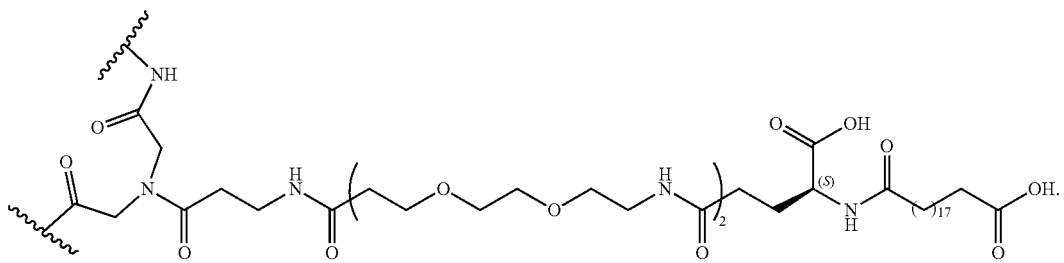

631. A peptide comprising the peptide of any one of embodiments 28-270.
632. A pharmaceutical composition comprising the peptide conjugate of any one of embodiments 1-630 or a peptide of embodiment 631, and a pharmaceutically acceptable excipient.
633. A method for treating a disease or condition in a subject in need thereof, the method comprising administering to the subject a composition comprising a therapeutically effective amount of the peptide conjugate of any one of embodiments 1-630 or the peptide of embodiment 631.
634. The method of embodiment 633, wherein the disease or condition is diabetes or obesity.
635. The method of embodiment 633, wherein the disease or condition is non-alcoholic fatty liver disease (NAFLD), nonalcoholic steatohepatitis (NASH), or cardiovascular disease.
636. The method of embodiment 633, wherein the disease or condition is short bowel syndrome (SBS).
637. The method of embodiment 633, wherein the disease or condition is inflammatory bowel disease (IBD), inflammatory bowel syndrome (IBS), or psoriasis.
638. The method of embodiment 633, wherein the disease or condition is Crohn's disease or ulcerative colitis.
639. The method of embodiment 633, wherein the disease or condition is Alzheimer's disease, Parkinson's disease or Huntington's disease.
640. The method of any one of embodiments 633-639, further comprising administering to the subject one or more additional therapeutic agents.
641. The method of embodiment 640, wherein the one or more additional therapeutic agents comprises an incretin hormone or a derivative thereof.
642. The method of embodiment 641, wherein the incretin hormone or derivative thereof is selected from GLP-1, exendin-4, glucagon (GCG), glucose-dependent insulinotropic polypeptide (GIP), oxyntomodulin, and combinations thereof.
643. The method of any one of embodiments 633-642, wherein the peptide conjugate is administered about once every 7 days.
644. The method of any one of embodiments 633-642, wherein the peptide conjugate is administered about once every 14 days.
645. The method of any one of embodiments 633-642, wherein the peptide conjugate is administered about once a month.
646. The method of any one of embodiments 633-642, wherein the peptide conjugate is administered about once every two months.
647. The method of any one of embodiments 633-642, wherein the peptide conjugate is administered about once every three months.

Pharmcokinetics

Mechanisms by which peptides and peptide conjugates positively influence pharmacokinetic or pharmacodynamic behavior include, but are not limited to, (i) preventing or mitigating in vivo proteolytic degradation or other activity-diminishing chemical modification of the therapeutic agent; (ii) improving half-life or other pharmacokinetic properties by reducing renal filtration, decreasing receptor-mediated clearance or increasing bioavailability; (iii) reducing toxicity; (iv) improving solubility; and/or (v) increasing biological activity and/or target selectivity of the unconjugated therapeutic agent. The therapeutic agent may comprise a peptide that modulates and/or binds to: a GLP-1 receptor, a GIP receptor, or a GLP-1 receptor and GIP receptor. The therapeutic agent may comprise a peptide comprising a sequence about or at least about 79%, 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOS: 1-61.

Peptide conjugates may enhance one or more pharmacokinetic properties of a therapeutic agent when attached to the therapeutic agent. Peptide conjugates disclosed herein may enhance the one or more pharmacokinetic properties of the therapeutic agent by at least about 200% as measured by pharmacodynamics when compared to the therapeutic agent or unmodified therapeutic peptide alone. Peptide conjugates disclosed herein may enhance the one or more pharmacokinetic properties of the therapeutic agent by at least about 300%, 400%, 500%, 600%, 700%, 800%, 900%, 1000% as measured by pharmacodynamics when compared to the therapeutic agent or unmodified therapeutic peptide alone.

The pharmacokinetic properties may comprise a half-life. The half-life of the peptide conjugate may be at least about two-fold longer compared to the half-life of the unmodified peptide alone. The half-life of the peptide conjugate disclosed herein may be at least about 3-fold, 4-fold, 5-fold, or 10-fold longer compared to the half-life of the therapeutic agent or unmodified therapeutic peptide alone. The half-life of a peptide conjugate disclosed herein may be at least about 6-, 7-, 8-, 9-, 10-, 15-, 20-, 25-, 30-, 35-, 40-, 45-, or 50-fold longer compared to the half-life of the unmodified peptide alone.

In some embodiments, the half-life of the peptide conjugate is at least about 2-fold greater than the half-life of an unmodified form of the peptide. In some embodiments, the half-life of the peptide conjugate is at least about 5-fold greater than the half-life of an unmodified form of the peptide. In some embodiments, the half-life of the peptide conjugate is at least about 10-fold greater than the half-life of an unmodified form of the peptide.

In addition, a peptide conjugate as described herein may have a positive effect on terms of increasing manufacturability, and/or reducing immunogenicity of the peptide, compared to an unconjugated form of the unmodified therapeutic peptide.

In some embodiments, peptides and peptide conjugates disclosed herein are administered weekly, or about every 7 days. In some cases, peptides and peptide conjugates disclosed herein are administered biweekly, or about every 14 days. In some cases, a peptide disclosed herein is administered every week, every two weeks, once a month, or once every three months. In some cases, a peptide conjugate disclosed herein is administered every week, every two weeks, once a month, or once every three months.

Therapeutic Use

In one aspect, peptides and peptide conjugates disclosed herein are useful for treating, alleviating, inhibiting and/or preventing one or more diseases and/or conditions. The disease and/or condition may be a chronic disease or condition. Alternatively, the disease and/or condition is an acute disease or condition. The disease or condition may be recurrent, refractory, accelerated, or in remission. The disease or condition may affect one or more cell types. The one or more diseases and/or conditions may be an autoimmune disease, inflammatory disease, or metabolic disease.

Disclosed herein are methods for treating a disease or condition in a subject in need thereof, the method comprising administering to the subject a peptide conjugate described herein. The disease or condition may be diabetes or obesity, or a medical condition associated with diabetes or obesity. The diabetes may be type 1 diabetes mellitus, type 2 diabetes mellitus, gestational diabetes, neonatal diabetes, maturity onset diabetes of the young, or latent autoimmune diabetes in adults, or any combination thereof. The disease or condition may be non-alcoholic fatty liver disease (NAFLD), nonalcoholic steatohepatitis (NASH), or cardiovascular disease. The disease or condition may be an autoimmune disorder. The disease or condition may be Crohn's disease or ulcerative colitis. The disease or condition may be short bowel syndrome (SBS). The disease or condition may be inflammatory bowel disease (IBD), inflammatory bowel syndrome (IBS), or psoriasis. The disease or condition may be Alzheimer's disease, Parkinson's disease or Huntington's disease. The peptide conjugate may be administered with one or more additional therapeutic agents. Disclosed herein are methods of treating a disease or condition in a subject in need thereof, the method comprising administering to the subject a composition disclosed herein comprising one or more peptide conjugates.

Provided herein is a method of preventing or treating a metabolic disease or condition in a subject in need thereof, the method comprising administering to the subject a peptide conjugate described herein. The metabolic disease or condition may be diabetes. The metabolic disease or condition may be obesity. The metabolic disease or condition may be glycogen storage disease, phenylketonuria, maple syrup urine disease, glutaric acidemia type 1, Carbamoyl phosphate synthetase I deficiency, alcaptonuria, Medium-chain acyl-coenzyme A dehydrogenase deficiency (MCADD), acute intermittent porphyria, Lesch-Nyhan syndrome, lipoid congenital adrenal hyperplasia, congenital adrenal hyperplasia, POMPC deficiency, LEPR deficiency, Bardet Biedl syndrome, Alstrome syndrome, Prader-Willi Syndrome, Kearns-Sayre syndrome, Zellweger syndrome, Gaucher's disease, or Niemann Pick disease.

Provided herein is a method of preventing or treating NAFLD, NASH, or cardiovascular disease in a subject in need thereof, the method comprising administering to the subject a peptide conjugate described herein.

Provided herein is a method of preventing or treating short bowel syndrome (SBS) in a subject in need thereof, the method comprising administering to the subject a peptide conjugate described herein.

Provided herein is a method of preventing or treating inflammatory bowel disease (IBD), inflammatory bowel syndrome (IBS), or psoriasis in a subject in need thereof, the method comprising administering to the subject a peptide conjugate described herein.

Provided herein is a method of preventing or treating Crohn's disease or ulcerative colitis in a subject in need thereof, the method comprising administering to the subject a peptide conjugate described herein.

Provided herein is a method of preventing or treating a sleep disorder.

Provided herein is a method of preventing or treating absence seizure.

Provided herein is a method of preventing or treating chronic kidney disease (for example complication of diabetes). Provided herein is a method of preventing or treating diabetic heart disease.

Provided herein is a method of preventing or treating cardiovascular events.

Provided herein is a method of preventing or treating Alzheimer's disease, Parkinson's disease or Huntington's disease in a subject in need thereof, the method comprising administering to the subject a peptide conjugate described herein.

Provided herein is a method of preventing or treating stomach and bowel-related disorders, such as the treatment of neonatals with compromised intestine function, osteoporosis, and DPP-IV (dipeptidylpeptidase-IV) mediated conditions. By way of example, the stomach and bowel-related disorders include ulcers, gastritis, digestion disorders, malabsorption syndromes, short-gut syndrome, cul-de-sac syndrome, inflammatory bowel disease, celiac sprue (for example arising from gluten induced enteropathy or celiac disease), tropical sprue, hypogammaglobulinemia sprue, enteritis, regional enteritis (Crohn's disease), ulcerative colitis, irritable bowel syndrome associated with diarrhea, Small intestine damage and short bowel syndrome.

Provided herein is a method of preventing or treating radiation enteritis, infectious or post-infectious enteritis, and small intestinal damage due to toxic or other chemotherapeutic agents. This may require administration of the peptide conjugate prior to, concurrently with or following a course of chemotherapy or radiation therapy in order to reduce side effects of chemotherapy such as diarrhea, abdominal cramping and vomiting, and reduce the consequent structural and functional damage of the intestinal epithelium resulting from the chemotherapy or radiation therapy.

Provided herein is a method of preventing or treating malnutrition, for example conditions such as the wasting syndrome cachexia and anorexia.

Provided herein is a method of preventing or treating a disease or condition which benefits from a modulator and/or binder of a GLP-1 receptor in a subject in need thereof comprising administering to the subject a peptide conjugate described herein.

Provided herein is a method of preventing or treating a disease or condition which benefits from a modulator and/or binder of a GLP-1/GIP receptor in a subject in need thereof comprising administering to the subject a peptide conjugate described herein.

Provided herein is a method of preventing or treating a disease or condition which benefits from a modulator and/or binder of a GIP receptor in a subject in need thereof comprising administering to the subject a peptide conjugate described herein.

In some embodiments, peptides disclosed herein are administered weekly, or about every 7 days. In some cases, peptides disclosed herein are administered biweekly, or about every 14 days.

In some embodiments, peptide conjugates disclosed herein are administered weekly, or about every 7 days. In some cases, peptide conjugates disclosed herein are administered biweekly, or about every 14 days.

Combinations

Disclosed herein are pharmaceutical compositions comprising a peptide or peptide conjugate described herein and one or more additional therapeutic agents.

The additional therapeutic agents may comprise one or more other diabetes drugs, DPP4 inhibitors, SGLT2 inhibitors, hypoglycemic drugs and biguanidine drugs, insulin secretogogues and sulfonyl urea drugs, TZD drugs, insulin and insulin analogs, FGF21 and analogs, leptin or leptin analogs, amylin and amylin analogs, an anti-inflammatory drug, cyclosporine A or FK506, 5-ASA, or a statin, or any combination thereof. The additional therapeutic agent may be aspirin.

The additional therapeutic agents may comprise a therapeutic incretin or derivative thereof. Non-limiting examples of incretins or derivatives thereof include GLP-1, glucagon, oxyntomodulin, exendin-4, GLP-2, GIP, and combinations thereof.

In some embodiments, combination treatment demonstrates superior glucose control, food intake reduction, and weight loss than administration of a single agent. In some embodiments, combination treatment mimics the beneficial effects of bariatric surgery in an obese patient.

Compositions

Disclosed herein are pharmaceutical compositions comprising a peptide or peptide conjugate described herein and a pharmaceutically acceptable excipients or vehicles. Pharmaceutically acceptable excipients or vehicles may include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with serum albumin are exemplary appropriate carriers. The pharmaceutical compositions may include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also may be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers may be conventional buffers such as acetate, borate, citrate, phosphate, bicarbonate, or Tris-HCl. Acetate buffer may be about pH 4-5.5, and Tris buffer can be about pH 7-8.5. Additional pharmaceutical agents are set forth in Remington's Pharmaceutical Sciences, 18th Edition, A. R. Gennaro, ed., Mack Publishing Company, 1990.

The composition may be in liquid form or in a lyophilized or freeze-dried form and may include one or more lyoprotectants, excipients, surfactants, high molecular weight structural additives and/or bulking agents. In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization. Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g., polysorbate 20, polysorbate 80); poloxamers (e.g., poloxamer 188); poly(ethylene glycol) phenyl ethers (e.g., Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl-or stearyl-sarcosine; linoleyl, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; and the MONAQUAT™ series (Mona Industries, Inc., Paterson, N.J.), polyethyl glycol, polypropyl glycol, and copolymers of ethylene and propylene glycol (e.g., Pluronics, PF68 etc). Exemplary amounts of surfactant that may be present in the pre-lyophilized formulation are from about 0.001-0.5%. High molecular weight structural additives (e.g., fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.1% to 10% by weight. In other embodiments, a bulking agent (e.g., mannitol, glycine) may be included.

Compositions may be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically may be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980.

Pharmaceutical compositions described herein may be formulated for controlled or sustained delivery in a manner that provides local concentration of the product (e.g., bolus, depot effect) and/or increased stability or half-life in a particular local environment. The compositions can include the formulation of peptide conjugates, polypeptides, nucleic acids, or vectors disclosed herein with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then can be delivered as a depot injection. Techniques for formulating such sustained-or controlled-delivery means are known, and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents (e.g., peptide conjugates).

Suitable and/or preferred pharmaceutical formulations may be determined in view of the present disclosure and general knowledge of formulation technology, depending upon the intended route of administration, delivery format, and desired dosage. Regardless of the manner of administration, an effective dose may be calculated according to patient body weight, body surface area, or organ size. Further refinement of the calculations for determining the appropriate dosage for treatment involving each of the formulations described herein are routinely made in the art and is within the ambit of tasks routinely performed in the art. Appropriate dosages may be ascertained through use of appropriate dose-response data.

Definitions

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below.

"Alkyl" refers to a straight or branched chain hydrocarbon monoradical, which may be fully saturated or unsaturated, having from one to about ten carbon atoms, or from one to six carbon atoms, wherein a sp3-hybridized carbon of the alkyl residue is attached to the rest of the molecule by a single bond. Examples of saturated hydrocarbon monoradical include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_1$-$C_9$ alkyl, a $C_1$-$C_8$ alkyl, a $C_1$-$C_7$ alkyl, a $C_1$-$C_6$ alkyl, a $C_1$-$C_5$ alkyl, a $C_1$-$C_4$ alkyl, a $C_1$-$C_3$ alkyl, a $C_1$-$C_2$ alkyl, or a $C_1$ alkyl. When the alkyl refers to an unsaturated straight or branched chain hydrocarbon monoradical it is known as an "alkenyl" or an "alkynyl". The alkenyl may be in either the cis or trans conformation about the double bond(s), and should be understood to include both isomers. Examples of alkenyls include, but are not limited to ethenyl (—CH=$CH_2$), 1-propenyl (—$CH_2$CH=$CH_2$), isopropenyl [—C($CH_3$)=$CH_2$], butenyl, 1,3-butadienyl and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms, or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Examples of alkynyl include, but are not limited to ethynyl, 2-propynyl, 2- and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. In some embodiments, the alkynyl is a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkyl group is optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —$CF_3$, —OH, —OMe, —$NH_2$, or —$NO_2$. In some embodiments, the alkyl is optionally substituted with oxo, halogen, —CN, —$CF_3$, —OH, or —OMe. In some embodiments, the alkyl is optionally substituted with halogen.

"Alkylene" refers to a straight or branched divalent hydrocarbon chain. Whenever it appears herein, a numerical range such as "$C_1$-$C_6$ alkylene" means that the alkylene consists of 1 carbon atom, 2 carbon atoms, 3 carbon atoms, 4 carbon atoms, 5 carbon atoms, or 6 carbon atoms, although the present definition also covers the occurrence of the term "alkylene" where no numerical range is designated. In some embodiments, the alkylene is a $C_1$-$C_{10}$ alkylene, a $C_1$-$C_9$ alkylene, a $C_1$-$C_8$ alkylene, a $C_1$-$C_7$ alkylene, a $C_1$-$C_6$ alkylene, a $C_1$-$C_5$ alkylene, a $C_1$-$C_4$ alkylene, a $C_1$-$C_3$ alkylene, a $C_1$-$C_2$ alkylene, or a $C_1$ alkylene. Unless stated otherwise specifically in the specification, an alkylene group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkylene is optionally substituted with oxo, halogen, —CN, —$CF_3$, —OH, —OMe, —$NH_2$, or —$NO_2$. In some embodiments, an alkylene is optionally substituted with oxo, halogen, —CN, —$CF_3$, —OH, or —OMe. In some embodiments, the alkylene is optionally substituted with halogen.

"Alkoxy" refers to a radical of the formula —$OR_a$ where $R_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkoxy is optionally substituted with oxo, halogen, —CN, —$CF_3$, —OH, —OMe, —$NH_2$, or —$NO_2$. In some embodiments, an alkoxy is optionally substituted with oxo, halogen, —CN, —$CF_3$, —OH, or —OMe. In some embodiments, the alkoxy is optionally substituted with halogen.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl is phenyl. Unless stated otherwise specifically in the specification, an aryl may be optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, an aryl is optionally substituted with halogen, methyl, ethyl, —CN, —$CF_3$, —OH, —OMe, —$NH_2$, or —$NO_2$. In some embodiments, an aryl is optionally substituted with halogen, methyl, ethyl, —CN, —$CF_3$, —OH, or —OMe. In some embodiments, the aryl is optionally substituted with halogen.

"Cycloalkyl" refers to a stable, partially or fully saturated, monocyclic or polycyclic carbocyclic ring, which may include fused (when fused with an aryl or a heteroaryl ring, the cycloalkyl is bonded through a non-aromatic ring atom) or bridged ring systems. Representative cycloalkyls include, but are not limited to, cycloalkyls having from three to fifteen carbon atoms ($C_3$-$C_{15}$ cycloalkyl), from three to ten carbon atoms ($C_3$-$C_{10}$ cycloalkyl), from three to eight carbon atoms ($C_3$-$C_8$ cycloalkyl), from three to six carbon atoms ($C_3$-$C_6$ cycloalkyl), from three to five carbon atoms ($C_3$-$C_8$ cycloalkyl), or three to four carbon atoms ($C_3$-$C_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —$CF_3$, —OH, —OMe, —$NH_2$, or —$NO_2$. In some embodiments, a cycloalkyl is optionally substituted with oxo, halogen, methyl, ethyl, —CN, —$CF_3$, —OH, or —OMe. In some embodiments, the cycloalkyl is optionally substituted with halogen.

"Halo" or "halogen" refers to bromo, chloro, fluoro, or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Heterocycloalkyl" refers to a stable 3- to 24-membered partially or fully saturated ring radical comprising 2 to 23 carbon atoms and from one to 8 heteroatoms selected from nitrogen, oxygen, phosphorous, and sulfur. Representative heterocycloalkyls include, but are not limited to, heterocycloalkyls having from two to fifteen carbon atoms ($C_2$-$C_{15}$ heterocycloalkyl), from two to ten carbon atoms ($C_2$-$C_{10}$ heterocycloalkyl), from two to eight carbon atoms ($C_2$-$C_8$ heterocycloalkyl), from two to six carbon atoms ($C_2$-$C_6$ heterocycloalkyl), from two to five carbon atoms ($C_2$-$C_5$ heterocycloalkyl), or two to four carbon atoms ($C_2$-$C_4$ heterocycloalkyl). In some embodiments, the heterocycloalkyl is a 3- to 6-membered heterocycloalkyl. In some embodiments, the heterocycloalkyl is a 5- to 6-membered heterocycloalkyl. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Partially saturated heterocycloalkyls include, for example dihydropyrrolyl or tetrahydropyridine. Unless stated otherwise specifically in the specification, a heterocycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heterocycloalkyl is optionally substituted with oxo, halogen, methyl, ethyl, —CN, —$CF_3$, —OH, —OMe, —$NH_2$, or —$NO_2$. In some embodiments, a heterocycloalkyl is optionally substituted with oxo, halogen, methyl, ethyl, —CN, —$CF_3$, —OH, or —OMe. In some embodiments, the heterocycloalkyl is optionally substituted with halogen.

"Heteroalkyl" refers to an alkyl group in which one or more skeletal atoms of the alkyl are selected from an atom other than carbon, e.g., oxygen, nitrogen (e.g. —NH—, —N(alkyl)-), sulfur, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, or combinations thereof wherein the heteroalkyl is attached to the rest of the molecule at a carbon atom of the heteroalkyl. Unless stated otherwise specifically in the specification, a heteroalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —$CF_3$, —OH, —OMe, —$NH_2$, or —$NO_2$. In some embodiments, a heteroalkyl is optionally substituted with oxo, halogen, methyl, ethyl, —CN, —$CF_3$, —OH, or —OMe. In some embodiments, the heteroalkyl is optionally substituted with halogen.

"Heteroaryl" refers to a 5- to 14-membered ring system radical comprising hydrogen atoms, one to thirteen carbon atoms, one to six heteroatoms selected from nitrogen, oxygen, phosphorous, and sulfur, and at least one aromatic ring. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 5-membered heteroaryl. In some embodiments, the heteroaryl is a 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroaryl is optionally substituted with halogen, methyl, ethyl, —CN, —$CF_3$, —OH, —OMe, —$NH_2$, or —$NO_2$. In some embodiments, a heteroaryl is optionally substituted with halogen, methyl, ethyl, —CN, —$CF_3$, —OH, or —OMe. In some embodiments, the heteroaryl is optionally substituted with halogen.

The term "percent identity" refers to a comparison between two nucleic acid or amino acid sequences. Such comparisons are measured using any number of alignment methods known in the art, including but not limited to global (e.g., Needleman-Wunsch algorithm) or local alignments (e.g., Smith-Waterman, Sellers, or other algorithm). Percent identity often refers to the percentage of matching positions of two sequences for a contiguous section of positions, wherein the two sequences are aligned in such a way to maximize matching positions and minimize gaps of non-matching positions. In some instances, alignments are conducted wherein there are no gaps between the two sequences. In some instances, the alignment results in less than 5% gaps, less than 3% gaps, or less than 1% gaps. Additional methods of sequence comparison or alignment are also consistent with the disclosure.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable salt" refers to a salt of a compound that is pharmaceutically acceptable and that possesses the desired pharmacological activity of the parent compound.

"Pharmaceutically acceptable excipient, carrier or adjuvant" refers to an excipient, carrier or adjuvant that may be administered to a subject, together with at least one antibody of the present disclosure, and which does not destroy the pharmacological activity thereof and is nontoxic when administered in doses sufficient to deliver a therapeutic amount of the compound.

"Pharmaceutically acceptable vehicle" refers to a diluent, adjuvant, excipient, or carrier with which at least one antibody of the present disclosure is administered.

Terms such as "treating" or "treatment" or "to treat" or "alleviating" or "to alleviate" may refer to: 1) therapeutic measures that cure, slow down, lessen symptoms of, and/or halt progression of a diagnosed pathologic condition or disorder; and/or 2) prophylactic or preventative measures that prevent and/or slow the development of a targeted pathologic condition or disorder. "Treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, and diminishment of any direct or indirect pathological consequences of the disease, preventing metastasis, decreasing the rate of disease progression, amelioration or palliation of the disease state, and remission or improved prognosis. Thus those in need of treatment may include those already with the disorder; those prone to have the disorder; and those in whom the disorder is to be prevented.

"Amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

"Disorder" or "disease" refers to a condition that would benefit from treatment with a substance/molecule (e.g., a peptide conjugate disclosed herein) or method disclosed herein. This includes chronic and acute disorders or diseases including those pathological conditions which predispose the mammal to the disorder in question.

"Mammal" for purposes of treatment refers to any animal classified as a mammal, including humans, rodents (e.g., mice and rats), and monkeys; domestic and farm animals; and zoo, sports, laboratory, or pet animals, such as dogs, cats, cattle, horses, sheep, pigs, goats, rabbits, etc. In some embodiments, the mammal is selected from a human, dog, rodent, or monkey. In some embodiments, the subject having a disease or condition in need of treating is a human. In some embodiments, the subject having a disease or condition in need of treating is a companion animal. In some embodiments, the subject having a disease or condition in need of treating is a dog. In some embodiments, the subject having a disease or condition in need of treating is a cat.

"Modulate" refers to the ability of a peptide to bind to a protein receptor. In some embodiments, the modulator is a ligand of the receptor. In some embodiments, the modulator is an agonist. In some embodiments, the modulator is an antagonist. For instance, a peptide that modulates the GLP-1 receptor binds to a GLP-1 receptor (GLP-1R). For instance, a peptide that modulates the GCG receptor binds to a GCG receptor (GCGR). For instance, a peptide that modulates the GIP receptor binds to a GIP receptor (GIPR). For instance, a peptide that modulates the PYY receptor binds to a PYY receptor (PYYR). As non-limiting examples, the peptide that modulates the GLP-1 receptor is a GLP-1R agonist. As non-limiting examples, the peptide that modulates both the GLP-1 receptor and the GCG receptor is a dual GLP-1R/GCGR agonist. As non-limiting examples, the peptide that modulates both the GLP-1 receptor and the GIP receptor is a dual GLP-1R/GIPR agonist. As non-limiting examples, the peptide that modulates the PYY receptor is a PYYR agonist.

"Unmodified peptide" refers to either an unmodified sequence (wild type peptide) or a modified sequence without a staple.

EXAMPLES

Peptides were synthesized by standard solid-phase peptide synthesis (SPPS) techniques and purified via HPLC.

Unless otherwise noted, all reagents were purchased from commercial suppliers and used without further purification. All reactions involving air or moisture sensitive reagents or intermediates were performed under an inert atmosphere of nitrogen or argon. All solvents used were of HPLC grade. Reactions were monitored by LC-MS or by thin-layer chromatography (TLC) on Merck 50×100 mm silica gel 60 aluminum sheets stained using an aqueous solution of KMnO4.

Flash chromatography purifications were performed on silica gel prepacked columns (40 µm, RediSep® Rf from Teledyne Isco) on a CombiFlash® Rf (Teledyne Isco). Purified final compounds were eluted as single and symmetrical peaks (thereby confirming a purity of ≥95%). Semi-preparative chromatography were performed on a Shimadzu HPLC with a Phenomenex Luna column (C18, 100 Å pore size, 10 µm particle size, 250×10.0 mm, flow: 4 mL/min) or on an Agilent 1200 HPLC with a Phenomenex Luna column (C18, 100 Å pore size, 5 µm particle size, 150×21.2 mm, flow: 20 mL/min).

$^1$H and $^{13}$C NMR spectra were recorded on a Bruker 400 system in d$_6$-DMSO, CDCl$_3$ or CD$_3$OD. Chemical shifts are given in parts per million (ppm) with tetramethylsilane as an internal standard. Abbreviations are used as follows: s=singlet, d=doublet, t=triplet, q=quartet, p=pentet, m=multiplet, dd=doublet of doublets, br=broad. Coupling constants (J values) are given in hertz (Hz). Low resolution mass spectra were recorded on a Waters Acquity UPLC with a Phemomenex Luna Omega C18 column (C18, 100 Å pore size, 1.6 µm particle size, 50×2.1 mm, flow: 0.4 mL/min). Solvents: A—H$_2$O+0.1% formic acid, B—MeCN+0.1% formic acid, gradient: 0-1 min 10-90% B, 1-1.6 min 90% B, 1.6-1.7 min 90-10% B, 1.7-2 min 10% B.

High resolution mass spectra (HRMS) were recorded on an Agilent 1200 Series Accurate Mass Time-of-Flight (TOF) with an Aeris Widepore column (XB-C8, 3.6 µm particle size, 150×2.1 mm, flow: 0.5 mL/min). Solvents: A—H$_2$O+0.1% formic acid, B—MeCN+0.1% formic acid, gradient: 0-2 min 5% B, 2-12 min 5-60% B, 12-13 min 60-80% B, 13-14 min 80-20% B, 14-15 min 20-80% B, 15-16 min 80-20% B, 16-17 min 20-95% B, 17-20 min 95% B, 20-21 min 95-5% B.

General Protocol A for Loading of Chlorotrityl Chloride Resin

Fmoc-Lys(ivDde)-OH (60 mg, 100 µmol) was coupled to 2-chlorotrityl chloride resin (Novabiochem) (100 mg, 80 µmol) by mixing the amino acid, resin, and DIEA (70 µL, 400 µmol) in 5 mL of DMF and stirring for 30 min. The resin was then washed with DMF (3×), DCM (3×) and treated with CH$_3$OH/DCM/DIEA (8:1:1) for 10 min to cap the unreacted trityl chloride sites, dried under vacuum and stored in a desiccator.

General Protocol B for Deprotection of Fmoc Protecting Group

To the resin was added piperidine in DMF (20%). The mixture was shaken for 5 min and drained. Fresh 20% piperidine was added and this time the mixture was shaken for 15 min. Positive ninhydrin and/or TNBS test was observed. The resin was then washed with DMF (3×), DCM (3×).

General Protocol C for Deprotection of ivDde Protecting Group

After washing with DMF and DCM, the resin was treated with 2% hydrazine in DMF (5 mL, 2×15 min). Positive ninhydrin and/or TNBS test was observed. The resin was then washed with DMF (3×), DCM (3×).

General Protocol D for Peptide Coupling

The resin was treated with the carboxylic acid derivative specified (3 eq) using coupling reagent HATU (3.3 eq), and DIEA (3.3 eq) in DMF (5 mL) for 2 h or repeated until a negative ninhydrin and/or TNBS test was observed. The resin was then washed with DMF (3×), DCM (3×).

General Protocol E for On-Resin Bromoacetylation

The resin was then treated with bromoacetic anhydride (2.4 eq), and DIEA (2.6 eq) in 200 mL of DCM for 30 min.

General Protocol F for Cleavage of Peptides from Chlorotrityl Resin

The resin was washed with DCM (3×), the product was cleaved from the resin using 5 mL of 10% TFA in DCM containing 10% H$_2$O and 10% triisopropylsilane for 1 h.

Example 1: Synthesis of a Fatty Acid Conjugation Reagent (FA2)

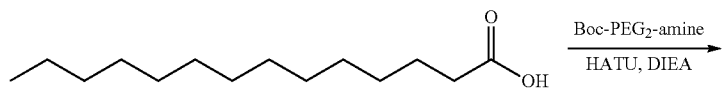

-continued

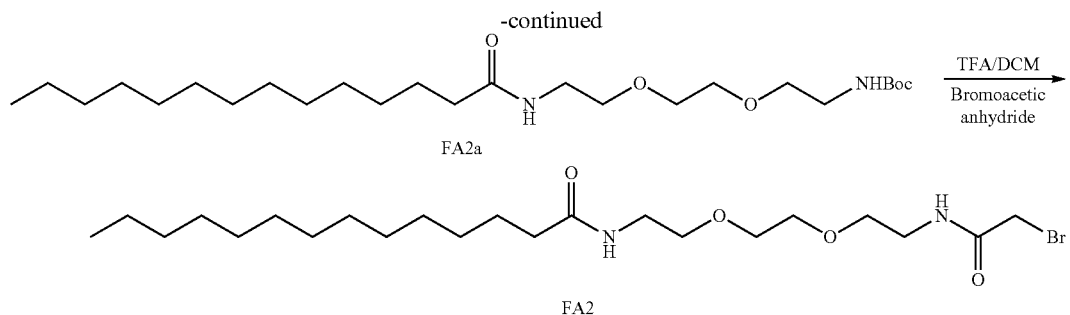

Intermediate FA2a. Myristic acid (0.46 g, 2 mmol) was dissolved in 5 mL of DMF. HATU (0.8 g, 2.1 mmol) and DIEA (0.4 mL, 2.2 mmol) were added followed by the addition of Boc-NH-PEG$_2$-COOH (0.5 g, 2 mmol). The reaction mixture was then stirred for 6 h, and the solvent was removed. The product was extracted with EtOAc (3×15 mL). The organic layer was successively washed with sat. NaHCO$_3$, cooled HCl (1 M) and brine, dried over Na$_2$SO$_4$, filtered, and concentrated. Purification by flash column chromatography on silica gel provided 0.81 g of tert-butyl (2-(2-(2-tetradecanamidoethoxy)ethoxy)ethyl)carbamate (FA2a) as a white solid in 90% product yield. MS (ES$^+$) m/z 459.6 ([M+H]$^+$), calcd MW 458.4.

FA2. A solution of FA2a (0.23 g, 0.5 mmol) in DCM (10 mL) was treated with TFA (2 mL) for 2 h. The mixture was concentrated, followed by the addition of bromoacetic anhydride (0.14 g, 0.55 mmol) and DIEA (0.17 mL, 1 mmol) in 10 mL of DCM at 0° C. The reaction mixture was then stirred for 2 h, and the solvent was removed. The product was extracted with EtOAc (3×15 mL). The organic layer was successively washed with sat. NaHCO$_3$, cooled HCl (1 M) and brine, dried over Na$_2$SO$_4$, filtered, and concentrated. Purification by flash column chromatography on silica gel provided 0.2 g of FA2 as a white solid in 83% product yield. MS (ES$^+$) m/z 480.4 ([M+H]$^+$), calcd MW 479.5.

Example 2: Synthesis of L1

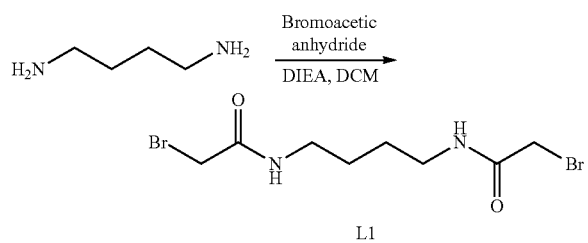

To a solution of 1,4-diaminobutane (80 µL, 0.795 mmol, 1 eq) in DCM (10 mL) at 0° C. were added DIEA (276 µL, 1.59 mmol, 2 eq) followed by bromoacetic anhydride (413 g, 1.59 mmol, 2 eq) dissolved in 1 mL of DCM. The reaction mixture was then stirred for 30 min at 0° C., 1.5 h at RT, and the solvent was removed. Purification by flash column chromatography on silica gel afforded L1 as a white solid (162 mg, 0.49 mmol, 61%). MS (ES$^+$) m/z 331.0 ([M+H]$^+$). $^1$H NMR (400 MHz, methanol-d$_4$) δ 3.94 (s, 4H), 3.40-3.30 (m, 4H), 1.68 (p, J=3.5 Hz, 4H).

Example 3: Synthesis of L1B

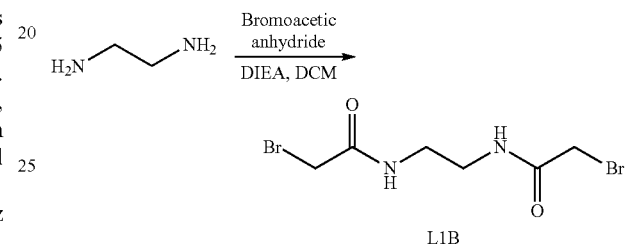

To a solution of 1,2-ethylenediamine (30 µL, 0.448 mmol, 1 eq) in DCM (5 mL) at 0° C. were added DIEA (172 µL, 0.985 mmol, 2.2 eq) followed by bromoacetic anhydride (233 mg, 0.897 mmol, 2 eq) dissolved in 1 mL of DCM. The reaction mixture was then stirred for 30 min at 0° C., 1.5 h at RT, and the solvent was removed. Purification by flash column chromatography on silica gel provided L1B as a white solid (43.9 mg, 0.145 mmol, 32%). MS (ES$^+$) m/z 302.55 ([M+H]$^+$), 304.54 ([M+H]$^+$). $^1$H NMR (400 MHz, methanol-d$_4$) δ 2.49 (s, 4H), 2.06 (s, 4H).

Example 4: Synthesis of L1C

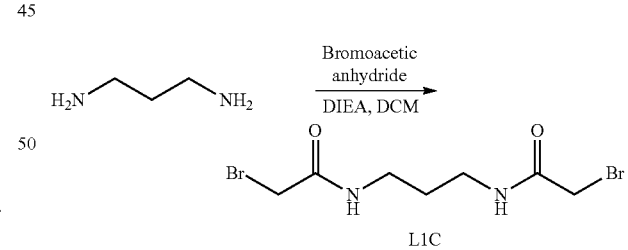

To a solution of 1,3-diaminopropane (30 µL, 0.359 mmol, 1 eq) in DCM (5 mL) at 0° C. were added DIEA (138 µL, 0.789 mmol, 2.2 eq) followed by bromoacetic anhydride (186 mg, 0.718 mmol, 2 eq) dissolved in 1 mL of DCM. The reaction mixture was then stirred for 30 min at 0° C., 1.5 h at RT, and the solvent was removed. Purification by flash column chromatography on silica gel afforded L1C as a white solid (60.8 mg, 0.19 mmol, 53%). MS (ES$^+$) m/z 316.32 ([M+H]$^+$), 318.6 ([M+H]$^+$). $^1$H NMR (400 MHz, methanol-d$_4$) δ 3.86 (s, 4H), 3.27 (t, J=6.8 Hz, 4H), 1.74 (p, J=6.8 Hz, 2H).

Example 5: Synthesis of L1D

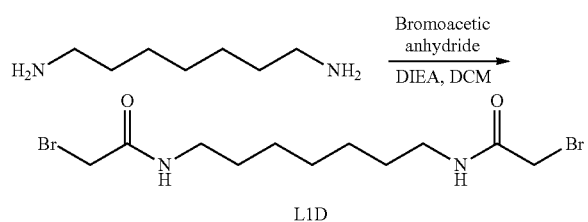

To a solution of 1,7-diaminohexane (65 mg, 0.499 mmol, 1 eq) in DCM (15 mL) at 0° C. were added DIEA (208 μL, 1.197 mmol, 2.4 eq) followed by bromoacetic anhydride (259 mg, 0.998 mmol, 2 eq) dissolved in 1 mL of DCM. The reaction mixture was then stirred for 30 min at 0° C., 1.5 h at RT, and the solvent was removed. Purification by flash column chromatography on silica gel afforded L1D as a white solid (120 mg, 0.322 mmol, 64%). MS (ES$^+$) m/z 372.71 ([M+H]$^+$), 374.70 ([M+3H]$^+$). $^1$H NMR (400 MHz, chloroform-d) δ 6.55 (s, 2H), 3.91 (s, 4H), 3.30 (q, J=7.1 Hz, 4H), 1.56 (p, J=7.1 Hz, 4H), 1.45-1.29 (m, 6H).

Example 6: Synthesis of L1E

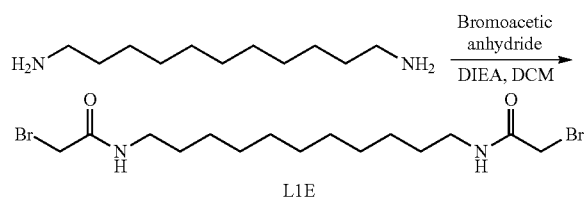

To a solution of 1,11-diaminoundecane (48 mg, 0.257 mmol, 1 eq) in DCM (10 mL) at 0° C. were added DIEA (108 μL, 0.616 mmol, 2.4 eq) followed by bromoacetic anhydride (134 mg, 0.515 mmol, 2 eq) dissolved in 1 mL of DCM. The reaction mixture was then stirred for 30 min at 0° C., 1.5 h at RT, and the solvent was removed. Purification by flash column chromatography on silica gel afforded L1E as a white solid (62.3 mg, 0.145 mmol, 56%). MS (ES$^+$) m/z 428.33 ([M+H]$^+$). $^1$H NMR (400 MHz, chloroform-d) δ 6.53 (s, 2H), 3.91 (s, 4H), 3.30 (q, J=6.8 Hz, 4H), 1.57 (q, J=7.2 Hz, 4H), 1.42-1.20 (in, 14H).

Example 7: Synthesis of L1F

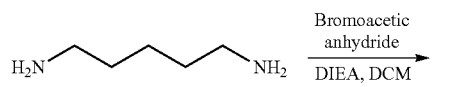

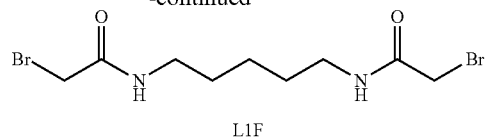

To a solution of cadaverine (48 mg, 0.257 mmol, 1 eq) in DCM (20 mL) at 0° C. were added DIEA (284 μL, 1.63 mmol, 2.4 eq) followed by bromoacetic anhydride (353 mg, 1.36 mmol, 2 eq) dissolved in 1 mL of DCM. The reaction mixture was then stirred for 30 min at 0° C., 1.5 h at RT, and the solvent was removed. Purification by flash column chromatography on silica gel afforded L1F as a white solid (156 mg, 0.453 mmol, 66%). MS (ES$^+$) m/z 344.65 ([M+H]$^+$), 346.64 ([M+H]$^+$). $^1$H NMR (400 MHz, methanol-d$_4$) δ 3.83 (s, 4H), 3.23 (q, J=6.8 Hz, 4H), 1.57 (p, J=7.2 Hz, 4H), 1.44-1.33 (m, 2H).

Example 8: Synthesis of L1G

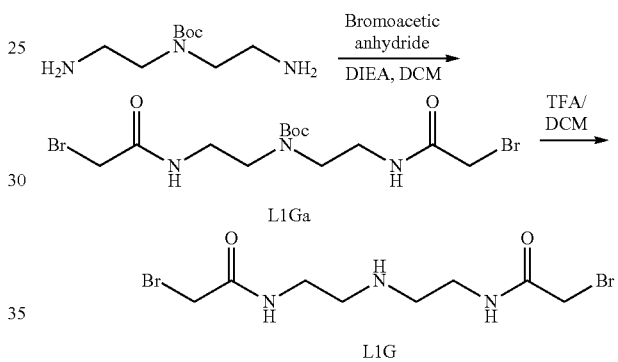

Intermediate L1Ga

To a solution of tert-butyl bis(2-aminoethyl)carbamate (167 mg, 0.82 mmol, 1 eq) in DCM (20 mL) at 0° C. were added DIEA (342 μL, 11.96 mmol, 2.4 eq) followed by bromoacetic anhydride (426 mg, 1.64 mmol, 2 eq) dissolved in 1 mL of DCM. The reaction mixture was then stirred for 30 min at 0° C., 1.5 h at RT, and the solvent was removed. Purification by flash column chromatography on silica gel afforded L1Ga as a white solid (289 mg, 0.65 mmol, 79%). MS (ES$^+$) m/z 445.71 ([M+H]$^+$), 447.7 ([M+H]$^+$). H NMR (400 MHz, methanol-d$_4$) δ 3.85 (s, 4H), 3.39 (s, 9H), 1.50 (s, 10H).

L1G

Compound L1Ga (20 mg) was dissolved in TFA/DCM (1:1, v/v, 2 mL), agitated 30 min at RT and evaporated (co-evaporation with hexane) to obtain compound LG as an oil. The product was directly used in further steps. MS (ES$^+$) m/z 345.2 ([M+H]$^+$).

Example 9: Synthesis of L3

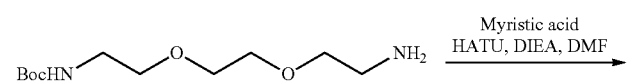

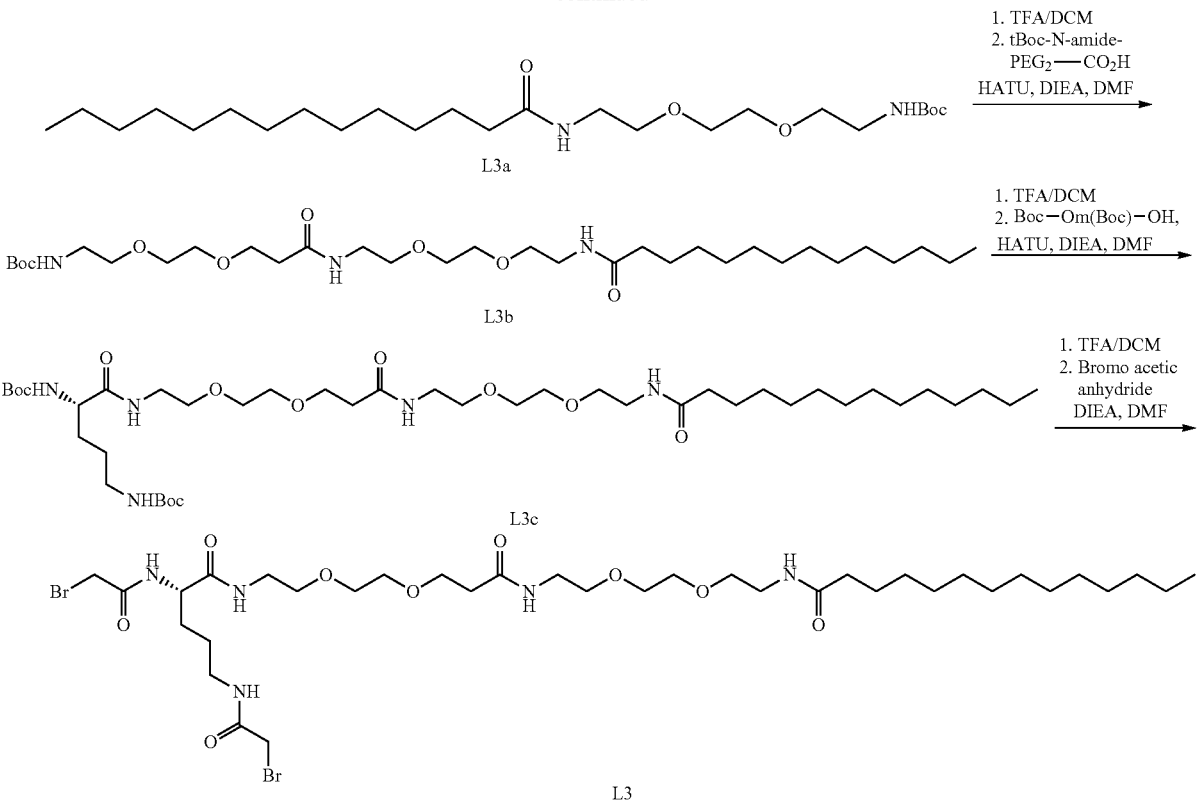

Intermediate L3a

Myristic acid (184 mg, 0.805 mmol, 1 eq) was dissolved in 4 mL of DMF. HATU (321 mg, 0.845 mmol, 1.1 eq) and DIEA (154 μL, 0.885 mmol, 1.1 eq) were added followed by the addition of Boc-NH-PEG$_2$-COOH (200 mg, 0.805 mmol, 1 eq). The reaction mixture was then stirred for 1.5 h, and the solvent was removed. The product was dissolved in EtOAc. The organic layer was successively washed with 1M HCl, sat. NaHCO$_3$, and brine, dried over Na$_2$SO$_4$, filtered, and concentrated. Purification by flash column chromatography on silica gel provided the desired compound L3a as a white solid (254 mg, 0.55 mmol, 69%). $^1$H NMR (400 MHz, chloroform-d) δ 3.66-3.54 (m, 8H), 3.49 (q, J=5.2 Hz, 2H), 3.35 (d, J=6.1 Hz, 2H), 2.20 (t, J=7.7 Hz, 2H), 1.63-1.58 (m, 2H), 1.47 (s, 8H), 1.33-1.24 (m, 21H), 0.90 (t, J=6.9 Hz, 3H). $t_R$=2.21 min (Agilent). MS (ES$^+$) m/z 459.6 ([M+H]$^+$)

Intermediate L3b

A solution of compound L3a (242 mg, 0.527 mmol, 1 eq) in DCM (2 mL) was treated with TFA (2 mL) for 30 min. The mixture was concentrated, co-evaporated with hexane. To a solution of BocNH-PEG$_2$-CO$_2$H (146 mg, 0.527 mol, 1 eq) dissolved in DMF (5 mL) was added HATU (224 mg, 0.59 mmol, 1.1 eq). Deprotected compound L3a and DIEA (183 μL, 1.05 mmol, 2 eq) in DMF were added to the reaction mixture. The reaction mixture was agitated for 2 h at RT. The product was diluted with EtOAc. The organic layer was successively washed with 1M HCl, sat. NaHCO$_3$, and brine, dried over Na$_2$SO$_4$, filtered, and concentrated. Purification by flash column chromatography on silica gel provided the desired compound L3b as an oil (129 mg, 0.209 mmol, 40%). $^1$H NMR (400 MHz, chloroform-d) δ 6.76 (s, 1H), 6.19 (s, 1H), 5.29 (s, 1H), 3.76 (t, J=5.8 Hz, 2H), 3.69-3.62 (m, 8H), 3.57 (dt, J=12.3, 5.0 Hz, 6H), 3.48 (dt, J=10.4, 5.5 Hz, 4H), 3.33 (s, 2H), 2.51 (t, J=5.8 Hz, 2H), 2.20 (t, J=7.0 Hz, 2H), 1.90-1.75 (m, 4H), 1.64 (p, J=7.3 Hz, 2H), 1.46 (s, 9H), 1.33-1.22 (m, 17H).

Intermediate L3c

A solution of Compound L3b (129 mg, 0.209 mmol, 1 eq) in DCM (2 mL) was treated with TFA (2 mL) for 30 min. The mixture was concentrated, co-evaporated with hexane. To a solution of Boc-Orn(Boc)-OH (69 mg, 0.209 mmol, 1 eq) dissolved in DMF (5 mL) was added HATU (88 mg, 0.23 mmol 1.1 eq). Deprotected compound L3b and DIEA (73 μL, 0.419 mmol, 2 eq) in DMF were added to the reaction mixture. The reaction mixture was agitated 2 h at RT. The product was diluted with EtOAc. The organic layer was successively washed with 1M HCl, sat. NaHCO$_3$, and brine, dried over Na$_2$SO$_4$, filtered, and concentrated. Purification by flash column chromatography on silica gel provided the desired compound L3c as an oil (137 mg, 0.164 mmol, 78%). $t_R$=4.07 min (Agilent). MS (ES$^+$) m/z 832.9 ([M+H]$^+$). $^1$H NMR (400 MHz, chloroform-d) δ 7.12 (s, 1H), 6.80 (s, 1H), 6.30 (s, 1H), 4.87 (s, 1H), 3.85-3.73 (m, 2H), 3.68-3.61 (m, 7H), 3.58 (p, J=6.1, 5.5 Hz, 7H), 3.53-3.36 (m, 6H), 3.29-3.00 (m, 2H), 2.51 (t, J=5.8 Hz, 2H), 2.20 (t, J=7.7 Hz, 2H), 2.00-1.74 (m, 6H), 1.71-1.51 (m, 5H), 1.45 (s, 18H), 1.35-1.22 (m, 21H).

L3

A solution of Compound L3c (137 mg, 0.165 mmol, 1 eq) in DCM (2 mL) was treated with TFA (2 mL) for 30 min. The mixture was concentrated, co-evaporated with hexane and dissolved in 10 mL of DCM and cooled at 0° C. DIEA (115 μL, 0.66 mmol, 4 eq) was added followed by bromoacetic anhydride (85.8 g, 0.33 mmol, 2 eq) dissolved in 1 mL of DCM. The reaction mixture was then stirred for 30 min at 0° C., 1.5 h at RT, and the solvent was removed. Purification by flash column chromatography on silica gel afforded L3 as a white solid (56 mg, 0.064 mmol, 39%). $t_R$=3.4 min (Agilent). MS (ES$^+$) m/z 872.4 ([M+H]$^+$), 874.3 ([M+H]$^+$).

Example 10: Synthesis of L4

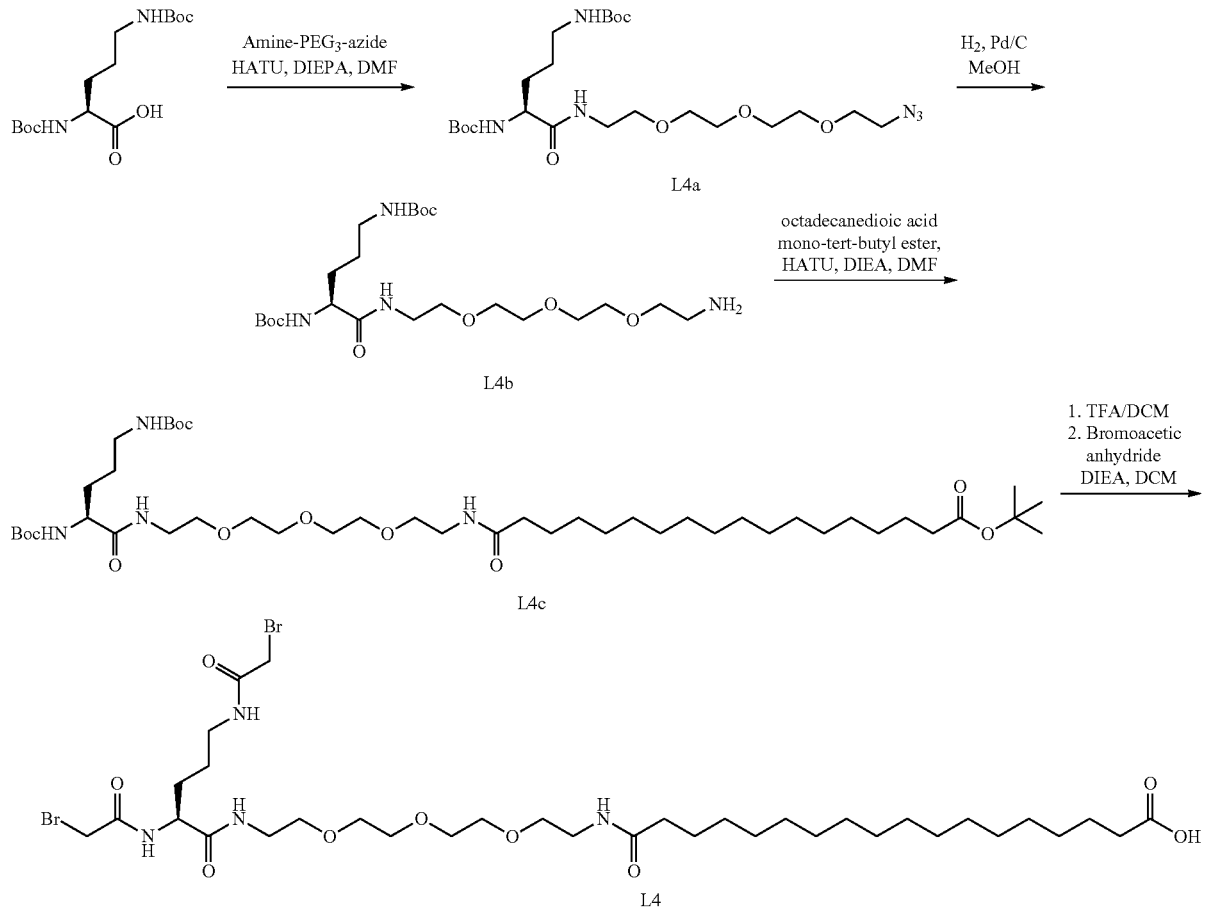

filtrated on celite and evaporated to afford compound L4b as an oil (516 mg, 1.02 mmol, quant). The product was used without any further purification.

Intermediate L4c

To a solution of octadecanedioic acid mono tert-butyl ester (370 mg, 1.02 mmol, 1 eq) dissolved in DMF (5 mL) was added HATU (387 mg, 1.02 mmol 1.1 eq), DIEA (186 µL, 1.07 mmol, 2 eq) and compound L4b (516 mg, 1.02 mmol, 1 eq) dissolved in 1 mL of DMF. The reaction mixture was agitated 3 h at RT. The product was diluted with EtOAc. The organic layer was successively washed with 1M HCl, sat. NaHCO$_3$, brine, dried over Na$_2$SO$_4$, filtered, and concentrated. Purification by flash column chromatography on silica gel provided the desired compound L4c as an oil (697 mg, 0.81 mmol, 79%). $^1$H NMR (400 MHz, chloroform-d) δ 6.94 (s, 1H), 6.42 (s, 1H), 4.81 (s, 11H), 4.20 (s, 1H), 3.65 (d, J=6.7 Hz, 8H), 3.59 (dt, J=9.7, 5.1 Hz, 4H), 3.51-3.35 (m, 4H), 3.31-3.18 (m, 1H), 3.17-3.06 (m, 1H), 2.20 (q, J=8.0 Hz, 4H), 1.87 (s, 4H), 1.71-1.53 (m, 6H), 1.45 (s, 26H), 1.26 (s, 24H).

L4

A solution of L4c (422 mg, 0.49 mmol, 1 eq) in DCM (2 mL) was treated with TFA (2 mL) for 30 min. The mixture was concentrated, co-evaporated with hexane and dissolved in 20 mL of DCM and cooled at 0° C. DIEA (327 µL, 1.96 mmol, 4 eq) was added followed by bromoacetic anhydride (254 mg, 0.98 mmol, 2 eq) dissolved in 1 mL of DCM. The reaction mixture was then stirred for 30 min at 0° C., 1.5 h at RT, and the solvent was removed. Purification by flash Intermediate L4a To a solution of Boc-Orn(Boc)-OH (595 mg, 1.79 mmol, 1 eq) dissolved in DMF (5 mL) was added HATU (750 mg, 1.79 mmol 1.1 eq), DIEA (343 µL, 1.97 mmol, 1.1 eq) and amine-PEG$_3$-N$_3$ (391 mg, 1.79 mmol, 1 eq) dissolved in 1 mL of DMF. The reaction mixture was agitated 16 h at RT. The product was diluted with EtOAc. The organic layer was successively washed with 1M HCl, sat. NaHCO$_3$, brine, dried over Na$_2$SO$_4$, filtered, and concentrated. Purification by flash column chromatography on silica gel provided the desired compound L4a as an oil (558 mg, 1.05 mmol, 58%). MS (ES$^+$) m/z 533.13 ([M+H]$^+$). $^1$H NMR (400 MHz, chloroform-d) δ 6.82 (s, 1H), 5.25 (d, J=8.3 Hz, 1H), 4.75 (s, 1H), 4.19 (s, 1H), 3.76-3.60 (m, 10H), 3.57 (t, J=5.1 Hz, 2H), 3.43 (t, J=4.6 Hz, 2H), 3.30-3.19 (m, 1H), 3.18-3.03 (m, 1H), 1.85 (s, 4H), 1.68-1.49 (m, 2H), 1.45 (s, 18H).

Intermediate L4b

To a solution of compound L4a (548 mg, 1.02 mmol, 1 eq) in anhydrous MeOH (10 mL) and under argon was added Pd/C (10.9 mg, 0.102 mmol, 0.1 eq) and argon was replaced with H$_2$. The reaction mixture was agitated for 6 h at RT, column chromatography on silica gel afforded L4 as a white solid (53 mg, 0.063 mmol, 12%). MS (ES$^+$) m/z 845.08 ([M+H]$^+$), 847.07 ([M+H]$^+$) $^1$H NMR (400 MHz, methanol-$d_4$) δ 3.68-3.60 (m, 8H), 3.54 (td, J=5.4, 3.4 Hz, 4H), 3.43-3.35 (m, 4H), 3.30-3.16 (m, 2H), 2.27 (t, J=7.5 Hz, 2H), 2.17 (t, J=7.6 Hz, 2H), 1.86-1.73 (m, 1H), 1.72-1.45 (m, 8H), 1.37-1.19 (m, 28H).

Intermediate L4Aa

To a solution of tert-butyl bis(2-aminoethyl)carbamate (500 mg, 2.45 mmol, 1 eq) and DIEA (1.02 mL, 5.88 mmol, 2 eq) in DCM (20 mL) at 0° C. was added dropwise bromoacetic anhydride (1.31 g, 5.04 mmol, 2.05 eq in 1 mL DCM). The reaction mixture was agitated 30 min at 0° C., 2 h at RT and evaporated in vacuo. Purification by flash chromatography afforded the product as an oil (883 mg, 81%). $^1$H NMR (400 MHz, methanol-$d_4$) δ 1.50 (s, 9H), 3.39 (s, 8H), 3.85 (s, 4H). $t_R$=1.04 min. MS (ES$^+$) m/z 445.71/447.70 ([M+H]$^+$).

Example 11: Synthesis of L4A

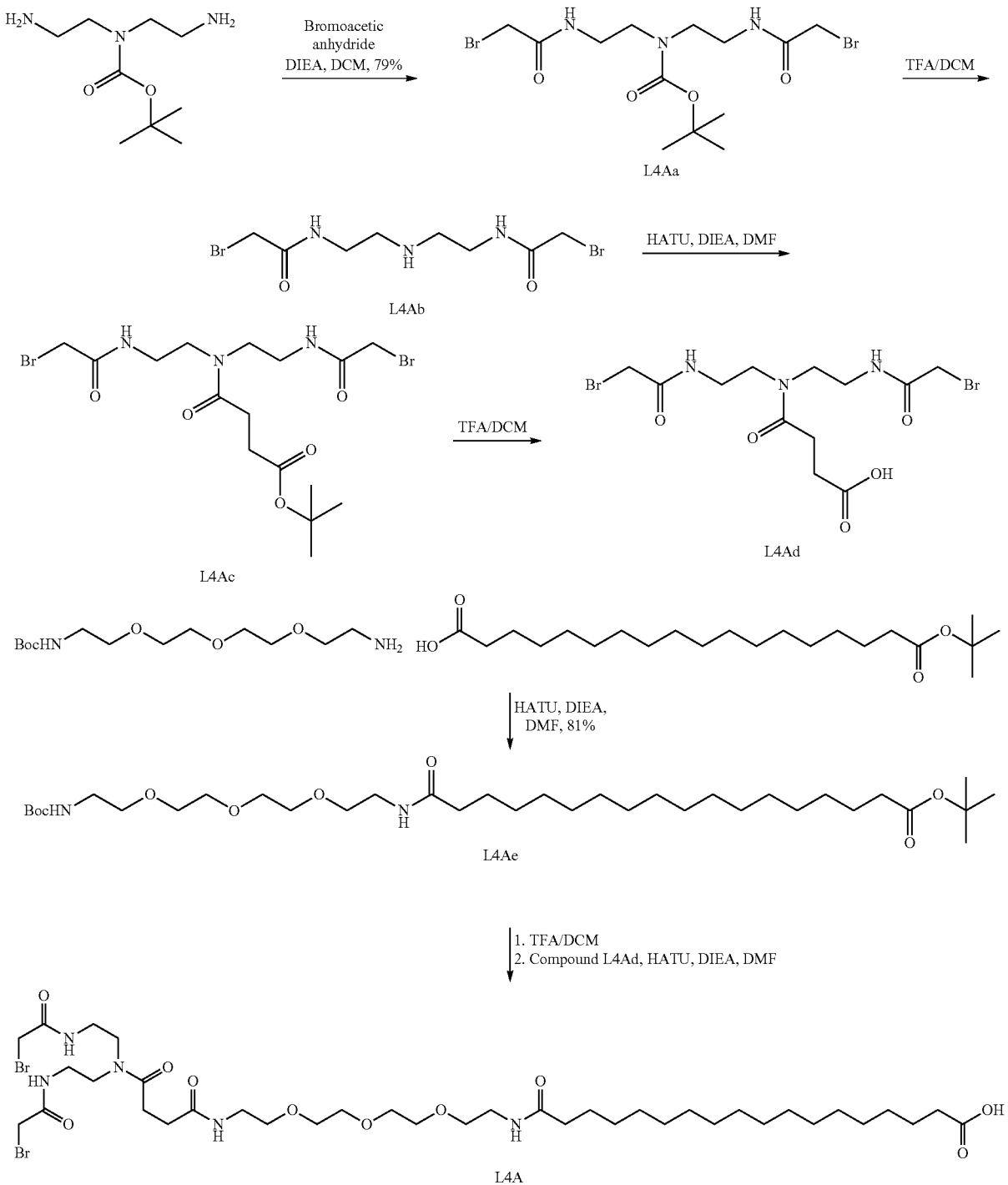

Intermediate L4Ab

A solution of compound L4Aa (1 eq) in DCM/TFA (1:1, v/v) was agitated at RT for 30 min and concentrated in vacuo (co-evaporated with heptane). Compound L4Ab was used directly in further steps without purification. $t_R$=0.58 min. MS (ES$^+$) m/z 345.65/347.67 ([M+H]$^+$).

Intermediate L4Ac

To a solution of mono-tert-butyl succinate (1.05 eq) in DMF was added HATU (1.05 eq). The reaction mixture was agitated at RT for 5 min. Compound L4Ab and DIEA (4 eq) were dissolved in DMF (1 mL) and added to the reaction mixture. The reaction was agitated overnight at RT and diluted with AcOEt. The organic phase was washed with HCl 1N, a solution of saturated NaHCO$_3$, dried over MgSO$_4$ and evaporated. Purification by flash chromatography afforded the product as an oil. $t_R$ 1.07 min. MS (ES$^+$) m/z 501.52/503.80 ([M+H]$^+$).

Intermediate L4Ad

A solution of compound L4Ac (1 eq) in DCM/TFA (1:1, v/v) was agitated at RT for 30 min and concentrated in vacuo (co-evaporated with heptane). Compound L4Ad was used directly in further steps without purification. $t_R$=0.57 min. MS (ES$^+$) m/z 445.71/447.73 ([M+H]$^+$).

Intermediate L4Ae

Octadecanedioic acid mono-tert-butyl ester acid (200 mg, 0.54 mmol, 1 eq) was dissolved in 5 mL of DMF. HATU (225 mg, 0.59 mmol, 1.1 eq) and DIEA (103 µL, 0.59 mmol, 1.1 eq) were added followed by the addition of Boc-NH-PEG$_3$-NH$_2$ (157.8 g, 0.54 mmol, 1 eq). The reaction mixture was then stirred for 3 h, and the solvent was removed. The product was dissolved in EtOAc. The organic layer was successively washed with sat. NaHCO$_3$, 1M HCl, brine, dried over Na$_2$SO$_4$, filtered, and concentrated. Purification by flash column chromatography on silica gel provided the desired product L4Ae as a white solid (281 mg, 0.43 mmol, 81%). MS (ES$^+$) m/z 645.5 ([M+H]$^+$). $^1$H NMR (400 MHz, chloroform-d) δ 3.76-3.61 (m, 8H), 3.63-3.54 (m, 4H), 3.48 (q, J=5.1 Hz, 2H), 3.34 (s, 2H), 2.20 (dt, J=9.8, 7.6 Hz, 4H), 1.67-1.55 (m, 4H), 1.49-1.44 (m, 17H), 1.30 (s, 6H), 1.30-1.24 (m, 19H).

L4A

A solution of compound L4Ae in DCM was treated with TFA for 30 min. The mixture was concentrated, co-evaporated with heptane, dissolved in DMF and added to a solution of compound L4Ad, HATU and DIEA in DMF. The reaction mixture was agitated 3 h and purified by semi-preparative HPLC to provide the desired product L4A.

Example 12: Synthesis of L5

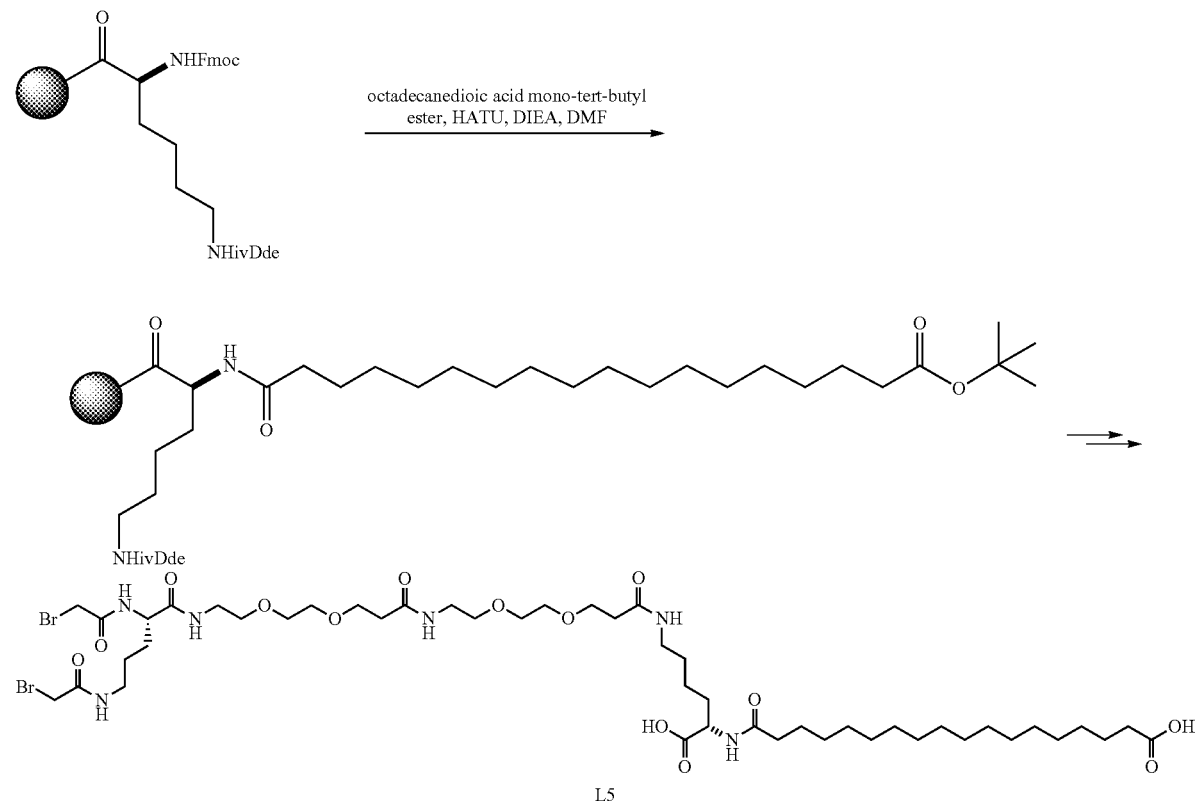

General Protocol A, B, D (Octadecanedioic Acid Mono-Tert Butyl Ester), C, D (Fmoc-PEG$_2$-Propionic Acid), B, D (Fmoc-PEG$_2$-Propionic Acid), B, D (Fmoc-Orn(Fmoc)-OH), B, E, F.

The crude was purified by semi-preparative HPLC with mass detection to afford the product L5 as a white solid (73 mg, 0.065 mmol, 11%). $^1$H NMR (400 MHz, methanol-d$_4$) δ 4.36 (td, J=8.9, 5.1 Hz, 2H), 3.89 (q, J=11.4 Hz, 2H), 3.82 (s, 2H), 3.74 (t, J=6.2 Hz, 2H), 3.60 (s, 4H), 3.54 (t, J=5.5 Hz, 2H), 3.37 (q, J=5.2 Hz, 2H), 3.29-3.11 (m, 5H), 2.44 (t, J=6.2 Hz, 2H), 2.26 (dt, J=12.3, 7.5 Hz, 4H), 1.89-1.77 (m, 2H), 1.76-1.49 (m, 10H), 1.48-1.38 (m, 2H), 1.37-1.25 (m, 25H).

Example 13: Synthesis of L5A and C20L5A

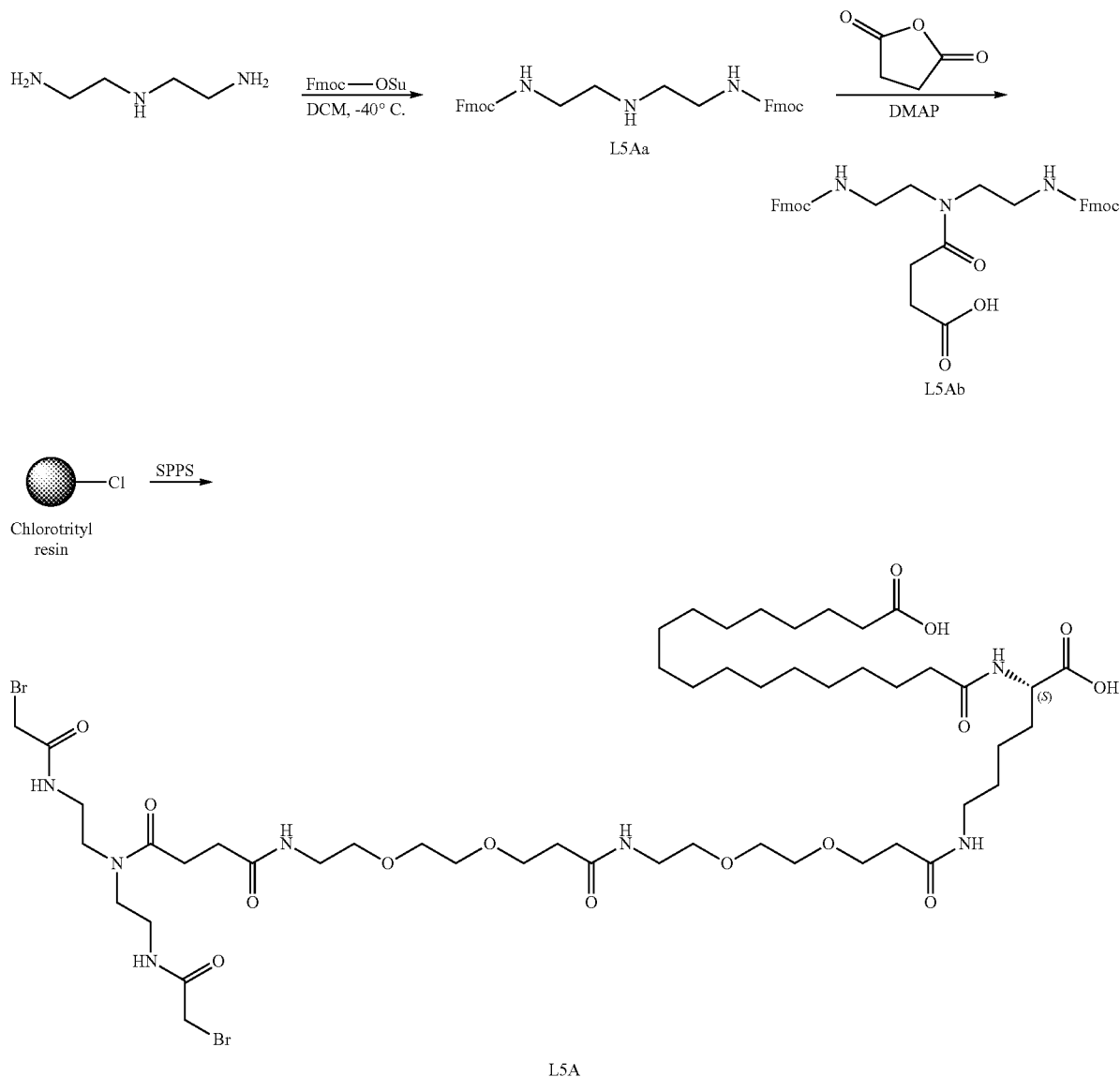

Intermediate L5Aa

A solution of Fmoc-OSu (131 g, 388 mmol) in DCM (200 mL) was added dropwise to a solution of diethylenetriamine (20 g, 194 mmol) in DCM (200 mL) at −40° C. under $N_2$, stirred for 2 h. LCMS showed the reaction was complete. The crude product in solution was not purified and used for the next step directly. $^1$H NMR (400 MHz, DMSO-$d_6$) δ 7.88 (d, J=7.6 Hz, 4H), 7.68 (d, J=7.6 Hz, 4H), 7.43-7.24 (m, 10H), 4.30 (d, J=6.4 Hz, 4H), 4.21 (d, J=6.4 Hz, 2H), 3.06 (d, J=5.6 Hz, 4H), 2.57 (d, J=7.6 Hz, 4H). MS (ES$^+$) m/z 548.2 ([M+H]$^+$).

Intermediate L5Ab

To a solution of compound L5Aa (106 g, 194 mmol) in DCM (400 mL) was added DMAP (4.74 g, 38.8 mmol) and tetrahydrofuran-2,5-dione (67.9 g, 678 mmol), stirred at 25° C. for 14 h. LCMS showed the reaction was complete. To the reaction mixture was added 1 N HCl until pH=5-6, stirred for 15 min, the organic phase was separated, then the organic phase was washed with water and saturated NaCl (500 mL) and the aqueous phase was extracted with DCM (500 mL) twice. The combined DCM was dried over anhydrous $Na_2SO_4$, concentrated under vacuum. The crude product was purified by column chromatography on silica gel using DCM/MeOH (80:0-5:1) as eluent to give compound L5Ab (57.6 g, 45% yield) as a white solid powder. $^1$H NMR (400 MHz, DMSO-$d_6$) δ 12.09 (s, 1H), 7.87 (d, J=7.5 Hz, 4H), 7.66 (d, J=7.0 Hz, 4H), 7.23-7.48 (m, 10H), 4.24-4.33 (m, 4H), 4.14-4.22 (m, 2H), 3.27 (s, 4H), 2.95-3.19 (m, 4H), 2.37-2.44 (m, 4H). MS (ES$^+$) m/z 648.2 ([M+H]$^+$). L5A General Protocol A, B, D (Octadecanedioic Acid Mono-Tert Butyl Ester), C, D (Fmoc-PEG$_2$-Propionic Acid), B, D (Fmoc-PEG$_2$-Propionic Acid), B, D (Compound L5Ab), B, E, F.

The crude was purified by HPLC to afford the product L5A as a white solid (5.2 g, 11% yield). MS (ES$^+$) m/z 1188.5 ([M+H]$^+$).

Synthesis of C20L5A

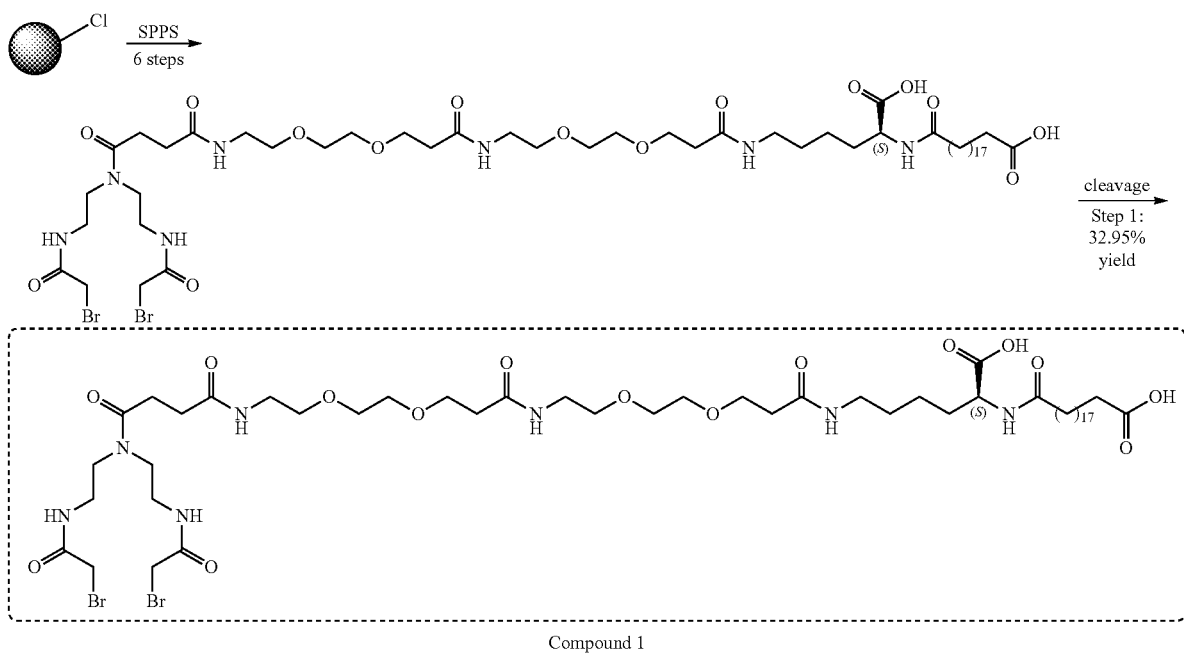

Compound 1

The peptide was synthesized using standard Fmoc chemistry.
1) Resin preparation: To the 1-chloro-2-[chloro(diphenyl)methyl]benzene (8.00 mmol, 2.00 eq, Sub 1.00 mmol/g) was added Fmoc-Lys(Dde)-OH (2.13 g, 4.00 mmol, 1.00 eq) and DIEA (2.76 mL, 16.0 mmol, 4.00 eq) in DCM (50.0 mL). The mixture was agitated with $N_2$ for 2 h at 20° C., then added MeOH (8.0 mL) and agitated with $N_2$ for another 30 min. The resin was washed with DMF (100 mL)*5. Then 20% PIPERIDINE (100 mL) in DMF was added and the mixture was agitated with $N_2$ for 15 min at 20° C. Then the mixture was filtered to get the resin. The resin was washed with DMF (100 mL)*5 and filtered to get the resin.
2) Coupling: a solution of 20-(tert-butoxy)-20-oxooctadecanoic acid (3.19, 8.00 mmol, 2.00 eq), HBTU (2.89 g, 7.60 mmol, 1.90 eq) and DIEA (2.06 g, 16.0 mmol, 2.76 mL, 4.00 eq) in DMF (30.00 mL) was added to the resin and agitated with $N_2$ for 20 min at 20° C. The resin was then washed with DMF (50.0 mL)*5.
3) Add 3% hydrazine hydrate/DMF and react on 15 min*2. Drain and wash with DMF (100 mL*5).
4) Repeat Step 2 for the following amino acid: (3)
Note:

| # | Materials | Coupling reagents |
|---|---|---|
| 3 | 3-[2-[2-(9H-fluoren-9-ylmethoxycarbonylamino)ethoxy]ethoxy]propanoic acid (2.00 eq) | HBTU (1.90 eq) and DIPEA (4.00 eq) |

5) Deprotection: 20% piperidine in DMF (100 mL) was added and agitated the resin with $N_2$ for another 30 min. The resin was washed with DMF (100 mL*5) and filtered to get the resin.
6) Repeat above step 2 and 5 for the coupling of following amino acids: (4-6)
Note:

| 4 | 3-[2-[2-(9H-fluoren-9-ylmethoxycarbonylamino)ethoxy]ethoxy]propanoic acid (2.00 eq) | HBTU (1.90 eq) and DIPEA (4.00 eq) |
|---|---|---|
| 5 | 4-[bis[2-(9H-fluoren-9-ylmethoxycarbonylamino)ethyl]amino]-4-oxo-butanoic acid (1.20 eq) | HATU (1.20 eq) and DIPEA (2.40 eq) |
| 6 | 2-bromoacetic acid (8.00 eq) | HOBt (4.00 eq) and DIC (8.00 eq) |

Peptide Cleavage and Purification:
1) Add cleavage buffer (90.0% TFA/2.5% TIS/2.5% H2O/5% methylsulfanylbenzene) to the flask containing the side chain protected peptide at room temperature and stir for 2.00 hours.
2) Precipitated the peptide was with cold isopropyl ether.
3) Filter and collect the filter cake.
4) Isopropyl ether washes two more times.
5) Dry the crude peptide under vacuum 2 hours.

The crude peptide was purified by prep-HPLC (A: 0.075% TFA in $H_2O$, B: ACN) to give the final product Compound 1 (1.85 g, 1.32 mmol, 32.95% yield, 86.65% purity) as an off-white solid.

Example 14: Synthesis of L6

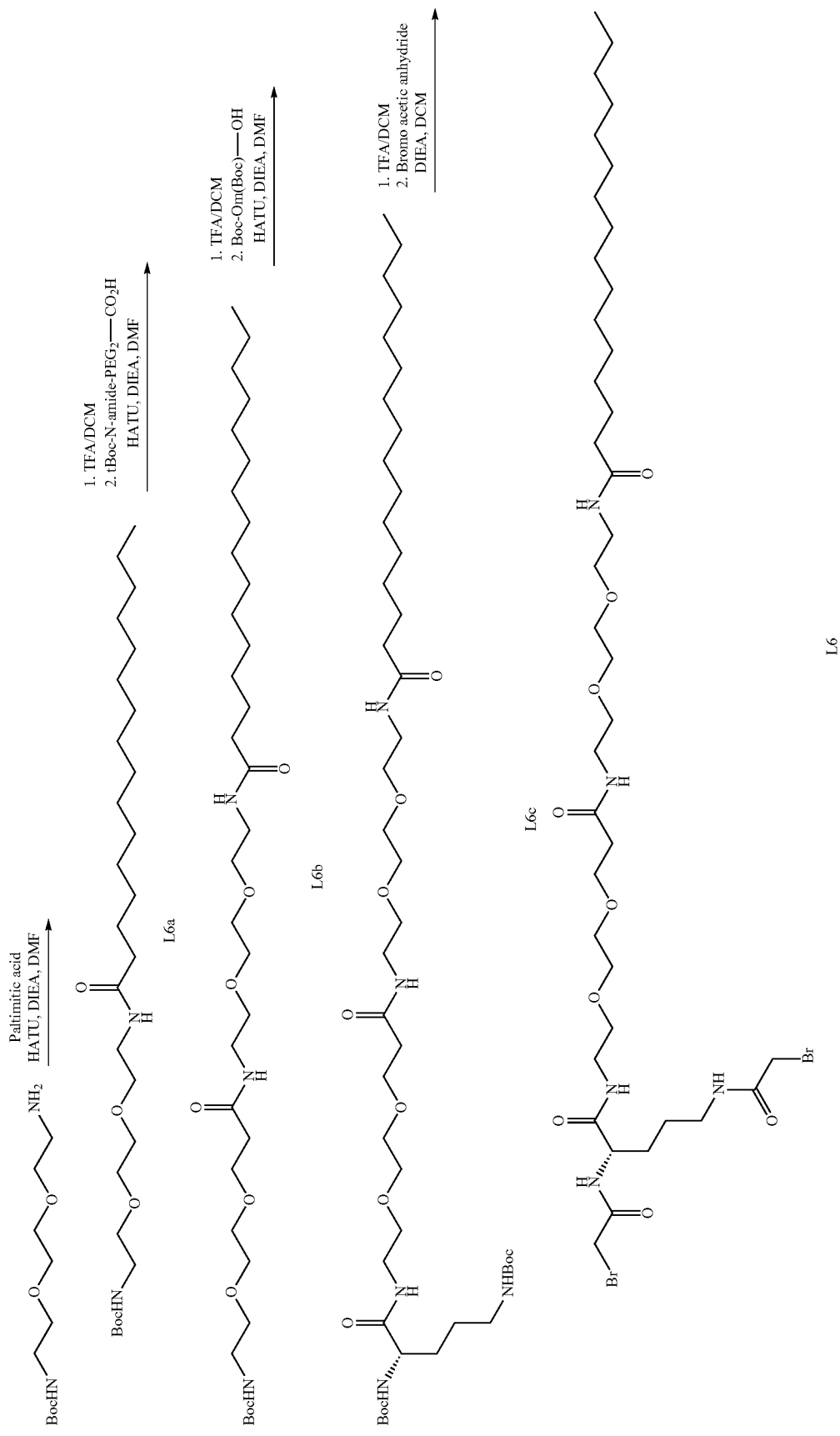

Intermediate L6a

Palmitic acid (235 mg, 0.919 mmol, 1.05 eq) was dissolved in 4 mL of DMF. HATU (349 mg, 0.919 mmol, 1.05 eq) and DIEA (167 µL, 0.963 mmol, 1.1 eq) were added followed by the addition of Boc-NH-PEG$_2$-NH$_2$ (200 mg, 0.875 mmol, 1 eq). The reaction mixture was then stirred for 2 h, and the solvent was removed. The product was dissolved in EtOAc. The organic layer was successively washed with 1M HCl, sat. NaHCO$_3$, HCl and brine, dried over Na$_2$SO$_4$, filtered, and concentrated to provide the desired compound L6a as a white solid (412 mg, 0.84 mmol, 97%). $^1$H NMR (400 MHz, chloroform-d) δ 6.17 (s, 1H), 5.07 (s, 1H), 3.58 (s, 4H), 3.53 (t, J=5.0 Hz, 3H), 3.43 (q, J=5.3 Hz, 2H), 3.36-3.21 (m, 2H), 2.15 (t, J=7.5 Hz, 2H), 1.66-1.54 (m, 2H), 1.32-1.15 (m, 26H), 0.84 (t, J=6.6 Hz, 3H).

Intermediate L6b

A solution of compound L6a (412 mg, 0.84 mmol, 1 eq) in DCM (2 mL) was treated with TFA (2 mL) for 30 min. The mixture was concentrated, co-evaporated with hexane. To a solution of BocNH-PEG$_2$-CO$_2$H (258 mg, 0.931 mmol, 1.1 eq) dissolved in DMF (5 mL) was added HATU (353 mg, 0.931 mmol, 1.1 eq). Deprotected compound L6a and DIEA (294 µL, 1.69 mmol, 2 eq) in DMF were added to the reaction mixture. The reaction mixture was agitated 2 h at RT. The product was diluted with EtOAc. The organic layer was successively washed with 1M HCl, sat. NaHCO$_3$, HCl and brine, dried over Na$_2$SO$_4$, filtered, and concentrated. Purification by flash column chromatography on silica gel provided the desired compound L6b as an oil (329 mg, 0.51 mmol, 60%). $^1$H NMR (400 MHz, chloroform-d) δ 6.79 (s, 1H), 6.28 (s, 1H), 5.28 (s, 1H), 3.68 (t, J=5.8 Hz, 2H), 3.61-3.44 (m, 14H), 3.38 (p, J=5.6 Hz, 4H), 3.24 (q, J=5.5 Hz, 2H), 2.42 (t, J=5.8 Hz, 2H), 2.11 (t, J=7.9 Hz, 2H), 1.55 (p, J=7.2 Hz, 2H), 1.38 (s, 9H), 1.32-1.10 (m, 24H), 0.81 (t, J=6.7 Hz, 3H).

Intermediate L6c

A solution of compound L6b (329 mg, 0.51 mmol, 1 eq) in DCM (2 mL) was treated with TFA (2 mL) for 30 min. The mixture was concentrated, co-evaporated with hexane. To a solution of Boc-Orn(Boc)-OH (186 mg, 0.56 mmol, 1.1 eq) dissolved in DMF (5 mL) was added HATU (213 mg, 0.56 mmol 1.1 eq). Deprotected compound L6b and DIEA (177 µL, 1.02 mmol, 2 eq) in DMF were added to the reaction mixture. The reaction mixture was agitated 2 h at RT. The product was diluted with EtOAc. The organic layer was successively washed with sat. NaHCO$_3$, 1M HCl and brine, dried over Na$_2$SO$_4$, filtered, and concentrated. Purification by flash column chromatography on silica gel provided the desired compound L6c as an oil (326 mg, 0.37 mmol, 94%). $^1$H NMR (400 MHz, chloroform-d) δ 7.18 (s, 1H), 6.92 (s, 1H), 6.48 (s, 1H), 5.61 (d, J=8.4 Hz, 1H), 5.08 (t, J=5.9 Hz, 1H), 4.13 (s, 1H), 3.73-3.65 (m, 2H), 3.59-3.44 (m, 14H), 3.42-3.29 (m, 8H), 3.19-2.86 (m, 2H), 2.42 (t, J=5.9 Hz, 2H), 2.10 (d, J=7.3 Hz, 2H), 1.78-1.63 (m, 1H), 1.60-1.40 (m, 5H), 1.35 (s, 18H), 1.26-1.09 (m, 22H), 0.80 (t, J=6.7 Hz, 3H).

L6

A solution of compound L6c (100 mg, 0.116 mmol, 1 eq) in DCM (2 mL) was treated with TFA (2 mL) for 30 min. The mixture was concentrated, co-evaporated with hexane and dissolved in 10 mL of DCM and cooled at 0° C. DIEA (80.8 µL, 0.46 mmol, 4 eq) was added followed by bromoacetic anhydride (61.9 mg, 0.238 mmol, 2.05 eq) dissolved in 1 mL of DCM. The reaction mixture was then stirred for 30 min at 0° C., 1.5 h at RT, and the solvent was removed. Purification by flash column chromatography on silica gel afforded L6 as a white solid (50.1 mg, 0.055 mmol, 40%). $^1$H NMR (400 MHz, methanol-d$_4$) δ 4.39 (dd, J=8.4, 5.5 Hz, 1H), 3.91 (q, J=11.4 Hz, 2H), 3.84 (s, 2H), 3.76 (t, J=6.2 Hz, 2H), 3.63 (d, J=7.1 Hz, 8H), 3.57 (q, J=5.5 Hz, 6H), 3.43-3.36 (m, 6H), 3.25 (t, J=13.9, 6.8 Hz, 2H), 2.49 (t, J=6.2 Hz, 2H), 2.21 (t, J=7.5 Hz, 2H), 1.91-1.79 (m, 1H), 1.75-1.53 (m, 5H), 1.42-1.25 (m, 24H), 0.92 (t, J=6.7 Hz, 3H).

Example 15: Synthesis of L7

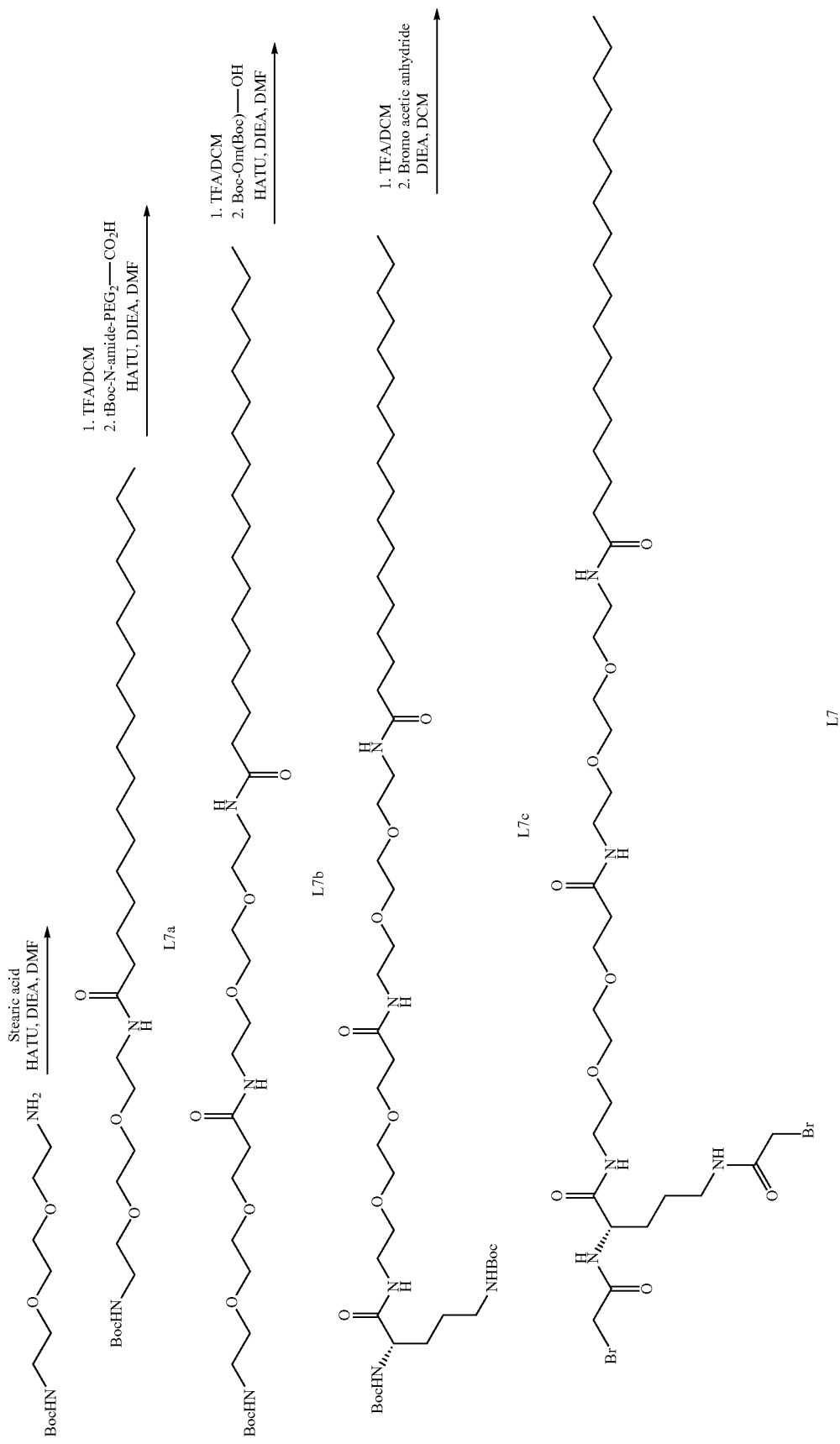

Intermediate L7a

Stearic acid (261 mg, 0.919 mmol, 1.05 eq) was dissolved in 4 mL of DMF. HATU (349 mg, 0.919 mmol, 1.05 eq) and DIEA (167 μL, 0.963 mmol, 1.1 eq) were added followed by the addition of Boc-NH-PEG$_2$-NH$_2$ (200 mg, 0.875 mmol, 1 eq). The reaction mixture was then stirred for 2 h, and the solvent was removed. The product was dissolved in EtOAc. The organic layer was successively washed with 1M HCl, sat. NaHCO$_3$, and brine, dried over Na$_2$SO$_4$, filtered, and concentrated to provide the desired compound L7a as a white solid (430 mg, 0.83 mmol, 95%). $^1$H NMR (400 MHz, chloroform-d) δ 3.69-3.59 (m, 4H), 3.56 (t, J=5.1 Hz, 4H), 3.46 (q, J=5.2 Hz, 2H), 3.40-3.23 (m, 2H), 2.18 (t, J=7.6 Hz, 2H), 1.62 (t, J=7.3 Hz, 2H), 1.45 (s, 9H), 1.35-1.19 (m, 30H), 0.88 (t, J=6.7 Hz, 4H).

Intermediate L7b

A solution of compound L7a (426 mg, 0.87 mmol, 1 eq) in DCM (2 mL) was treated with TFA (2 mL) for 30 min. The mixture was concentrated, co-evaporated with hexane. To a solution of BocNH-PEG$_2$-CO$_2$H (266 mg, 0.96 mmol, 1.1 eq) dissolved in DMF (5 mL) was added HATU (366 mg, 0.96 mmol, 1.1 eq). Deprotected compound L7a and DIEA (304 μL, 1.75 mmol, 2 eq) in DMF were added to the reaction mixture. The reaction mixture was agitated 2 h at RT. The product was diluted with EtOAc. The organic layer was successively washed with 1M HCl, sat. NaHCO$_3$, and brine, dried over Na$_2$SO$_4$, filtered, and concentrated. Purification by flash column chromatography on silica gel provided the desired compound L7b as an oil (360 mg, 0.53 mmol, 61%). $^1$H NMR (400 MHz, chloroform-d) δ 6.75 (s, 1H), 6.18 (s, 1H), 5.26 (s, 1H), 3.75 (t, J=5.8 Hz, 2H), 3.69-3.52 (m, 14H), 3.47 (p, J=5.4 Hz, 4H), 3.33 (q, J=5.5 Hz, 2H), 2.50 (t, J=5.8 Hz, 2H), 2.19 (t, J=7.5 Hz, 2H), 2.07 (s, 1H), 1.63 (p, J=7.3 Hz, 2H), 1.46 (s, 9H), 1.37-1.19 (m, 29H), 0.89 (t, J=6.7 Hz, 3H).

Intermediate L7c

A solution of compound L7b (360 mg, 0.53 mmol, 1 eq) in DCM (2 mL) was treated with TFA (2 mL) for 30 min. The mixture was concentrated, co-evaporated with hexane. To a solution of Boc-Orn(Boc)-OH (195 mg, 0.58 mmol, 1.1 eq) dissolved in DMF (5 mL) was added HATU (223 mg, 0.58 mmol 1.1 eq). Deprotected compound L7b and DIEA (186 μL, 1.07 mmol, 2 eq) in DMF were added to the reaction mixture. The reaction mixture was agitated 2 h at RT. The product was diluted with EtOAc. The organic layer was successively washed with 1M HCl, sat. NaHCO$_3$, and brine, dried over Na$_2$SO$_4$, filtered, and concentrated. Purification by flash column chromatography on silica gel provided the desired compound L7c as an oil (373 mg, 0.42 mmol, 78%). $^1$H NMR (400 MHz, chloroform-d) δ 7.14 (s, 1H), 6.84 (s, 1H), 6.35 (s, 1H), 5.53 (d, J=8.2 Hz, 1H), 5.05-4.88 (m, 1H), 4.20 (s, 1H), 3.82-3.69 (m, 2H), 3.65-3.31 (m, 22H), 3.23-3.00 (m, 2H), 2.48 (t, J=5.8 Hz, 2H), 2.17 (t, J=7.8 Hz, 2H), 1.87-1.72 (m, 1H), 1.67-1.48 (m, 5H), 1.42 (s, 18H), 1.34-1.14 (m, 29H), 0.87 (t, J=6.9 Hz, 3H).

L7

A solution of compound L7c (100 mg, 0.112 mmol, 1 eq) in DCM (2 mL) was treated with TFA (2 mL) for 30 min. The mixture was concentrated, co-evaporated with hexane and dissolved in 10 mL of DCM and cooled at 0° C. DIEA (78 μL, 0.44 mmol, 4 eq) was added followed by bromoacetic anhydride (62 mg, 0.24 mmol, 2.05 eq) dissolved in 1 mL of DCM. The reaction mixture was then stirred for 30 min at 0° C., 1.5 h at RT, and the solvent was removed. The product was dissolved in EtOAc. The organic layer was successively washed with 1M HCl, sat. NaHCO$_3$, and brine, dried over Na$_2$SO$_4$, filtered, and concentrated. Purification by flash column chromatography on silica gel afforded L7 as a white solid (95 mg, 0.10 mmol, 91%). MS (ES$^+$) m/z 931.31 ([M+H]$^+$), 933.25 ([M+H]$^+$). $^1$H NMR (400 MHz, methanol-d$_4$) δ 4.39 (dd, J=8.5, 5.4 Hz, 1H), 3.91 (q, J=11.3 Hz, 2H), 3.84 (s, 2H), 3.76 (t, J=6.2 Hz, 2H), 3.63 (d, J=7.0 Hz, 8H), 3.57 (t, J=5.5 Hz, 6H), 3.42-3.35 (m, 6H), 3.31-3.13 (m, 4H), 2.49 (t, J=6.2 Hz, 2H), 2.20 (t, J=7.4 Hz, 2H), 1.91-1.79 (m, 11H), 1.75-1.56 (m, 6H), 1.39-1.26 (m, 26H), 0.92 (t, J=6.3 Hz, 3H).

Example 16: Synthesis of L8

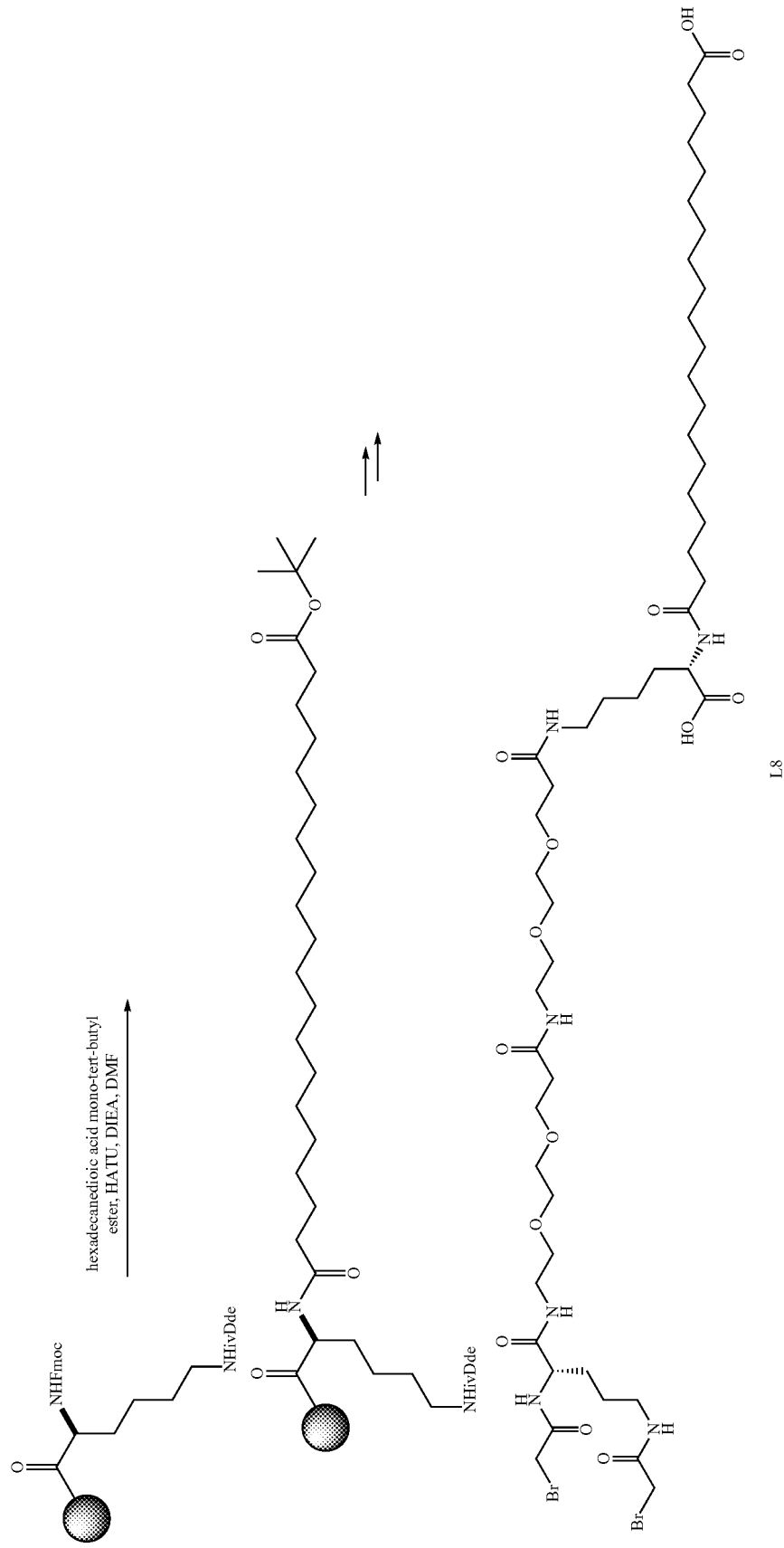

General Protocol A, B, D (Hexadecanedioic Acid Mono-Tert Butyl Ester), C, D (Fmoc-PEG$_2$-Propionic Acid), B, D (Fmoc-PEG$_2$-Propionic Acid), B, D (Fmoc-Orn(Fmoc)-OH), B, E, F.

The crude was purified by semi-preparative HPLC with mass detection to afford the product L8 as a white solid (42.6 mg, 0.038 mmol, 22%). $^1$H NMR (400 MHz, methanol-d$_4$) δ 4.38 (td, J=8.6, 5.1 Hz, 2H), 3.91 (q, J=11.3 Hz, 2H), 3.84 (s, 2H), 3.76 (q, J=6.1 Hz, 4H), 3.65-3.59 (m, 8H), 3.56 (td, J=5.5, 1.7 Hz, 4H), 3.43-3.37 (m, 4H), 3.31-3.16 (m, 4H), 2.48 (dt, J=15.7, 6.2 Hz, 4H), 2.28 (dt, J=12.6, 7.5 Hz, 4H), 1.95-1.79 (m, 1H), 1.77-1.51 (m, 10H), 1.49-1.41 (m, 2H), 1.40-1.26 (m, 31H).

Example 17: Synthesis of L9

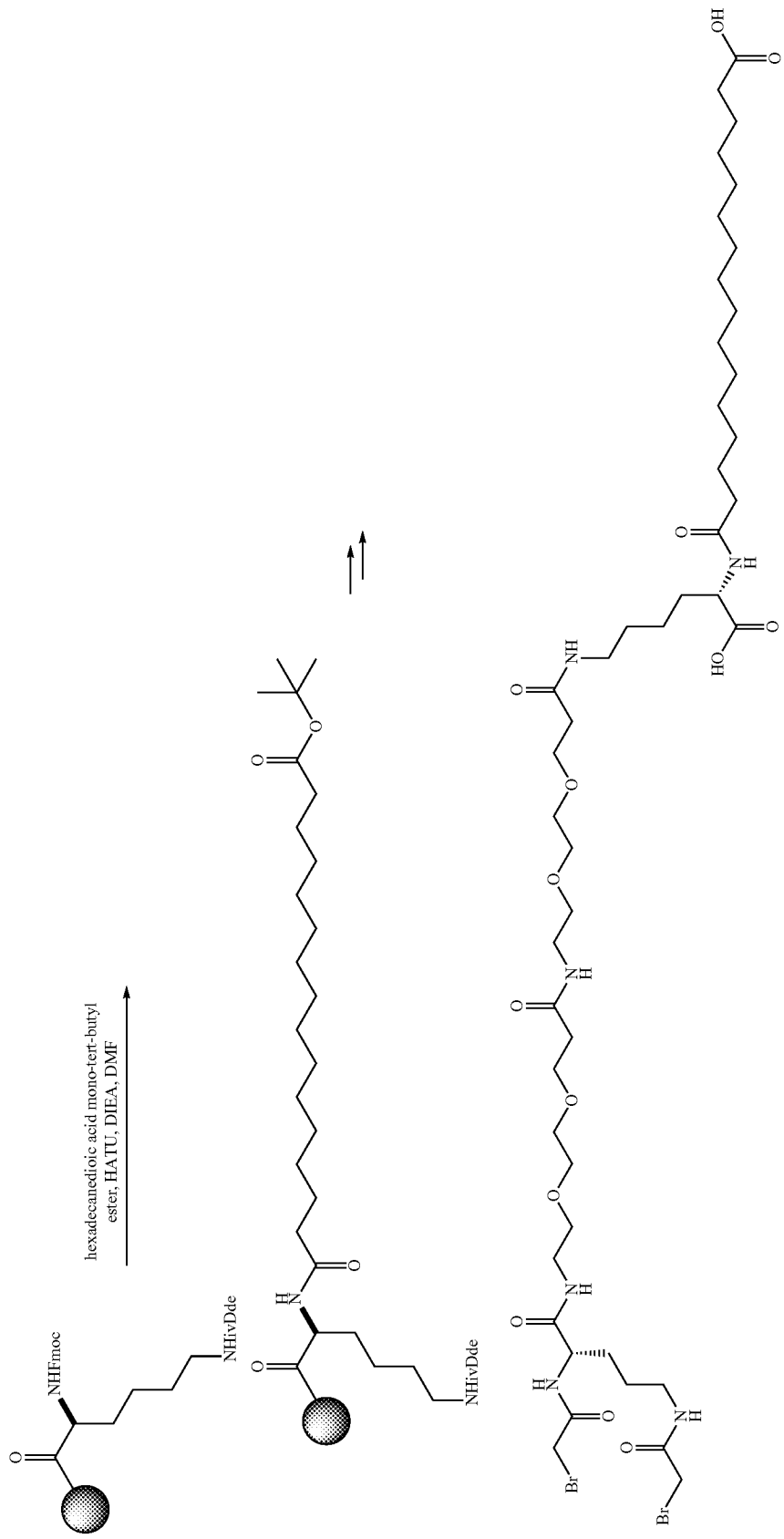

General Protocol A, B, D (Heptadecanedioic Acid Mono-Tert Butyl Ester), C, D (Fmoc-PEG$_2$-Propionic Acid), B, D (Fmoc-PEG$_2$-Propionic Acid), B, D (Fmoc-Orn(Fmoc)-OH), B, E, F.

The crude was purified by semi-preparative HPLC with mass detection to afford the product L9 as a white solid (49 mg, 0.089 mmol, 9%). $^1$H NMR (400 MHz, methanol-d$_4$) δ 4.45-4.33 (m, 2H), 3.92 (t, J=10.9 Hz, 2H), 3.85 (d, J=1.1 Hz, 2H), 3.77 (q, J=6.0 Hz, 4H), 3.63 (s, 8H), 3.57 (t, J=5.6 Hz, 4H), 3.40 (t, J=5.5 Hz, 4H), 3.25 (dq, J=22.7, 6.7 Hz, 4H), 2.48 (dt, J=15.6, 6.2 Hz, 4H), 2.29 (dt, J=13.2, 7.4 Hz, 4H), 1.95-1.79 (m, 2H), 1.80-1.50 (m, 10H), 1.51-1.41 (m, 2H), 1.40-1.27 (m, 20H).

Example 18: Synthesis of L12

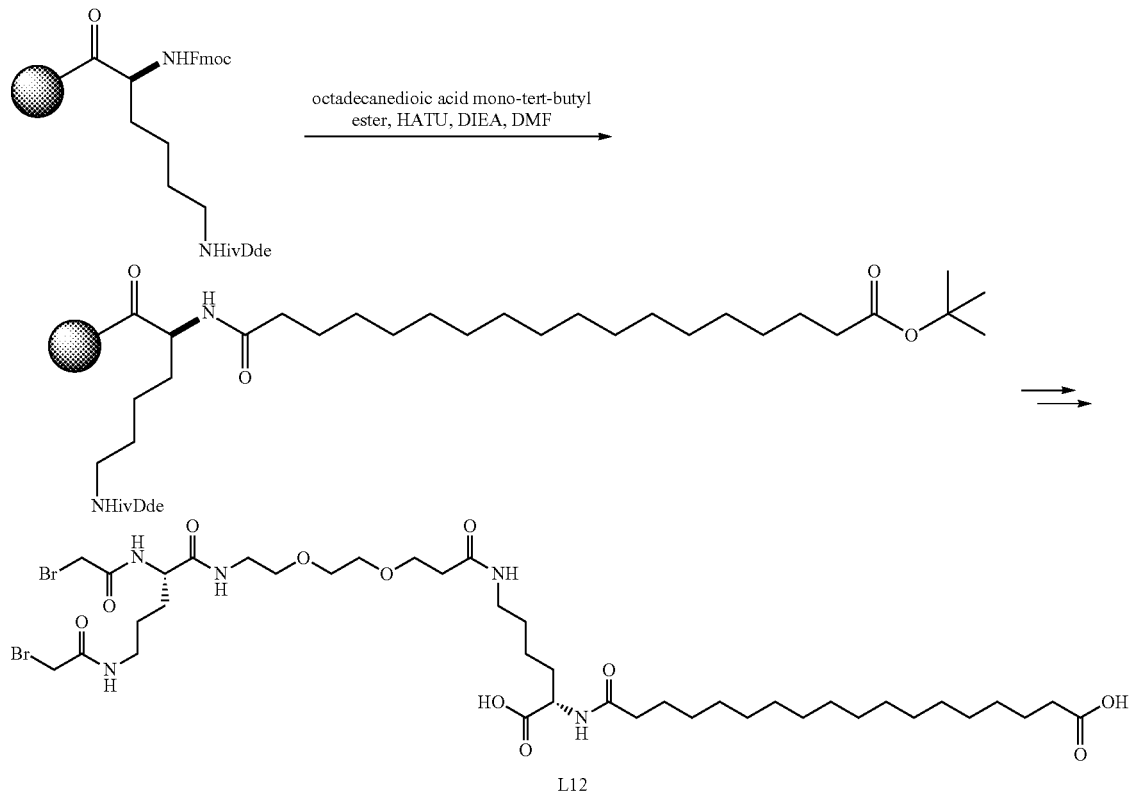

General Protocol A, B, D (Octadecanedioic Acid), C, D (Fmoc-PEG$_2$-Propionic Acid), B, D (Fmoc-Orn(Fmoc)-OH), B, E, F.

The crude was purified by semi-preparative HPLC with mass detection to afford the product L12 as a white solid (51.7 mg, 0.054 mmol, 3%). $^1$H NMR (400 MHz, methanol-d$_4$) δ 4.39 (td, J=9.2, 5.1 Hz, 2H), 3.92 (qd, J=11.4, 1.2 Hz, 2H), 3.85 (s, 2H), 3.76 (t, J=6.2 Hz, 2H), 3.63 (s, 4H), 3.57 (t, J=5.5 Hz, 2H), 3.40 (q, J=5.1 Hz, 2H), 3.30-3.12 (m, 6H), 2.47 (t, J=6.1 Hz, 2H), 2.29 (dt, J=12.1, 7.4 Hz, 4H), 1.95-1.77 (m, 2H), 1.78-1.50 (m, 10H), 1.48-1.40 (m, 2H), 1.39-1.26 (m, 22H).

Example 19: Synthesis of L14

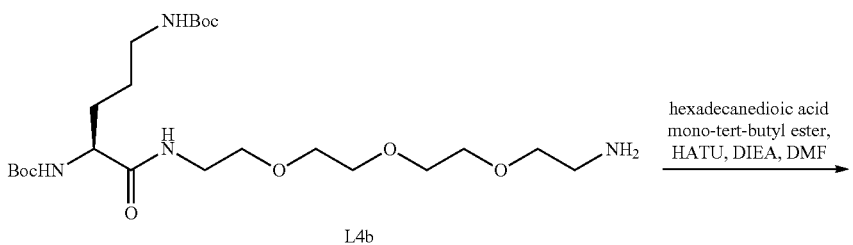

-continued

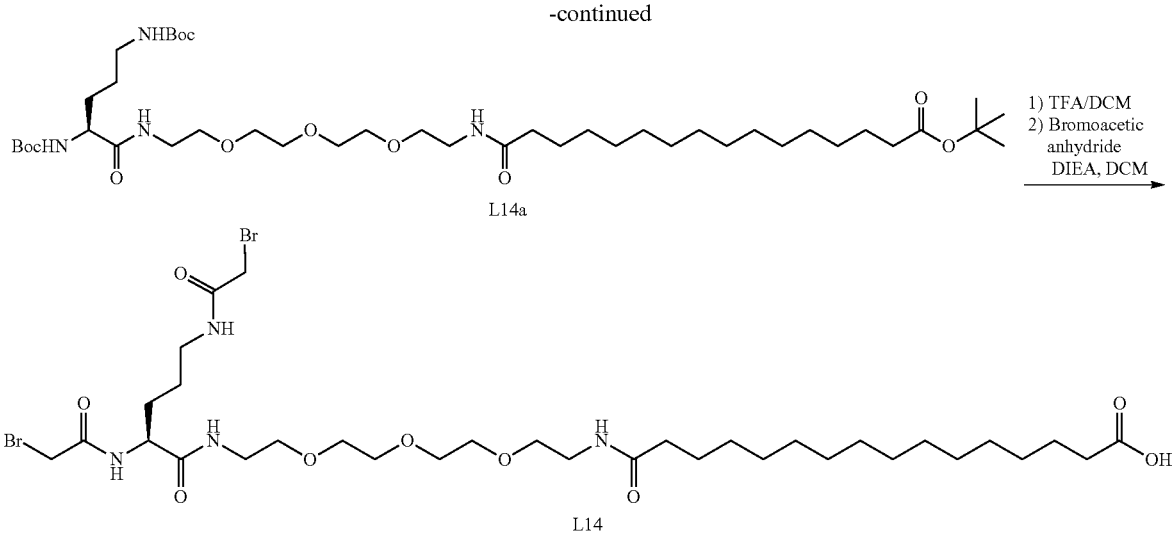

Intermediate L14a

To a solution of hexadecanedioic acid mono tert-butyl ester (102 mg, 0.30 mmol, 1 eq) dissolved in DMF (5 mL) was added HATU (125 mg, 0.33 mmol 1.1 eq), DIEA (51 μL, 0.33 mmol, 1.1 eq) and compound L4b (151.9 mg, 0.3 mmol, 1 eq) dissolved in 1 mL of DMF. The reaction mixture was agitated 3 h at RT. The product was diluted with EtOAc. The organic layer was successively washed with 1M HCl, sat. NaHCO$_3$, brine, dried over Na$_2$SO$_4$, filtered, and concentrated. Purification by flash column chromatography on silica gel provided the desired compound L14a as an oil (147 mg, 0.176 mmol, 59%). $^1$H NMR (400 MHz, chloroform-d) δ 6.87 (s, 11H), 6.40 (s, 1H), 5.32 (s, 2H), 4.79 (s, 1H), 4.20 (s, 1H), 3.66 (d, J=7.0 Hz, 8H), 3.60 (dt, J=10.0, 5.1 Hz, 4H), 3.49-3.45 (m, 3H), 3.31-3.18 (m, 1H), 3.13-3.06 (m, 1H), 2.21 (td, J=7.8, 6.0 Hz, 4H), 1.88-1.78 (m, 1H), 1.66-1.53 (m, 7H), 1.51-1.42 (m, 27H), 1.36-1.19 (m, 20H).

L14

A solution of compound L14a (40 mg, 0.048 mmol, 1 eq) in DCM (2 mL) was treated with TFA (2 mL) for 30 min. The mixture was concentrated, co-evaporated with hexane and dissolved in 20 mL of DCM and cooled at 0° C. DIEA (34 μL, 0.1924 mmol, 4 eq) was added followed by bromoacetic anhydride (23.63 mg, 0.098 mmol, 2.05 eq) dissolved in 1 mL of DCM. The reaction mixture was then stirred for 30 min at 0° C., 1.5 h at RT, and the solvent was removed. Purification by flash column chromatography on silica gel afforded L14 as a white solid (18.3 mg, 0.022 mmol, 46%). MS (ES$^+$) m/z 817.1 ([M+H]$^+$), 819.09 ([M+H]$^+$). $^1$H NMR (400 MHz, methanol-d$_4$) δ 4.38 (dd, J=8.4, 5.5 Hz, 1H), 3.92 (q, J=11.2, 10.6 Hz, 2H), 3.84 (s, 2H), 3.69-3.61 (m, 8H), 3.56 (td, J=5.5, 2.6 Hz, 4H), 3.44-3.36 (m, 4H), 3.30-3.14 (m, 2H), 2.29 (t, J=7.4 Hz, 2H), 2.21 (t, J=7.5 Hz, 2H), 1.91-1.78 (m, 11H), 1.76-1.67 (m, 1H), 1.67-1.54 (m, 6H), 1.40-1.29 (m, 20H).

Example 20: Synthesis of L15

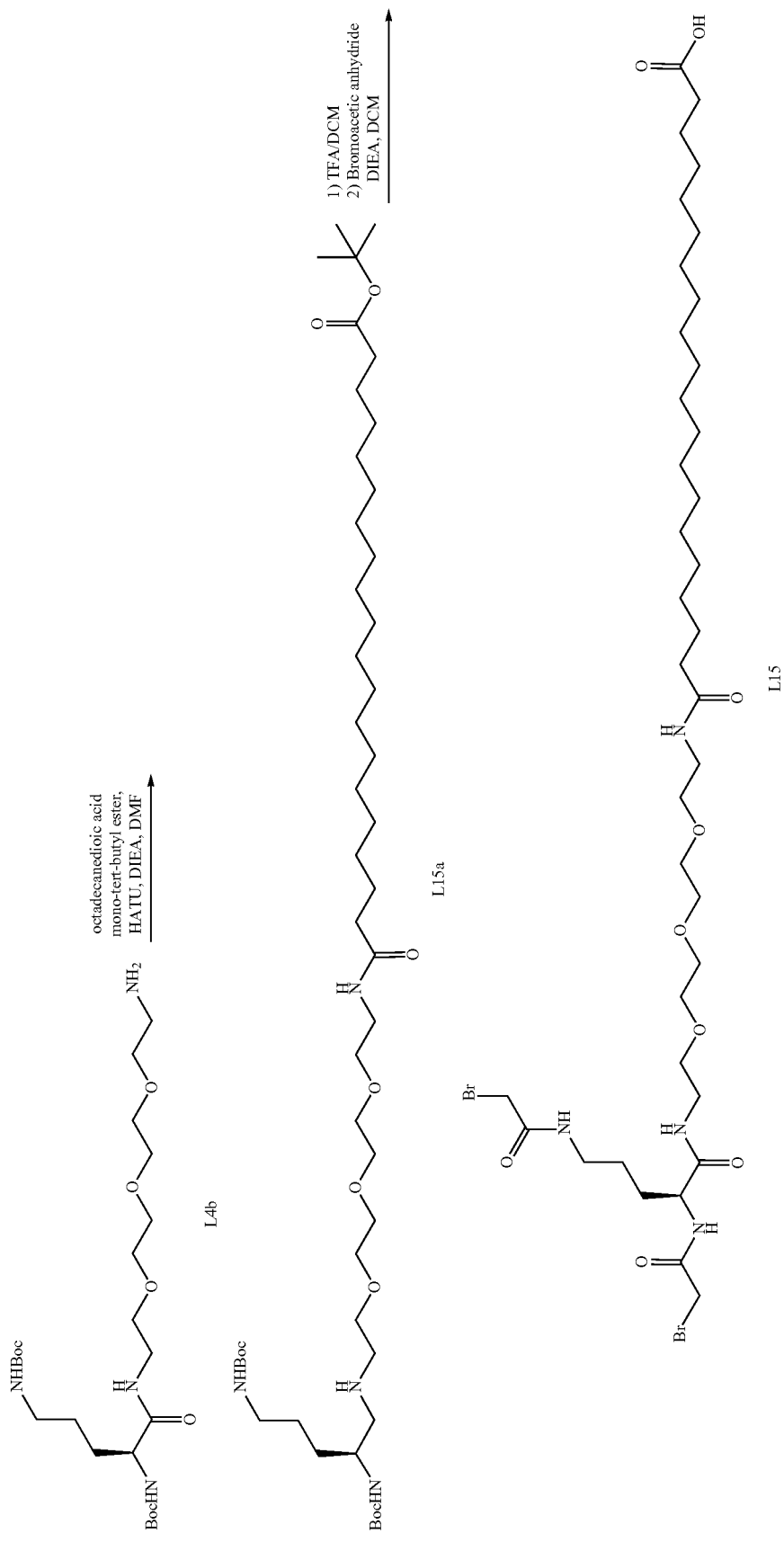

Intermediate L15a

To a solution of 20-(tert-butoxy)-20-oxoicosanoic acid (360 mg, 0.90 mmol, 1.05 eq) dissolved in DMF (5 mL) was added HATU (343 mg, 0.90 mmol 1.05 eq), DIEA (300 µL, 1.71 mmol, 2 eq) and compound L4b (435 mg, 0.858 mmol, 1 eq) dissolved in 1 mL of DMF. The reaction mixture was agitated 3 h at RT. The product was diluted with EtOAc. The organic layer was successively washed with 1M HCl, sat. NaHCO$_3$, brine, dried over Na$_2$SO$_4$, filtered, and concentrated. Purification by flash column chromatography on silica gel provided the desired compound L15a as an oil (555 mg, 0.625 mmol, 72%). $^1$H NMR (400 MHz, chloroform-d) δ 6.87 (s, 1H), 6.40 (s, 1H), 4.79 (s, 1H), 4.21 (s, 1H), 3.76-3.53 (m, 15H), 3.47 (s, 5H), 3.32-3.05 (m, 3H), 2.29-2.17 (m, 4H), 1.90-1.76 (m, 4H), 1.69-1.53 (m, 2H), 1.52-1.41 (m, 33H), 1.36-1.20 (m, 29H).

L15

A solution of compound L15a (100 mg, 0.112 mmol, 1 eq) in DCM (2 mL) was treated with TFA (2 mL) for 30 min. The mixture was concentrated, co-evaporated with hexane and dissolved in 20 mL of DCM and cooled at 0° C. DIEA (79 µL, 0.45 mmol, 4 eq) was added followed by bromoacetic anhydride (60 mg, 0.231 mmol, 2.05 eq) dissolved in 1 mL of DCM. The reaction mixture was then stirred for 30 min at 0° C., 1.5 h at RT, and the solvent was removed. Purification by flash column chromatography on silica gel afforded L15 as a white solid (17.5 mg, 0.02 mmol, 18%). MS (ES$^+$) m/z 873.21 ([M+H]$^+$), 875.20 ([M+H]$^+$) $^1$H NMR (400 MHz, methanol-d$_4$) δ 4.38 (dd, J=8.4, 5.5 Hz, 1H), 3.91 (q, J=11.4 Hz, 2H), 3.84 (s, 2H), 3.72-3.61 (m, 8H), 3.56 (td, J=5.5, 2.7 Hz, 4H), 3.44-3.35 (m, 5H), 3.30-3.17 (m, 2H), 2.29 (t, J=7.4 Hz, 2H), 2.21 (t, J=7.5 Hz, 2H), 1.92-1.77 (m, 1H), 1.75-1.53 (m, 7H), 1.40-1.27 (m, 27H).

Example 21: Synthesis of L16

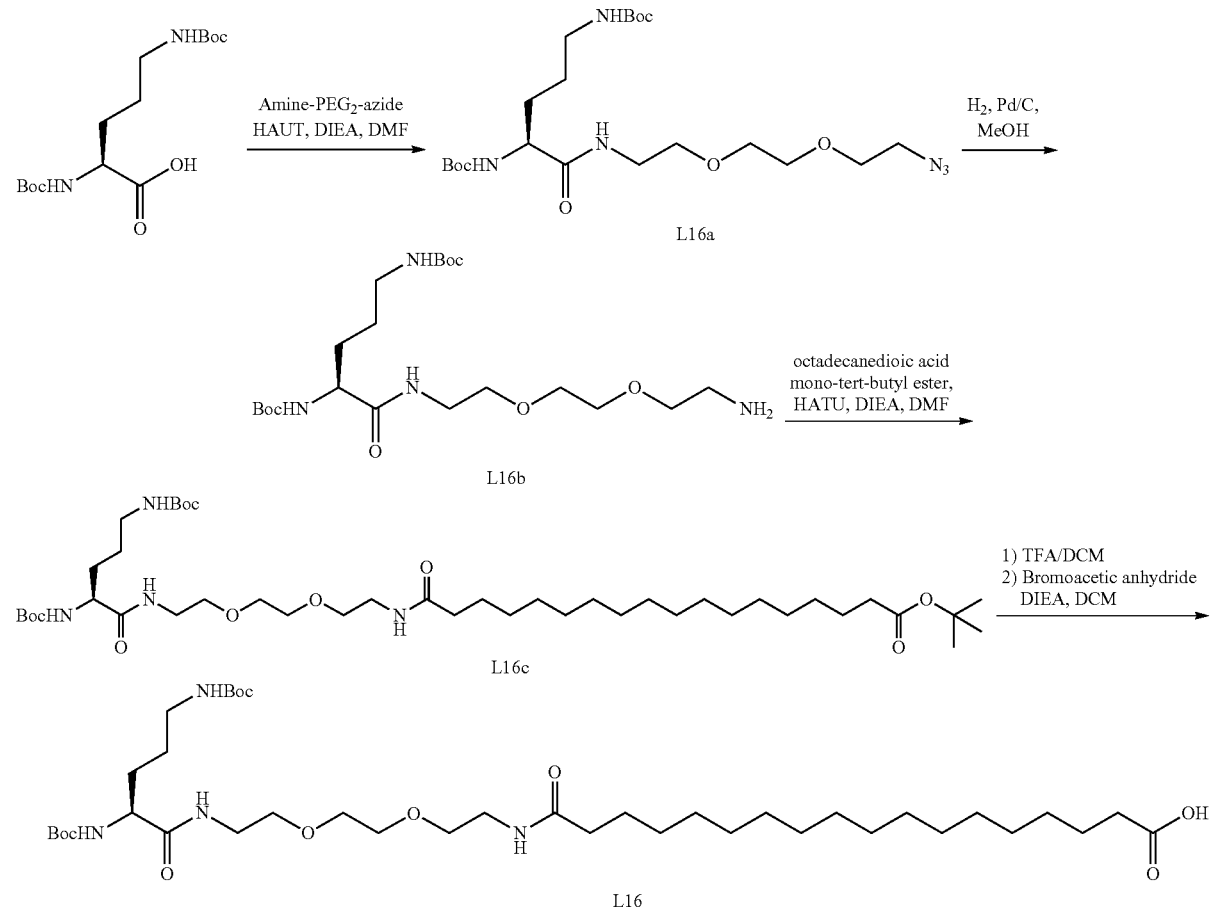

Intermediate L16a

To a solution of Boc-Orn(Boc)-OH (400 mg, 1.2 mmol, 1 eq) dissolved in DMF (10 mL) was added HATU (504 mg, 1.32 mmol 1.1 eq), DIEA (230 µL, 1.32 mmol, 1.1 eq) and amine-PEG$_2$-N$_3$ (210 mg, 1.20 mmol, 1 eq) dissolved in 1 mL of DMF. The reaction mixture was agitated 4 h at RT. The product was diluted with EtOAc. The organic layer was successively washed with 1M HCl, sat. NaHCO$_3$, brine, dried over Na$_2$SO$_4$, filtered, and concentrated. Purification by flash column chromatography on silica gel provided the desired compound L16a as an oil (471 mg, 0.96 mmol, 80%). $^1$H NMR (400 MHz, methanol-d$_4$) δ 4.01 (t, J=6.6 Hz, 1H), 3.71-3.60 (m, 6H), 3.55 (t, J=5.5 Hz, 2H), 3.41-3.37 (m, 3H), 3.04 (t, J=6.2 Hz, 2H), 1.78-1.66 (m, 1H), 1.62-1.48 (m, 3H), 1.48-1.39 (m, 18H).

Intermediate L16b

To a solution of compound L16a (471 mg, 0.9 mmol, 1 eq) in anhydrous MeOH (10 mL) and under argon was added Pd/C (10.2 mg, 0.09 mmol, 0.1 eq) and argon was replaced with H$_2$. The reaction mixture was agitated for 6 h at RT, filtrated on celite and evaporated to afford compound L16b as an oil (295.5 mg, 0.64 mmol, 71%). The product was used without any further purification. MS (ES$^+$) m/z 462.51 ([M+H]$^+$).

Intermediate L16c

To a solution of octadecanedioic acid mono tert-butyl ester (281 mg, 0.76 mmol, 1 eq) dissolved in DMF (5 mL) was added HATU (288 mg, 0.76 mmol, 1 eq), DIEA (132 µL, 0.76 mmol, 1 eq) and compound L16b (351 mg, 0.76 mmol, 1 eq) dissolved in 1 mL of DMF. The reaction mixture was agitated 3 h at RT. The product was diluted with EtOAc. The organic layer was successively washed with 1M HCl, sat. $NaHCO_3$, brine, dried over $Na_2SO_4$, filtered, and concentrated. Purification by flash column chromatography on silica gel provided the desired compound L16c as an oil (351 mg, 0.43 mmol, 57%). $^1$H NMR (400 MHz, methanol-$d_4$) δ 3.61 (s, 4H), 3.54 (td, J=5.6, 2.3 Hz, 4H), 3.40-3.34 (m, 4H), 3.04 (t, J=6.6 Hz, 2H), 2.20 (td, J=7.6, 5.9 Hz, 4H), 1.77-1.68 (m, 2H), 1.64-1.48 (m, 2H), 1.48-1.42 (m, 28H), 1.35-1.26 (m, 26H).

L16

A solution of compound L16c (31 mg, 0.038 mmol, 1 eq) in DCM (2 mL) was treated with TFA (2 mL) for 30 min. The mixture was concentrated, co-evaporated with hexane and dissolved in 20 mL of DCM and cooled at 0° C. DIEA (27 µL, 0.152 mmol, 4 eq) was added followed by bromoacetic anhydride (21 mg, 0.078 mmol, 2.05 eq) dissolved in 1 mL of DCM. The reaction mixture was then stirred for 30 min at 0° C., 1.5 h at RT, and the solvent was removed. Purification by flash column chromatography on silica gel afforded L16 as a white solid (12.6 mg, 0.015 mmol, 41%). MS (ES$^+$) m/z 801.13 ([M+H]$^+$), 803.12 ([M+H]$^+$). $^1$H NMR (400 MHz, methanol-$d_4$) δ 4.37 (dd, J=8.5, 5.4 Hz, 1H), 3.91 (q, J=11.3 Hz, 2H), 3.84 (s, 2H), 3.63 (s, 4H), 3.57 (td, J=5.6, 2.6 Hz, 4H), 3.43-3.36 (m, 4H), 3.31-3.17 (m, 1H), 2.29 (t, J=7.4 Hz, 2H), 2.21 (t, J=7.5 Hz, 2H), 1.90-1.79 (m, 1H), 1.76-1.54 (m, 7H), 1.41-1.30 (m, 26H).

Example 22: Synthesis of L17

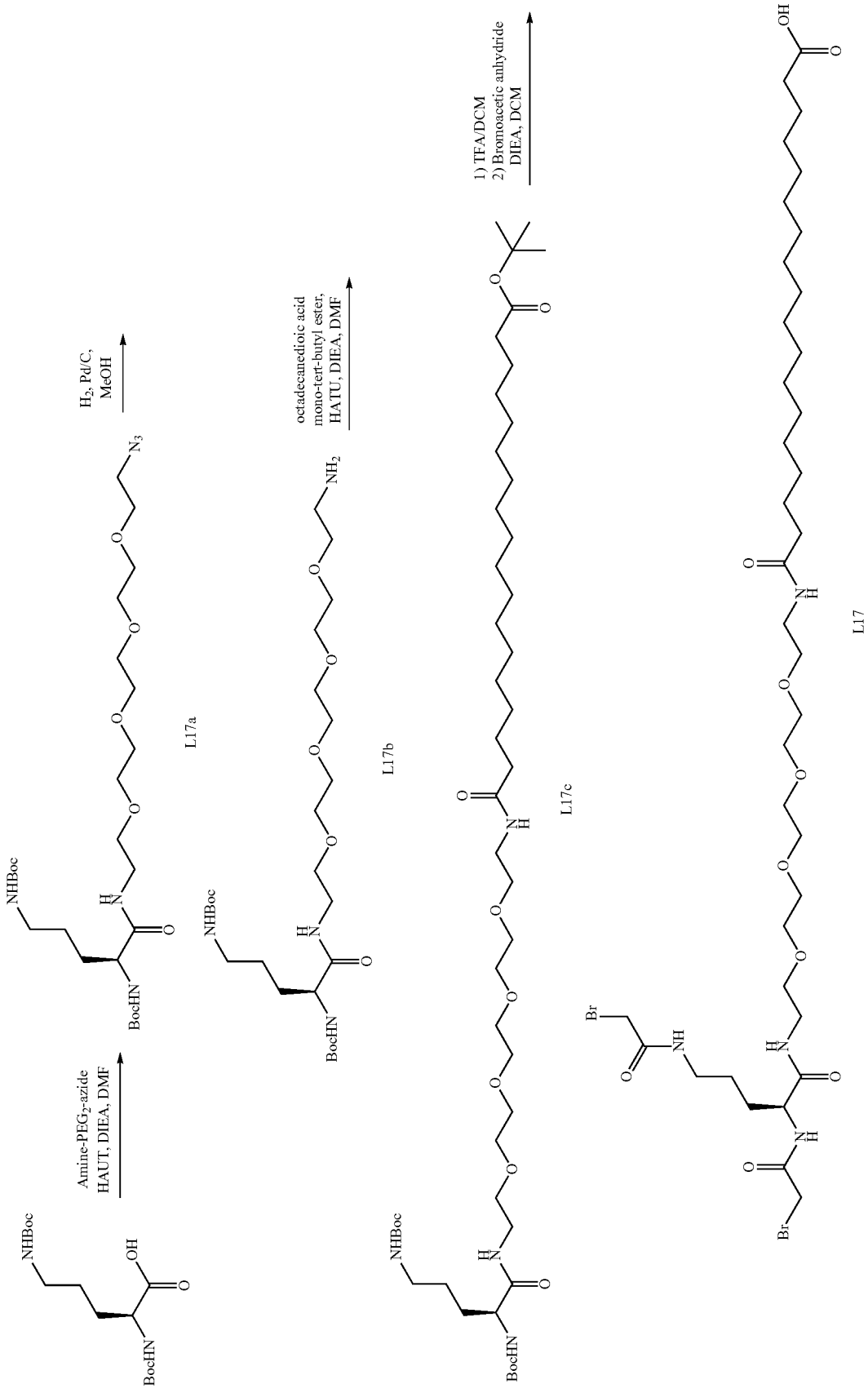

Intermediate L17a

To a solution of Boc-Orn(Boc)-OH (400 mg, 1.2 mmol, 1 eq) dissolved in DMF (10 mL) was added HATU (504 mg, 1.32 mmol 1.1 eq), DIEA (230 µL, 1.32 mmol, 1.1 eq) and amine-PEG$_2$-N$_3$ (316 mg, 1.20 mmol, 1 eq) dissolved in 1 mL of DMF. The reaction mixture was agitated 4 h at RT. The product was diluted with EtOAc. The organic layer was successively washed with 1M HCl, sat. NaHCO$_3$, brine, dried over Na$_2$SO$_4$, filtered, and concentrated. Purification by flash column chromatography on silica gel provided the desired compound L17a as an oil (454 mg, 0.78 mmol, 66%). $^1$H NMR (400 MHz, methanol-d$_4$) δ 4.04-3.97 (m, 11H), 3.71-3.58 (m, 14H), 3.54 (t, J=5.4 Hz, 2H), 3.37 (t, J=5.0 Hz, 4H), 3.04 (t, J=6.6 Hz, 2H), 1.75-1.67 (m, 1H), 1.62-1.48 (m, 3H), 1.48-1.41 (m, 18H).

Intermediate L17b

To a solution of compound L17a (454 mg, 0.9 mmol, 1 eq) in anhydrous MeOH (10 mL) and under argon was added Pd/C (8.3 mg, 0.078 mmol, 0.1 eq) and argon was replaced with H$_2$. The reaction mixture was agitated for 6 h at RT, filtrated on celite and evaporated to afford compound L17b as an oil (192 mg, 0.35 mmol, 45%). The product was used without any further purification.

Intermediate L17c

To a solution of octadecanedioic acid mono tert-butyl ester (225 mg, 0.61 mmol, 1 eq) dissolved in DMF (5 mL) was added HATU (231 mg, 0.61 mmol 1 eq), DIEA (106 µL, 0.61 mmol, 1 eq) and compound L17b (335 mg, 0.61 mmol, 1 eq) dissolved in 1 mL of DMF. The reaction mixture was agitated 2 h at RT. The product was diluted with EtOAc. The organic layer was successively washed with 1M HCl, sat. NaHCO$_3$, brine, dried over Na$_2$SO$_4$, filtered, and concentrated. Purification by flash column chromatography on silica gel provided the desired compound L17c as an oil (178 mg, 0.20 mmol, 32%). $^1$H NMR (400 MHz, chloroform-d) δ 5.32 (s, 2H), 3.74-3.63 (m, 11H), 3.59 (dt, J=10.9, 5.0 Hz, 4H), 3.52-3.43 (m, 4H), 3.27-3.08 (m, 2H), 2.22 (d, J=7.6 Hz, 4H), 1.69-1.52 (m, 6H), 1.51-1.42 (m, 27H), 1.27 (s, 26H).

L17

A solution of compound L17c (45.6 mg, 0.05 mmol, 1 eq) in DCM (2 mL) was treated with TFA (2 mL) for 30 min. The mixture was concentrated, co-evaporated with hexane and dissolved in 20 mL of DCM and cooled at 0° C. DIEA (36 µL, 0.202 mmol, 4 eq) was added followed by bromoacetic anhydride (27 mg, 0.103 mmol, 2.05 eq) dissolved in 1 mL of DCM. The reaction mixture was then stirred for 30 min at 0° C., 1.5 h at RT, and the solvent was removed. Purification by flash column chromatography on silica gel afforded L17 as a white solid (14.9 mg, 0.017 mmol, 33%). MS (ES$^+$) m/z 889.18 ([M+H]$^+$), 891.17 ([M+H]$^+$) $^1$H NMR (400 MHz, methanol-d$_4$) δ 4.38 (dd, J=8.3, 5.5 Hz, 1H), 3.92 (q, J=11.3 Hz, 2H), 3.84 (s, 2H), 3.67-3.60 (m, 7H), 3.56 (td, J=5.5, 3.5 Hz, 4H), 3.45-3.35 (m, 5H), 3.32-3.15 (m, 3H), 2.29 (t, J=7.4 Hz, 2H), 2.21 (t, J=7.5 Hz, 2H), 1.90-1.76 (m, 1H), 1.74-1.57 (m, 7H), 1.41-1.26 (m, 25H).

Example 23: Synthesis of L18

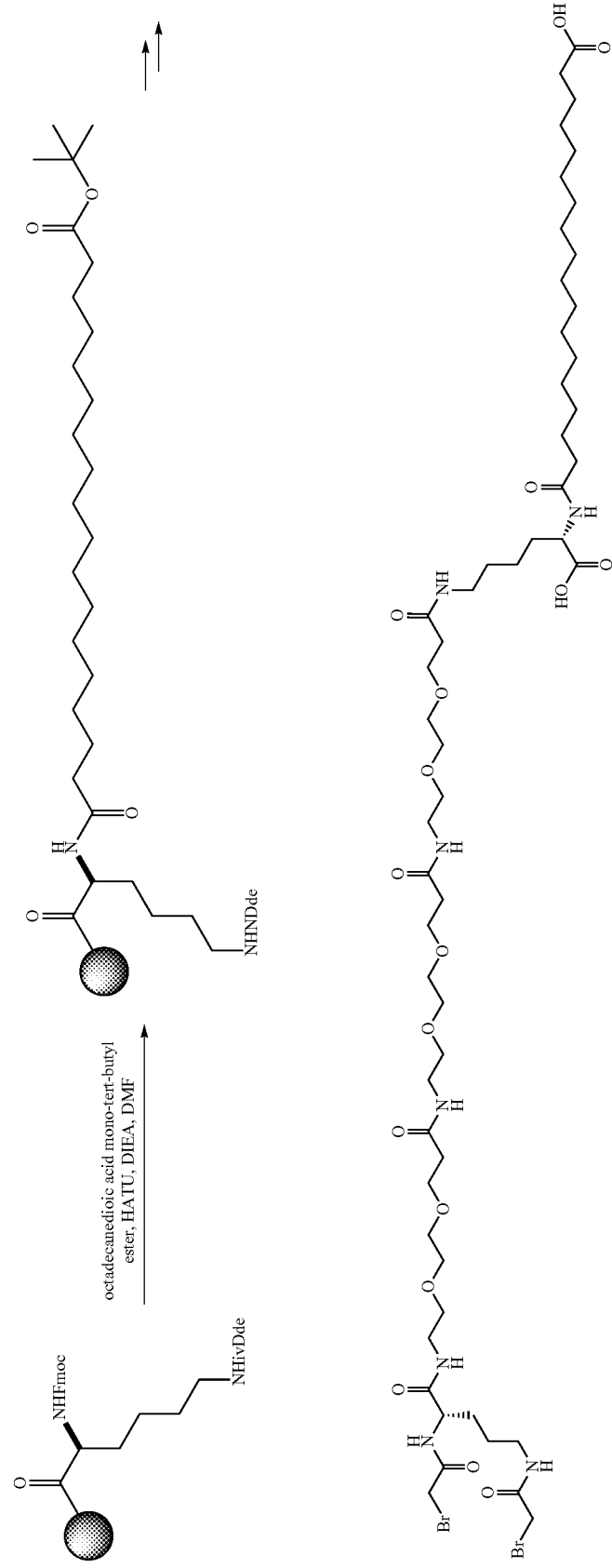

General Protocol A, B, D (Octadecanedioic Acid), C, D (Fmoc-PEG$_2$-Propionic Acid), B, (Fmoc-PEG$_2$-Propionic Acid), B, (Fmoc-PEG$_2$-Propionic Acid), B, D (Fmoc-Orn (Fmoc)-OH), B, E, F.

The crude was purified by semi-preparative HPLC with mass detection to afford the product L18 as a white solid (47 mg, 0.036 mmol, 10%). MS (ES$^+$) m/z 1276.39 ([M+H]$^+$), 1278.37 ([M+H]$^+$).

General Procedure for Bromoacetyl Peptide Stapling/Conjugation

Peptides were dissolved at a concentration of 2 mM with 1.5 eq of bromoacetyl staple in 1:3 (v/v) MeCN/30 mM NH$_4$HCO$_3$ buffer (pH 8.5). The pH of the reaction mixture was readjusted with ammonium hydroxide to correct the drop in pH caused by the peptide TFA counterion. More MeCN was added for particularly insoluble peptides. The reaction was stirred at RT for 2-4 h, before acidification to pH 5 via dropwise addition of acetic acid. The resulting solution was lyophilized and purified by reversed-phase HPLC.

General Solid-Phase Protocols for Lactam Stapling

Peptide-resin bearing amine side chain orthogonal protection (Dde/Mmt) at each stapling position was swollen in DMF for 1 h. The Dde protecting group was removed from the first side chain via treatment with 2% hydrazine solution in DMF (2×15 min). Positive TNBS test was observed. The linker building block specified below was coupled as described and a negative TNBS test was observed. The solvent was exchanged for DCM and the Mmt group was removed from the second side chain via treatment with 1% TFA in DCM containing 5% TIPS, 5×2 min. The resin was washed with DCM, 10% DIEA in DMF, DMF and a positive TNBS test was observed. The linker was cyclized and the PEG-fatty acid portion of the staple (if applicable) elongated as described below. The complete stapled peptide was cleaved from the resin using 95% TFA, 2.5% TIPS, 2.5% H$_2$O, 3 h. The peptide cleavage mixture was evaporated to an oil, triturated and washed with diethyl ether and purified via reversed-phase HPLC. A Dde/Alloc protection scheme can also be used for this approach, which requires the addition of allyl alcohol to the Dde deprotection cocktail as a scavenger to prevent concurrent reduction of the Alloc allyl moiety.

Synthesis of K(Fmoc) Linker

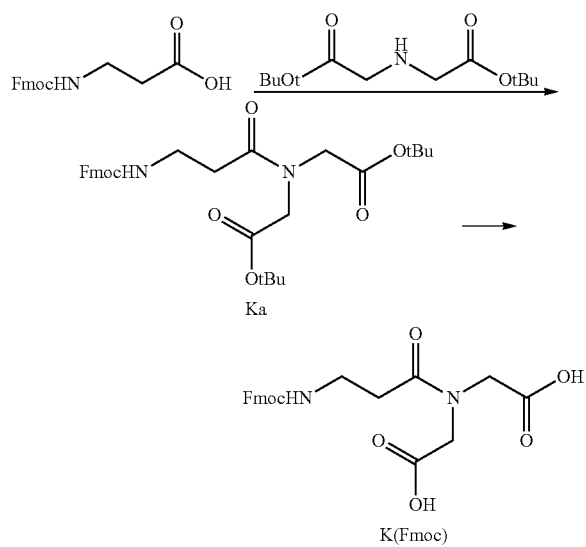

Intermediate Ka

Fmoc-β-Ala-OH (1.00 g, 3.21 mmol) and di-tert-butyl iminodiacetate (0.461 g, 2.68 mmol) were suspended in 100 mL DCM. HATU (1.02 g, 2.68 mmol) and DIEA (3.32 mL, 12.8 mmol) were added and the reaction was stirred at RT for 3.5 h. The solvent was evaporated and the residue dissolved in MeOH and purified via flash column chromatography on silica gel (hexane/EtOAc) to afford the product as a white solid (0.802 g, 56%). $^1$H NMR (400 MHz, chloroform-d) δ 7.78 (d, J=7.4 Hz, 2H), 7.62 (d, J=7.4 Hz, 2H), 7.42 (t, J=7.4 Hz, 2H), 7.33 (t, J=7.4 Hz, 2H), 5.66 (t, J=5.7 Hz, 1H), 4.35 (d, J=7.3 Hz, 2H), 4.23 (t, J=7.3 Hz, 1H), 4.10 (s, 2H), 4.02 (s, 2H), 3.56 (q, J=5.7 Hz, 2H), 2.55 (t, J=5.7 Hz, 2H), 1.49 (s, 18H).

K(Fmoc) Linker

Compound Ka was treated with 20 mL 1:1 TFA/DCM for 2 h. The solvent was evaporated and the residue triturated and washed with diethyl ether to afford K(Fmoc) linker as a white solid (0.371 g, 58%). MS (ES$^+$) m/z 427.15 ([M+H]$^+$).

Synthesis of A(Fmoc) Linker

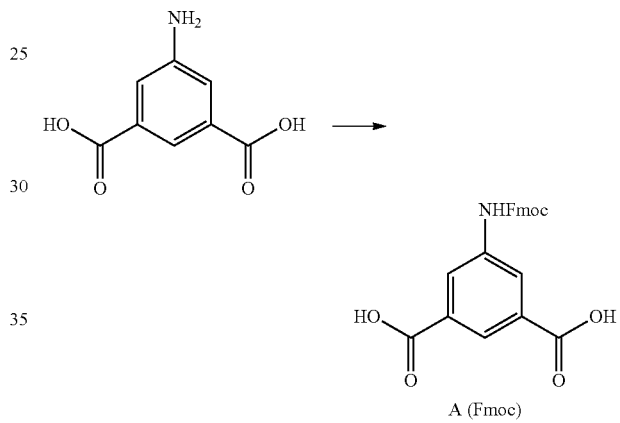

A solution of 5-Aminoisophthalic acid (1.00 g, 5.5 mmol) in 10 mL dioxane was added to a degassed solution of Na$_2$CO$_3$ (1.46 g, 5.5 mmol) in 15 mL water. The solution was cooled on ice and a solution of Fmoc chloride (1.42 g, 5.5 mmol) in 10 mL dioxane was then added dropwise with stirring over 15 min. The reaction was then stirred for 1 h and then 24 h at RT. The dioxane was removed under vacuum and the remaining aqueous solution acidified with 1M HCl. The resulting solid precipitate was then washed with diethyl ether (4×10 mL), redissolved in EtOAc, filtered, washed with brine, dried over Na$_2$SO$_4$ filtered and concentrated to give A (Fmoc) linker as a white solid (119 mg, 5%). $^1$H NMR (500 MHz, DMSO-d$_6$) δ 13.24 (s, 2H), 10.12 (s, 1H), 8.33 (d, J=1.5 Hz, 2H), 8.12 (t, J=1.5 Hz, 1H), 7.91 (d, J=7.6 Hz, 2H), 7.76 (dd, J=7.6, 1.2 Hz, 2H), 7.43 (t, J=7.6 Hz, 2H), 7.36 (td, J=7.6, 1.2 Hz, 2H), 4.50 (d, J=6.8 Hz, 2H), 4.33 (t, J=6.8 Hz, 1H).

General Protocol G for 'A1' and 'K1' Series Simple Lactam Staples

For linker coupling the appropriate diacid building block (2 eq) was attached using HATU (4 eq) and DIEA (4 eq) in DMF, 1×2 h. The cyclization step was achieved using HATU (1 eq) and DIEA (2 eq) in DMF, 1×2 h.

General Protocol H for 'K' PEG-Fatty Acid Trifunctional Lactam Staples

For linker coupling the intramolecular symmetric anhydride of building block K(Fmoc) linker (2 eq) was preformed using DIC (2 eq) and catalytic DMAP in dry DCM for 10 min at RT. The peptide-resin solvent was exchanged for DCM and the anhydride was then added and agitated overnight. The resin was drained, washed with DCM and DMF. The linker was cyclized overnight via treatment with DIC (1 eq) and HOBt or HOAt (1 eq) in DMF, and a negative TNBS was observed. Remaining uncyclized linker was capped via treatment with 10% acetic anhydride in DMF (30 min). The linker Fmoc group was deprotected via treatment with 20% piperidine in DMF (2×10 min). A positive TNBS was observed. Subsequent staple PEG and fatty acid building blocks were attached sequentially to the linker free amine via standard coupling chemistry: building block (3 eq), HATU (3 eq) and DIEA (6 eq) in DMF, 1 h at RT, using 20% piperidine in DMF for deprotection cycles (5+10 min, RT).

General Protocol I for 'A' PEG-Fatty Acid Trifunctional Lactam Staples

For linker coupling the building block A(Fmoc) linker (2 eq) was attached using HATU (4 eq) and DIEA (4 eq) in DMF, 1×2 h. The cyclization step was achieved using HATU (1 eq) and DIEA (2 eq) in DMF, 1×2 h. Remaining uncyclized linker was capped via treatment with 10% acetic anhydride in DMF (30 min). The linker Fmoc group was deprotected via treatment with 20% piperidine in DMF (2×10 min). It was not possible to observe a positive TNBS test for the aniline nitrogen. Fmoc-R-Ala-OH (3 eq) was coupled using HATU (3 eq) and DIEA (6 eq) in DMF, 4×1 h at RT or as the symmetric anhydride using DIC/DMAP in DCM (2 h, RT). Subsequent staple PEG and fatty acid building blocks were attached sequentially to the linker free amine via standard coupling chemistry: building block (3 eq), HATU (3 eq) and DIEA (6 eq) in DMF, 1 h at RT, using 20% piperidine in DMF for deprotection cycles (5+10 min, RT).

In some embodiments, the peptide conjugate described herein comprises a half-life extending moiety or a staple of Table 2 or Table 3.

Example 24: Peptide Synthesis for mCMZ370(C (14-21)-L5A(S)) and mCMZ371(C(17-24)-L5A(S))

mCMZ370(C(14-21)-L5A(S)) comprises Compound 2 (266: SEQ ID NO. 5) and L5A.
mCMZ371(C(17-24)-L5A(S)) comprises Compound 3 (268: SEQ ID NO. 6) and L5A.

General Procedure for Preparation of Compound 1:

The peptide was synthesized using standard Fmoc chemistry.
1) Resin preparation: To the 2-CTC 1-chloro-2-[chloro (diphenyl)methyl]benzene (20.0 mmol, 1.00 eq) (Sub: 1.00 mmol/g) was added Fmoc-Lys(Dde)-OH (15.0 mmol, 1.00 eq) and DIEA (10.0 mL, 4.00 eq) in DCM (150 mL). The mixture was agitated with $N_2$ for 2 hrs at 20° C., then added MeOH (15.0 mL) and agitated with $N_2$ for another 30 mins. The resin was washed with DMF (300 mL*5).
2) Deprotection: 20% piperidine in DMF (300 mL) was added and agitated the resin with $N_2$ for another 30 mins. The resin was washed with DMF (300 mL*5) and filtered to get the resin.
3) Coupling: A solution of 18-(tert-butoxy)-18-oxooctadecanoic acid (2.00 eq) and DIEA (4.00 eq) in DMF (150 mL) was added HATU (1.90 eq) to the resin and agitated with $N_2$ for 30 mins at 20° C. The resin was then washed with DMF (300 mL*5).
4) Deprotection: 3% hydrazine hydrate in DMF (300 mL) was added and agitated the resin with $N_2$ for another 15 min for twice. The resin was washed with DMF (300 mL*5) and filtered to get the resin.
5) Repeat above step 2 to 3 for the coupling of following amino acids: (3-5).
6) Repeat above step 3 for the coupling of following amino acids: 2-bromoacetic acid.

Note:

| # | Materials | Coupling reagents |
|---|---|---|
| 3 | Fmoc-NH-PEG2-CH$_2$CH$_2$COOH (1.50 eq) | HBTU (1.42 eq) and DIEA (3.00 eq) |
| 4 | Fmoc-NH-PEG2-CH$_2$CH$_2$COOH (1.50 eq) | HBTU (1.42 eq) and DIEA (3.00 eq) |
| 5 | ![structure] (2.00 eq) | HBTU (1.90 eq) and DIEA (4.00 eq) |
| 6 | 2-bromoacetic acid (12.0 eq) | DIC (6.00 eq) |

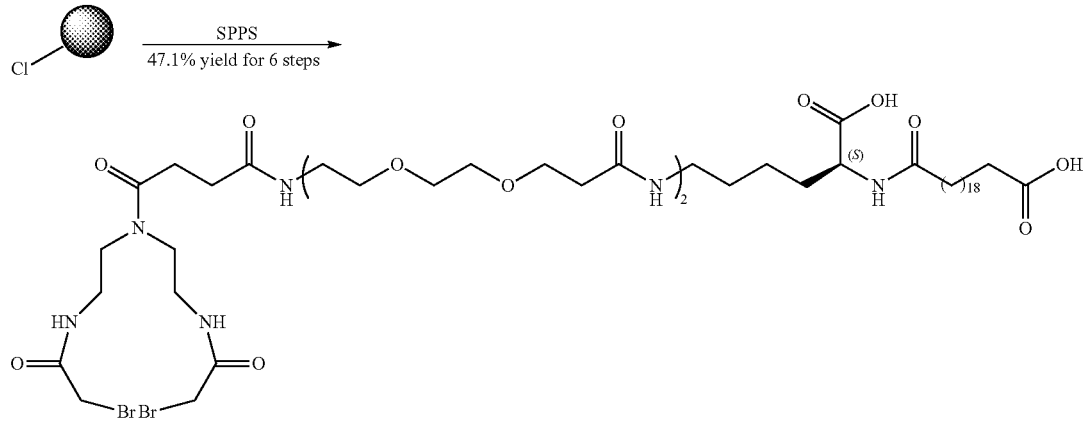

20% piperidine in DMF was used for Fmoc deprotection for 30 mins. The coupling reaction was monitored by ninhydrin test, and the resin was washed with DMF for 5 times.

Peptide Cleavage and Purification:
1) After coupling, the resin was washed with DMF (200 ml) for 5 times. After last step, the resin was washed with MeOH (200 mL) for 3 times and dried under vacuum. Then the peptide resin (35.0 g) was treated with the cleavage cocktail (350 mL, 95% TFA/5% $H_2O$) for 1.5 hours. The mixture was filtered to remove the cleavage cocktail, concentrated under reduced pressure to give a residue. LCMS (EW33512-2-P1A1, Rt=1.524 min).
2) The crude peptide was purified by prep-HPLC (A: 0.075% TFA in $H_2O$, B: ACN) to give the Compound 1 (8.92 g, 7.07 mmol, 47.11% yield, 94.13% purity) was obtained as a white solid and comfirmed by LCMS (EW33512-2-P1A, Rt=1.544 min), and HPLC (EW33515-2-P1B, Rt=13.396 min, purity: 94.13%).

Purification Conditions:

| Separation condition | |
| --- | --- |
| Dissolution condition | Dissolve in 50% TFA - $H_2O$ |
| Instrument | Gilson GX-281 |
| Mobile Phase | A: $H_2O$ (0.075% TFA in $H_2O$) |
|  | B: $CH_3CN$ |
| Gradient | 38-68%-50 min. Retention time: 50 min |
| Column | luna, C18, 10 um, 100 A |
| Flow Rate | 20 mL/Min |
| Wavelength | 214/254 nm |
| Oven Tem. | 30° C. |

General Procedure for Preparation of Compound 2: (266: SEQ ID NO. 5)

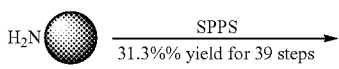

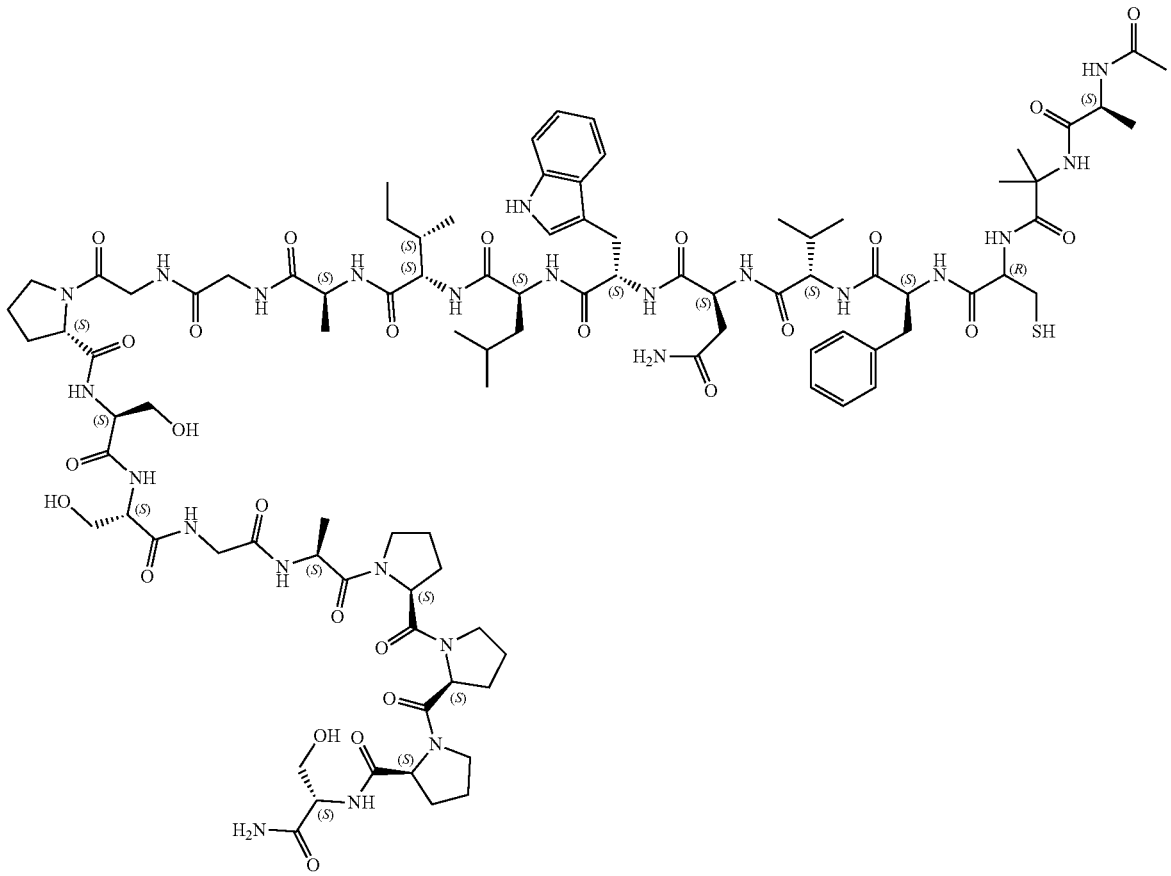

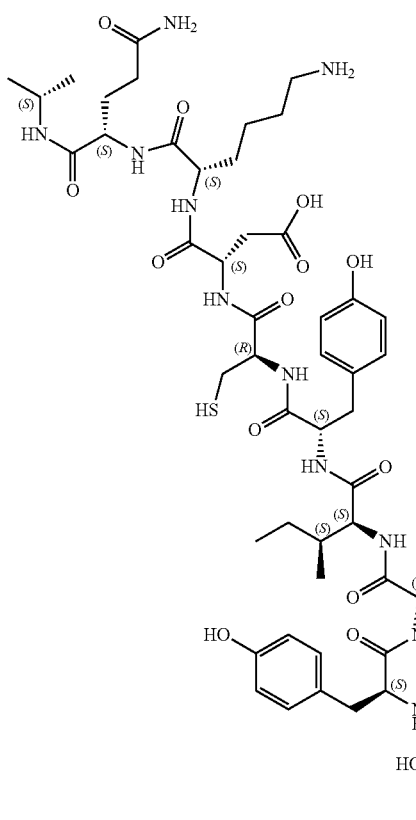
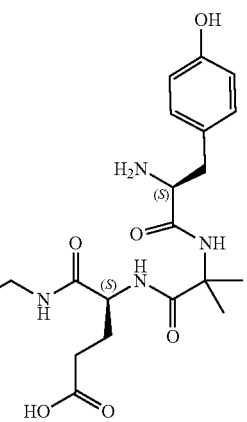

Peptide Synthesis:
The peptide was synthesized using standard Fmoc chemistry.
1) Resin preparation: To the 9H-fluoren-9-ylmethyl N-[(2,4-dimethoxyphenyl)-[4-[2-oxo-2-[[phenyl(p-tolyl)methyl]amino]ethoxy]phenyl]methyl]carbamate (5.00 mmol, 1.00 eq) (Sub: 0.28 mmol/g) in DMF (300 mL) was agitated with N₂ for 2 hrs at 20° C. Then the mixture was filtered to get the resin.
2) Deprotection: 20% piperidine in DMF (300 mL) was added and agitated the resin with N₂ for another 30 mins. The resin was washed with DMF (300 mL*5) and filtered to get the resin.
3) Coupling: A solution of Fmoc-Ser(tBu)-OH (15.0 mmol, 5.75 g, 3.00 eq), DIEA (30.0 mmol, 5.20 mL, 6.00 eq) in DMF (100 mL), then HBTU (5.41 g, 14.2 mmol, 2.85 eq) was added to the resin and agitated with N₂ for 20 mins at 20° C. The resin was then washed with DMF (450 mL*5).
4) Repeat above step 2 to 3 for the coupling of following amino acids: (2~34).

Note:

| # | Materials | Coupling reagents |
|---|---|---|
| 2 | Fmoc-Pro-OH (3.00 eq) | HBTU (2.85 eq) and DIEA (6.00 eq) |
| 3 | Fmoc-Pro-OH (3.00 eq) | HBTU (2.85 eq) and DIEA (6.00 eq) |
| 4 | Fmoc-Pro-OH (3.00 eq) | HBTU (2.85 eq) and DIEA (6.00 eq) |
| 5 | Fmoc-Ala-OH (3.00 eq) | HBTU (2.85 eq) and DIEA (6.00 eq) |
| 6 | Fmoc-Gly-OH (3.00 eq) | HBTU (2.85 eq) and DIEA (6.00 eq) |
| 7 | Fmoc-Ser(tBu)-OH (3.00 eq) | HBTU (2.85 eq) and DIEA (6.00 eq) |
| 8 | Fmoc-Ser(tBu)-OH (3.00 eq) | HBTU (2.85 eq) and DIEA (6.00 eq) |
| 9 | Fmoc-Pro-OH (3.00 eq) | HBTU (2.85 eq) and DIEA (6.00 eq) |
| 10 | Fmoc-Gly-OH (3.00 eq) | HBTU (2.85 eq) and DIEA (6.00 eq) |
| 11 | Fmoc-Gly-OH (3.00 eq) | HBTU (2.85 eq) and DIEA (6.00 eq) |
| 12 | Fmoc-Ala-OH (3.00 eq) | HBTU (2.85 eq) and DIEA (6.00 eq) |
| 13 | Fmoc-Ile-OH (3.00 eq) | HBTU (2.85 eq) and DIEA (6.00 eq) |
| 14 | Fmoc-Leu-OH (3.00 eq) | HBTU (2.85 eq) and DIEA (6.00 eq) |
| 15 | Fmoc-Trp(Boc)-OH (3.00 eq) | HBTU (2.85 eq) and DIEA (6.00 eq) |
| 16 | Fmoc-Asn(Trt)-OH (3.00 eq) | HBTU (2.85 eq) and DIEA (6.00 eq) |
| 17 | Fmoc-Val-OH (3.00 eq) | HBTU (2.85 eq) and DIEA (6.00 eq) |
| 18 | Fmoc-Phe-OH (3.00 eq) | HBTU (2.85 eq) and DIEA (6.00 eq) |
| 19 | Fmoc-Cys(Trt)-OH (3.00 eq) | HBTU (2.85 eq) and DIEA (6.00 eq) |
| 20 | Fmoc-Aib-OH (3.00 eq) | HBTU (2.85 eq) and DIEA (6.00 eq) |
| 21 | Fmoc-Ala-OH (3.00 eq) | HBTU (2.85 eq) and DIEA (6.00 eq) |

-continued

| # | Materials | Coupling reagents |
|---|---|---|
| 22 | Fmoc-Ala-OH (3.00 eq) | HBTU (2.85 eq) and DIEA (6.00 eq) |
| 23 | Fmoc-Gln(Trt)-OH (3.00 eq) | HBTU (2.85 eq) and DIEA (6.00 eq) |
| 24 | Fmoc-Lys(Boc)-OH (3.00 eq) | HBTU (2.85 eq) and DIEA (6.00 eq) |
| 25 | Fmoc-Asp(OtBu)-OH (3.00 eq) | HATU (2.85 eq) and DIEA (6.00 eq) |
| 26 | Fmoc-Cys(Trt)-OH (3.00 eq) | HATU (2.85 eq) and DIEA (6.00 eq) |
| 27 | Fmoc-Tyr(tBu)-OH (3.00 eq) | HATU (2.85 eq) and DIEA (6.00 eq) |
| 28 | Fmoc-Ile-OH (3.00 eq) | HATU (2.85 eq) and DIEA (6.00 eq) |
| 29 | Fmoc-Ser(tBu)-OH (3.00 eq) | HATU (2.85 eq) and DIEA (6.00 eq) |
| 30 | Fmoc-Tyr(tBu)-OH (3.00 eq) | HATU (2.85 eq) and DIEA (6.00 eq) |
| 31 | Fmoc-Asp(OtBu)-OH (3.00 eq) | HATU (2.85 eq) and DIEA (6.00 eq) |
| 32 | Fmoc-Ser(tBu)-OH (3.00 eq) | HATU (2.85 eq) and DIEA (6.00 eq) |
| 33 | Fmoc-Thr(tBu)-OH (3.00 eq) | HATU (2.85 eq) and DIEA (6.00 eq) |
| 34 | Fmoc-Phe-OH (3.00 eq) | HATU (2.85 eq) and DIEA (6.00 eq) |
| 35 | Fmoc-Thr(tBu)-OH (3.00 eq) | HATU (2.85 eq) and DIEA (6.00 eq) |
| 36 | Fmoc-Gly-OH (3.00 eq) | HATU (2.85 eq) and DIEA (6.00 eq) |
| 37 | Fmoc-Glu(OtBu)-OH (3.00 eq) | HATU (2.85 eq) and DIEA (6.00 eq) |
| 38 | Fmoc-Aib-OH (3.00 eq) | HATU (2.85 eq) and DIEA (6.00 eq) |
| 39 | Boc-Tyr(tBu)-OH (3.00 eq) | HATU (2.85 eq) and DIEA (6.00 eq) |

Note:
20% piperidine in DMF was used for Fmoc deprotection for 15 mins. The coupling reaction was monitored by ninhydrin test, and the resin was washed with DMF for 5 times.

Peptide Cleavage and Purification:

1) After coupling, the resin was washed with DMF (200 mL) for 5 times. After last step, the resin was washed with MeOH (200 mL) for 3 times and dried under vacuum. Then the peptide resin (45.6 g) was treated with the cleavage cocktail (460 mL, 92.5% TFA/2.5% TIS/2.5% Mpr/2.5% $H_2O$) for 2.5 hours. The mixture was filtered to remove the cleavage cocktail. The peptide is precipitated with cold isopropyl ether, filtered and concentrated under reduced pressure to give a residue. LCMS (EW33512-1-P1A1, Rt=1.539 min).

2) The residue was purified by prep-HPLC (A: 0.075% TFA in $H_2$, B: ACN) to give the Compound 2 (7.70 g, 1.57 mmol, 31.33% yield, 85.12% purity, TFA) was obtained as a white solid and comfirmed by LCMS (EW33512-1-P1A, Rt=1.515 min) and HPLC (EW33515-1-P1B, Rt=12.103 min).

Purification Conditions:

| | Separation condition |
|---|---|
| Dissolution condition | Dissolve in 20% ACN - $H_2O$ |
| Instrument | Gilson GX-281 |
| Mobile Phase | A: $H_2O$ (0.075% TFA in $H_2O$) |
| | B: $CH_3CN$ |
| Gradient | 20-50%-60 min. Retention time: 45 min |
| Column | Gemini, 5 um, c18, 110 A + luna, c18, 10 um, 100 A |
| Flow Rate | 100 mL/Min |
| Wavelength | 214/254 nm |
| Oven Tem. | 30° C. |

General Procedure for Preparation of mCMZ370(C(14-21)-L5A(S))

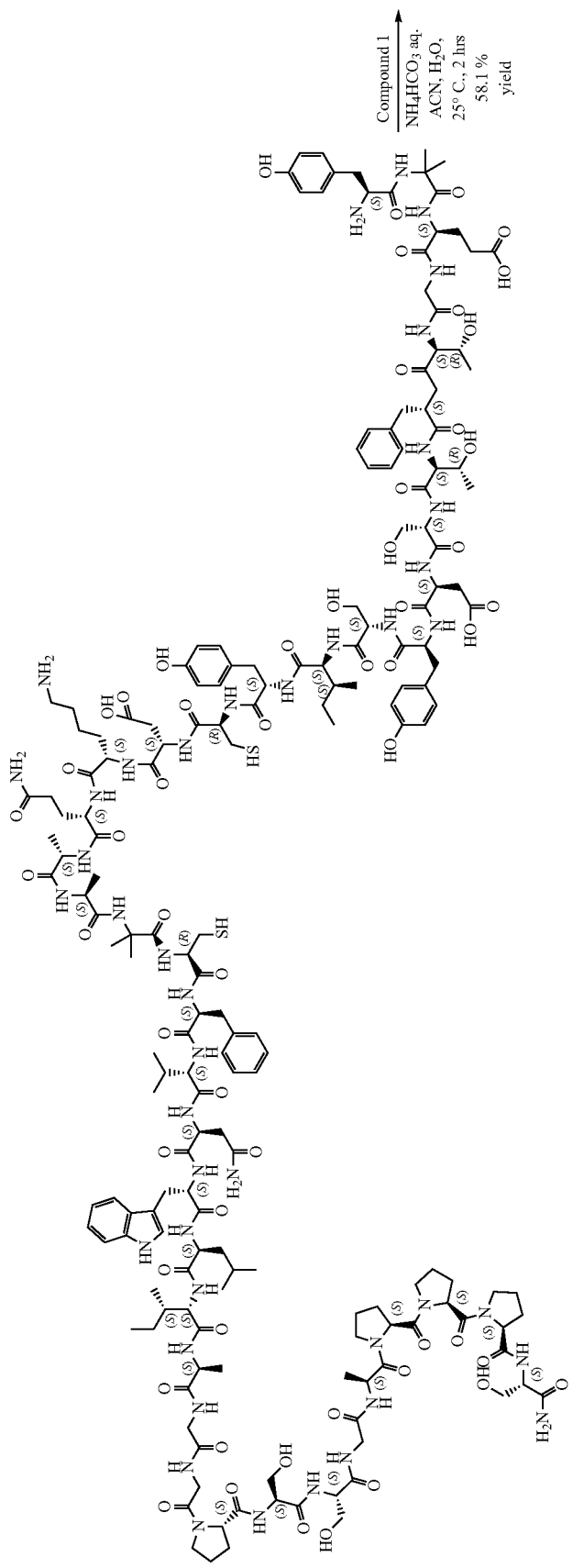

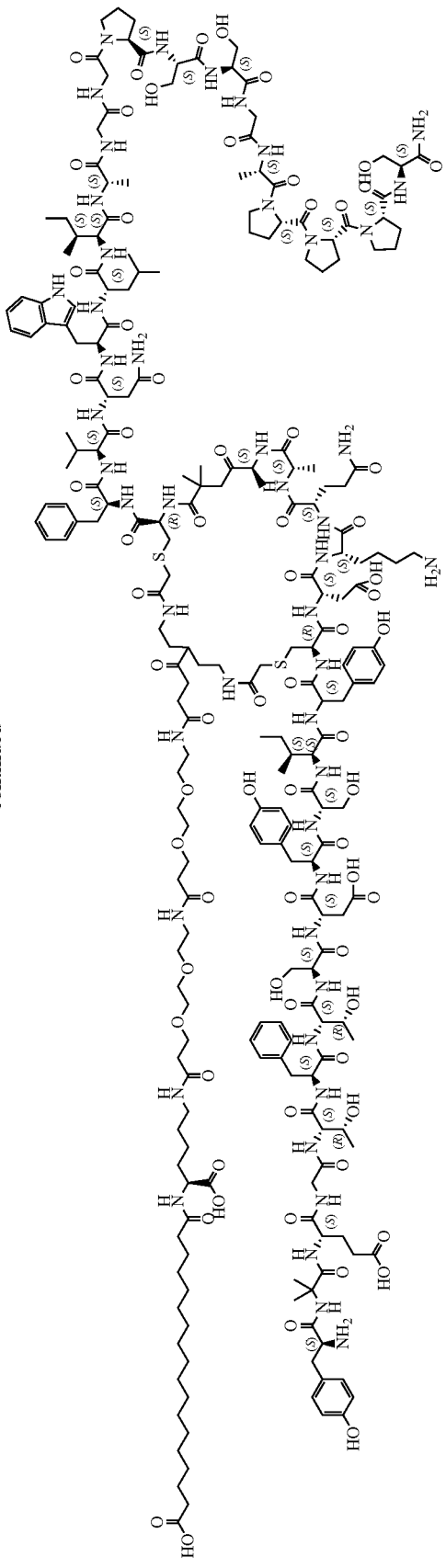

To a mixture of compound 2 (2.80 g, 570.44 umol, 85.12 purity, 1.20 eq, TFA) in MeCN (200 mL) and H$_2$O (300 mL) was added NH$_4$HCO$_3$ (1 M, 475.37 uL, 1.00 eq) until the pH=8~9, then was added drop-wise Compound 1 (600 mg, 475.37 umol, 94.13% purity, 1.00 eq) in MeCN (60.0 mL) and H$_2$O (90.0 mL). The mixture was stirred at 25° C. for 2 hrs. LCMS (EW33512-3-P1A1, product: Rt=1.652 mi) showed Reactant 1 was consumed completely and one main peak with desired m/z was detected. The reaction mixture was adjust pH=5-6 with 1 M HCl aq., then was lyophilized. The residue was purified by prep-HPLC (TFA condition: A: 0.075% TFA in H$_2$O, B: ACN), a) then was second purified by prep-HPLC (HOAc condition: A: 0.5% HOAc in H$_2$O, B: ACN) to give the mCMZ370(C(14-21)-L5A(S)) (1.45 g, 276.45 umol, 58.15% yield, 96.85% purity, HAC) was obtained as a white solid and confirmed by LCMS (EW33512-3-P1A, product: Rt=1.661 min) & HPLC (EW33512-3-P1B, product: Rt=13.316 min, purity: 96.85%).

Purification Conditions:

| Separation condition | |
|---|---|
| Dissolution condition | Dissolve in 30% ACN - H$_2$O |
| Instrument | Gilson GX-281 |
| Mobile Phase | A: H$_2$O (0.075% TFA in H$_2$O) |
| | B: CH$_3$CN |
| Gradient | 24-54%-60 min. Retention time: 30 min |
| Column | luna, C8, 10 um, 100 A |
| Flow Rate | 100 ml/Min |
| Wavelength | 214/254 nm |
| Oven Tem. | 30° C. |
| Second separation condition | |
| Dissolution condition | Dissolve in 20% ACN - 50% TFA in H$_2$O |
| Instrument | Gilson GX-281 |
| Mobile Phase | A: H$_2$O (0.5% HAC in H$_2$O) |
| | B: CH$_3$CN |
| Gradient | CH$_3$COONH$_4$ (0.2 mol/L in H$_2$O) for 25 min. |
| | 0.5% CH$_3$COOH in H$_2$O for 10 min. |
| | 32-62% ACN in 0-30 min Retention time: 59 min |
| Column | Gemini, 5 um, C18, 110 A + luna, C18, 10 um, 100 A |
| Flow Rate | 20 mL/Min |
| Wavelength | 214/254 nm |
| Oven Tem. | 30° C. |

General Procedure for Preparation of Compound 3: (268: SEQ ID NO. 6)

Peptide Synthesis:

Compound 1 was synthesized according to the above protocol.

The peptide was synthesized using standard Fmoc chemistry.

5) Resin preparation: To the 9H-fluoren-9-ylmethyl N-[(2,4-dimethoxyphenyl)-[4-[2-oxo-2-[[phenyl(p-tolyl)methyl]amino]ethoxy]phenyl]methyl]carbamate (5.00 mmol, 1.00 eq) (Sub: 0.28 mmol/g) in DMF (300 mL) was agitated with N$_2$ for 2 hrs at 20° C. Then the mixture was filtered to get the resin.

6) Deprotection: 20% piperidine in DMF (300 mL) was added and agitated the resin with N$_2$ for another 30 mins. The resin was washed with DMF (300 mL*5) and filtered to get the resin.

7) Coupling: A solution of Fmoc-Ser(tBu)-OH (15.0 mmol, 5.75 g, 3.00 eq), DIEA (30.0 mmol, 5.20 mL, 6.00 eq) in DMF (100 mL), then HBTU (5.41 g, 14.2 mmol, 2.85 eq) was added to the resin and agitated with N$_2$ for 20 mins at 20° C. The resin was then washed with DMF (450 mL*5).

8) Repeat above step 2 to 3 for the coupling of following amino acids: (2-34).

9) Note:

| # | Materials | Coupling reagents |
|---|---|---|
| 2 | Fmoc-Pro-OH (3.00 eq) | HBTU (2.85 eq) and DIEA (6.00 eq) |
| 3 | Fmoc-Pro-OH (3.00 eq) | HBTU (2.85 eq) and DIEA (6.00 eq) |
| 4 | Fmoc-Pro-OH (3.00 eq) | HBTU (2.85 eq) and DIEA (6.00 eq) |
| 5 | Fmoc-Ala-OH (3.00 eq) | HBTU (2.85 eq) and DIEA (6.00 eq) |
| 6 | Fmoc-Gly-OH (3.00 eq) | HBTU (2.85 eq) and DIEA (6.00 eq) |
| 7 | Fmoc-Ser(tBu)-OH (3.00 eq) | HBTU (2.85 eq) and DIEA (6.00 eq) |
| 8 | Fmoc-Ser(tBu)-OH (3.00 eq) | HBTU (2.85 eq) and DIEA (6.00 eq) |
| 9 | Fmoc-Pro-OH (3.00 eq) | HBTU (2.85 eq) and DIEA (6.00 eq) |
| 10 | Fmoc-Gly-OH (3.00 eq) | HBTU (2.85 eq) and DIEA (6.00 eq) |
| 11 | Fmoc-Gly-OH (3.00 eq) | HBTU (2.85 eq) and DIEA (6.00 eq) |
| 12 | Fmoc-Ala-OH (3.00 eq) | HBTU (2.85 eq) and DIEA (6.00 eq) |
| 13 | Fmoc-Ile-OH (3.00 eq) | HBTU (2.85 eq) and DIEA (6.00 eq) |
| 14 | Fmoc-Leu-OH (3.00 eq) | HBTU (2.85 eq) and DIEA (6.00 eq) |
| 15 | Fmoc-Trp(Boc)-OH (3.00 eq) | HBTU (2.85 eq) and DIEA (6.00 eq) |
| 16 | Fmoc-Cys(Trt)-OH (3.00 eq) | HBTU (2.85 eq) and DIEA (6.00 eq) |
| 17 | Fmoc-Val-OH (3.00 eq) | HBTU (2.85 eq) and DIEA (6.00 eq) |
| 18 | Fmoc-Phe-OH (3.00 eq) | HBTU (2.85 eq) and DIEA (6.00 eq) |
| 19 | Fmoc-Glu-OH (3.00 eq) | HBTU (2.85 eq) and DIEA (6.00 eq) |
| 20 | Fmoc-Aib-OH (3.00 eq) | HBTU (2.85 eq) and DIEA (6.00 eq) |
| 21 | Fmoc-Ala-OH (3.00 eq) | HBTU (2.85 eq) and DIEA (6.00 eq) |
| 22 | Fmoc-Ala-OH (3.00 eq) | HBTU (2.85 eq) and DIEA (6.00 eq) |
| 23 | Fmoc-Cys(Trt)-OH (3.00 eq) | HBTU (2.85 eq) and DIEA (6.00 eq) |
| 24 | Fmoc-Lys(Boc)-OH (3.00 eq) | HBTU (2.85 eq) and DIEA (6.00 eq) |
| 25 | Fmoc-Asp(OtBu)-OH (3.00 eq) | HATU (2.85 eq) and DIEA (6.00 eq) |
| 26 | Fmoc-Leu-OH (3.00 eq) | HATU (2.85 eq) and DIEA (6.00 eq) |
| 27 | Fmoc-Tyr(tBu)-OH (3.00 eq) | HATU (2.85 eq) and DIEA (6.00 eq) |
| 28 | Fmoc-Ile-OH (3.00 eq) | HATU (2.85 eq) and DIEA (6.00 eq) |
| 29 | Fmoc-Ser(tBu)-OH (3.00 eq) | HATU (2.85 eq) and DIEA (6.00 eq) |
| 30 | Fmoc-Tyr(tBu)-OH (3.00 eq) | HATU (2.85 eq) and DIEA (6.00 eq) |
| 31 | Fmoc-Asp(OtBu)-OH (3.00 eq) | HATU (2.85 eq) and DIEA (6.00 eq) |
| 32 | Fmoc-Ser(tBu)-OH (3.00 eq) | HATU (2.85 eq) and DIEA (6.00 eq) |
| 33 | Fmoc-Thr(tBu)-OH (3.00 eq) | HATU (2.85 eq) and DIEA (6.00 eq) |
| 34 | Fmoc-Phe-OH (3.00 eq) | HATU (2.85 eq) and DIEA (6.00 eq) |
| 35 | Fmoc-Thr(tBu)-OH (3.00 eq) | HATU (2.85 eq) and DIEA (6.00 eq) |
| 36 | Fmoc-Gly-OH (3.00 eq) | HATU (2.85 eq) and DIEA (6.00 eq) |
| 37 | Fmoc-Glu(OtBu)-OH (3.00 eq) | HATU (2.85 eq) and DIEA (6.00 eq) |

-continued

| # | Materials | Coupling reagents |
|---|---|---|
| 38 | Fmoc-Aib-OH (3.00 eq) | HATU (2.85 eq) and DIEA (6.00 eq) |
| 39 | Boc-Tyr(tBu)-OH (3.00 eq) | HATU (2.85 eq) and DIEA (6.00 eq) |

Note:
20% piperidine in DMF was used for Fmoc deprotection for 15 mins. The coupling reaction was monitored by ninhydrin test, and the resin was washed with DMF for 5 times.

Peptide Cleavage and Purification:
3) After coupling, the resin was washed with DMF (200 mL) for 5 times. After last step, the resin was washed with MeOH (200 mL) for 3 times and dried under vacuum. Then the peptide resin (45.6 g) was treated with the cleavage cocktail (460 mL, 92.5% TFA/2.5%/TIS/2.5% Mpr/2.5% H₂O) for 2.5 hours. The mixture was filtered to remove the cleavage cocktail. The peptide is precipitated with cold isopropyl ether, filtered and concentrated under reduced pressure to give a residue. LCMS (EW33512-1-P1A1, Rt=1.539 min).
4) The residue was purified by prep-HPLC (A: 0.075% TFA in H₂O, B: ACN) to give the Compound 3 (7.70 g, 1.57 mmol, 31.33% yield, 85.12% purity, TFA) was obtained as a white solid and comfirmed by LCMS (EW33512-1-P1A, Rt=1.515 min) and HPLC (EW33515-1-P1B, Rt=12.103 min).

Purification Conditions:

| Separation condition | |
|---|---|
| Dissolution condition | Dissolve in 20% ACN - H₂O |
| Instrument | Gilson GX-281 |
| Mobile Phase | A: H₂O (0.075% TFA in H₂O) B: CH₃CN |
| Gradient | 20-50%-60 min. Retention time: 45 min |
| Column | Gemini, 5 um, c18, 110 A + luna, c18, 10 um, 100 A |
| Flow Rate | 100 mL/Min |
| Wavelength | 214/254 nm |
| Oven Tem. | 30° C. |

General Procedure for Preparation of mCMZ371(C(17-24)-L5A(S))
To a mixture of compound 3 (2.80 g, 570.44 umol, 85.12% purity, 1.20 eq, TFA) in MeCN (200 mL) and H₂O (300 mL) was added NH₄HCO₃ (1 M, 475.37 uL, 1.00 eq) until the pH=8-9, then was added drop-wise Compound 1 (600 mg, 475.37 umol, 94.13% purity, 1.00 eq) in MeCN (60.0 mL) and H₂O (90.0 mL). The mixture was stirred at 25° C. for 2 hrs. LCMS (EW33512-3-P1A1, product: Rt=1.652 min) showed Reactant 1 was consumed completely and one main peak with desired m/z was detected. The reaction mixture was adjust pH=5-6 with 1 M HCl aq., then was lyophilized. The residue was purified by prep-HPLC (TFA condition: A: 0.075% TFA in H₂O, B: ACN), and then was second purified by prep-HPLC (HOAc condition: A: 0.5% HOAc in H₂O, B: ACN) to give the mCMZ371(C(17-24)-L5A(S)) (1.45 g, 276.45 umol, 58.15% yield, 96.85% purity, HAC) was obtained as a white solid and confirmed by LCMS (EW33512-3-P1A, product: Rt=1.661 min) & HPLC (EW33512-3-P1B, product: Rt=13.316 min, purity: 96.85%).

Purification Conditions:

| Separation condition | |
|---|---|
| Dissolution condition | Dissolve in 30% ACN - H₂O |
| Instrument | Gilson GX-281 |
| Mobile Phase | A: H₂O (0.075% TFA in H₂O) B: CH₃CN |
| Gradient | 24-54%-60 min. Retention time: 30 min |
| Column | luna, C8, 10 um, 100 A |
| Flow Rate | 100 mL/Min |
| Wavelength | 214/254 nm |
| Oven Tem. | 30° C. |
| Second separation condition | |
| Dissolution condition | Dissolve in 20% ACN - 50% TFA in H₂O |
| Instrument | Gilson GX-281 |
| Mobile Phase | A: H₂O (0.5% HAC in H₂O) B: CH₃CN |
| Gradient | CH₃COONH₄ (0.2 mol/L in H₂O) for 25 min. 0.5% CH₃COOH in H₂O for 10 min. 32-62% ACN in 0-30 min Retention time: 59 min |
| Column | Gemini, 5 um, C18, 110 A + luna, C18, 10 um, 100 A |
| Flow Rate | 20 mL/Min |
| Wavelength | 214/254 nm |
| Oven Tem. | 30° C. |

Example A: A Stapled GLP-1R/GIPR Dual Agonist Peptide Exhibit Improved Anorexigenic Properties and Metabolic Parameters Over Commercial GLP-1R Agonists and Preclinical GLP-1R/GCGR Candidates Peptide conjugates were generated as full dual agonists (Table 4) with EC$_{50}$ values of 4-35 pM and 11-40 pM, for the human GIP and GLP-1 receptors respectively. By adjusting the linker, the length of fatty acid chain, functional group at the end of the fatty acid chain and a limited number of amino acid changes in the peptide sequence, it was possible to vary the terminal half-lives of the DI compounds in mice from 2 to 20 hours.

TABLE 4

Peptide Sequences

| SEQ ID | Label | Peptide sequence | Peptide Name | |
|---|---|---|---|---|
| 31 | SEQ-1 | H₂N-Y(Aib)EGT-FTSDY-SIYLD-KQAA(Aib)-EFVNW-LLAGG-PSSGA-PPPS-CONH₂ | | SEQ ID NO: 28 |
| 32 | SEQ-2 | H₂N-Y(Aib)EGT-FTSDY-SIYLD-KKAA(Aib)-EFVKW-LLAGG-PSSGA-PPPS-CONH₂ | ZA-40 | SEQ ID NO: 18, where each X is K |

TABLE 4-continued

Peptide Sequences

| SEQ ID | Label | Peptide sequence | Peptide Name | |
|---|---|---|---|---|
| 33 | SEQ-3 | H$_2$N-Y(Aib)EGT-FTSDY-SIYKD-KQAA(Aib)-KFVNW-LLAGG-PSSGA-PPPS-CONH$_2$ | ZA-39 | SEQ ID NO: 1, where each X is K |
| 34 | SEQ-4 | H$_2$N-Y(Aib)EGT-FTSDY-SIYKD-KQAA(Aib)-KFKNW-LKAGG-PSSGA-PPPS-CONH$_2$ | 14k, 21k, staple K23-27 | SEQ ID NO: 29, where each X is K |
| 35 | SEQ-5 | H$_2$N-Y(Aib)EGT-FTSDY-SIYLD-KKAQ(Aib)-AFVKW-LIAQG-PSSGA-PPPS-CONH$_2$ | 19Q-21A, 27I, 29Q, K17-24 staple | SEQ ID NO: 19, where each X is K |
| 36 | SEQ-6 | H$_2$N-Y(Aib)EGT-FHSDY-DIYKD-KQAA(Aib)-KFVQW-LLAGG-PSSGA-PPPS-CONH$_2$ | ZA-41 | SEQ ID NO: 2, where each X is K |
| 37 | SEQ-7 | H$_2$N-Y(Aib)EGT-FHSDY-DIYKD-KQAA(Nle)-KFVAW-LLAGG-PSSGA-PPPS-CONH$_2$ | ZA-42 | SEQ ID NO: 3, where each X is K |
| 38 | SEQ-8 | H$_2$N-Y(Aib)EGT-FTsDY-SIYKD-KQAA(Nle)-KFVAW-LLAGG-PSSGA-PPPS-CONH$_2$ | ZA-43 | SEQ ID NO: 4, where each X is K |

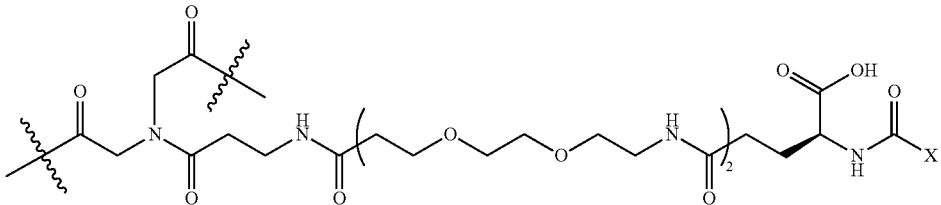

Linker L1

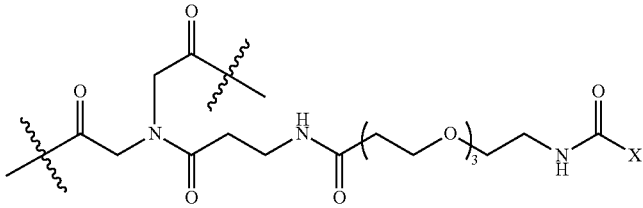

Linker L2

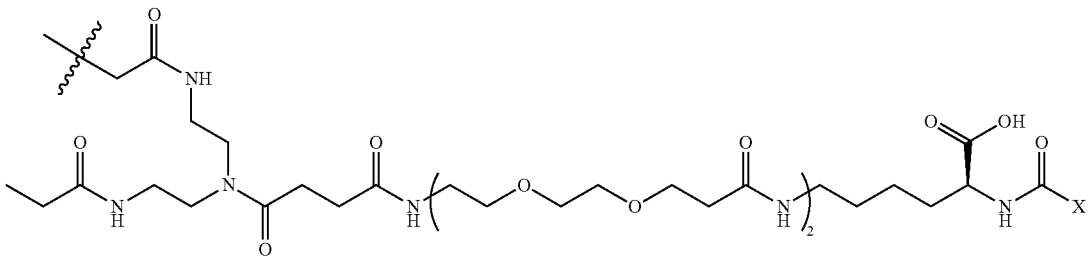

Linker L3 mCMD307 (2050-K4) Decreased Body Weight and Improved Glucose Intolerance and Dyslipidemia and Attenuated Hepatic Steatosis in DIO Mice Encouraged by the preliminary PK and PD results, the efficacy of chronic administration of mCMD307 (2050-K4) was assessed in a high-fat-diet-induced obesity (DIO) mouse model. DIO mice (C$_{57}$BL/6, male, 25-week old) were randomized based on their body weight and then treated for 5 weeks by s.c. dosing of either PBS, mCMD307 (2050-K4) (40 µg/kg), or semaglutide (40 µg/kg; positive control). Wide-type lean mice were used as normal controls.

Figure 5A:
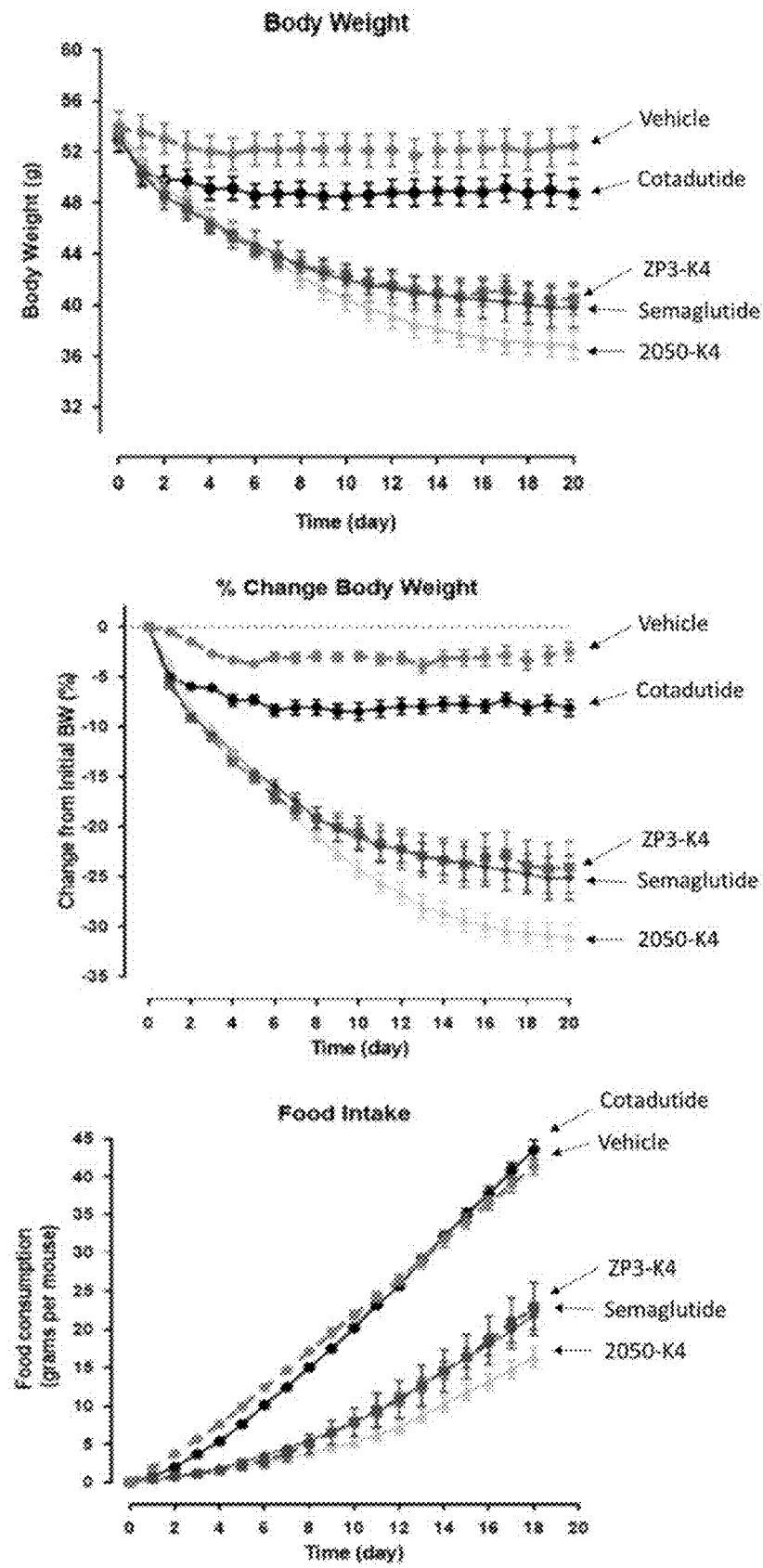
FIGS. 5A-5E show in vivo efficacy of mCMD307 (2050-K4) in high-fat-diet-induced obesity (DIO) mice treated for 24 days. Effects on body weight and food intake change (FIG. 5A), oral glucose tolerance test at day 21, fasted blood glucose prior to the OGTT (day 20) and fed glucose after the OGTT (day 21) (FIG. 5B). Upon termination at day 24, measurement of liver enzyme ALT, AST, ALP levels and plasma cholesterol and triglyceride levels (FIG. 5C) and liver weight, liver triglyceride, liver/body weight ratio and fat weight (FIG. 5D); and steatosis score and liver lipid accumulation measurement by Oil-red staining (FIG. 5E). C57BL/6 mice (male, 37 weeks old) were treated with PBS (s.c., twice daily), mCMD307 (K4) (s.c. once daily; 10 nmol kg-1) or semaglutide (s.c. once daily; 10 nmol kg-1) for 24 days. Data are means±SE, n=6 per group. Statistics: AUC and fasted glucose data were compared by one-way ANOVA followed by Dunnett's multiple comparison tests vs. PBS-treated mice: **$P<0.0001$; *$P<0.001$; **$P<0.01$.
Figure 5B:
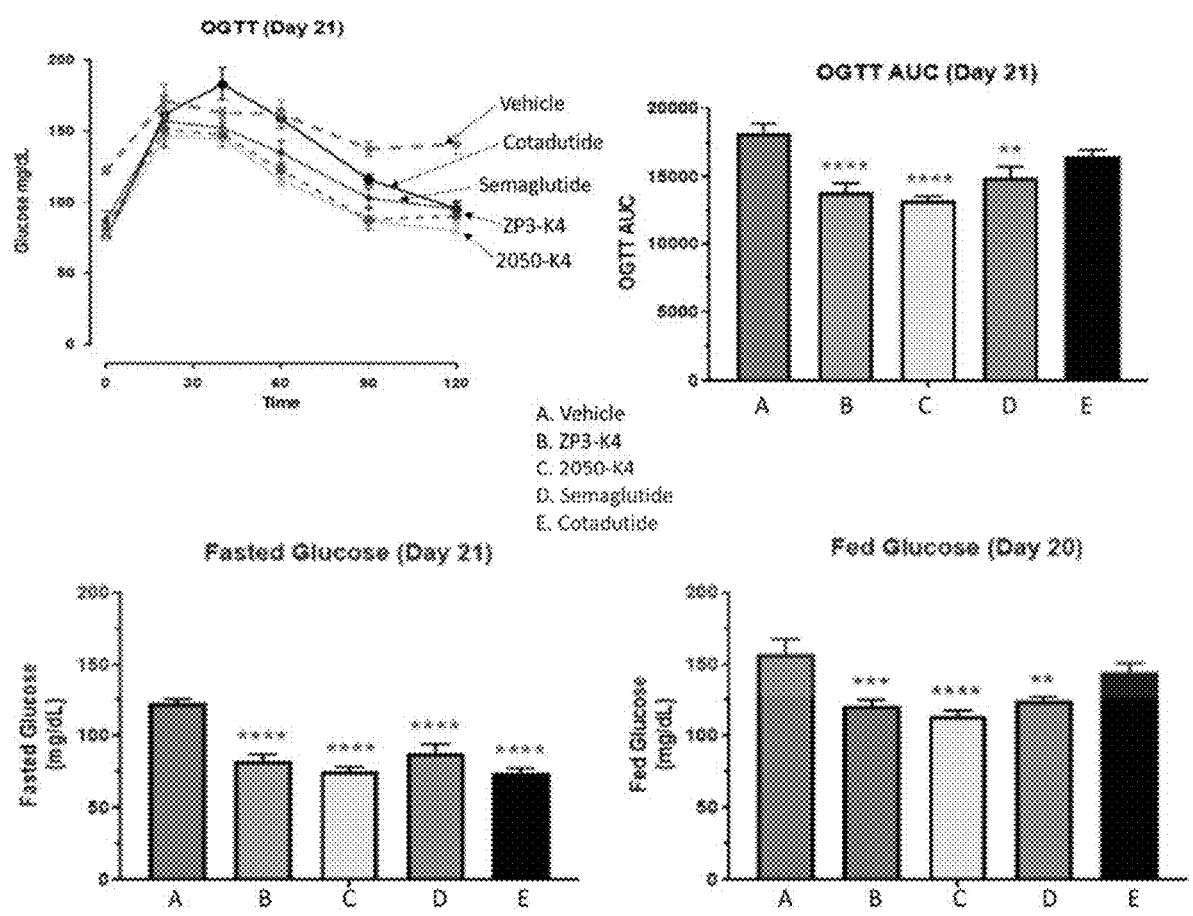
Figure 5C:
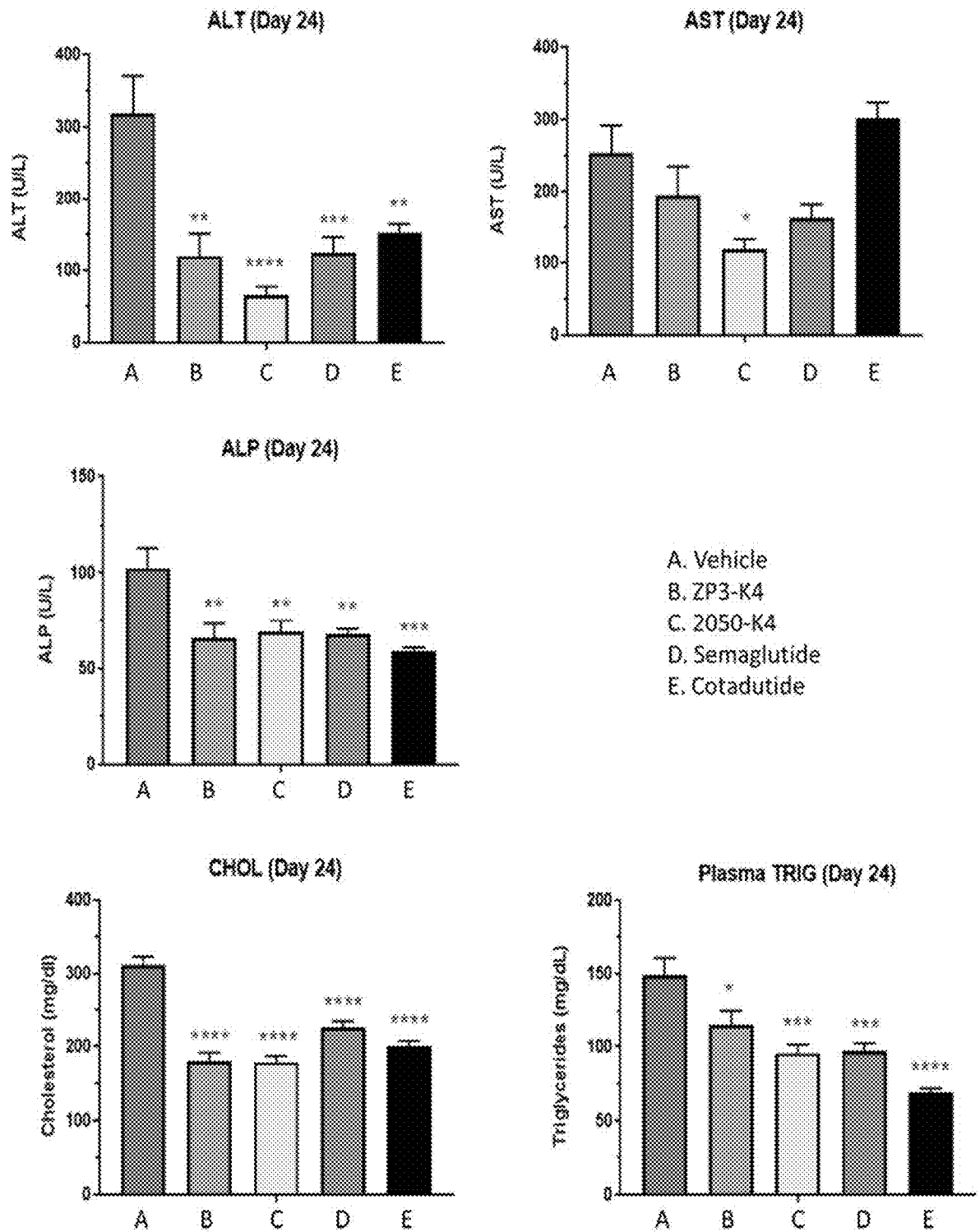
Figure 5D:
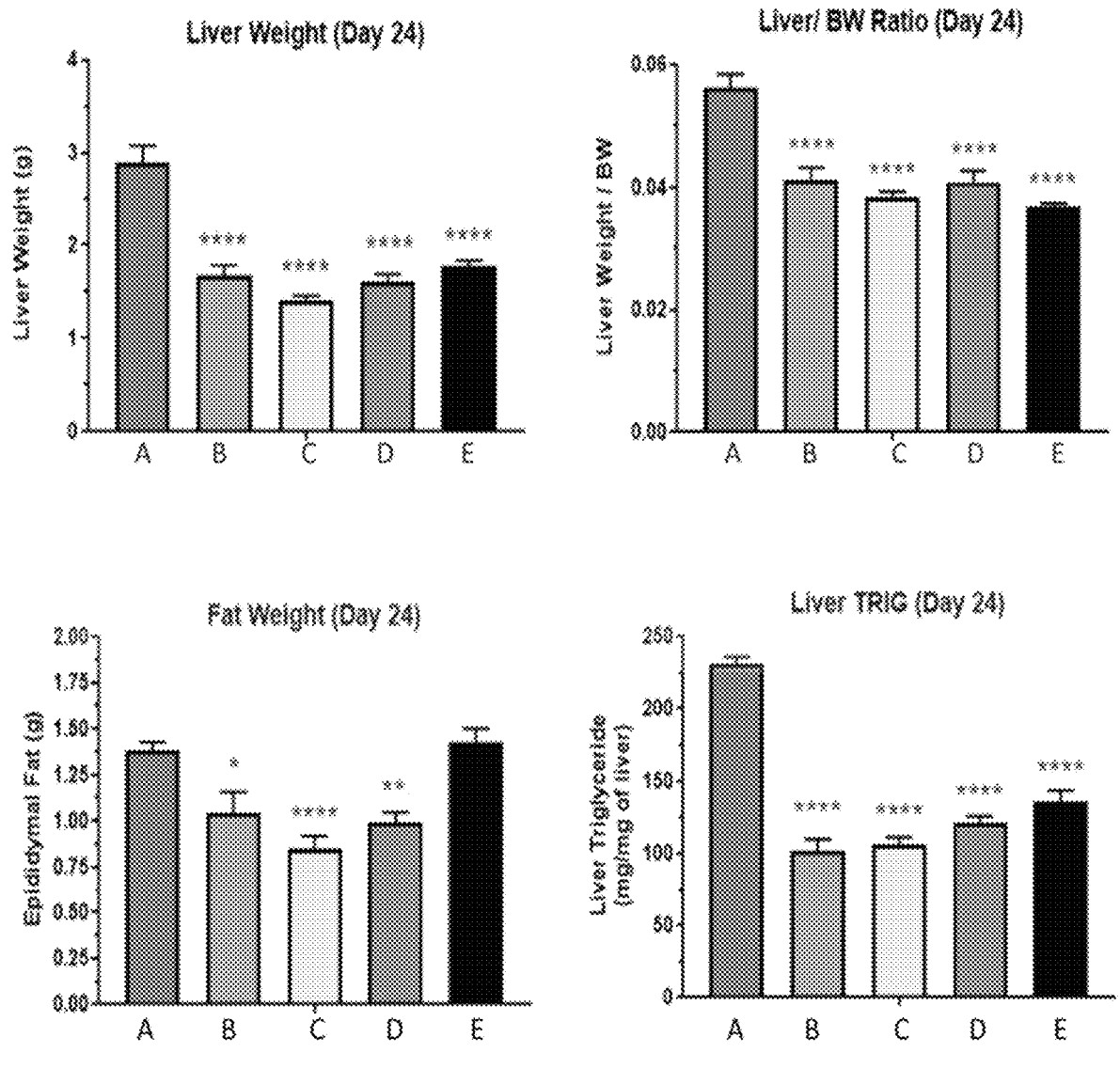
Figure 5E:
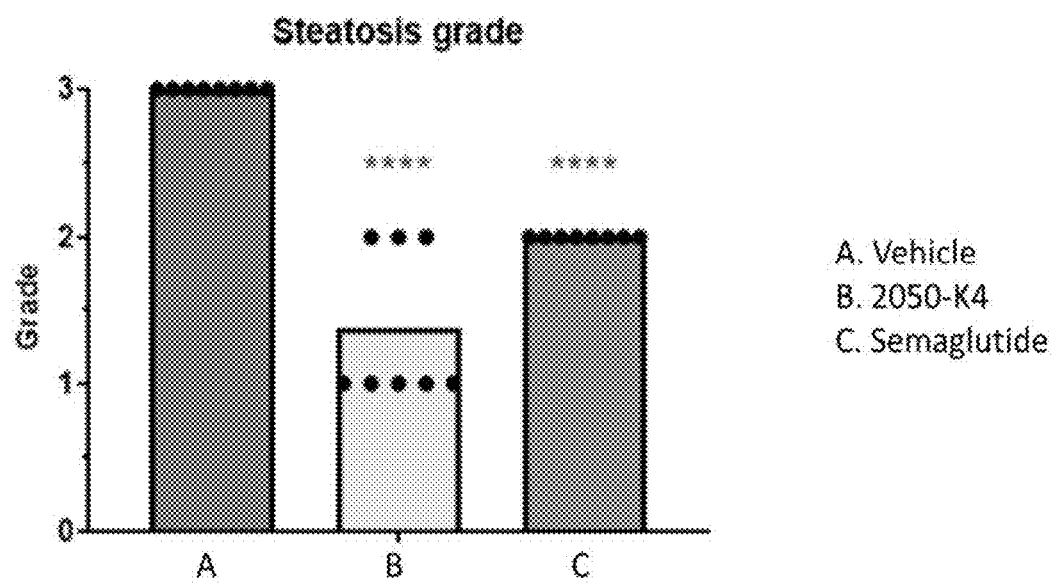
Figure 5E:
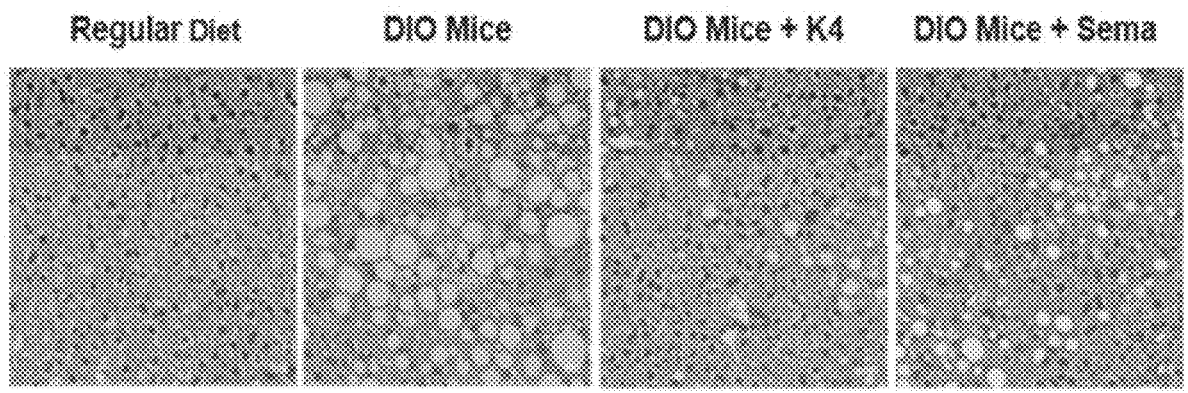
Figure 6A:
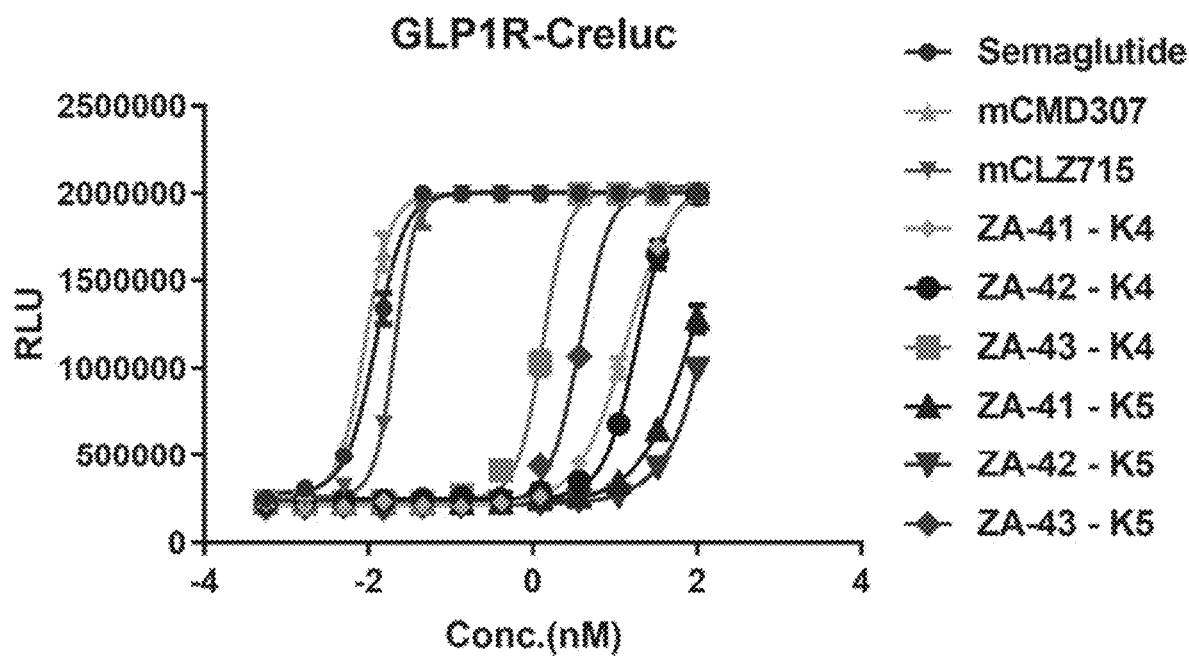
FIG. 6A depicts the results of a GLP1 receptor activation reporter assay comparing the activity of semaglutide with the activities of various peptide conjugates.
Figure 6B:
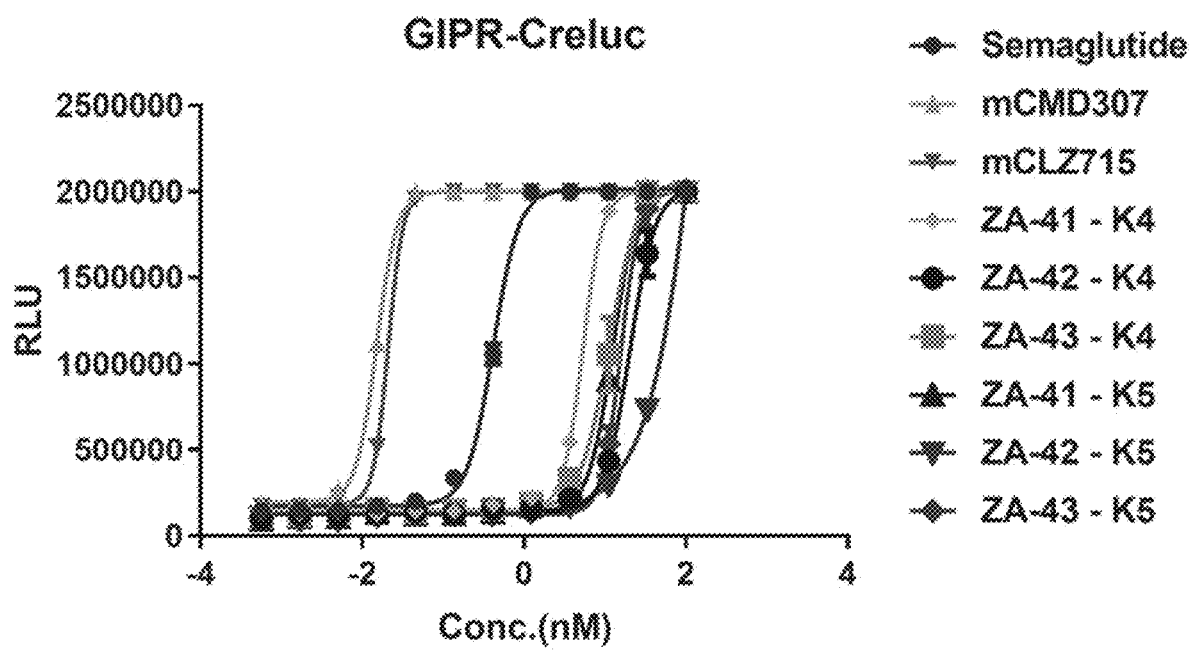
FIG. 6B depicts the results of a GIP receptor activation reporter assay comparing the activity of semaglutide with the activities of various peptide conjugates.
Figure 7A:
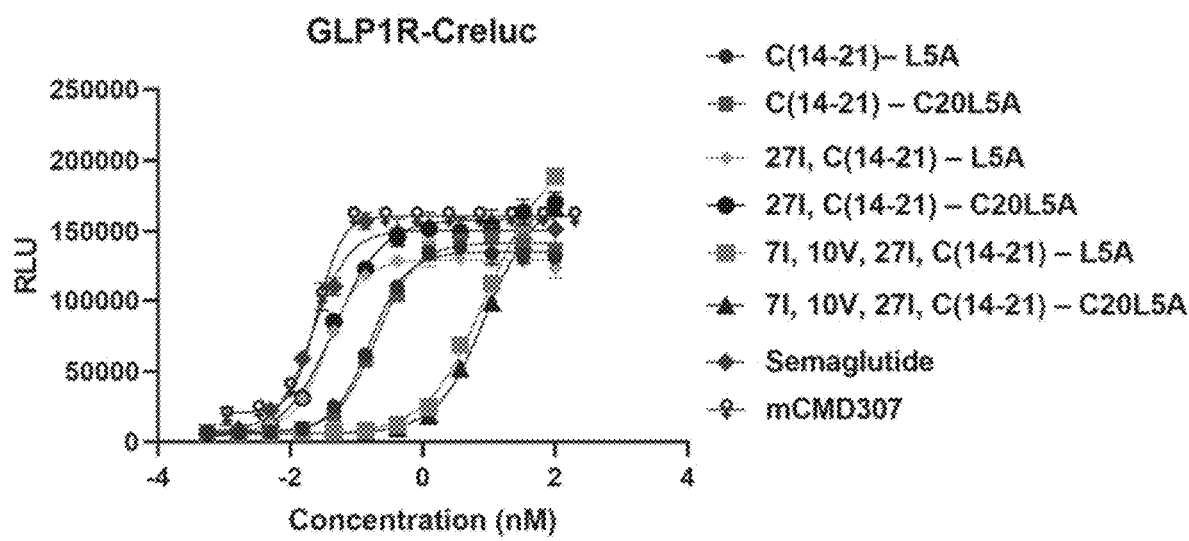
FIG. 7A depicts the results of a GLP1 receptor activation reporter assay comparing the activity of semaglutide with the activities of various peptide conjugates.
Figure 7B:
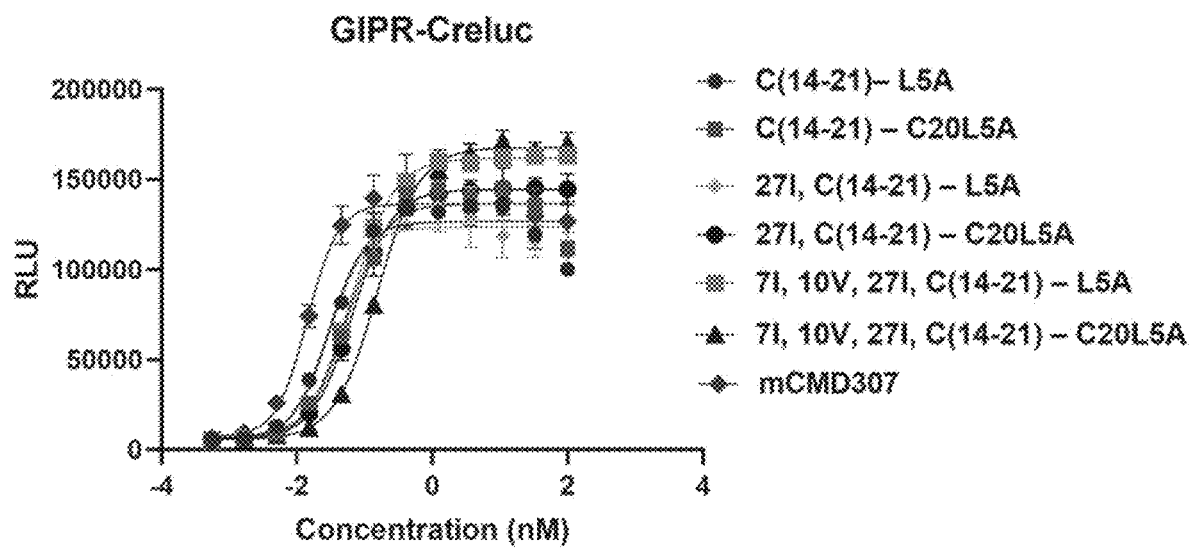
FIG. 7B depicts the results of a GIP receptor activation reporter assay comparing the activity of semaglutide with the activities of various peptide conjugates.
Figure 8A:
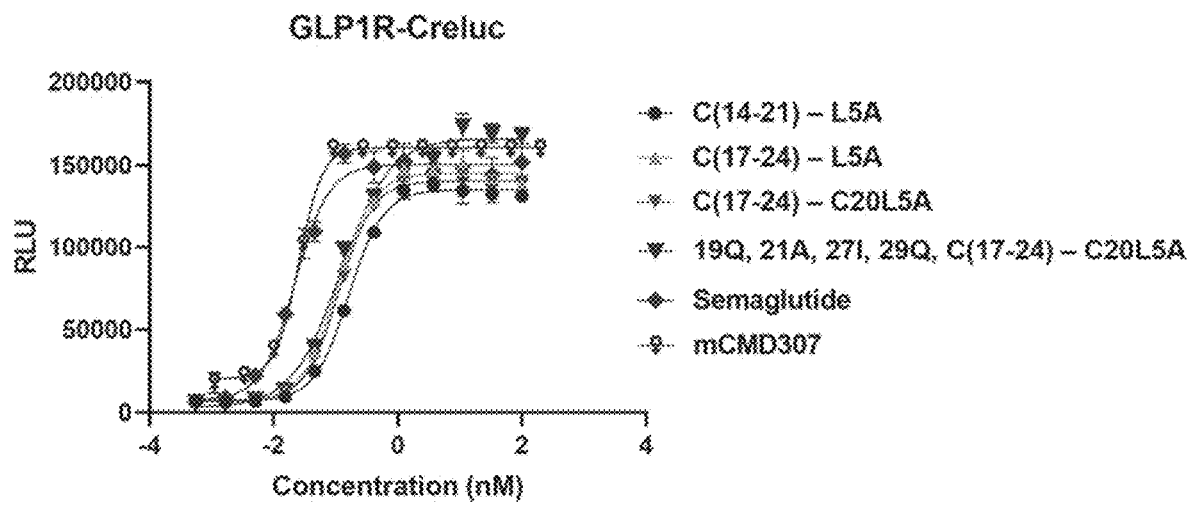
FIG. 8A depicts the results of a GLP1 receptor activation reporter assay comparing the activity of semaglutide with the activities of various peptide conjugates.
Figure 8B:
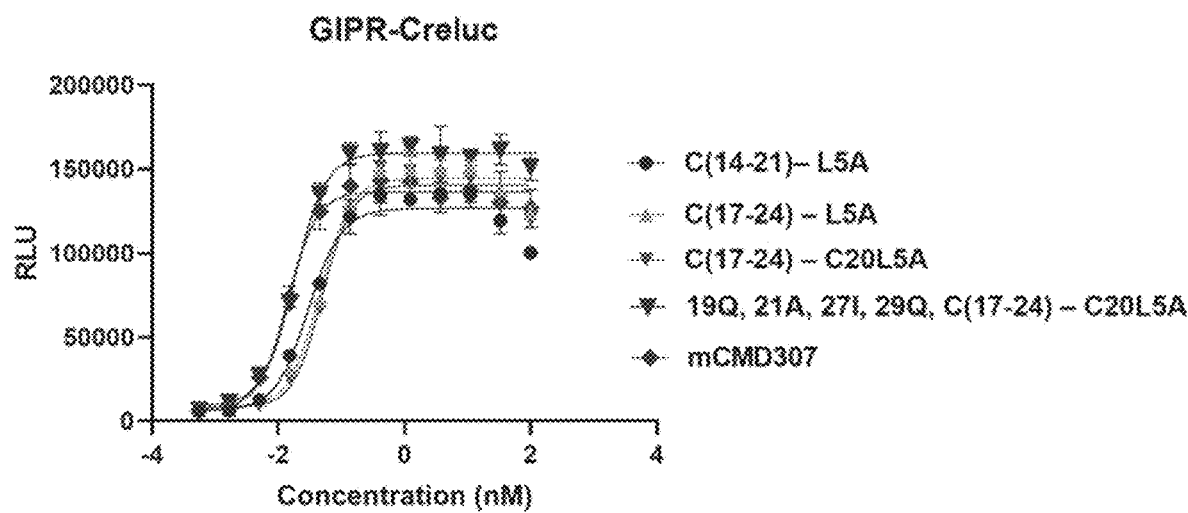
FIG. 8B depicts the results of a GIP receptor activation reporter assay comparing the activity of semaglutide with the activities of various peptide conjugates.
Figure 9A:
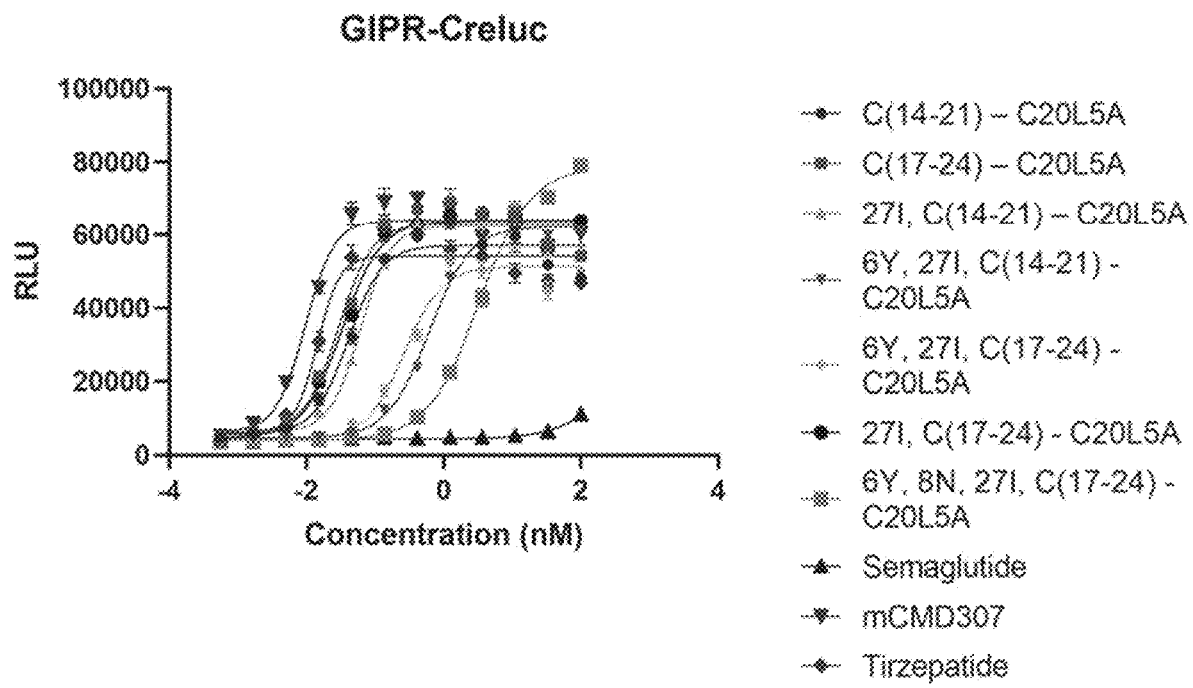
FIG. 9A depicts the results of a GIP1 receptor activation reporter assay comparing the activity of semaglutide with the activities of various peptide conjugates.
Figure 9B:
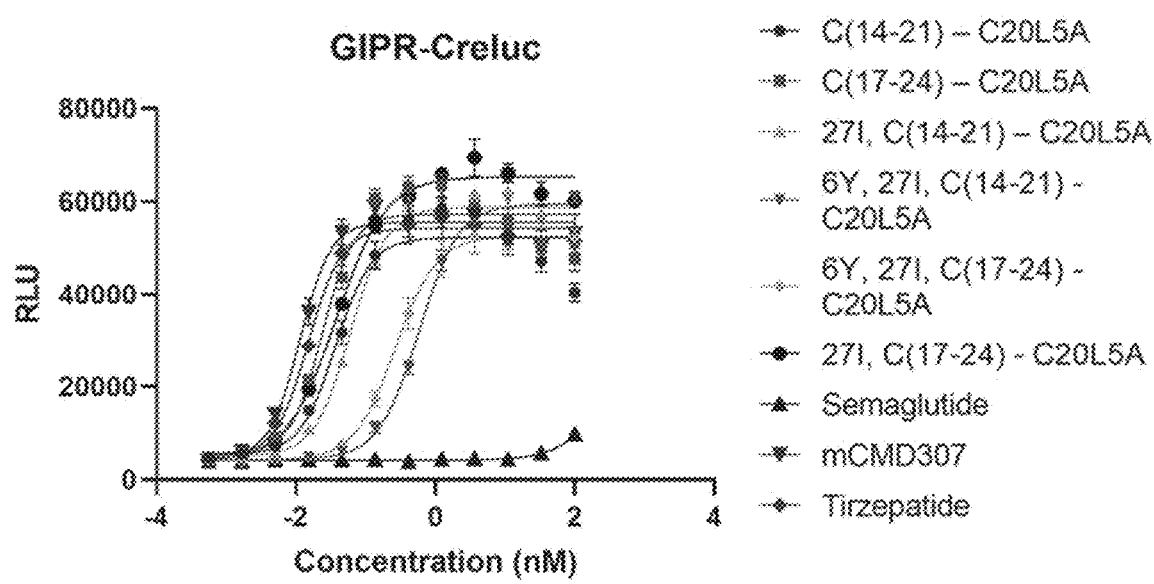
FIG. 9B depicts the results of a GIP receptor activation reporter assay comparing the activity of semaglutide with the activities of various peptide conjugates.
Figure 10:
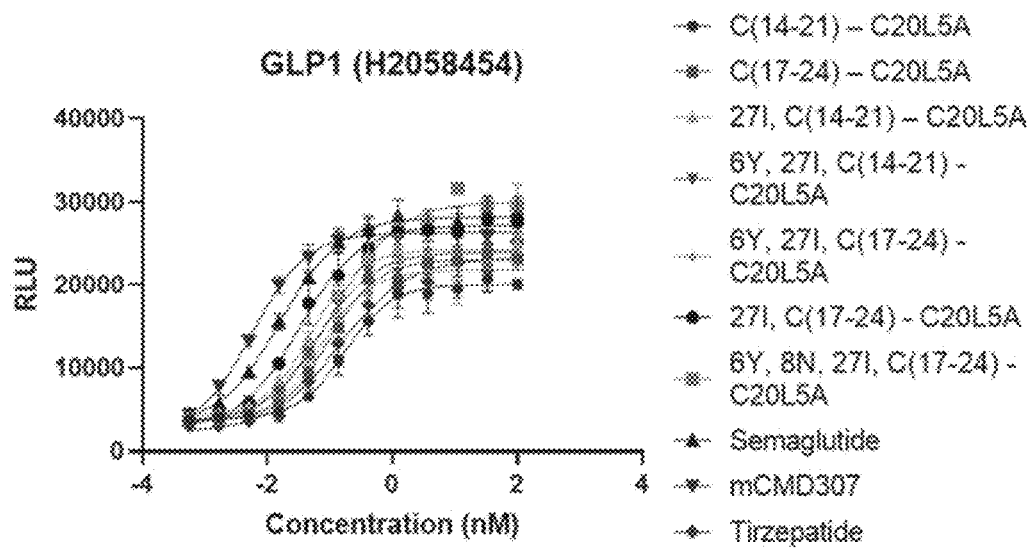
FIG. 10 depicts the results of a GIP1 receptor activation reporter assay comparing the activity of semaglutide with the activities of various peptide conjugates.

Fruitfully, mCMD307 (2050-K4)-treated DIO mice exhibited a steady reduction in body weight and fasting blood glucose levels, with better efficacy than semaglutide-treated group (FIG. 5A). At an efficacious dose of 40 µg/kg, mCMD307 (2050-K4) significantly reduced body weight food intake (FIG. 5A), Apart from a reduction in fasting blood glucose levels, in an OGTT on day 21 and OGTT on day 21, the levels of fed blood glucose in mCMD307 (2050-K4)-treated DIO mice were also significantly lower than compared to PBS-treated DIO mice (FIG. 5B). At the termination of the study at day 24, liver enzyme ALT, AST, ALP levels and plasma cholesterol and triglyceride levels (FIG. 5C) and liver weight, liver triglyceride, liver/body weight ratio and fat weight (FIG. 5D); and steatosis score and liver lipid accumulation measurement by Oil-red staining (FIG. 5E). C57BL/6 mice (male, 37 weeks old) were treated with PBS (s.c., twice daily), mCMD307 (K4) (s.c. once daily; 10 nmol kg-1) or semaglutide (s.c. once daily; 10 nmol kg-1) for 24 days. Data are means±SE, n=6 per group. Accordingly, these results suggest that mCMD307 (2050-K4) could offer potential clinical benefit for the treatment of fatty liver diseases such as non-alcoholic fatty liver disease (NAFLD) and non-alcoholic steatohepatitis (NASH).

Figure 2A:
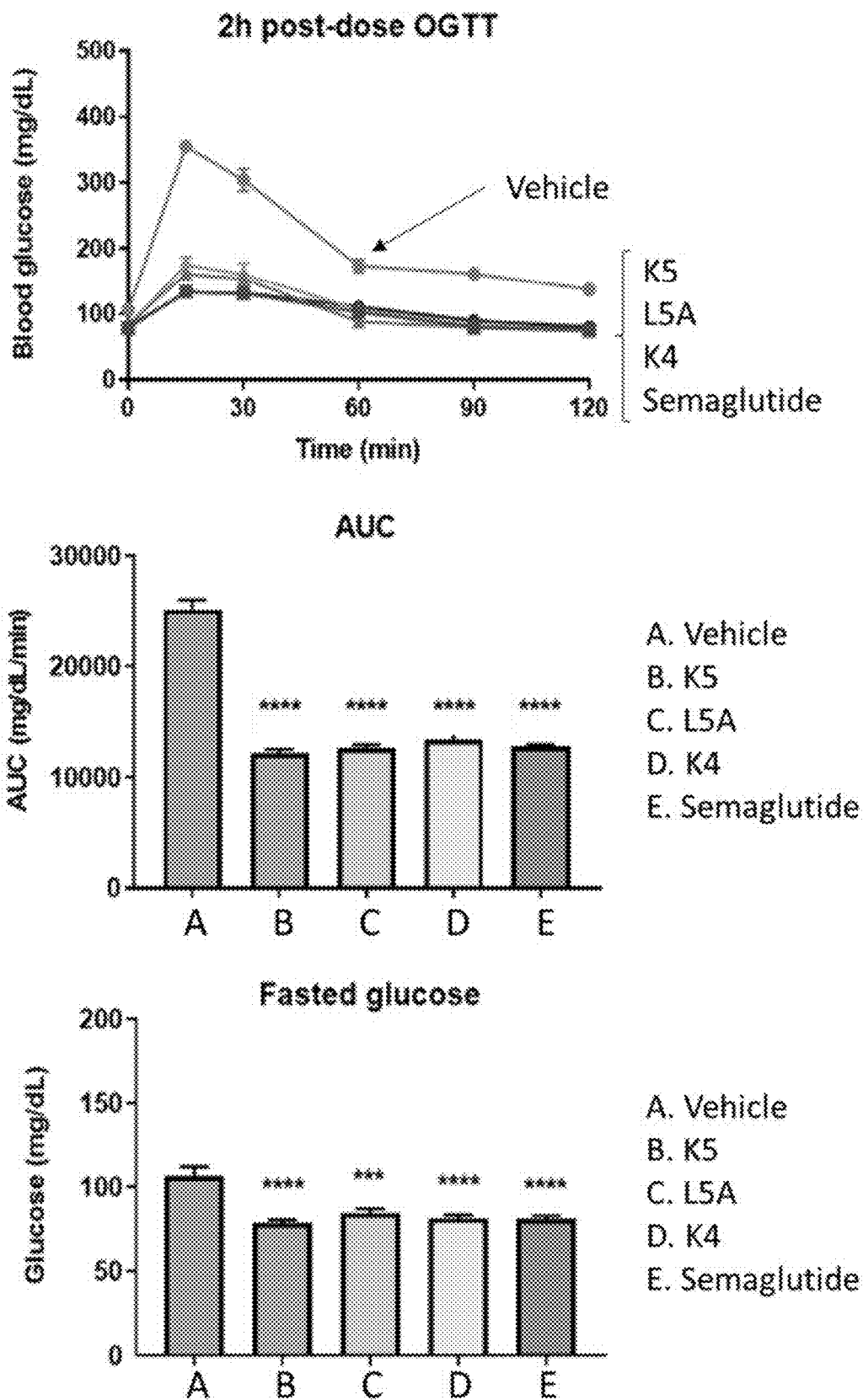
FIGS. 2A-2B are graphs showing plasma glucose excursion during oral glucose tolerance tests (OGTT) in normal mice after 2 h (FIG. 2A) and 96 h (FIG. 2B) post injection. C57B6 mice were s.c. injected with vehicle, L5A (mCMC759), K5 (mCLZ715), K4 (mCMD307), or semaglutide (at 10 nmol/kg each) 2 h prior to the glucose challenge. The bar graph shows the levels of glucose in mice obtained by measuring the area under curve [AUC] as well as the effects on fasted blood glucose. Data are means±SE, n=6 per group. Statistics: AUC and fasted glucose data were compared by one-way ANOVA followed by Dunnett's multiple comparison tests vs. PBS-treated mice: **$P<0.0001$; *$P<0.001$.
Figure 2B:
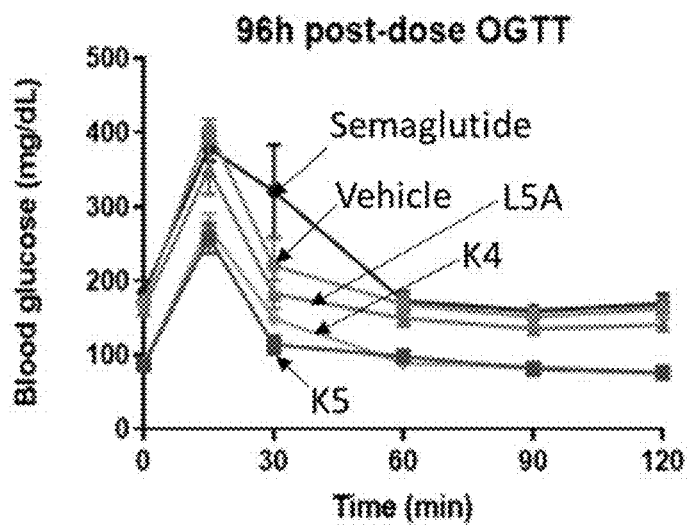
Figure 2B:
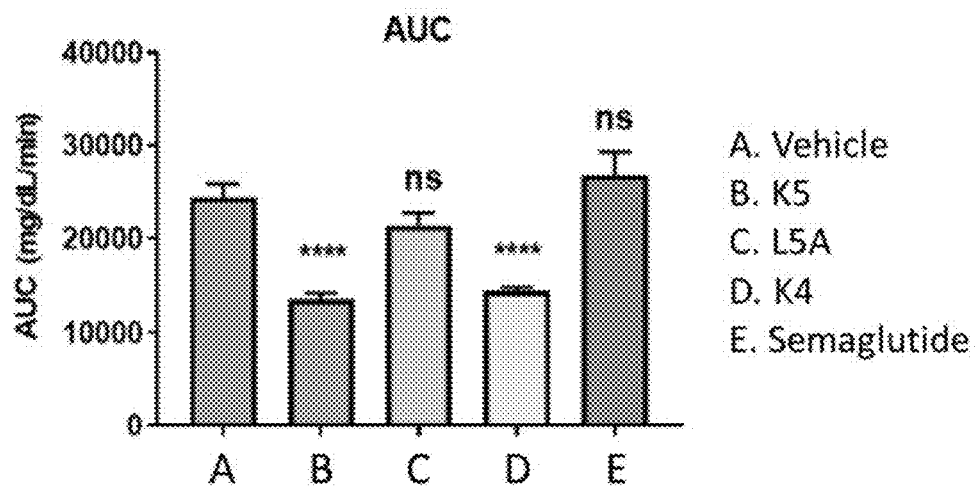
Figure 2B:
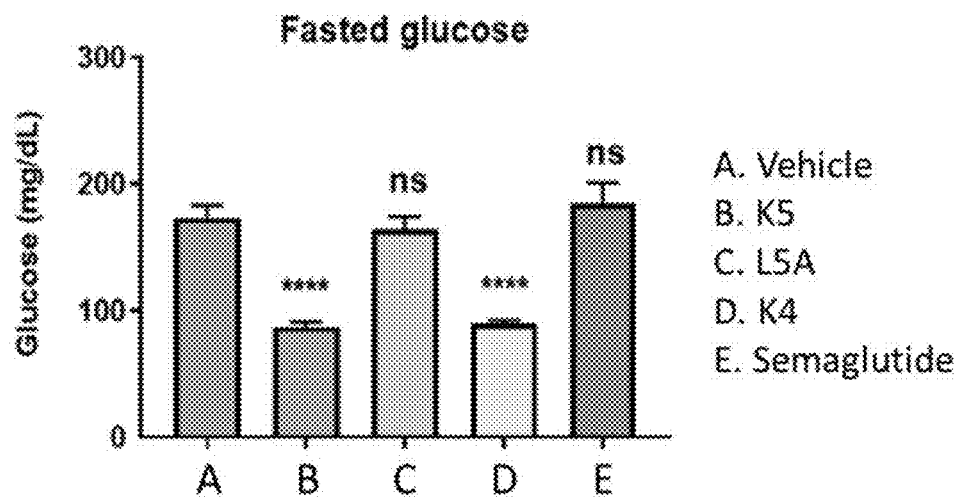

The Acute Effects of Dual Incretin Agonists on Glucose Tolerance in Wild-Type Mice Selected GLP-1R/GIPR dual agonists were evaluated for their acute effects in oral glucose tolerance tests (OGTT) in wild-type mice. The single GLP-1R agonist semaglutide was employed as a positive control in this experiment. All peptides significantly improved glucose tolerance to a similar level after 2 h of from administration when compared to the vehicle (FIG. 2A). Similar results were observed for fasted blood glucose for all peptides. However, significant differences in glucose levels were observed after 96 h from administration of the peptides. Semaglutide did not exhibit any improvement over the vehicle after 96 h. On the other hand, mice treated with mCMD307 (K4) and mCLZ715 (K5) showed more significant improvements in handling glucose (FIG. 2B). Moreover, mCMD307 (K4) and mCLZ715 (K5) were able to significantly reduce fasted glucose levels while the rest of the peptides resulted in no improvements in efficacy. The increased in vivo efficacy of mCMD307 (K4) and mCLZ715 (K5) observed here likely result from both higher dual agonistic activity and the extended in vivo half-life. Assuming a direct relationship between pharmacokinetics and pharmacokinetics, the results of this experiment indicate that peptide mCMD307 (K4) and mCLZ715 (K5) exhibits a longer half-life than semaglutide, and thus has the potential to be developed as a once weekly or semi-monthly with an appropriate formulation.

Pharmacokinetics in Wild-Type Mice

Figure 3:
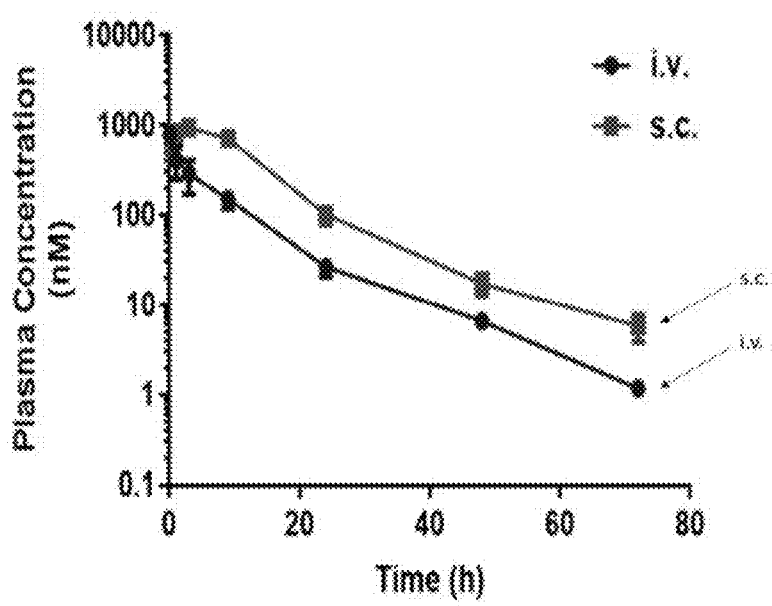
FIG. 3 is a graph showing the pharmacokinetic profile of peptide mCMD307 (K4) after a single s.c. administration (1 mg kg-1) or i.v. administration (0.3 mg kg-1) in mice. Peptide dissolved in PBS (pH 8.2) was administered via i.v. or s.c. route into CD1 mice (n=3 per group). Blood samples were collected at the indicated time points and analyzed by in vitro GLP-1R activity assay. The assay was performed in triplicate. Pharmacokinetic analyses were determined by noncompartmental analysis with WinNonLin.
Figure 4A:
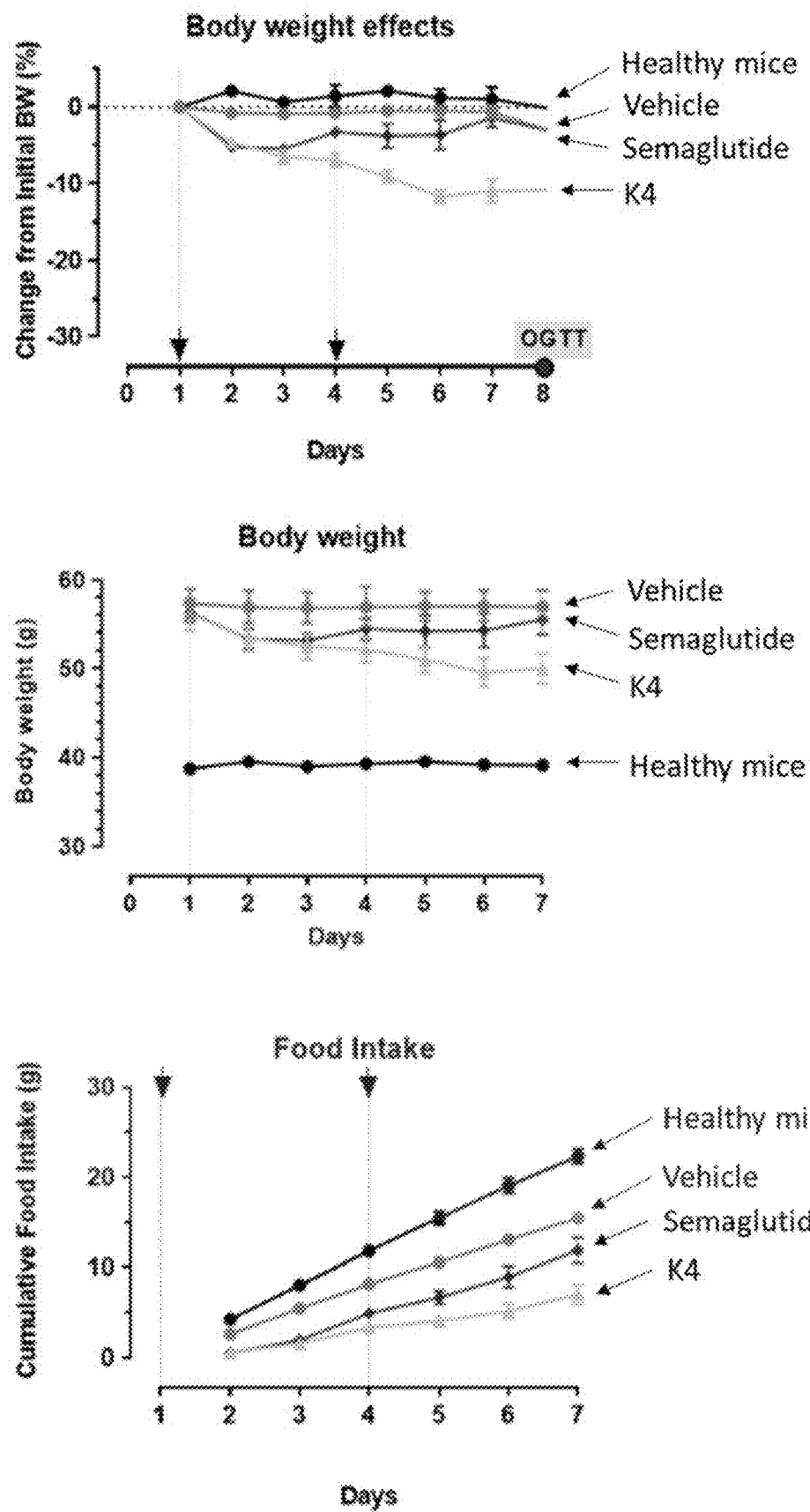
FIGS. 4A-4B show in vivo efficacy of mCMD307 (K4) in DIO mice treated for 7 days. Effects on body weight change (FIG. 4A, top), crude body weight (FIG. 4A, middle), cumulative food intake (FIG. 4A, bottom), OGTT on day 7 (FIG. 4B, top and middle), and fasted blood glucose on day 7 (FIG. 4B, bottom). C57BL/6 mice (male, 37 weeks old) were treated with PBS (s.c., twice daily), mCMD307 (K4) (s.c. once daily; 10 nmol kg-1) or semaglutide (s.c. once daily; 10 nmol kg-1) for 7 days. The arrows indicate the day of administration. Data are means±SE, n=6 per group. Statistics: AUC and fasted glucose data were compared by one-way ANOVA followed by Dunnett's multiple comparison tests vs. PBS-treated mice: **$P<0.0001$; *$P<0.001$; **$P<0.01$.
Figure 4B:
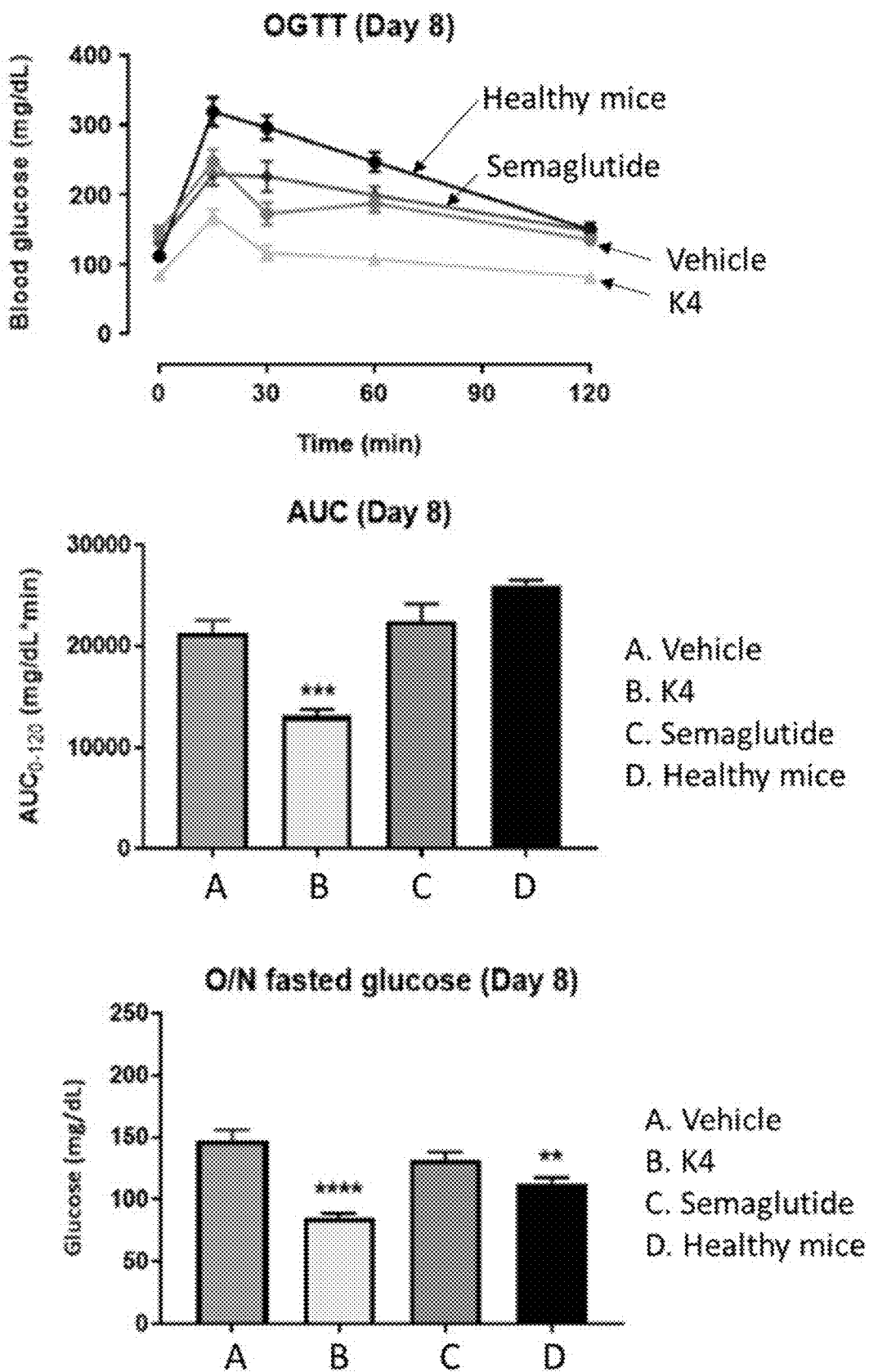

To determine the in vivo half-life of the potent analog mCMD307 (2050-K4), pharmacokinetic (PK) studies were performed in CD1 female mice by i.v. or s.c. injection of the peptide at 40 μg/kg. Plasma level of the peptide at indicated time points was determined using the in vitro GLP-1R reporter assay. mCMD307 (2050-K4) exhibited higher $T_{max}$ and $C_{max}$ (11.6 h and 4710 nM, respectively) after s.c. administration (FIG. 3). Notably, the terminal mouse plasma half-life of mCMD307 (2050-K4) is longer than that of semaglutide (rodent half-life is ~8 h), which has been clinically approved for once-weekly application in T2DM patients. It is also noteworthy that although our focus for half-life extension was on the serum-binding ability of the stapled peptide, there may be a combination of effects, for example self-assembly and depoting at the injection site, that led to the delayed onset of $C_{max}$ and the extended half-life.

TABLE 6

PK Parameters of Peptide mCMD307 (K4) in Plasma

| $T_{max}$ | 2.33 ± 1.16 h | $C_{max}$ | 4710 ± 659 ng mL$^{-1}$ |
|---|---|---|---|
| $T_{1/2}$ | 11.6 ± 0.85 h | $AUC_{0\text{-}last}$ | 59200 ± 6810 ng h mL$^{-1}$ |
| $V_{ss}$ | 0.18 ± 0.05 L Kg$^{-1}$ | Clearance | 0.28 ± 0.04 mL min$^{-1}$ kg$^{-1}$ |

Experimental Procedures

Peptide cross-linking. The dicysteine-containing peptide (2 mM, >85% pure) (Shanghai Apeptide Co., Shanghai, China) and the cross-linker (1.5 eq) were dissolved in $CH_3CN$/30 mM $NH_4HCO_3$ buffer (v/v; 1:3) pH 8.5), and the reaction was stirred at room temperature for 2-4 h. Under ice cooling, acetic acid was then added dropwise to reduce the pH of the mixture to around 5 and the crude cross-linked peptide was then purified by semi-preparative chromatography on Agilent 1200 with a Phenomenex Luna column ($C_{18}$, 100 Å pore size, 5 μm particle size, 150×21.2 mm). A linear gradient from 30% to 60% $CH_3CN$/$H_2O$ containing 0.05% trifluoroacetic acid was applied for 60 min at a flow rate of 20 mL min$^{-1}$. The fractions containing the products were collected and lyophilized to afford the products as a powder with >90% purity.

The identity and purity of the peptide were determined using an Agilent 6520 accurate-mass quadrupole-time-of-light (QTOF) instrument equipped with reversed-phase liquid chromatography and an electrospray ionization (ESI). Aeris Widepore column (XB-$C_{18}$, 3.6 μm particle size, 150×2.1 mm) was used with a flow rate of 0.5 mL min$^{-1}$ and peptides were detected using a UV-Vis detection wavelength of 214 nm.

Generation of CRE-Luc stable cell line overexpressing GLP-1R or GIP. HEK293 cells were infected with lentivirus encoding firefly luciferase gene under the control of cAMP responsive element (CRE) promoter (Qiagen, The Netherlands) and then were selected using 1 μg mL$^{-1}$ puromycin (Life Technologies, Carlsbad) for 1 week. The surviving cells (referred to as CRE-HEK293) were expanded and then transfected with a G418 selective mammalian expression plasmid encoding human GLP-1R or GIPR. In brief, GLP-1R or GIPR plasmid was transfected into CRE-HEK293 cells using Lipofectamine 2000 and selected with 400 μg mL$^{-1}$ Geneticin (Life Technologies, Carlsbad, CA). Single colony stable cell line overexpressing CRE-luciferase and GLP-1R or GIPR (HEK293-GLP-1R-CRE or HEK293-GIPR-CRE) was then established for in vitro activity assay.

In vitro receptor activation reporter assay (receptor-mediated cAMP synthesis) HEK293-GLP-1R-CRE or HEK293-GIPR-CRE cells were seeded in 384-well plates at a density of 5000 cells per well and cultured for 18 h in DMEM with 10% FBS at 37° C. and 5% $CO_2$. Cells were treated with peptides in a dose-dependent manner for 24 h, and receptor activation was reported by luminescence intensities, using One-Glo (Promega, WI) luciferase reagent following manufacturer's instruction. The $EC_{50}$ of each peptide was determined using GraphPad Prism 6 software (GraphPad, San Diego, CA).

cAMP Assay

CHOK1 cells stably overexpressed human GLP-1R or GIPR (20 μL of 5000 cells per well) were seeded in a white solid 384 well plate covered with metal lid and incubated overnight. On day 2, the culture medium was replaced by fresh medium containing no FBS (for 0% FBS group). Cells were treated with 5 μL peptide in 12-point dose response, in culture medium with 0.5 mM IBMX in triplicate for 30 min at 37° C., 5% $CO_2$. cAMP dynamic 2 kit from Cisbio was used to detect cAMP level. Briefly, 25 µL of cAMP detection reagent (1:1:38 of cAMP-d2, Cryptate conjugate, lysis buffer) per well was added and incubated at room temperature for 1 h. For cell negative control wells, cAMP detection reagent without d2 was added. Plates were then read at Ex320 nm, Em-1 665 nm and, EM-2 620 nm. Graphs were plotted with Ratio or ΔF using Prism software and $EC_{50}$ values were then obtained:

Ratio=$A_{665\ nm}/B_{620\ nm}$×10$^4$

% ΔF=(standard or sample ratio−ratio$_{neg}$)/ratio$_{neg}$×100.

Animals Animal care and experimental procedures were approved by the Institutional Animal Care and Use Committee (IACUC) of Calibr at the Scripps Research Institute, strictly following the NIH guidelines for humane treatment of animals.

Pharmacokinetics of peptides in mice Female CD-1 mice (n=4 per group) from Charles River Laboratory were fasted overnight and administered 100 µL of each peptide in phosphate buffered saline by intravenous (i.v.) or subcutaneous (s.c.) route. Food was provided to mice after blood collection at 3 h time point. Blood was collected into heparin tubes and centrifuged at 3,000×g for 15 min. The resulting plasma were then stored at −80° C. for peptide concentration determination. The concentrations of peptides in plasma at each time point were determined by in vitro cell based activity assay. Briefly, HEK293-GLP-1R-CRE cells were treated with plasma samples at different time points (5-point dose response, starting from 1:10 to 1:100 dilution of each plasma sample) and incubated for 16 h in DMEM with 10% FBS at 37° C. with 5% $CO_2$, and the firefly luciferase activity was then measured. Simultaneously, the same peptides were used to obtain standard curves and parameters for Bottom, Top, $EC_{50}$, and Hill Slope. Relative luciferase unit (RLU) for each plasma sample was used to calculate the peptide concentrations in plasma (nmol/L), using parameters derived from the standard curve:

(RLU=Bottom+(Top−Bottom)/(1+10$^{(Log\ EC50-Conc.)\times Hill\ Slope)}$))

Peptide concentrations in plasma were obtained and plotted against time points to obtain in vivo half-life of each peptide, using WinNonLin Phoenix software (Pharsight Corp, St. Louis, MO).

Oral glucose tolerance test (OGTT) Female Charles River CD-1 mice were fasted overnight and then administrated 150 µL of each peptide in PBS (pH=8.2) by i.v. or s.c. route. After 6 h, mice were orally or intraperitoneally administrated with 2 gram of glucose solution per kg body weight and their blood glucose levels were measured (by tail nick) before (0 min) and after glucose challenge for 2 to 3 h.

DIO Study DIO mice ($C_{57}BL/6$, male, 25 weeks old, or 19 weeks on high fat diet) were randomized based on their body weight and were treated with daily subcutaneous injections of mCMD307 (2050-K4) or vehicle (n=5). Body weight and food intake were monitored daily throughout the study. At the end of the experiment, mice were sacrificed, and visceral fat mass was weighed. Collected plasma was used for cholesterol level determination according to the manufacturer's guide (cholesterol assay kit, Abcam, Cambridge, England) and triglyceride level using a triglyceride colorimetric assay kit (Cayman chemical, Ann Arbor, Michigan). Oil red staining Frozen tissue sections of liver were cut at 10 µm and air dried onto the slides. After fixation in 10% formalin for 5 min, the slides were briefly washed with running tap water for 10 min, followed by rinsing with 60% isopropanol. Subsequently, oil red 0 working solution (0.3% oil red 0) was used to stain lipid for 15 min. Slides were again rinsed with 60% isopropanol, and then nuclei were lightly stained with alum hematoxylin, followed by rinsing with distilled water, and mounted in glycerin jelly. Pictures were taken under a microscope.

Biochemical and Histological analyses Terminal serum analytes including ALT, AST, and ALP were determined by Alfa Wassermann Vet Axcel clinical analyzer. Hepatic triglycerides were measured in liver homogenates generated with a colorimetric triglyceride kit (Cayman Chemical). Paraformaldehyde-fixed liver were paraffin-embedded, sectioned and stained with hematoxylin-eosin and Picro-Sirius red by HistoTox Labs (Boulder, CO). All histological assessment (steatosis, fibrosis scoring) were performed by a certified histopathologist blind to treatment (HistoTox Labs) based on classification outlined by Kleiner et al.

Example B: In Vitro Receptor Activation Reporter Assay (Receptor-Mediated cAMP Synthesis) HEK293

Generation of CRE-Luc Stable Cell Line Overexpressing GLP-1R

HEK293 cells were infected with lentivirus encoding firefly luciferase gene under the control of cAMP responsive element (CRE) promoter (Qiagen, The Netherlands) and then were selected using 1 µg/mL puromycin (Life Technologies, Carlsbad) for 1 week. The surviving cells (referred to as CRE-HEK293) were expanded and then transfected with a G418 selective mammalian expression plasmid encoding human GLP-1R. In brief, GLP-1R plasmid was transfected into CRE-HEK293 cells using Lipofectamine 2000 and selected with 400 µg/mL Geneticin (Life Technologies, Carlsbad, CA). Single colony stable cell line overexpressing CRE-luciferase and GLP1R was then established for in vitro activity assay.

GLP-1R-CRE or HEK293-GIPR-CRE cells were seeded in 384-well plates at a density of 5000 cells per well and cultured for 18 h in DMEM with 10% FBS at 37° C. and 5% $CO_2$. Cells were treated with peptides in a dose dependent manner for 24 h, and receptor activation was reported by luminescence intensities, using One-Glo (Promega, WI) luciferase reagent following manufacturer's instruction. The $EC_{50}$ of each peptide was determined using GraphPad Prism 6 software (GraphPad, San Diego, CA). Results are depicted in FIGS. 6A-6B, FIGS. 7A-7B, FIGS. 8A-8B, FIGS. 9A-9B, and Tables 7-12. Measurements of peptide conjugate potency were expressed as half maximal effective concentration ($EC_{50}$) values.

Measurements indicate distinct and separable in vitro activation potencies of a number of peptide conjugates described herein. In some instances, novel peptide conjugates were tested against known GLP1R or dual GLP1R/GIPR agonists under the same assay conditions. Table 11 shows the results of testing mCMZ371, cCMV268, Tirzepatide, Sesmaglutide and hGIP (as a control) for human GLP1R and GIPR activation in this in vitro assay. The testing recapitulated previously published results for Tirzepatide indicating comparable GIPR activation to wild-type human GIP (hGIP). Tirzepatide is known to bind human GIPR with a comparable affinity than that of hGIP and approximately five times lower GLP-1 receptor binding than native hGLP-1 (T. Coskun et al. *Mol Metab.* 2018 December; 18:3-14). Surprisingly, mCMZ371 showed a much different in vitro activation profile compared to Tirzepatide with approximately 4-fold more potency in activating GLP1R but 2-fold less potency in activating GIPR. Thus, mCMZ371 functions as a GLP1R/GIPR dual agonist with a distinct agonist profile when compared with Tirzepatide. mCMZ371 has much stronger activation of GLP1R signaling and weaker activation of GIPR signaling than does Tirzepatide. This profile of mCMZ371 for differentially modulating the extent of two metabolic hormone receptor signaling pathways compared to a known dual agonist creates a unique activation profile of GLP1R and GIPR in subjects upon treatment. This unique activation profile in mCMZ371 is beneficial for treating a subject in need of GLP1R activation to a greater extent and GIPR activation to a lesser extent than that afforded by the use of other known GLP1R/GIPR dual agonists or combination therapy with single GLP1R and GIPR agonists. Also noteworthy in Table 11 is the comparison in activation profiles between mCMZ371 and mCMV268. These two peptide conjugates share identical amino acid sequences but differ in their lipid staples. mCMZ371 showed approximately three-fold more potent activation of GLP1R signaling and a more modest increase in potency of GIPR activation.

TABLE 8

$EC_{50}$ of receptor-mediated cAMP synthesis by various peptide conjugates

| EC50 [nM] | GLP1R | GIPR |
|---|---|---|
| Semaglutide | 0.03 | — |
| mCMD307 | 0.03 | 0.01 |
| C(14-21) - L5A | 0.16 | 0.03 |
| C(14-21) - C20L5A | 0.20 | 0.05 |
| 27I, C(14-21) - L5A | 0.04 | 0.03 |
| 27I, C(14-21) - C20L5A | 0.05 | 0.07 |
| 7I, 10V, 27I, C(14-21) - L5A | 83.92 | 12.55 |
| 7I, 10V, 27I, C(14-21) - C20L5A | ~13663 | 303.00 |

TABLE 9

$EC_{50}$ of receptor-mediated cAMP synthesis by various peptide conjugates

| EC50 [nM] | GLP1R | GIPR |
|---|---|---|
| Semaglutide | 0.03 | — |
| mCMD307 | 0.03 | 0.01 |
| C(14-21) - L5A | 0.16 | 0.03 |
| C(17-24) - L5A | 0.11 | 0.05 |
| C(17-24) - C20L5A | 0.11 | 0.05 |
| 19Q, 21A, 27I, 29Q, C(17-24) - C20L5A | 0.12 | 0.02 |

TABLE $EC_{50}$ of receptor-mediated cAMP synthesis by various peptide conjugates

| [EC50] | GLP1R (nM) | | | | GIPR (nM) | | | |
|---|---|---|---|---|---|---|---|---|
| | 02/19 | 3/25 | 03/26 | average | 02/19 | 03/25 | 03/26 | average |
| C(14-21)-C20L5A | 0.17 | 0.17 | 0.19 | 0.18 | 0.07 | 0.04 | 0.04 | 0.05 |
| C(17-24)-C20L5A | 0.07 | 0.10 | 0.09 | 0.09 | 0.04 | 0.02 | 0.03 | 0.03 |
| 27I, C(14-21)-C20L5A (mCMV266) | 0.03 | 0.05 | 0.06 | 0.05 | 0.08 | 0.06 | 0.06 | 0.07 |
| 6Y, 27I, C(14-21)-C20L5A | 0.04 | 0.07 | 0.07 | 0.06 | 0.50 | 0.58 | 0.60 | 0.56 |
| 6Y, 27I, C(17-24)-C20L5A | 0.05 | 0.07 | 0.06 | 0.06 | 0.27 | 0.27 | 0.25 | 0.26 |
| 27I, C(17-24)-C20L5A (mCMV268) | 0.02 | 0.03 | 0.03 | 0.03 | 0.05 | 0.04 | 0.03 | 0.04 |
| 6Y, 8N, 27I, C(17-24)-C20L5A | 0.06 | 0.11 | 0.07 | 0.08 | 2.48 | — | 3.29 | 2.88 |
| Semaglutide | 0.05 | 0.02 | 0.02 | 0.03 | — | — | — | — |
| mCMD307 | 0.01 | 0.01 | 0.01 | 0.01 | 0.04 | 0.01 | 0.01 | 0.02 |
| Tirzepatide | | 0.15 | 0.09 | 0.12 | | 0.02 | 0.02 | 0.02 |

TABLE 7

$EC_{50}$ of receptor-mediated cAMP synthesis by various peptide conjugates

| EC50 [nM] | GLP1R | GIPR |
|---|---|---|
| Semaglutide | 0.01 | 0.41 |
| mCMD307 | 0.01 | 0.02 |
| mCLZ715 | 0.02 | 0.02 |
| ZA-41- K4 | 13.77 | 5.31 |
| ZA-42 - K4 | 18.77 | 20.43 |
| ZA-43 - K4 | 1.32 | 11.29 |
| ZA-41 - K5 | 83.92 | 12.55 |
| ZA-42 - K5 | ~13663 | 303.00 |
| ZA-43 - K5 | 3.74 | 15.66 |

TABLE 11

Potency summary in human GLP1R and GIPR activation ($EC_{50}$ of receptor-mediated cAMP synthesis by various peptide conjugates)

| | In Vitro Potency GLP1R $EC_{50}$ [nM] | | In Vitro Potency GIPR $EC_{50}$ [nM] | |
|---|---|---|---|---|
| Peptide | 10% FBS | No Serum | 10% FBS | No Serum |
| Semaglutide | 0.42 ± 0.10 | 0.17 ± 0.09 | — | — |
| hGIP | — | — | 0.01 ± 0.00 | 0.05 ± 0.00 |
| mCMV268 | 1.96 ± 0.46 | 0.42 ± 0.12 | 0.09 ± 0.02 | 0.01 ± 0.01 |
| mCMZ371 | 0.56 ± 0.15 | 0.14 ± 0.06 | 0.04 ± 0.01 | 0.01 ± 0.00 |
| Tirzepatide | 2.35 ± 0.27 | 0.57 ± 0.25 | 0.02 ± 0.00 | 0.006 ± 0.00 |

TABLE 12

Potency summary in mouse, cynomolgous monkey, and dog GLP1R and GIPR activation (EC$_{50}$ of receptor-mediated cAMP synthesis by various peptide conjugates)

| Peptide | In Vitro Potency GLP1R EC$_{50}$ [nM] | | | In Vitro Potency GIPR EC$_{50}$ [nM] | | |
|---|---|---|---|---|---|---|
| | Mouse | Cyno | Dog | Mouse | Cyno | Dog |
| Semaglutide | 0.10 ± 0.01 | 0.13 ± 0.00 | 0.67 ± 0.08 | — | — | — |
| hGIP | — | — | — | 0.34 ± 0.05 | 0.69 ± 0.30 | 0.70 ± 0.25 |
| mCMV268 | 0.26 ± 0.08 | 0.22 ± 0.04 | 1.48 ± 0.20 | 0.26 ± 0.11 | 0.16 ± 0.04 | 0.42 ± 0.13 |
| mCMZ371 | 0.09 ± 0.01 | 0.11 ± 0.00 | 1.34 ± 0.13 | 0.27 ± 0.08 | 0.13 ± 0.02 | 0.47 ± 0.12 |
| Tirzepatide | 0.16 ± 0.02 | 0.55 ± 0.08 | 6.98 ± 1.23 | 0.42 ± 0.27 | 0.08 ± 0.02 | 0.10 ± 0.15 |

To investigate the stability of the conjugates in mouse, cyno monkey, dog, and human plasma, conjugate mCMD307 was incubated in plasma for 24 h (Table 13). At certain time intervals a sample of plasma was taken and plasma proteins precipitated. Samples were analyzed using LC-MS.

TABLE 13

Plasma stability

| | Area under the peak (%) | Cleavage point |
|---|---|---|
| 24 h Stability Data in Mouse | | |
| mCMD307 | 53% | N/A |
| Impurity 1 | 7.10% | Pro(31)/Ser(32) |
| Impurity 2 | 22.4% (Impurities 2 & 3 co-elute) | Thr(7)/Ser(8) |
| Impurity 3 | | Phe(6)/Thr(7) |
| Impurity 4 | 13.20% | Tyr(10)/Ser(11) |
| Impurity 5 | 4.7% (Impurities 5 & 6 co-elute) | Leu(26)/Leu(27) |
| Impurity 6 | | Tyr(13)/Lys(14) |

TABLE 13-continued

Plasma stability

| | Area under the peak (%) | Cleavage point |
|---|---|---|
| 24 h Stability Data in Cyno | | |
| mCMD307 | 87% | N/A |
| Impurity 1 | 3.14% | Pro(31)/Ser(32) |
| Impurity 2 | 5.39% | Aib(2)/Glu(3) |
| 24 h Stability Data in Dog and Human | | |
| mCMD307 | 92% | N/A |

Example D: Pharmacokinetics Studies

The pharmacokinetic profile of conjugates (27, C(14-21)-C20L5A) and (271, C(17-24)-C20L5A) was evaluated in mice upon s.c. or i.v. injection at 1 mg/kg. The peptide plasma concentration at various time points was determined using LC-MS.

Figure 11A:
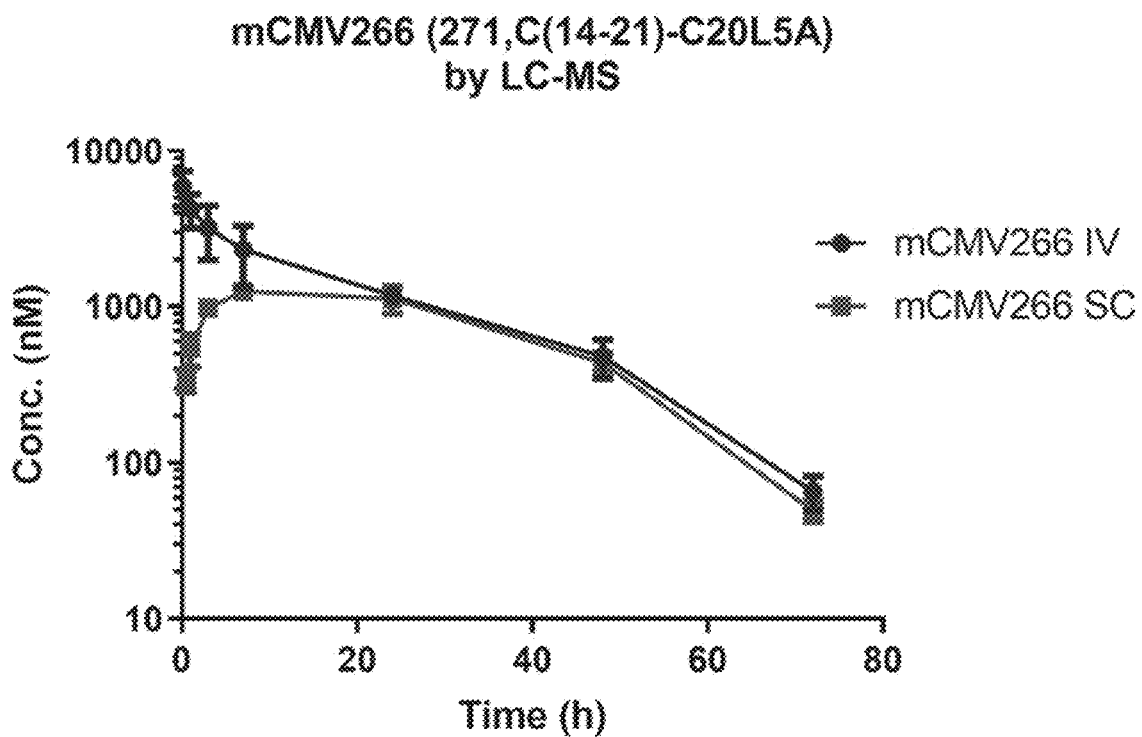
FIGS. 11A-11B show the plasma concentration in mice versus time for peptide mCMV266 (FIG. 11A) and mCMV268 (FIG. 11B) administered via IV and SC.
Figure 11B:
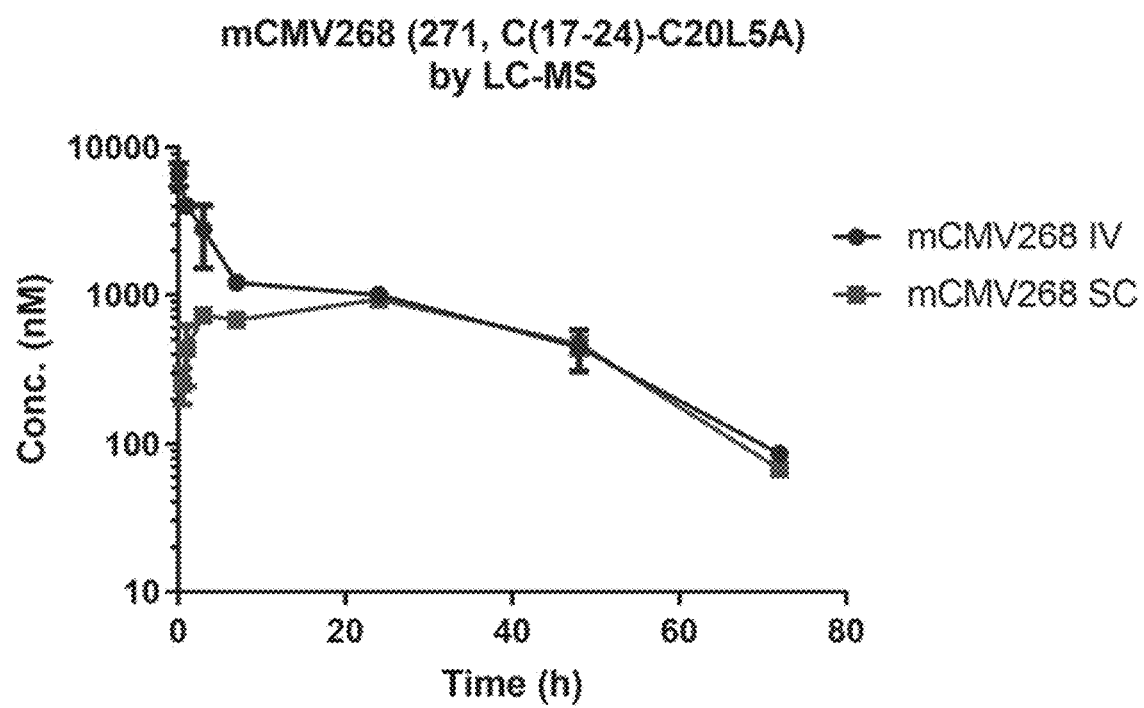

FIGS. 11A-11B show the plasma concentration in mice versus times for peptides administered via IV and SV.

TABLE 14

Summary of mCMV266 and mCMV268 Pharmacokinetics in CD-1 Mouse (ng/mL)

| Dose (mg/kg) | Cmpd | Route | T$_{1/2}$ (hr) | C$_{max}$ (ng/mL) | T$_{max}$ (hr) | AUC$_{0-24}$ (hr*ng/mL) | AUC$_{LAST}$ (hr*ng/mL) | AUC$_{INF}$ (hr*ng/mL) | Vd (L/kg) | Cl (mL/min/kg) | MRT$_{LAST}$ (hr) | F (%) |
|---|---|---|---|---|---|---|---|---|---|---|---|---|
| 1 | mCMV 268 | IV | 14.8 | 33967 | 0.5 | 204267 | 315067 | 326967 | 0.067 | 0.050 | 19.5 | 64% |
| 1 | mCMV 268 | SC | 12.8 | 4783 | 24 | 92093 | 200467 | 208433 | 0.087 | 0.080 | 27.8 | |
| 1 | mCMV 266 | IV | 11.5 | 30367 | 0.50 | 269233 | 390433 | 397167 | 0.043 | 0.043 | 18.6 | 63% |
| 1 | mCMV 266 | SC | 10.7 | 6610 | 12.7 | 135267 | 246767 | 251600 | 0.063 | 0.067 | 24.3 | |

The pharmacokinetic profile of conjugates mCMZ370 and mCMZ371 was evaluated in mice upon I.V. or S.C. injection at 1 mg/kg. (Table 15 and Table 16). The peptide plasma concentration at various time points was determined using LC-MS. Notably, mCMZ371 demonstrated a longer half-life (t Z) and significantly larger area under the curve (AUC) calculations than mCMZ370 after either I.V. or S.C. administration. This extended pharmacokinetic profile of mCMZ37 allows for lower effective dosing strategies than would be available for mCMZ370. This feature is important given the desire to mitigate any potential adverse drugs reactions which may be dose dependent. Additionally, the extended pharmacokinetic profile of mCMZ371 will allow for an longer dose interval during treatment of a subject in need thereof.

TABLE 15

Summary of mCMZ370 and mCMZ371 Pharmacokinetics in CD-1 Mouse (I.V. administration)

| Sample Name | Animal | Dose (mg/kg) | Route | Rsq_adjusted | $C_0$ (ng/mL) | $C_{max}$ (ng/mL) | $t_{1/2}$ (hr) | $T_{max}$ (hr) | $T_{last}$ (hr) |
|---|---|---|---|---|---|---|---|---|---|
| mCMZ370 | 1 | 1 | I.V. | 0.985 | 15210 | 14564 | 8.82 | 0.08 | 72 |
|  | 2 | 1 | I.V. | 0.993 | 8380 | 8230 | 8.82 | 0.08 | 72 |
|  | 3 | 1 | I.V. | 0.976 | 10006 | 9829 | 9.87 | 0.08 | 72 |
| mCMZ371 | 7 | 1 | I.V. | 0.972 | 15533 | 15134 | 9.13 | 0.08 | 72 |
|  | 8 | 1 | I.V. | 0.995 | 21060 | 20910 | 10 | 0.08 | 72 |
|  | 9 | 1 | I.V. | 1 | 24603 | 24203 | 10.31 | 0.08 | 72 |

| Sample Name | Animal | Dose (mg/kg) | Route | $AUC_{0\_24}$ (hr*ng/mL) | $AUC_{last}$ (hr*ng/mL) | $AUC_{INF\_pred}$ (hr*ng/mL) | $V_{ss\_pred}$ (L/kg) | $V_{z\_pred}$ (L/kg) | $Cl_{\_pred}$ (mL/min/kg) |
|---|---|---|---|---|---|---|---|---|---|
| mCMZ370 | 1 | 1 | I.V. | 120757 | 148290 | 148865 | 0.098 | 0.085 | 0.112 |
|  | 2 | 1 | I.V. | 107856 | 127615 | 128099 | 0.106 | 0.099 | 0.13 |
|  | 3 | 1 | I.V. | 85158 | 102411 | 103033 | 0.133 | 0.138 | 0.162 |
| mCMZ371 | 7 | 1 | I.V. | 242246 | 341205 | 343780 | 0.054 | 0.038 | 0.048 |
|  | 8 | 1 | I.V. | 255418 | 355565 | 359258 | 0.051 | 0.04 | 0.046 |
|  | 9 | 1 | I.V. | 285442 | 403090 | 407964 | 0.046 | 0.036 | 0.041 |

| Sample Name | Animal | Dose (mg/kg) | Route | $MRT_{last}$ (hr) | $MRT_{INF\_pred}$ (hr) | $AUC_{\_\% Extrap\_pred}$ (%) | $AUMC_{\_\% Extrap\_pred}$ (%) | No_points_lambda_z (L/kg) |
|---|---|---|---|---|---|---|---|---|
| mCMZ370 | 1 | 1 | I.V. | 14.35 | 14.63 | 0.39 | 2.24 | 4 |
|  | 2 | 1 | I.V. | 13.29 | 13.56 | 0.38 | 2.36 | 4 |
|  | 3 | 1 | I.V. | 13.3 | 13.74 | 0.6 | 3.79 | 4 |
| mCMZ371 | 7 | 1 | I.V. | 18.19 | 18.69 | 0.75 | 3.41 | 3 |
|  | 8 | 1 | I.V. | 17.72 | 18.43 | 1.03 | 4.82 | 3 |
|  | 9 | 1 | I.V. | 17.83 | 18.65 | 1.19 | 5.56 | 3 |

TABLE 16

Summary of mCMZ370 and mCMZ371 Pharmacokinetics in CD-1 Mouse (S.C. administration)

| Sample Name | Animal | Dose (mg/kg) | Route | Rsq_adjusted | $C_{max}$ (ng/mL) | $t_{1/2}$ (hr) | $T_{max}$ (hr) | $T_{last}$ (hr) |
|---|---|---|---|---|---|---|---|---|
| mCMZ370 | 4 | 1 | S.C. | 1 | 2460 | 7.5 | 7 | 72 |
|  | 5 | 1 | S.C. | 0.998 | 2221 | 7.06 | 24 | 72 |
|  | 6 | 1 | S.C. | 0.998 | 3993 | 7.05 | 3 | 72 |
| mCMZ371 | 10 | 1 | S.C. | 0.999 | 9259 | 10.66 | 24 | 72 |
|  | 11 | 1 | S.C. | 0.91 | 3389 | 12.36 | 24 | 72 |
|  | 12 | 1 | S.C | 0.994 | 6337 | 11.01 | 24 | 72 |

| Sample Name | Animal | Dose (mg/kg) | Route | $AUC_{0\_24}$ (hr*ng/mL) | $AUC_{all}$ (hr*ng/mL) | $AUC_{INF\_pred}$ (hr*ng/mL) | $V_{F\_pred}$ (L/kg) | $Cl_{Fpred}$ (mL/min/kg) |
|---|---|---|---|---|---|---|---|---|
| mCMZ370 | 4 | 1 | S.C. | 41870 | 53345 | 53483 | 0.2 | 0.24 |
|  | 5 | 1 | S.C. | 44691 | 68029 | 68240 | 0.15 | 0.21 |
|  | 6 | 1 | S.C | 63474 | 80522 | 80676 | 0.13 | 0.06 |
| mCMZ371 | 10 | 1 | S.C. | 127402 | 267216 | 273625 | 0.06 | 0.12 |
|  | 11 | 1 | S.C. | 67917 | 138868 | 143707 | 0.12 | 0.08 |
|  | 12 | 1 | S.C. | 95280 | 197314 | 202468 | 0.08 | 0.24 |

| Sample Name | Animal | Dose (mg/kg) | Route | $MRT_{last}$ (hr) | $MRT_{INF\_pred}$ (hr) | $AUC_{\_\% Extrap\_pred}$ (%) | $AUMC_{\_\% Extrap\_pred}$ (%) | No_points_lambda_z (L/kg) |
|---|---|---|---|---|---|---|---|---|
| mCMZ370 | 4 | 1 | S.C. | 16.06 | 16.23 | 0.26 | 1.32 | 3 |
|  | 5 | 1 | S.C. | 20.45 | 20.64 | 0.31 | 1.23 | 3 |
|  | 6 | 1 | S.C. | 15.69 | 15.82 | 0.19 | 0.99 | 3 |

TABLE 16-continued

Summary of mCMZ370 and mCMZ371 Pharmacokinetics in CD-1 Mouse (S.C. administration)

Figure 17:
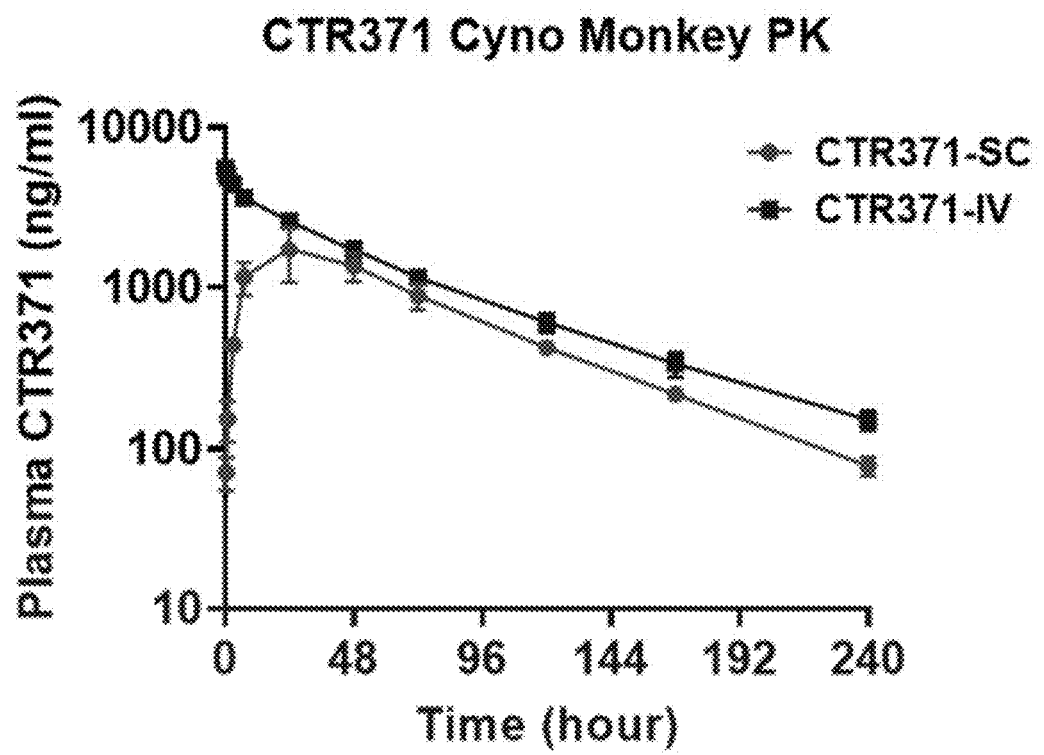
FIG. 17 shows the plasma concentration in cynomolgus monkeys versus time for peptide mCMZ371 (CTR371) and mCMV268 administered via IV and SC.
Figure 17:
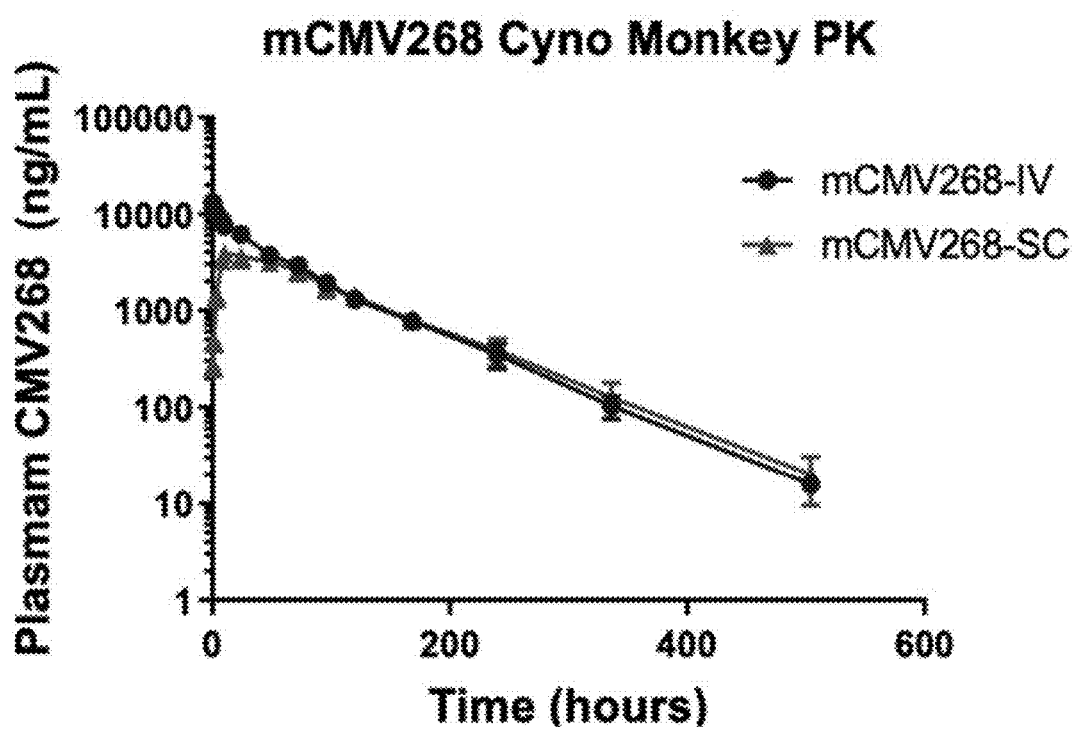
Figure 18:
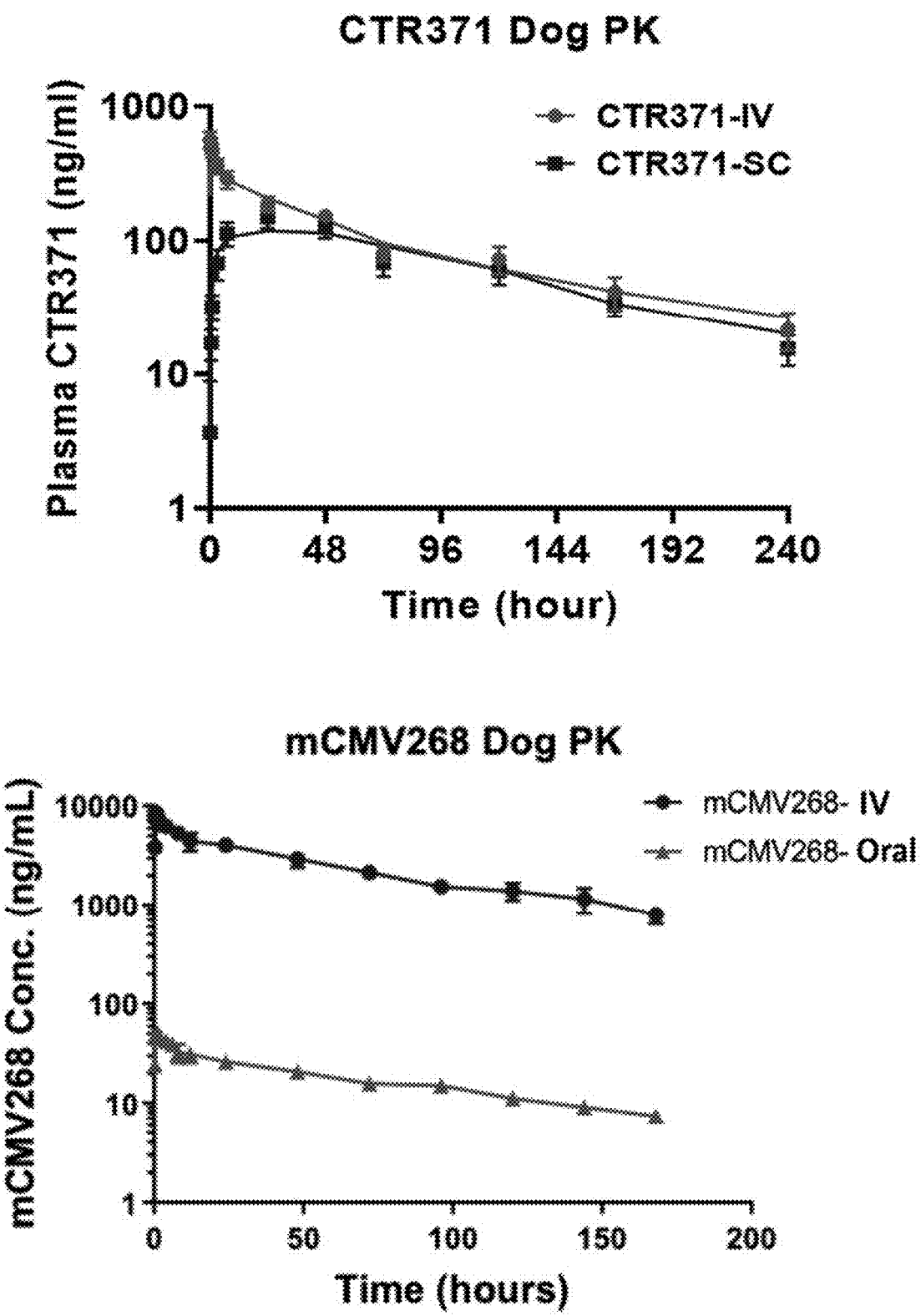
FIG. 18 shows the plasma concentration in dogs versus time for peptide mCMZ371 (CTR371) and mCMV268. CTR371 was administered via IV and SC. mCMV268 was administered via IV and PO.

| mCMZ371 | 10 | 1 | S.C. | 27.64 | 29.04 | 2.34 | 7.05  | 3 |
|---------|----|---|------|-------|-------|------|-------|---|
|         | 11 | 1 | S.C. | 26.63 | 28.76 | 3.37 | 10.52 | 3 |
|         | 12 | 1 | I.V. | 27.22 | 28.77 | 2.55 | 7.78  | 3 | mCMZ371 exhibited cross-reactivity with mouse, cynomolgus monkey, dog and human GLP1R and GIPR. Data for cynomolgus monkey assays are shown in FIG. 17 and Table 17. Data for dog assays are shown in FIG. 18 and Table 18. In addition to cross-reactivity, mCMZ371 demonstrated an extended pharmacokinetic profile with a long $t_{1/2}$ in both cynomolgus monkeys and dogs.

TABLE 17

Summary of mCMZ371 and mCMV268 Pharmacokinetics in cynomolgus monkey mCMZ371 (CTR371)

| PK Parameters | CTR371 - I.V. | CTR371 - S.C. |
|---|---|---|
| $C_{max}$ (ng/ml) | — | 1737 |
| $T_{1/2}$ (h) | 60.2 | 49.3 |
| $Vd_{ss}$ (L/kg) | 0.0538 | — |
| Cl (mL/min/kg) | 0.0126 | — |
| $T_{max}$ (h) | — | 24 |
| $T_{last}$ (h) | 240 | 240 |
| AUC $_{0-last}$ | 266594 | 155915 |
| Bioavailability (%) | — | 58.5 |

| PK Parameters | mCMV268 - I.V. | mCMV268 - S.C. |
|---|---|---|
| $C_{max}$ (ng/ml) | — | 3927 |
| $T_{1/2}$ (h) | 58.8 | 60.5 |
| $Vd_{ss}$ (L/kg) | 0.0612 | — |
| Cl (mL/min/kg) | 0.0140 | — |
| $T_{max}$ (h) | — | 14.7 |
| $T_{last}$ (h) | 504 | 504 |
| AUC $_{0-last}$ | — | 437624 |
| Bioavailability (%) | — | 73.7 |

TABLE 18

Summary of mCMZ371 and mCMV268 Pharmacokinetics in dog mCMZ371 (CTR371)

| PK Parameters | CTR371 - I.V. | CTR371 - S.C. |
|---|---|---|
| $C_{max}$ (ng/mL) | — | 150 |
| $T_{1/2}$ (h) | 71.9 | 62.7 |
| $Vd_{ss}$ (L/kg) | 0.110 | — |
| Cl (mL/min/kg) | 0.0198 | — |
| $T_{max}$ (h) | — | 24 |
| $T_{last}$ (h) | 240 | 240 |
| AUC $_{0-last}$ | 25585 | 17575 |
| Bioavailability (%) | — | 68.7 |

| PK Parameters | mCMV268 - I.V. | mCMV268 Oral |
|---|---|---|
| $C_{max}$ (ng/ml) | 8497 | 31.4 |
| $T_{1/2}$ (h) | 63.9 | 77.8 |
| $Vd_{ss}$ (L/kg) | 0.0957 | — |
| Cl (mL/min/kg) | 0.0181 | 21.6 |
| $T_{max}$ (h) | 0.693 | 1.00 |
| $T_{last}$ (h) | 168 | 144 |
| AUC $_{0-last}$ | 59235 | 1699 |
| Bioavailability (%) | — | 0.27%, 0.27%, 0.04%, 0.06%, 0 |

Example E: In Vivo Oral Glucose Tolerance Test (OGTT)

Figure 16:
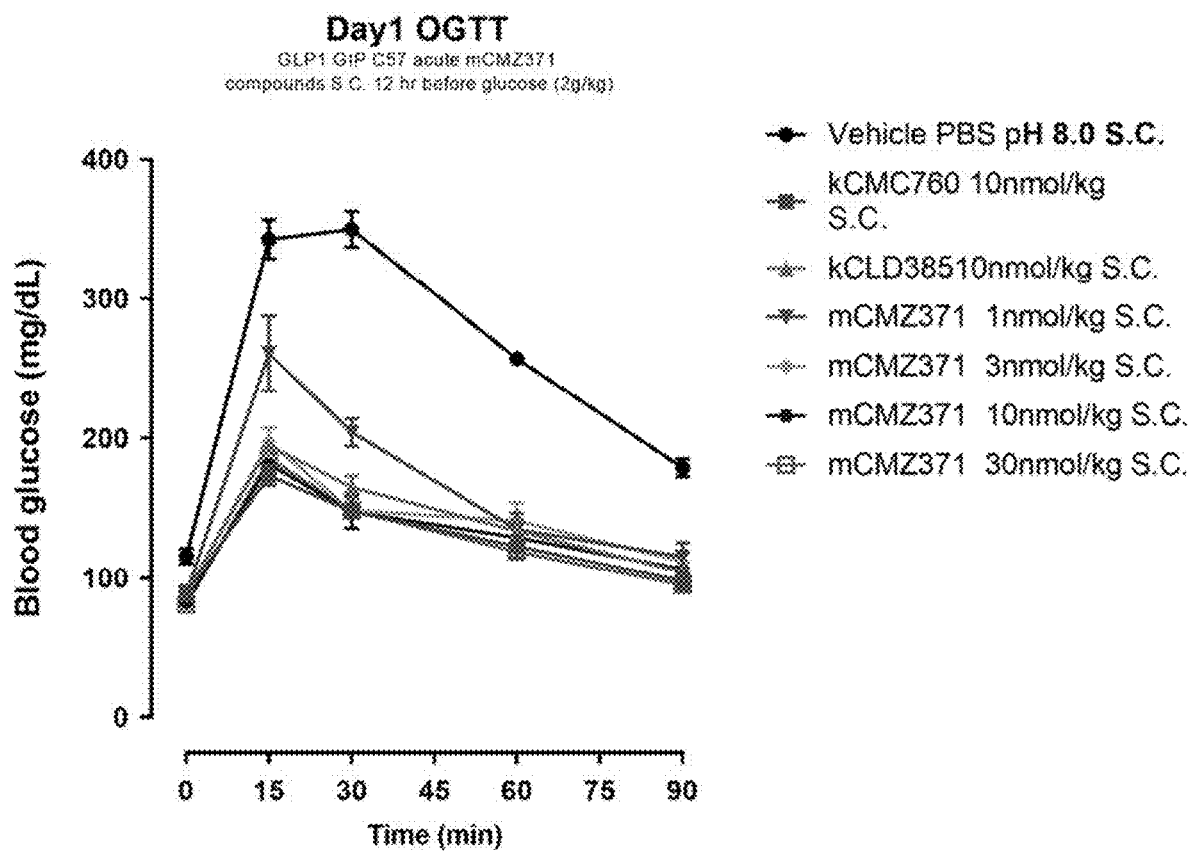
FIG. 16 shows plasma glucose excursion during oral glucose tolerance tests (OGTT) in normal mice after 12 h post injection. C57B6 mice were single-dose SC injected with vehicle, Tirzepatide (kCMC760) (10 nmol/kg), kCLD385 (10 nmol/kg), or mCMZ371 (1, 3, 10 or 30 nmol/kg) 12 hours prior to glucose challenge.
Figure 16:
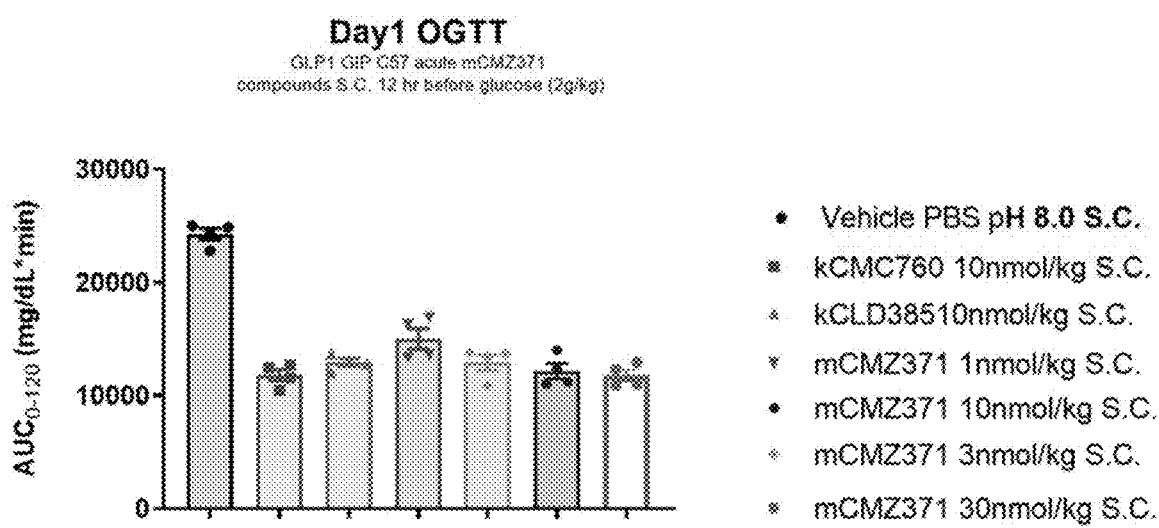

Mice were fasted overnight prior to the oral glucose tolerance test (OGTT), and then dosed with peptide. After 12 h, 1 g of glucose solution per kg body weight was administered orally, and mouse tail blood glucose levels were measured before (0 min) and after glucose challenge for 90 minutes (with measurements at 15, 30, 60 and 90 minutes) (FIG. 16). The data were compared using the unpaired Student's t test. Where appropriate, data were compared using repeated measures or one-way analysis of variance, followed by the Student-Newman-Keuls post hoc test. Calculations for $AUC_{0-120}$ (mg/dL*min) were also analyzed and graphed in FIG. 16. The effects of mCMZ371 at various dosages (1, 3, 10, and 30 nmol/kg S.C.) on oral glucose tolerance was tested and compared to that of Tirzepatide (kCMC760) (10 nmol/kg S.C.) and kCLD385 (10 nmol/kg S.C.). The graphs of $AUC_{0-120}$ mean and standard error demonstrate a glucose tolerance response for mCMZ371 at 1 nmol/kg S.C. and more robust responses at the higher dosages (3 nmol/kg S.C., 10 nmol/kg S.C., and 30 nmol/kg S.C.) indicating a clear dose response effect. The response of mice to mCMZ371, tirzepatide (kCMC760), and semaglutide (kCLD385) all at a dosage of 10 nmol/kg S.C. produced indistinguishable effects on glucose tolerance. Of note, mice treated with a single dose of mCMZ371 at 3 nmol/kg S.C. produced glucose tolerance responses that were indistinguishable from the responses to tirzepatide and semaglutide at 10 nmol/kg S.C. This indicates the extent of pharmacodynamic potency of mCMZ371 at modest concentrations allowing for a lower effective dose than the use of tirzepatide or semaglutide for subjects in need of treatment. This lower effective dose of mCMZ371 reduces both the likelihood and severity of adverse drug responses in subjects in need of treatment.

Figure 12:
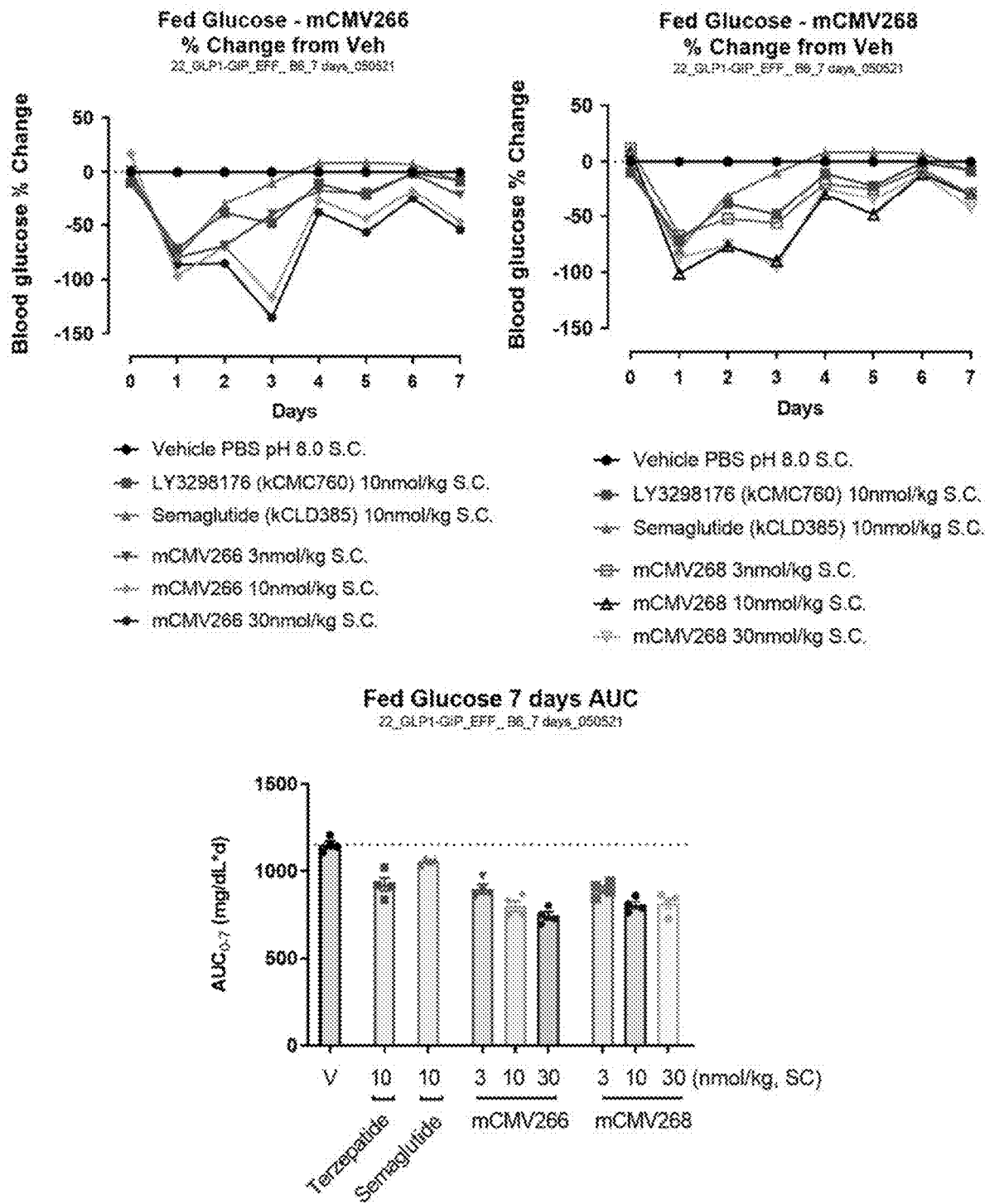
FIG. 12 demonstrate extended PD effects of mCMV266 and mCMV268 peptide conjugates on fed glucose in C57B6 mice after a single SC dose of mCMV266 (3, 10 and 30 nmol/kg) and mCMV268 (3, 10 and 30 nmol/kg).

Example F: Dose Related, Long-Acting PD Effects on Fed Glucose and Body Weight in Mice Mice were single dosed with peptide conjugates and assayed for fed glucose level and body weight for up to seven days. As shown in FIG. 12, mCMV266 and mCMV268 demonstrate a robust and durable impact on fed glucose in wild-type mice. A dose response PD effect was observed for both compounds, with a more dramatic effect with high dose mCMV266. The mCMV266 and mCMV268 peptide conjugates demonstrated better efficacy than semaglutide, and more potency in vivo than Tirzepatide.

Figure 13:
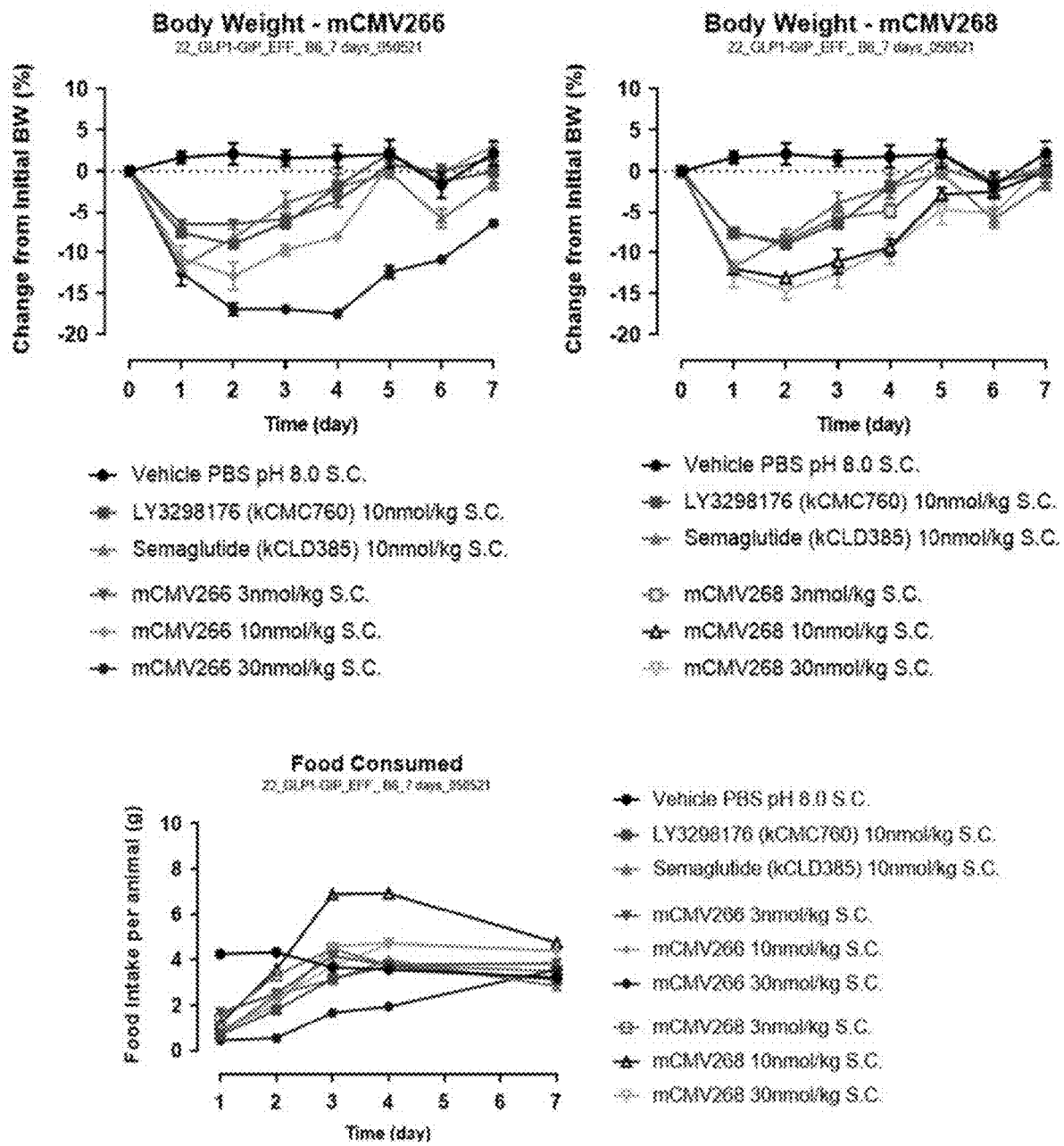
FIG. 13 demonstrate the effects of mCMV266 and mCMV268 peptide conjugates on body weight and food consumption in wild-type C57B6 mice after a single SC dose of mCMV266 (3, 10 and 30 nmol/kg) and mCMV268 (3, 10 and 30 nmol/kg).
Figure 14:
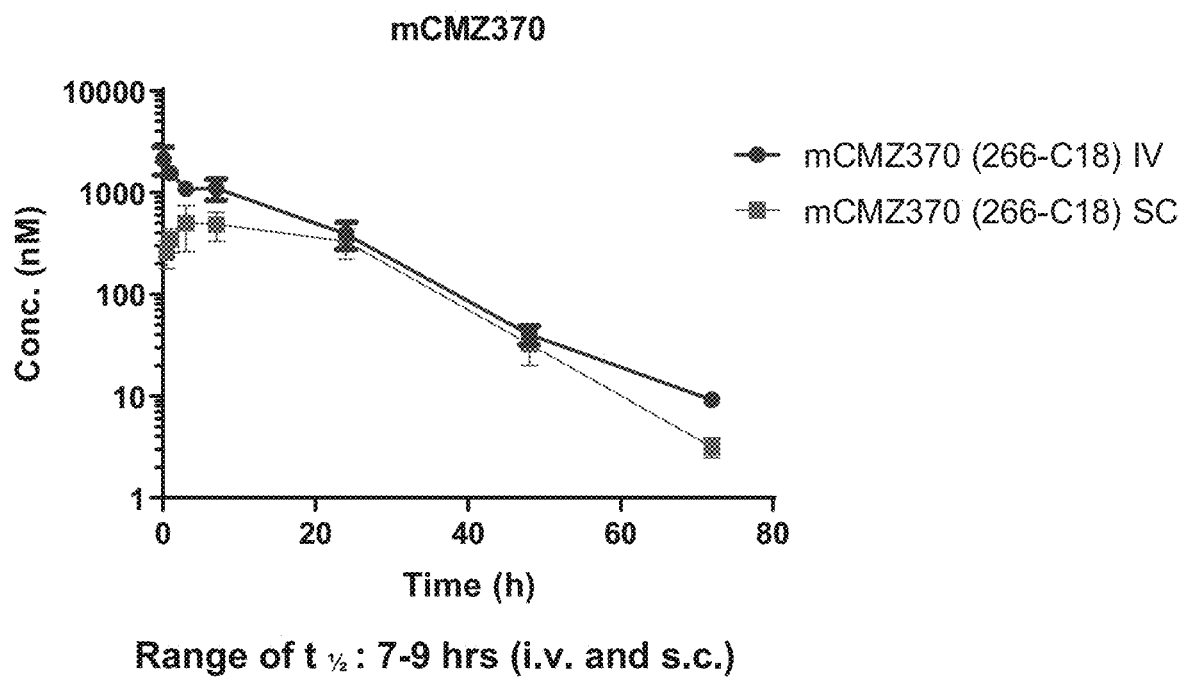
FIG. 14 shows the plasma concentration in mice versus time for peptide mCMZ370 and mCMZ371 administered via IV and SC.
Figure 14:
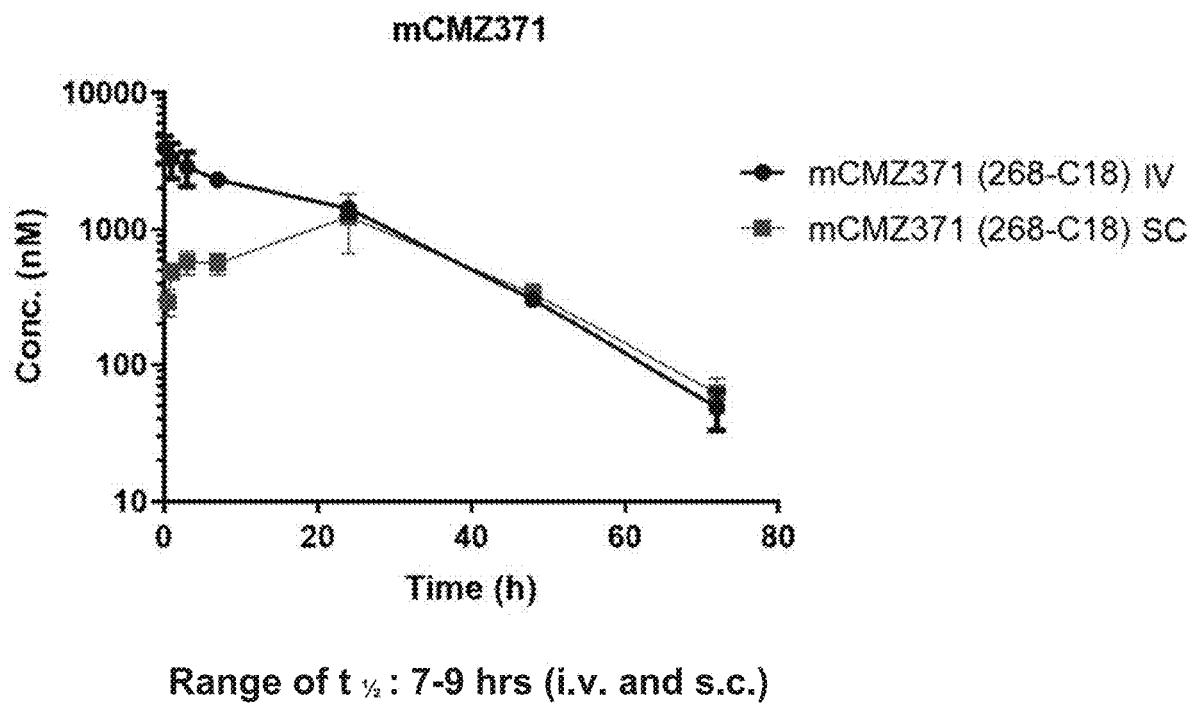

As shown in FIG. 13, mCMV266 and mCMV268 peptide conjugates demonstrate durable impact on body weight reduction in mice. The peptide conjugates demonstrated better efficacy than semaglutide, and were more potent in vivo than tirzepatide.

Figure 15:
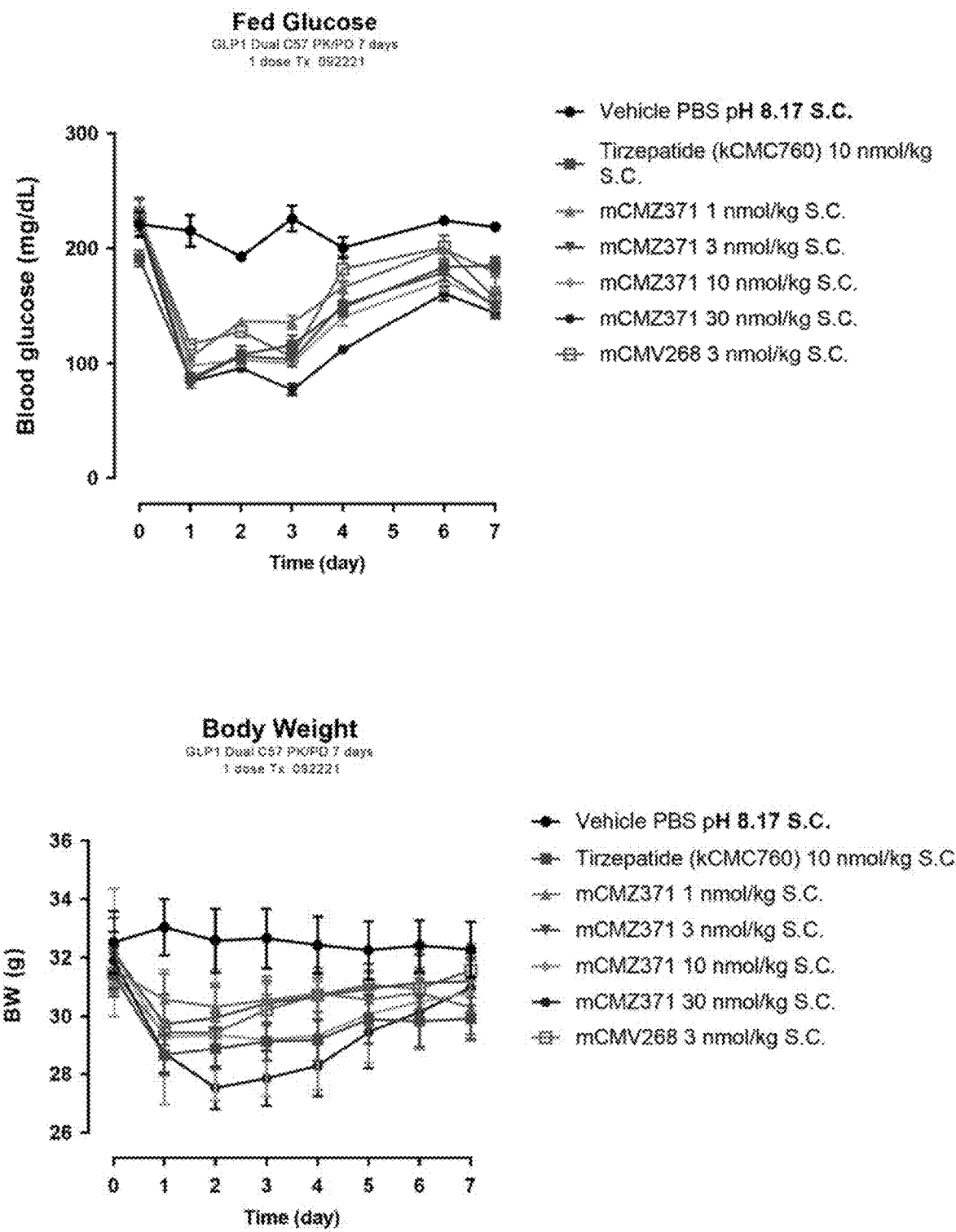
FIG. 15 demonstrates extended PD effects of mCMZ371 and mCMV268 peptide conjugates on fed glucose in C57B6 mice after a single SC dose of mCMZ371 (1, 3, 10 and 30 nmol/kg) and mCMV268 (3 nmol/kg). Results are compared to those testing Tirzepatide (kCMC760) after a single SC dose (10 nmol/kg). Effects on body weight in the same animals was also graphed at each time point.

As shown in FIG. 15, mCMZ371 demonstrated a robust and durable impact on fed glucose in wild-type mice. mCMZ371 was efficacious even from a single dose at 1 nmol/kg. mCMZ371 was more potent in reducing fed levels than mCMV268 treatment at 3 nmol/kg and more potent than Tirzepatide at 10 nmol/kg indicating clear dose response efficacy. mCMZ371 showed a stronger reduction in fed glucose than mCMV268 (both at 3 nmol/kg S.C.) and achieved similar reduction of fed glucose to Tirzepatide at 3 times higher dosages (10 nmol/kg S.C.). As shown in FIG. 15, mCMZ371 peptide conjugate demonstrated durable impact on body weight reduction in mice. A dose response was evident, but all doses of mCMZ371 tested (including 1 nmol/kg S.C.) led to a reduction in body weight. mCMZ371 and mCMV268 treatment (each at 3 nmol/kg S.C.) achieved similar efficacy in weight reduction. These effects of mCMZ371 and mCMV268 (at 3 nmol/kg S.C.) produced similar responses to higher dose treatment with Tirzepatide (at 10 nmol/kg S.C.). At 30 nmol/kg S.C., mCMZ371 treatment produced superior efficacy in reduction of body weight compared with other dosages and molecules tested. These robust pharmacodynamic responses to mCMZ371 provide opportunities for developing a treatment dosing regimen with a lower effective dose range than Tirzepatide thereby mitigating the risk of occurrence and extent of adverse drug responses in subjects in need of treatment. Based on the superior efficacy in reduction of body weight of mCMZ371 at the highest dose tested, a treatment dosing regimen can be developed yielding more extensive weight loss than treatment with Tirzepatide.

What is claimed is:

1. A peptide conjugate comprising a staple, and a peptide comprising YAibEGTFTSDYSIYLDKCAAAibEFVCWLIAGGPSSGAPPPS (SEQ ID NO: 61), wherein the staple is

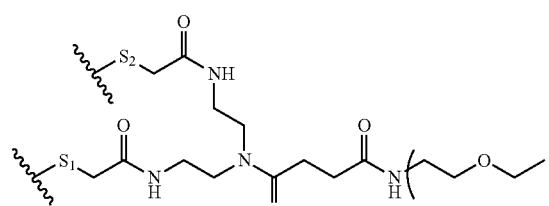

-continued

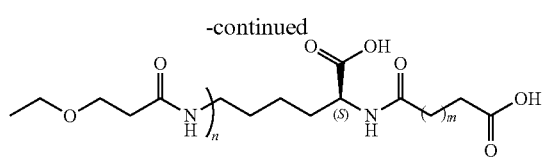

wherein n is 1-4;

m is 6-20;

—$S_2$— is a sulfur atom of the first cysteine of SEQ ID NO:61; and

—$S_1$— is a sulfur atom of the second cysteine of SEQ ID NO:61.

2. The peptide conjugate of claim 1, wherein n is 2.

3. The peptide conjugate of claim 1, wherein n is 2 and m is 13-17.

4. A pharmaceutical composition comprising the peptide conjugate of claim 1, and a pharmaceutically acceptable excipient or vehicle.

5. A peptide conjugate comprising a staple, and a peptide comprising YAibEGTFTSDYSIYLDKCAAAib-EFVCWLIAGGPSSGAPPPS (SEQ ID NO: 61), wherein the peptide conjugate has the following formula:

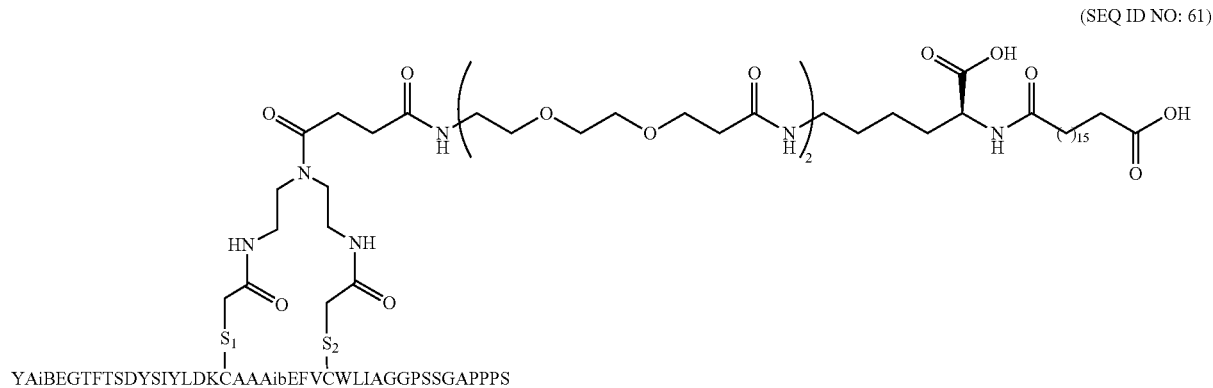

(SEQ ID NO: 61)

wherein —S$_1$— is a sulfur atom of the first cysteine of SEQ ID NO:61, and —S$_2$— is a sulfur atom of the second cysteine of SEQ ID NO:61.

6. A pharmaceutical composition comprising the peptide conjugate of claim 5, and a pharmaceutically acceptable excipient or vehicle.

7. A peptide conjugate comprising a staple, and a peptide comprising YAibEGTFTSDYSIYLDKCAAAib-EFVCWLIAGGPSSGAPPPS (SEQ ID NO: 61), wherein the staple is:

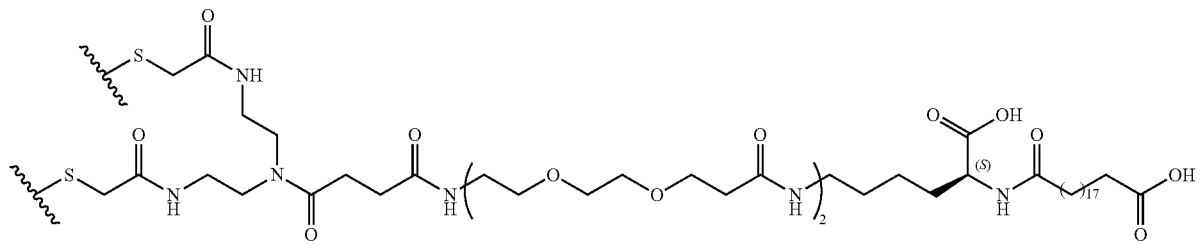

wherein each —S is a sulfur atom of a cysteine of SEQ ID NO:61.

8. A pharmaceutical composition comprising the peptide conjugate of claim 7, and a pharmaceutically acceptable excipient or vehicle.

* * * * *